United States Patent
Bolling et al.

(10) Patent No.: US 9,795,480 B2
(45) Date of Patent: Oct. 24, 2017

(54) RECONFIGURING TISSUE FEATURES OF A HEART ANNULUS

(71) Applicant: Millipede, Inc., Santa Rosa, CA (US)

(72) Inventors: Steven F. Bolling, Ann Arbor, MI (US); Jeremy A. Abbs, Minneapolis, MN (US); Brian A. Biancucci, Chelsea, MI (US)

(73) Assignee: Millipede, Inc., Santa Rosa, CA (US)

( * ) Notice: Subject to any disclaimer, the term of this patent is extended or adjusted under 35 U.S.C. 154(b) by 81 days.

(21) Appl. No.: 14/567,872

(22) Filed: Dec. 11, 2014

(65) Prior Publication Data
US 2015/0142105 A1    May 21, 2015

Related U.S. Application Data

(62) Division of application No. 12/868,624, filed on Aug. 25, 2010, now abandoned.
(Continued)

(51) Int. Cl.
*A61F 2/24* (2006.01)

(52) U.S. Cl.
CPC .......... *A61F 2/2445* (2013.01); *A61F 2/2466* (2013.01); *A61F 2/243* (2013.01);
(Continued)

(58) Field of Classification Search
CPC .......... A61F 2/24; A61F 2/2427; A61F 2/243; A61F 2/2442; A61F 2/2445;
(Continued)

(56) References Cited

U.S. PATENT DOCUMENTS

| 3,143,742 A | 8/1964 | Cromie |
| 4,602,911 A | 7/1986 | Ahmadi et al. |

(Continued)

FOREIGN PATENT DOCUMENTS

| AT | 470701 T | 6/2010 |
| AU | 2006238892 A1 | 11/2006 |

(Continued)

OTHER PUBLICATIONS

B. Braun Medical Inc., "Pulmonary Embolism: IVC Filters." Retrieved from the Internet: http://www.bbraunusa.com/pe/pe05a.html [retrieved on Dec. 14, 2006], 4 pages.
(Continued)

*Primary Examiner* — Melanie Tyson
(74) *Attorney, Agent, or Firm* — Knobbe, Martens, Olson & Bear, LLP

(57) ABSTRACT

Among other things, a tool to attach a support to a heart valve annulus includes a stabilizing body that includes features to stabilize an axial position of the tool relative to the annulus, and an attachment device connected to the stabilizing body, the stabilizing body and the attachment device being movable relative to one another under control from a location remote from the tool. The support may have an expandable tubular body having a plurality of struts, a plurality of tissue anchors extending from distally facing apexes in a distal direction post-deployment, wherein axial distal advance of the implantable annulus support causes the plurality of tissue anchors to axially engage tissue, and the implantable annulus support is self-contractible from a radially enlarged engagement configuration for engaging tissue of the mitral valve annulus, to a reduced, deployed configuration for modifying mitral valve annulus geometry.

10 Claims, 125 Drawing Sheets

Related U.S. Application Data

(60) Provisional application No. 61/376,614, filed on Aug. 24, 2010.

(52) U.S. Cl.
CPC .............. *A61F 2210/0014* (2013.01); *A61F 2220/0016* (2013.01); *A61F 2230/0069* (2013.01)

(58) Field of Classification Search
CPC ............ A61F 2/2466; A61F 2210/0014; A61F 2220/016; A61B 17/0057; A61B 2017/00579; A61B 2017/00592
See application file for complete search history.

(56) References Cited

U.S. PATENT DOCUMENTS

| | | | |
|---|---|---|---|
| 4,820,299 A | 4/1989 | Philippe et al. | |
| 5,254,127 A | 10/1993 | Wholey et al. | |
| 5,370,685 A | 12/1994 | Stevens | |
| 5,674,280 A | 10/1997 | Davidson et al. | |
| 5,769,816 A | 6/1998 | Barbut et al. | |
| 5,772,590 A | 6/1998 | Webster, Jr. | |
| 5,810,882 A | 9/1998 | Bolduc | |
| 5,824,066 A | 10/1998 | Gross | |
| 5,968,053 A | 10/1999 | Revelas | |
| 5,984,959 A | 11/1999 | Robertson et al. | |
| 6,001,127 A | 12/1999 | Schoon et al. | |
| 6,210,432 B1 | 4/2001 | Soleme et al. | |
| 6,254,642 B1 | 7/2001 | Taylor | |
| 6,355,030 B1 | 3/2002 | Aldrich et al. | |
| 6,582,460 B1 | 6/2003 | Cryer | |
| 6,652,537 B2 | 11/2003 | Mercereau et al. | |
| 6,702,826 B2 | 3/2004 | Liddicoat et al. | |
| 6,726,716 B2 | 4/2004 | Marquez | |
| 6,776,791 B1 | 8/2004 | Stallings et al. | |
| 6,790,231 B2 | 9/2004 | Liddicoat et al. | |
| 6,913,608 B2 | 7/2005 | Liddicoat et al. | |
| 6,942,694 B2 | 9/2005 | Liddicoat et al. | |
| 6,951,571 B1 | 10/2005 | Srivastava | |
| 7,007,698 B2 | 3/2006 | Thornton | |
| 7,063,722 B2 | 6/2006 | Marquez | |
| 7,081,131 B2 | 7/2006 | Thornton | |
| 7,087,064 B1 | 8/2006 | Hyde | |
| 7,329,280 B2 | 2/2008 | Bolling et al. | |
| 7,357,815 B2 | 4/2008 | Shaoulian et al. | |
| 7,404,824 B1 | 7/2008 | Webler et al. | |
| 7,482,936 B2 | 1/2009 | Bolling | |
| 7,556,647 B2 | 7/2009 | Drews et al. | |
| 7,655,040 B2 | 2/2010 | Douk et al. | |
| 7,988,725 B2 | 8/2011 | Gross et al. | |
| 8,012,202 B2 | 9/2011 | Alameddine | |
| 8,226,707 B2 | 7/2012 | White | |
| 8,287,591 B2 | 10/2012 | Keidar et al. | |
| 8,430,926 B2 | 4/2013 | Kirson | |
| 8,551,161 B2 | 10/2013 | Dolan | |
| 8,579,964 B2 | 11/2013 | Lane et al. | |
| 8,784,482 B2 | 7/2014 | Rahdert et al. | |
| 8,998,979 B2 | 4/2015 | Seguin | |
| 9,180,005 B1 | 11/2015 | Lashinski et al. | |
| 9,610,156 B2 | 4/2017 | Lashinski | |
| 2001/0044637 A1 | 11/2001 | Jacobs et al. | |
| 2002/0002401 A1* | 1/2002 | McGuckin, Jr. | A61B 17/12109 623/1.19 |
| 2002/0042621 A1 | 4/2002 | Liddicoat et al. | |
| 2002/0151961 A1 | 10/2002 | Lashinski et al. | |
| 2002/0161377 A1 | 10/2002 | Rabkin | |
| 2002/0173841 A1 | 11/2002 | Ortiz et al. | |
| 2003/0040793 A1 | 2/2003 | Marquez | |
| 2003/0093148 A1 | 5/2003 | Bolling | |
| 2003/0158570 A1 | 8/2003 | Ferrazzi | |
| 2003/0199975 A1 | 10/2003 | Gabbay | |
| 2003/0199987 A1 | 10/2003 | Berg et al. | |
| 2003/0212453 A1 | 11/2003 | Mathis et al. | |
| 2003/0225420 A1 | 12/2003 | Wardle | |
| 2003/0233142 A1 | 12/2003 | Morales et al. | |
| 2004/0010275 A1 | 1/2004 | Jacobs et al. | |
| 2004/0049266 A1 | 3/2004 | Anduiza et al. | |
| 2004/0067544 A1 | 4/2004 | Vogel et al. | |
| 2004/0092965 A1 | 5/2004 | Parihar | |
| 2004/0122516 A1 | 6/2004 | Fogarty et al. | |
| 2004/0127982 A1 | 7/2004 | Machold et al. | |
| 2004/0148019 A1 | 7/2004 | Vidlund et al. | |
| 2004/0148020 A1 | 7/2004 | Vidlund et al. | |
| 2004/0148021 A1 | 7/2004 | Cartledge et al. | |
| 2004/0167620 A1 | 8/2004 | Ortiz et al. | |
| 2004/0172063 A1 | 9/2004 | Li et al. | |
| 2004/0186565 A1 | 9/2004 | Schreck | |
| 2004/0193191 A1 | 9/2004 | Starksen et al. | |
| 2004/0193261 A1 | 9/2004 | Berreklouw | |
| 2004/0236419 A1 | 11/2004 | Milo | |
| 2004/0243104 A1 | 12/2004 | Seddon | |
| 2004/0243227 A1 | 12/2004 | Starksen et al. | |
| 2004/0243230 A1* | 12/2004 | Navia | A61F 2/2445 623/2.36 |
| 2004/0249400 A1 | 12/2004 | Vargas et al. | |
| 2004/0249453 A1 | 12/2004 | Cartledge et al. | |
| 2004/0260394 A1* | 12/2004 | Douk | A61F 2/2433 623/2.36 |
| 2005/0004665 A1 | 1/2005 | Aklog | |
| 2005/0004668 A1 | 1/2005 | Aklog et al. | |
| 2005/0038508 A1 | 2/2005 | Gabbay | |
| 2005/0049692 A1 | 3/2005 | Numamoto | |
| 2005/0075713 A1 | 4/2005 | Biancucci et al. | |
| 2005/0080454 A1 | 4/2005 | Drews et al. | |
| 2005/0131533 A1 | 6/2005 | Alfieri et al. | |
| 2005/0137701 A1 | 6/2005 | Salahieh et al. | |
| 2005/0177180 A1 | 8/2005 | Kaganov et al. | |
| 2005/0182290 A1 | 8/2005 | Lau et al. | |
| 2005/0182486 A1 | 8/2005 | Gabbay | |
| 2005/0192629 A1 | 9/2005 | Saadat et al. | |
| 2005/0234508 A1* | 10/2005 | Cummins | A61B 17/0057 606/213 |
| 2005/0267560 A1 | 12/2005 | Bates | |
| 2005/0288776 A1 | 12/2005 | Shaoulian et al. | |
| 2005/0288783 A1 | 12/2005 | Shaoulian et al. | |
| 2006/0025855 A1 | 2/2006 | Lashinski et al. | |
| 2006/0025858 A1 | 2/2006 | Alameddine | |
| 2006/0106305 A1 | 5/2006 | Lau | |
| 2006/0106456 A9 | 5/2006 | Machold et al. | |
| 2006/0129235 A1 | 6/2006 | Seguin et al. | |
| 2006/0149349 A1 | 7/2006 | Garbe | |
| 2006/0178733 A1 | 8/2006 | Pinchuk et al. | |
| 2006/0184240 A1 | 8/2006 | Jimenez et al. | |
| 2006/0184241 A1 | 8/2006 | Marquez | |
| 2006/0195012 A1 | 8/2006 | Mortier et al. | |
| 2006/0206203 A1 | 9/2006 | Yang et al. | |
| 2006/0241746 A1 | 10/2006 | Shaoulian et al. | |
| 2006/0241747 A1 | 10/2006 | Shaoulian et al. | |
| 2007/0005129 A1 | 1/2007 | Damm et al. | |
| 2007/0016287 A1 | 1/2007 | Cartledge et al. | |
| 2007/0027533 A1 | 2/2007 | Douk | |
| 2007/0050019 A1 | 3/2007 | Hyde | |
| 2007/0055368 A1 | 3/2007 | Rhee et al. | |
| 2007/0112423 A1 | 5/2007 | Chu | |
| 2007/0112425 A1 | 5/2007 | Schaller et al. | |
| 2007/0142907 A1 | 6/2007 | Moaddeb et al. | |
| 2007/0156233 A1 | 7/2007 | Kapadia et al. | |
| 2007/0161846 A1 | 7/2007 | Nikolic et al. | |
| 2007/0239272 A1 | 10/2007 | Navia et al. | |
| 2007/0244553 A1 | 10/2007 | Rafiee et al. | |
| 2007/0250161 A1* | 10/2007 | Dolan | A61F 2/2445 623/2.11 |
| 2007/0276478 A1 | 11/2007 | Marmureanu et al. | |
| 2007/0282436 A1 | 12/2007 | Pinchuk | |
| 2007/0293942 A1 | 12/2007 | Mirzaee | |
| 2007/0299543 A1 | 12/2007 | Cartledge et al. | |
| 2008/0027483 A1 | 1/2008 | Cartledge et al. | |
| 2008/0067713 A1 | 3/2008 | Bordener | |
| 2008/0077235 A1 | 3/2008 | Kirson | |
| 2008/0167713 A1 | 7/2008 | Bolling | |
| 2008/0177380 A1 | 7/2008 | Starksen et al. | |
| 2008/0255661 A1 | 10/2008 | Straubinger et al. | |

(56) References Cited

U.S. PATENT DOCUMENTS

| | | |
|---|---|---|
| 2008/0288060 A1 | 11/2008 | Kaye et al. |
| 2009/0082857 A1 | 3/2009 | Lashinski et al. |
| 2009/0087414 A1 | 4/2009 | Edelman et al. |
| 2009/0149872 A1 | 6/2009 | Gross et al. |
| 2009/0177276 A1 | 7/2009 | Carpentier et al. |
| 2009/0182419 A1 | 7/2009 | Bolling |
| 2009/0198316 A1 | 8/2009 | Laske et al. |
| 2009/0264996 A1 | 10/2009 | Vanermen et al. |
| 2009/0276040 A1 | 11/2009 | Rowe et al. |
| 2009/0287299 A1 | 11/2009 | Tabor et al. |
| 2009/0287304 A1 | 11/2009 | Dahlgren et al. |
| 2010/0004740 A1 | 1/2010 | Seguin et al. |
| 2010/0049315 A1 | 2/2010 | Kirson |
| 2010/0087855 A1 | 4/2010 | Leung et al. |
| 2010/0121433 A1 | 5/2010 | Bolling |
| 2010/0152838 A1 | 6/2010 | Kang et al. |
| 2010/0152840 A1 | 6/2010 | Seguin et al. |
| 2010/0185229 A1 | 7/2010 | Horan |
| 2010/0249920 A1 | 9/2010 | Bolling |
| 2010/0298929 A1 | 11/2010 | Thornton |
| 2011/0022166 A1 | 1/2011 | Dahlgren et al. |
| 2011/0066224 A1 | 3/2011 | White |
| 2011/0106247 A1 | 5/2011 | Miller et al. |
| 2011/0172760 A1 | 7/2011 | Anderson |
| 2011/0202127 A1 | 8/2011 | Mauch et al. |
| 2011/0224785 A1 | 9/2011 | Hacohen |
| 2011/0288632 A1 | 11/2011 | White |
| 2011/0319989 A1 | 12/2011 | Lane et al. |
| 2012/0022640 A1 | 1/2012 | Gross et al. |
| 2012/0027116 A1 | 2/2012 | Etemad |
| 2012/0053680 A1 | 3/2012 | Bolling et al. |
| 2012/0109288 A1 | 5/2012 | Bolling |
| 2012/0109289 A1 | 5/2012 | Bolling |
| 2012/0215303 A1 | 8/2012 | Quadri |
| 2012/0283757 A1 | 11/2012 | Miller et al. |
| 2012/0308610 A1 | 12/2012 | Edelman et al. |
| 2013/0006295 A1 | 1/2013 | Chanduszko |
| 2013/0046373 A1 | 2/2013 | Cartledge |
| 2013/0123910 A1 | 5/2013 | Cartledge et al. |
| 2013/0138207 A1 | 5/2013 | Quadri |
| 2013/0177600 A1 | 7/2013 | Edelman et al. |
| 2013/0325118 A1 | 12/2013 | Cartledge |
| 2014/0039612 A1 | 2/2014 | Dolan |
| 2014/0163690 A1 | 6/2014 | White |
| 2014/0222136 A1 | 8/2014 | Geist et al. |
| 2014/0277427 A1 | 9/2014 | Ratz et al. |
| 2014/2777563 | 9/2014 | White |
| 2014/0296962 A1 | 10/2014 | Cartledge et al. |
| 2014/0309731 A1 | 10/2014 | Quadri et al. |
| 2015/0142105 A1 | 5/2015 | Bolling et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0038285 A1 | 2/2016 | Glenn et al. |
| 2016/0128829 A1 | 5/2016 | Oba |
| 2016/0235526 A1 | 8/2016 | Lashinski et al. |
| 2017/0035564 A1 | 2/2017 | Ryan |
| 2017/0086974 A1 | 3/2017 | Lashinski et al. |
| 2017/0143488 A1 | 5/2017 | Lashinski et al. |
| 2017/0143489 A1 | 5/2017 | Lashinski et al. |
| 2017/0156860 A1 | 6/2017 | Lashinski et al. |

FOREIGN PATENT DOCUMENTS

| | | |
|---|---|---|
| AU | 2006238892 B2 | 11/2006 |
| CA | 2456991 | 3/2003 |
| CA | 2605080 A1 | 11/2006 |
| CN | 101268183 A | 9/2008 |
| CN | 101268183 B | 11/2008 |
| EP | 1874919 A1 | 11/2006 |
| EP | 1874919 B1 | 6/2010 |
| EP | 2 047 824 | 5/2012 |
| EP | 2 656 816 | 10/2013 |
| ES | 2347078 T3 | 10/2010 |
| HK | 1116829 A1 | 10/2015 |
| JP | H588612 | 12/1993 |
| JP | 2002-525169 | 8/2002 |
| JP | 2005-537067 | 12/2005 |
| JP | 2008-528117 | 7/2008 |
| JP | 2008-534086 | 8/2008 |
| JP | 2008-538587 A | 10/2008 |
| JP | 2008-538937 | 11/2008 |
| JP | 2010-284536 | 12/2010 |
| JP | 2012-224644 A | 11/2012 |
| JP | 05174656 B2 | 4/2013 |
| WO | WO 90/09153 | 8/1990 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 99/29269 | 6/1999 |
| WO | WO 99/49816 | 10/1999 |
| WO | WO 00/07521 | 2/2000 |
| WO | WO 00/18333 | 4/2000 |
| WO | WO 00/44311 | 8/2000 |
| WO | WO 00/62715 | 10/2000 |
| WO | WO 01/89440 A2 | 11/2001 |
| WO | WO 01/89440 A3 | 11/2001 |
| WO | WO 02/094132 | 11/2002 |
| WO | WO 03/017874 | 3/2003 |
| WO | WO 03/053289 | 7/2003 |
| WO | WO 03/080150 | 10/2003 |
| WO | WO 03/105670 | 12/2003 |
| WO | WO 03/105730 | 12/2003 |
| WO | WO 2004/014282 | 2/2004 |
| WO | WO 2004/019816 | 3/2004 |
| WO | WO 2004/019826 | 3/2004 |
| WO | WO 2004/030569 A2 | 4/2004 |
| WO | WO 2004/030569 A3 | 4/2004 |
| WO | WO 2004/031717 | 4/2004 |
| WO | WO 2004/032717 | 4/2004 |
| WO | WO 2004/103223 | 12/2004 |
| WO | WO 2004/112657 A1 | 12/2004 |
| WO | WO 2005/002424 A2 | 1/2005 |
| WO | WO 2005/002424 A3 | 1/2005 |
| WO | WO 2005/007037 | 1/2005 |
| WO | WO 2005/046488 | 5/2005 |
| WO | WO 2005/087139 | 9/2005 |
| WO | WO 2006/011275 | 2/2006 |
| WO | WO 2006/052687 | 5/2006 |
| WO | WO 2006/086135 | 8/2006 |
| WO | WO 2006/086434 | 8/2006 |
| WO | WO 2006/105084 | 10/2006 |
| WO | WO 2006/116129 A2 | 11/2006 |
| WO | WO 2006/116357 A1 | 11/2006 |
| WO | WO 2007/021834 | 2/2007 |
| WO | WO 2008/088716 | 7/2008 |
| WO | WO 2009/140268 A1 | 11/2009 |
| WO | WO 2010/011699 | 1/2010 |
| WO | WO 2012/027116 | 3/2012 |
| WO | WO 2012/167095 | 12/2012 |
| WO | WO 2013/088327 | 6/2013 |

OTHER PUBLICATIONS

Bonow, et al., "ACC/AHA 2006 Guidelines for the Management of Patients with Valvular Heart Disease," J. American College of Cardiology, 48(3):1-148 (2006).

Boston Scientific, "Device Details." Retrieved from the Internet: http://bostonscientific.com/rned_specialty/deviceDetail.jsp [retrieved on Aug. 31, 2006], 1 page.

Braunberger et al., "Very Long-Term Results (More Than 20 years) of Valve Repair with Carpentier's Techniques in Nonrheumatic Mitral Valve Insufficiency," Circulation, 104:I8-I11 (2001).

Braunwald et al., "Conservative Management of tricuspid Regurgitation in Patients Undergoing Mitral Valve Replacement," Circulation, XXXV and XXXVI:I63-I69 (1967).

Carpentier et al., "Surgical Management of Acquired Tricuspid Valve Disease," J. Thoracic and Cardiovascular Surgery, 67(1):53-65 (1974).

Center for Devices and Radiological Health, U.S. Dept. of Health and Human Services Food and Drug Administration "Guidance for

(56) References Cited

OTHER PUBLICATIONS

Annuloplasty Rings 510(k) Submissions; Final Guidance for Industry and FDA Staff," 1-15 (2001).
Cosgrove et al., "Mitral Valvuloplasty," Curro. Probl. Cardiol., 359-405 (1989).
Dreyfus et al., "Secondary Tricuspid Regurgitation or Dilatation: Which Should Be the Criteria for Surgical Repair?," Ann. Thorac. Surg., 79:127-32 (2005).
Google Images, Recurved Hooks. Retrieved from the Internet: www.implementology.org.pf and personal.cityu.edu.hk [retrieved on Dec. 14, 2006], 1 page.
Leung et al., "Barbed, Bi-directional Surgical Sutures: In Vivo Strength and Histopathology Evaluations," Society for Biomaterials 28th Annual Meeting Transactions, #724 (2003).
Magovern et al., "Sutureless Artificial Heart Valves," Circulation, 27:784-788 (1963).
McCarthy et al., "Tricuspid Valve Repair: Durability and Risk Factors for Failure," J. Thoracic and Cardiovascular Surgery, 127:674-85 (2004).
Nath et al., "Impact of Tricuspid Regurgitation on Long-Term Survival," J. American College of Cardiology, 43(3):405-409 (2004).
Navia et al., "Surgical Management of Secondary Tricuspid Valve Regurgitation: Anulus, Commissure, or Leaflet Procedure?," Abstract presented at American Association for Thoracic Surgery Annual Meeting (2009).
Rogers et al., "The Tricuspid Valve: Current Perspective and Evolving Management of Tricuspid Regurgitation," Circulation, 119:2718-2725 (2009).
Sagie et al., "Determinants of Functional Tricuspid Regurgitation in Incomplete Tricuspid Valve Closure: Doppler Color Flow Study of 109 Patients," J. American College of Cardiology, 24:446-53 (1994).
Savage et al., "Use of Mitral Valve Repair: Analysis of Contemporary United States Experience Reported to the Society of Thoracic Surgeons National Cardiac Database," Ann. Thorac. Surg., 75:820-825 (2003).
Shiran et al., "Tricuspid Regurgitation in Mitral Valve Disease," J. American College of Cardiology, 53(5):401-408 (2009).
Song et al., "Factors Associated with Development of Late Significant Tricuspid Regurgitation after Successful Left-Sided Valve Surgery," Heart, 95:931-936 (2009).
Tang et al., "Tricuspid Valve Repair with an Annuloplasty Ring Results in Improved Long-Term Outcomes," Circulation, 114:1577-1581 (2006).
Thompson, "Percutaneous Heart Valve Technology: The Mitral Challenge," Medtech Insight, 11(2):38-52 (2009).
Zlotnick et al., "A Perfectly Functioning Magovem-Cromie Sutureless Prosthetic Aortic Valve 42 Years After Implantation," Circulation, 117:e1-e2 (2008).
U.S. Appl. No. 11/620,955, filed Jan. 8, 2007.
U.S. Appl. No. 12/794,235, filed Jun. 4, 2010.
U.S. Appl. No. 12/868,624, filed Aug. 25, 2010.
U.S. Appl. No. 13/347,051, filed Jan. 10, 2012.
U.S. Appl. No. 13/347,052, filed Jan. 10, 2012.
Japanese Decision to Grant; Application No. 2009-544986; pp. 3 dated Mar. 25, 2013.
European Office Action; Application No. 08727364.5-1651; pp. 6 dated Jan. 2, 2014.
European Search Report; Application No. 10754160.9-1659 / 2408400; pp. 6 dated May 3, 2013.
European Search Report; Application No. 11186500.2-1659; pp. 5 dated Sep. 20, 2013.
European Search Report; Application No. 08727364.5-1651; pp. 3 dated Oct. 8, 2013.
European Office Action; Application No. 11186500.2-1659; pp. 6 dated Oct. 11, 2013.
International Search Report; Application No. PCT/US2008/050224; pp. 3 dated Jul. 1, 2008.
International Preliminary Report on Patentability; Application No. PCT/US08/050224; pp. 9 dated Jul. 14, 2009.
International Preliminary Report on Patentability; Application No. PCT/US2010/027943; pp. 12 dated Sep. 20, 2011.
International Preliminary Report on Patentability; Application No. PCT/US2011/047345; pp. 9, dated Feb. 26, 2013.
International Search Report and Written Opinion; Application No. PCT/US2014/026333; pp. 13 dated Jul. 21, 2014.
International Search Report and Written Opinion; Application No. PCT/US2011/047345, pp. 9 dated Dec. 7, 2011.
International Search Report and Written Opinion; Application No. PCT/US2011/039022; pp. 11 dated Sep. 22, 2011.
International Search Report and Written Opinion; Application No. PCT/US2010/027943; pp. 16 dated Jul. 13, 2010.
International Search Report and Written Opinion; Application No. PCT/US2013/059751; pp. 8 dated Dec. 11, 2013.
Japanese Office Action with English translation; Application No. 2012-500990; pp. 8 dated Jan. 8, 2014.
Japanese Office Action; Application No. 2009-544986; pp. 6 dated Aug. 13, 2012.
Partial European Search Report; Application No. 11186500.2-1659 / 2412316; pp. 7 dated Jun. 5, 2013.

* cited by examiner

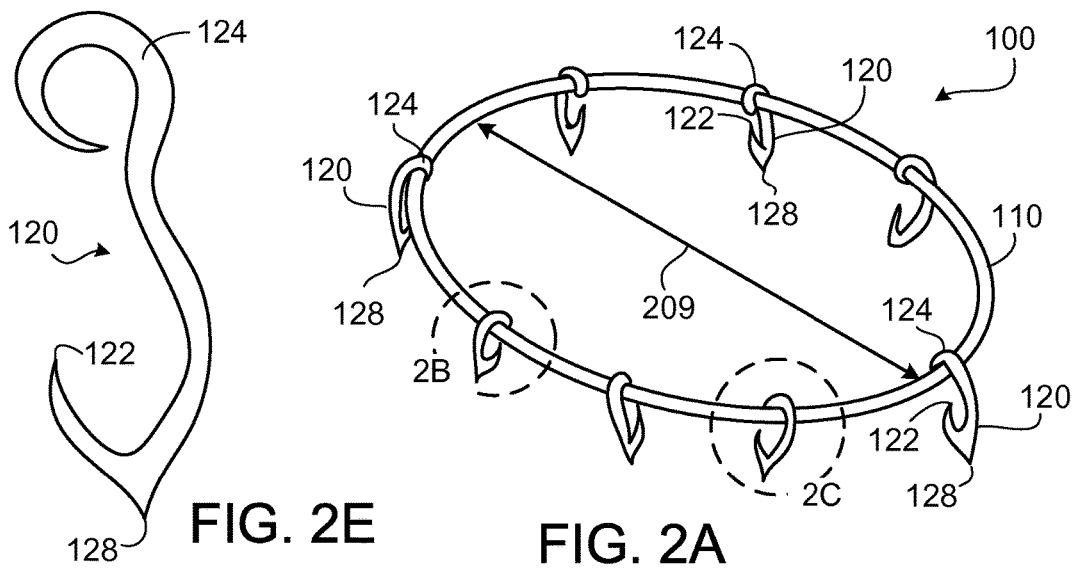
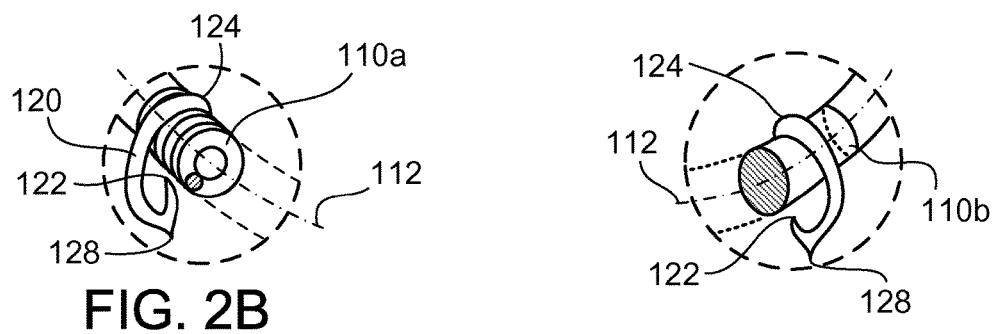
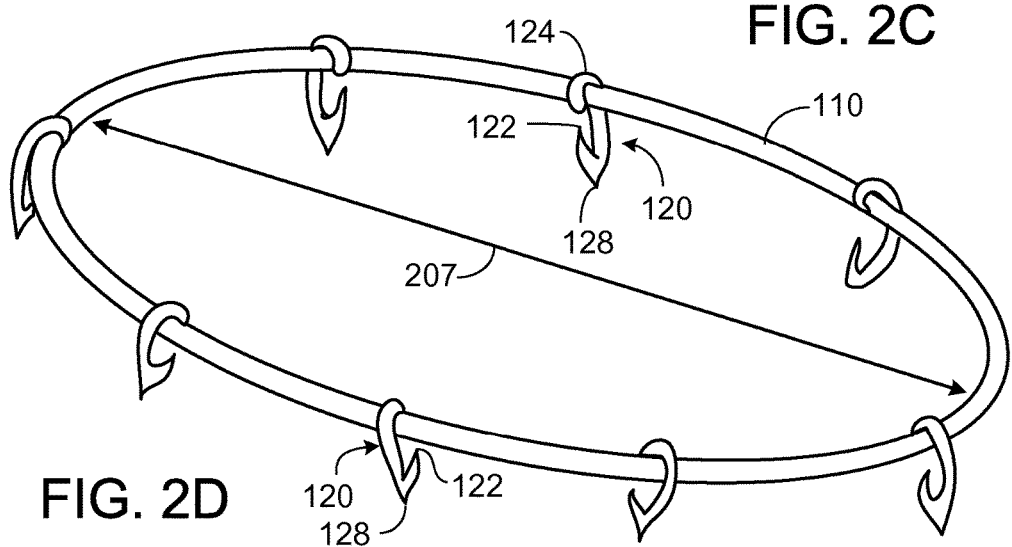

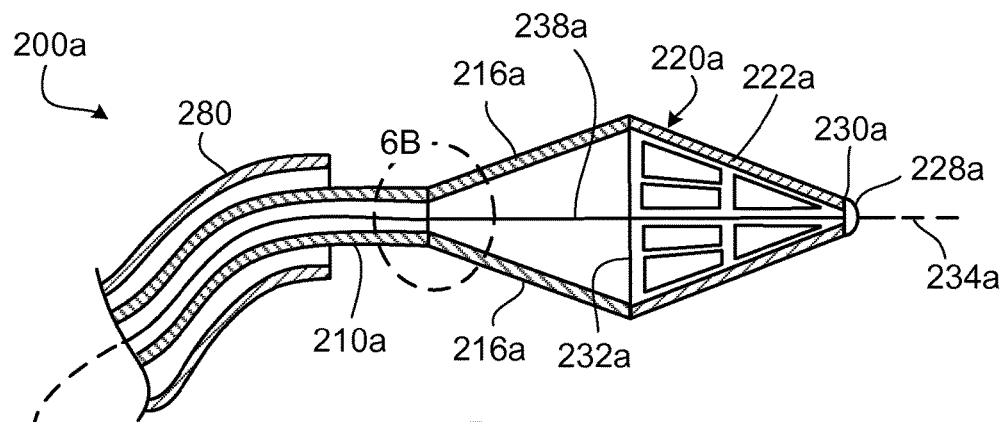
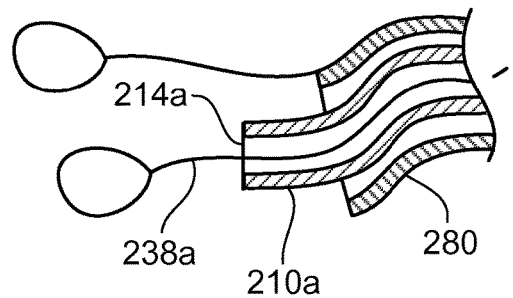
FIG. 6A
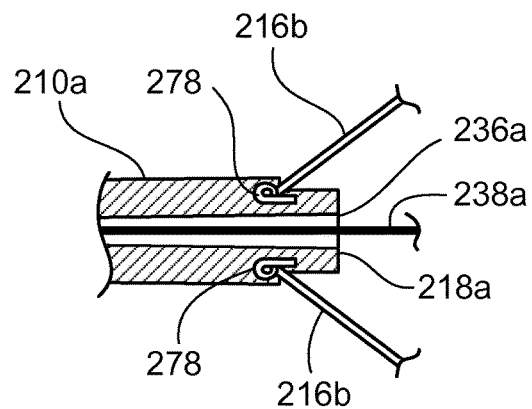
FIG. 6B

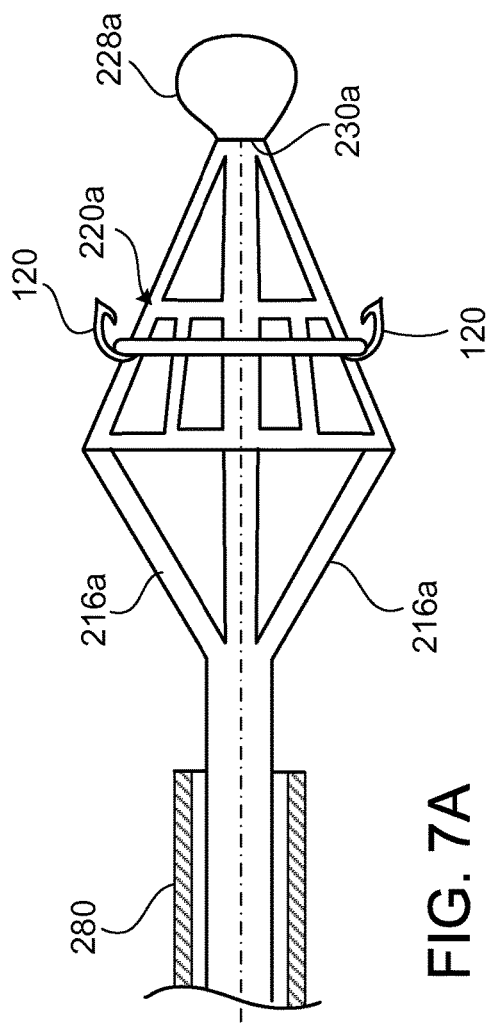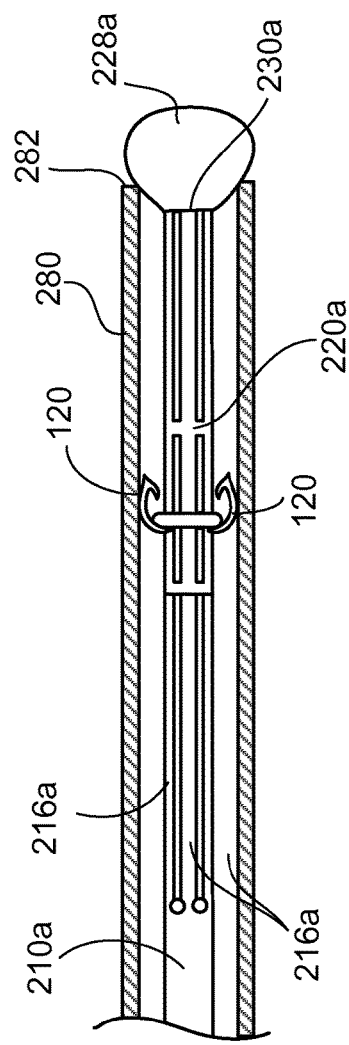
FIG. 7A
FIG. 7B

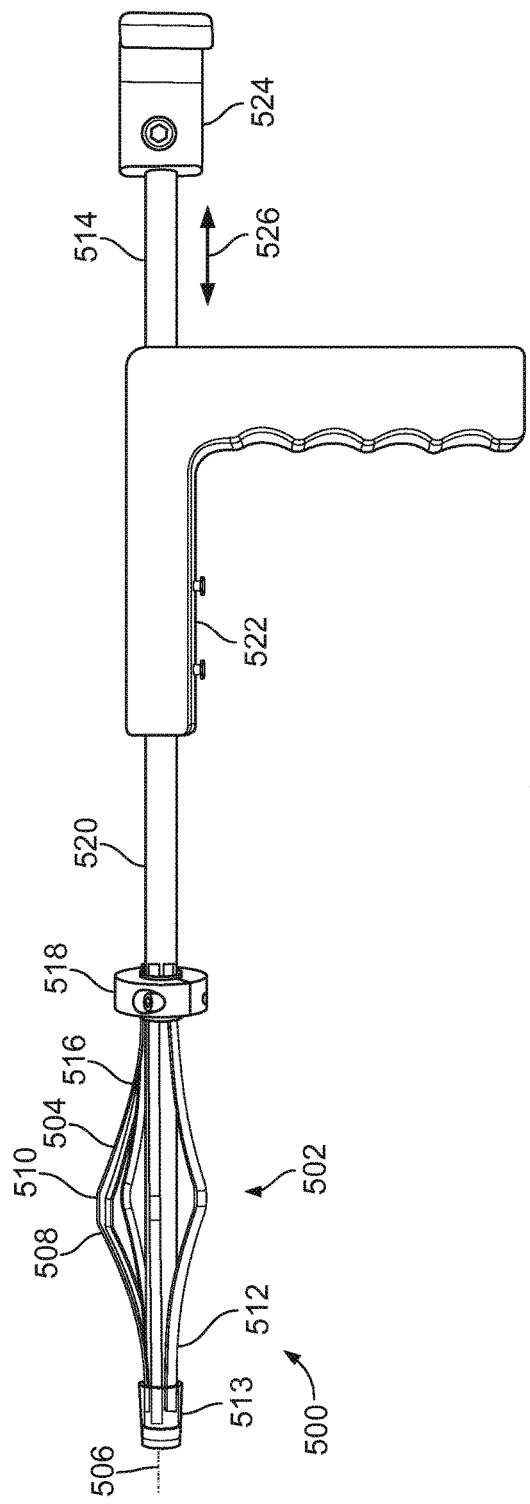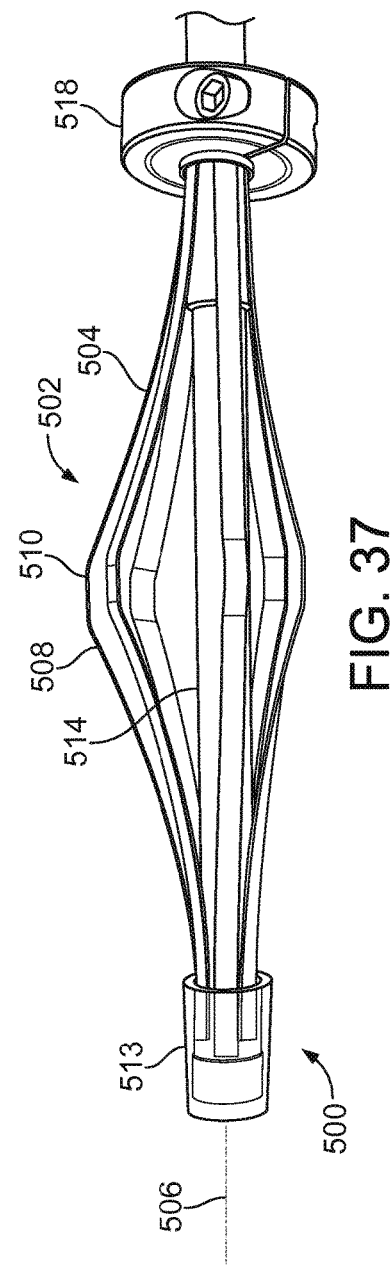
FIG. 36
FIG. 37

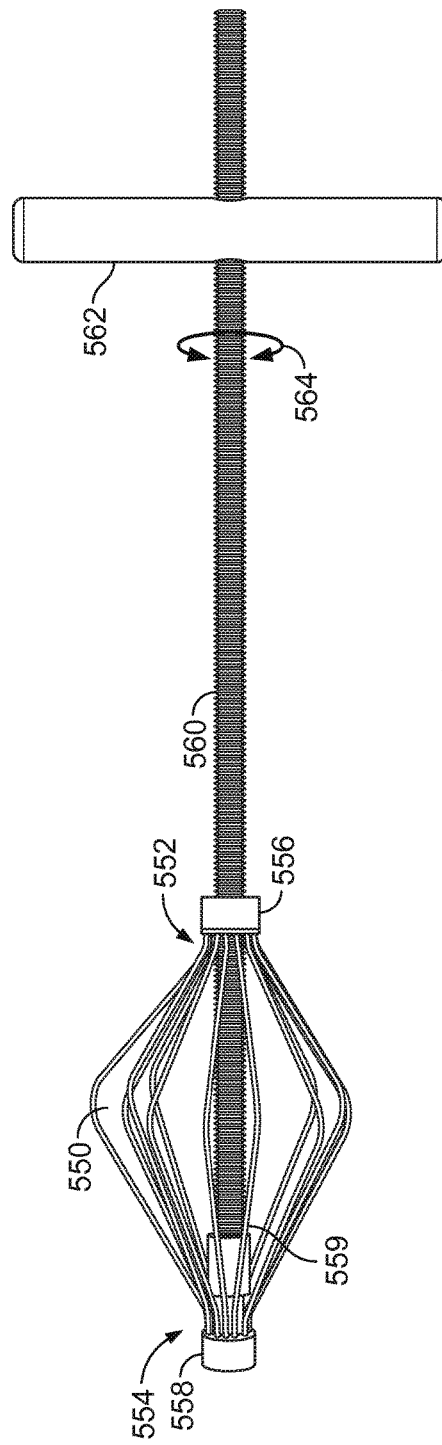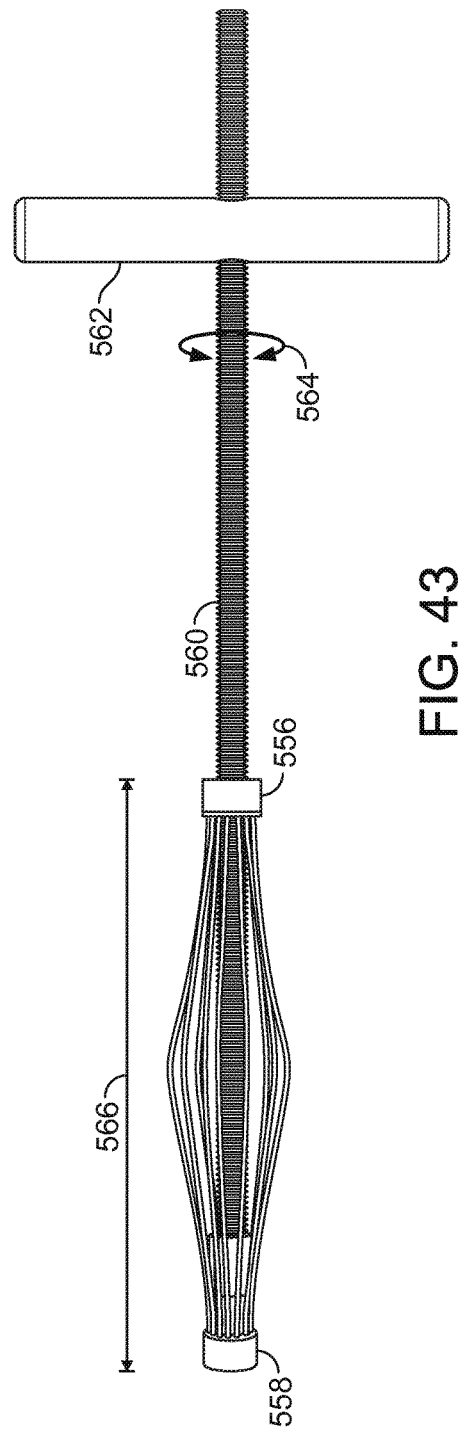

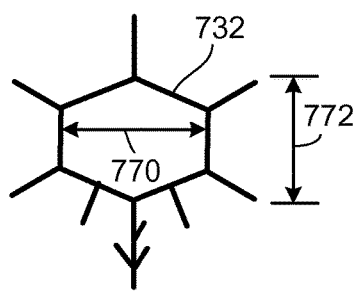
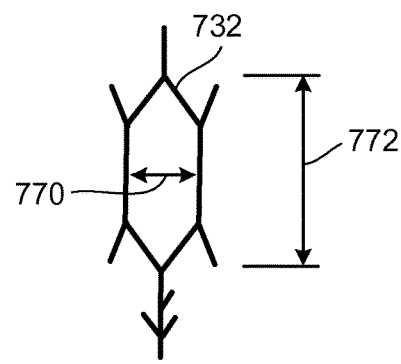
FIG. 60A  FIG. 60B
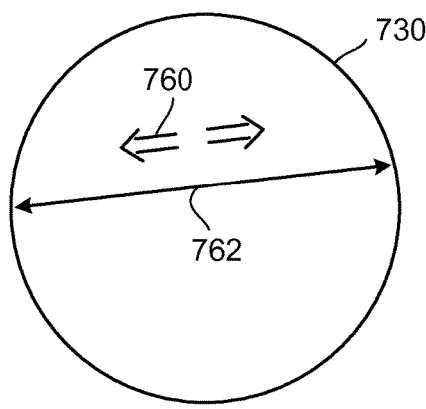
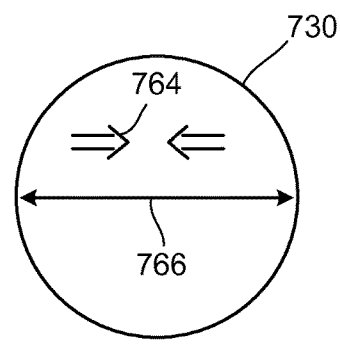
FIG. 61A  FIG. 61B

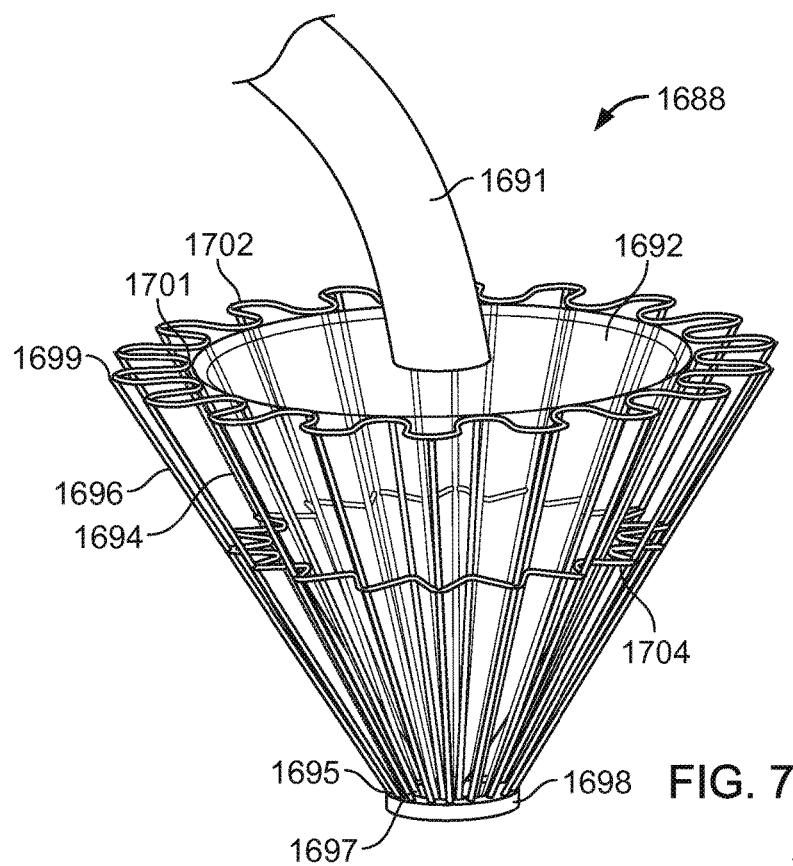
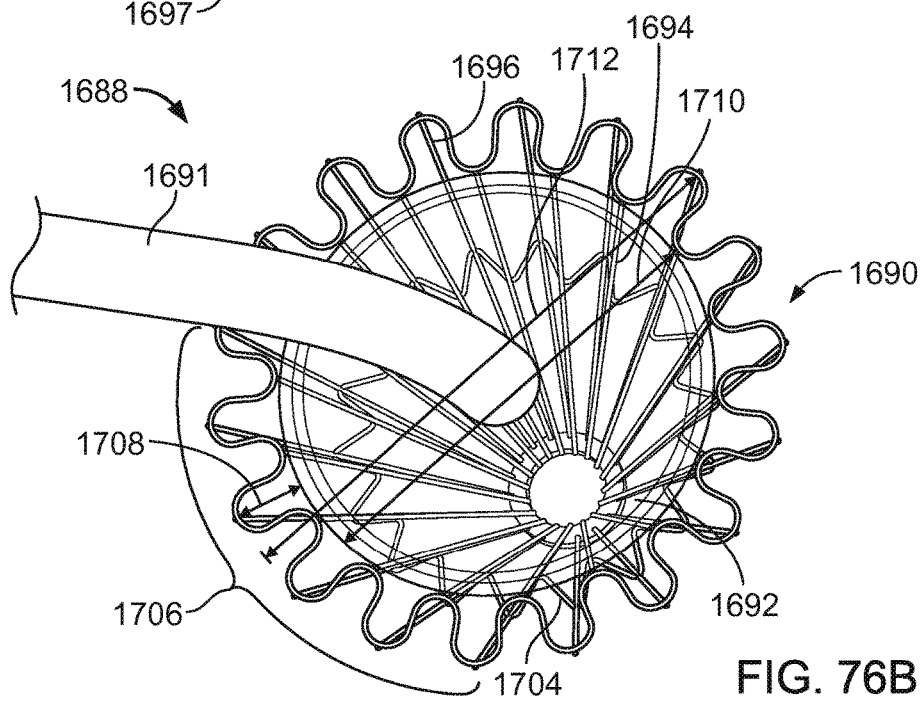
FIG. 76A
FIG. 76B

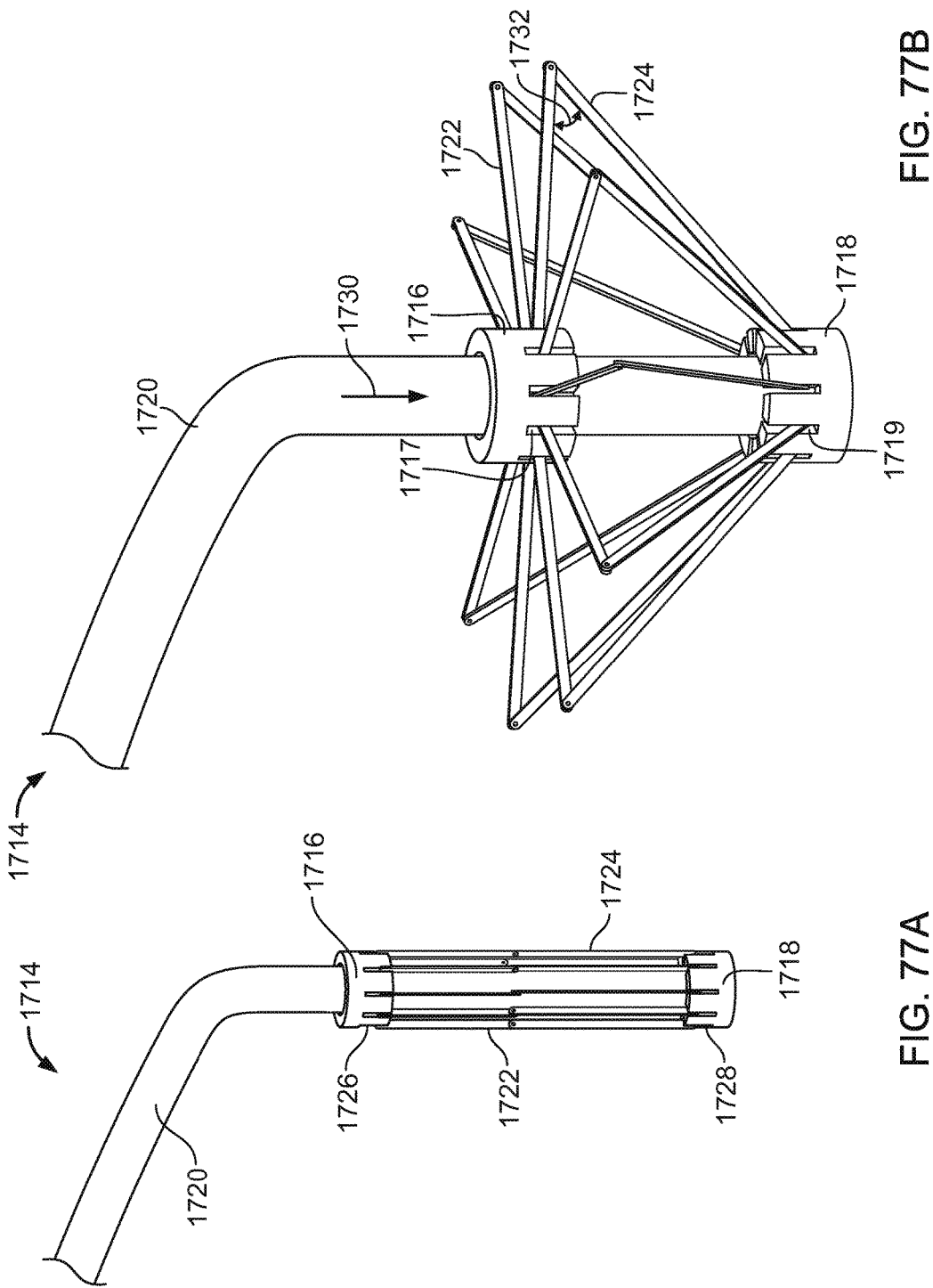

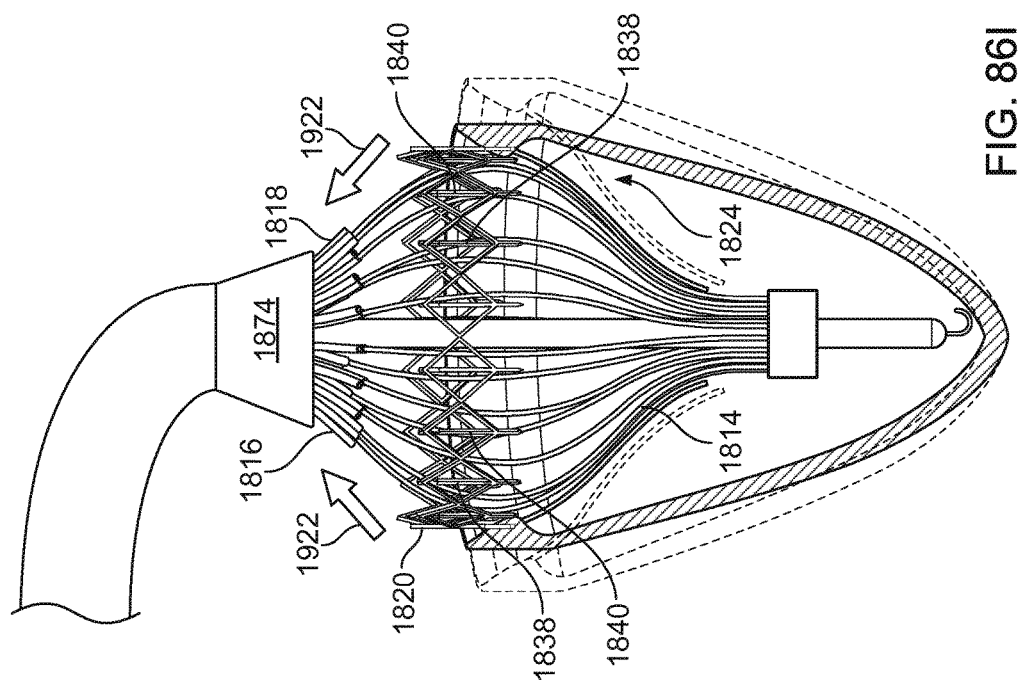
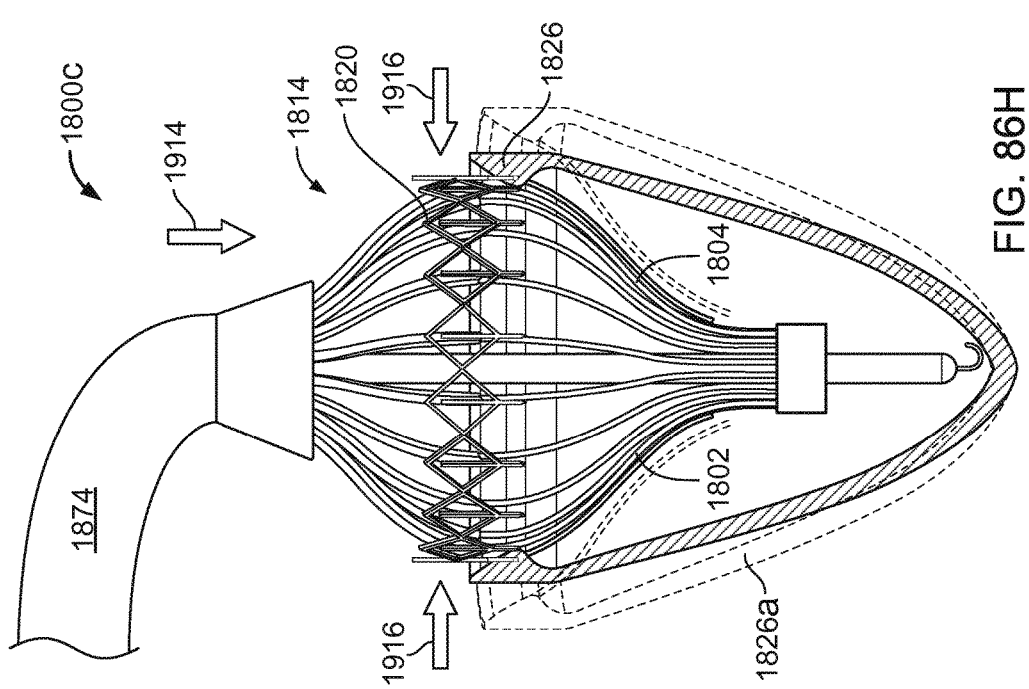

RECONFIGURING TISSUE FEATURES OF A HEART ANNULUS

CROSS-REFERENCE TO RELATED APPLICATIONS

The present application is a divisional of U.S. application Ser. No. 12/868,624, filed Aug. 25, 2010, entitled "RECONFIGURING TISSUE FEATURES OF A HEART ANNULUS," now abandoned, which claims priority to U.S. Provisional Patent Application No. 61/376,614, filed on Aug. 24, 2010, entitled "RECONFIGURING HEART FEATURES," which is incorporated here in its entirety by reference.

BACKGROUND OF THE INVENTION

Field of the Invention

This description relates to reconfiguring heart features.

Description of the Related Art

The annulus of a heart valve (a fibrous ring attached to the wall of the heart), for example, maintains the shape of the valve opening and supports the valve leaflets. In a healthy heart, the annulus is typically round and has a diameter that enables the leaflets to close the valve tightly, ensuring no blood regurgitation during contraction of the heart. Because the annuluses of atrioventricular valves, for example, are supported more stably by the heart tissue on one side of the annulus than on the other side, and for other reasons, the size and shape of an annulus may become distorted over time. The distortion may prevent the valve from closing properly, allowing blood to regurgitate backwards through the valve. The distortion can be corrected, for example, during open heart surgery, by attaching a ring or other support around the annulus to restore its shape and size.

SUMMARY OF THE INVENTION

In one aspect, in general, a tool to attach a support to a heart valve annulus, includes a stabilizing body that includes features to stabilize an axial position of the tool relative to the annulus, and an attachment device connected to the stabilizing body, the stabilizing body and the attachment device being movable relative to one another under control from a location remote from the tool, from one configuration in which the support is held in a pre-attachment contracted state to another configuration in which the support is held in an expanded state for attachment at multiple locations around the annulus by action from the remote location.

Implementations may include one or more of the following features. The tool may be configured to permit blood to flow through during attachment. The attachment device may be connected to the stabilizing body in a configuration to permit the attachment device to be withdrawn from the support after attachment by action from the remote location. The tool may be for use with an annular support that includes sharp elements for attachment of the support to the annulus and connection elements to connect the support temporarily to the attachment device until the support has been attached to the annulus. The stabilizing body and the attachment device may form a tracking mechanism and the attachment device is configured to track the tracking mechanism during relative motion of the attachment device and the stabilizing body. The stabilizing body may be configured to match topological features of the annulus to provide stabilization without applying more than small radial forces to the annulus. The stabilizing body may be configured to support leaflets of the valve of the heart in at least a nearly closed position when the tool is in place in the valve. The stabilizing body may comprise a set of preformed flexible wires arranged around a central axis. The attachment device may comprise a set of tubes arranged around a central axis and extending to the remote location.

In one aspect, in general, a tool to attach a support to a heart valve annulus, includes flexible tubes that together carry the support, and flexible wires passing through the flexible tubes, the flexible wires forming a basket that is contoured to contact a heart valve annulus at multiple points along its periphery.

Implementations may include one or more of the following features. The basket may be collapsible for delivery to the annulus. The tool may include a sheath over the collapsed basket. The sheath may include tubes sized to receive the flexible wires. The basket may be expandable and the sheath resists expansion of the basket. The flexible wires may provide a passage through which blood can flow. Each of the flexible tubes may have at least two lumens. Each of the flexible wires may have a free end that passes through one of the two lumens of the corresponding tube. The support may be attached to another of the two lumens of each of the corresponding tube. Each of the flexible tubes may be configured to receive a strut feature of the support. The basket may be shaped to allow heart valve leaflets to partially close when the basket is deployed in a heart valve. The basket may conform to a shape of the heart valve annulus. The tool may include a guide catheter configured to guide the flexible wires along a common direction of travel. The tool may include a collar attached to the flexible wires and sized to receive the guide catheter.

In one aspect, in general, an apparatus includes an annular structure to be attached to a heart valve annulus, the annular structure being expandable and contractible between a contracted pre-attachment configuration and an expanded post attachment configuration, the structure including holding elements that are configured (a) to be held by an attachment tool to enable the attachment tool to cause expansion and contraction of the annular structure in connection with attaching the annular structure to the annulus, and (b) to restrain the annular structure from being expanded, after the annular structure has been attached and the holding elements of the structure are no longer held by the attachment tool.

In one aspect, in general, an apparatus includes structural elements connected to form a ring, the structural elements being capable of expanding and contracting to make the ring bigger or smaller, gripping elements attached to the structural elements to penetrate and grip heart tissue, and configuration elements attached to the respective structural elements and each controllable to permit or prevent the ring from expanding.

Implementations may include one or more of the following features. The configuration elements may be each sized to be received by a corresponding lumen of a delivery tool. The ring may include polygonal elements. The configuration elements may be capable of a first position flush with the polygonal elements and capable of a second position angled away from the polygonal elements. The polygonal elements may include diamond-shaped elements. The configuration elements may resist contraction of the polygonal elements when the configuration elements are in the position flush with the polygonal elements. The configuration elements may resist horizontal contraction of the polygonal elements. The configuration elements may resist vertical contraction of the polygonal elements. The configuration elements may resist horizontal expansion of the polygonal elements. The configuration elements may resist vertical expansion of the polygonal elements.

In one aspect, in general, a method includes positioning a delivery head near to or in contact with a heart valve annulus, causing a heart valve support to expand by moving the heart valve support along a basket of the delivery head, and attaching the expanded heart valve support to the heart valve annulus.

Implementations may include one or more of the following features. Aligning the delivery head with a heart valve annulus may include filling the annulus with the delivery head. The method may include contracting the heart valve support after attachment.

These and other aspects and features, and combinations of them, may be expressed as apparatus, methods, systems, and in other ways.

Other features and advantages will be apparent from the description and the claims.

BRIEF DESCRIPTION OF THE DRAWINGS

FIGS. 2A through 2D are perspective views of a heart valve support.

FIG. 2E is a plan view of a recurved hook.

FIGS. 6A and 6B are sectional side views of a catheter delivery tool.

FIGS. 7A through 7B show delivery of a heart valve support.

FIGS. 36 through 39 are side views of an insertion tool that includes a dilator formed of six arms arranged at equal intervals around an insertion axis.

FIGS. 42 and 43 show a dilator that can include round wire arms that are evenly spaced around the insertion axis and have each been shape set to the expanded configuration.

FIGS. 60A and 60B are views of a hexagonal section of a support when the support expands and contracts.

FIGS. 61A and 61B are top views of a support when the support expands and contracts.

FIGS. 76A through 76C show a delivery tool having a cone-shaped wire cage enclosing a balloon.

FIGS. 77A and 77B show a delivery tool that has splaying projections spanning an upper ring and a base ring arranged around a shaft.

FIGS. 86A through 86J show delivery of a heart valve support that uses a guide catheter that can be used to stabilize the delivery tool within the heart valve annulus.

DETAILED DESCRIPTION OF THE PREFERRED EMBODIMENTS

Figure 1A:
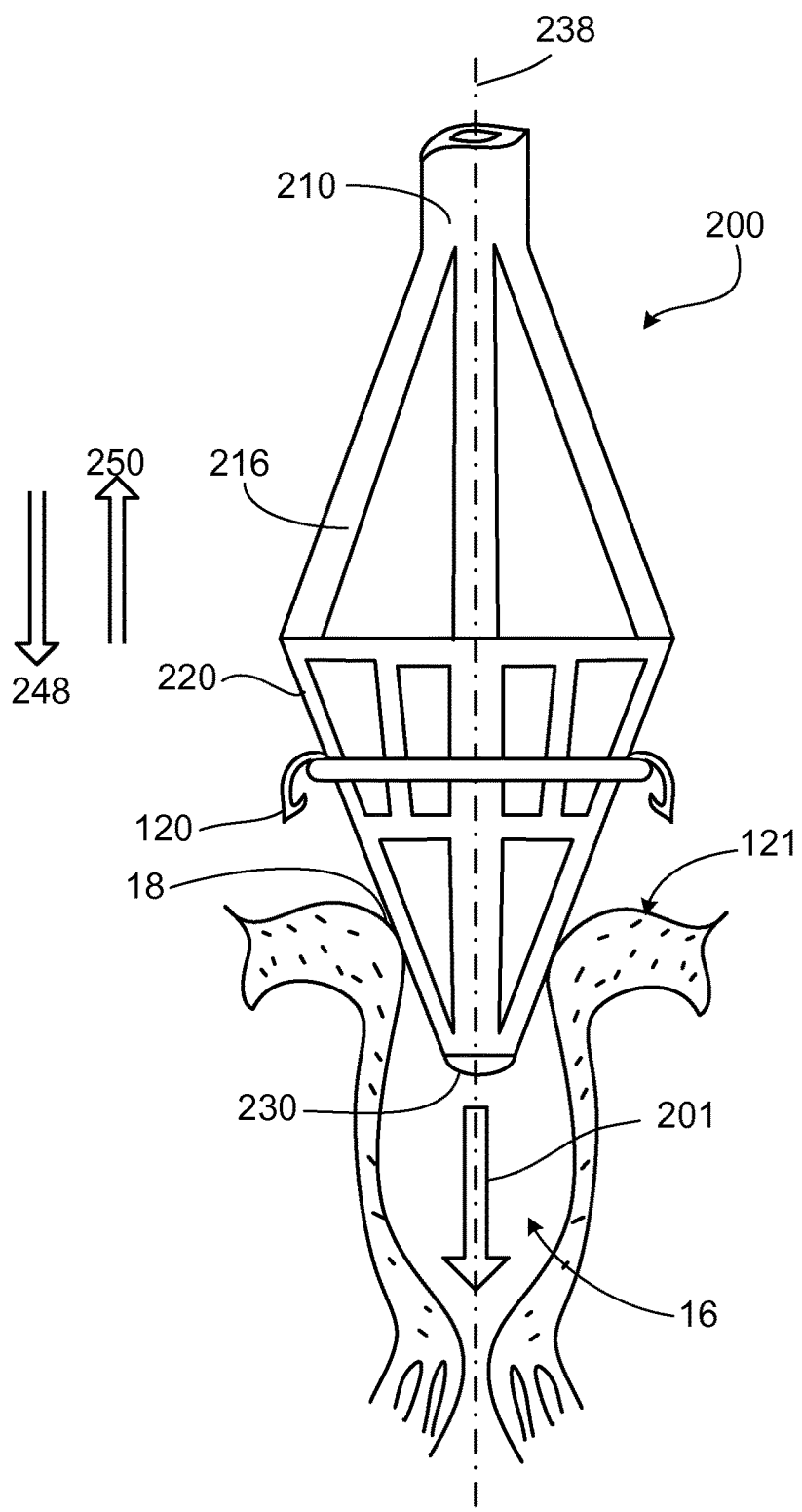
FIGS. 1A through 1E show delivery of a heart valve support where a delivery tool is pushed into the valve, the hooks of a support are embedded into valve tissue, and the delivery tool is pulled away.
Figure 1B:
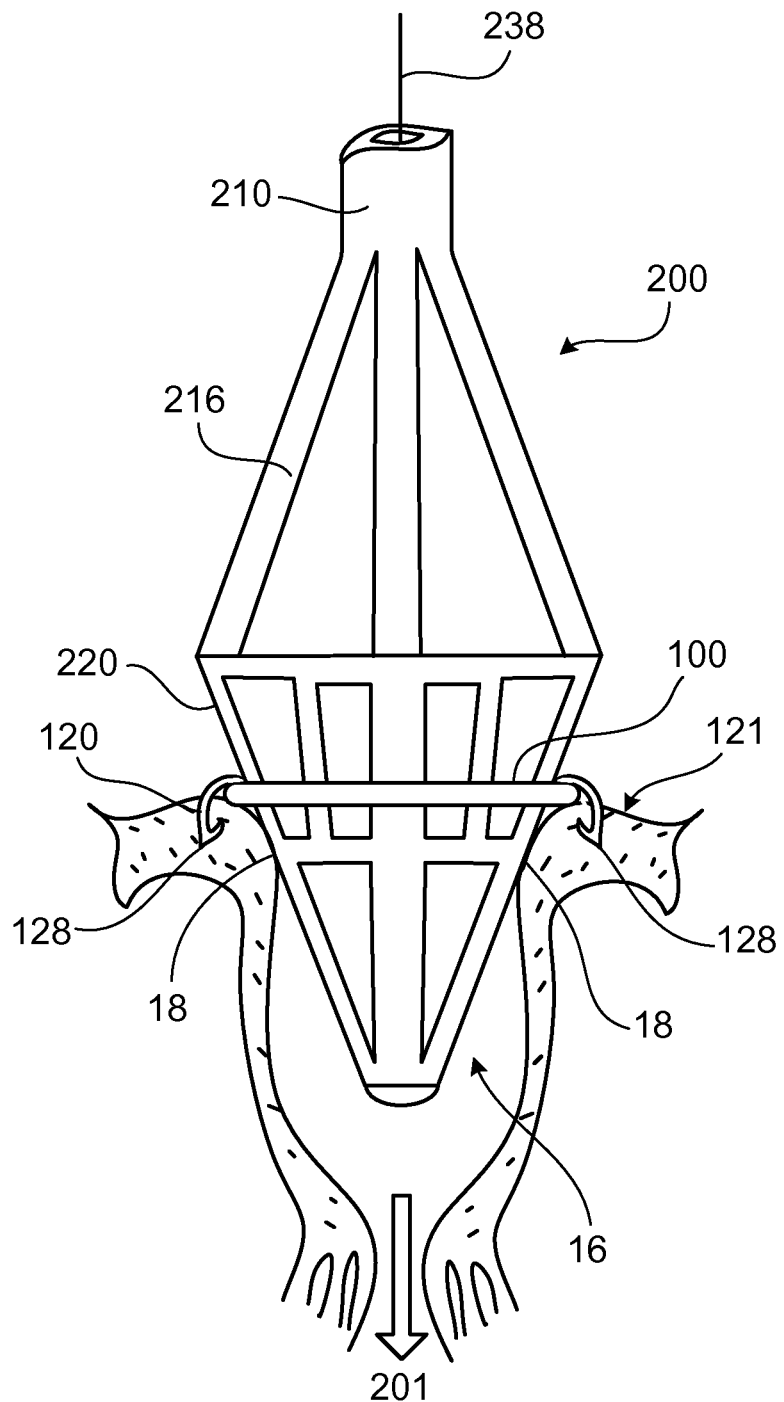
Figure 1C:
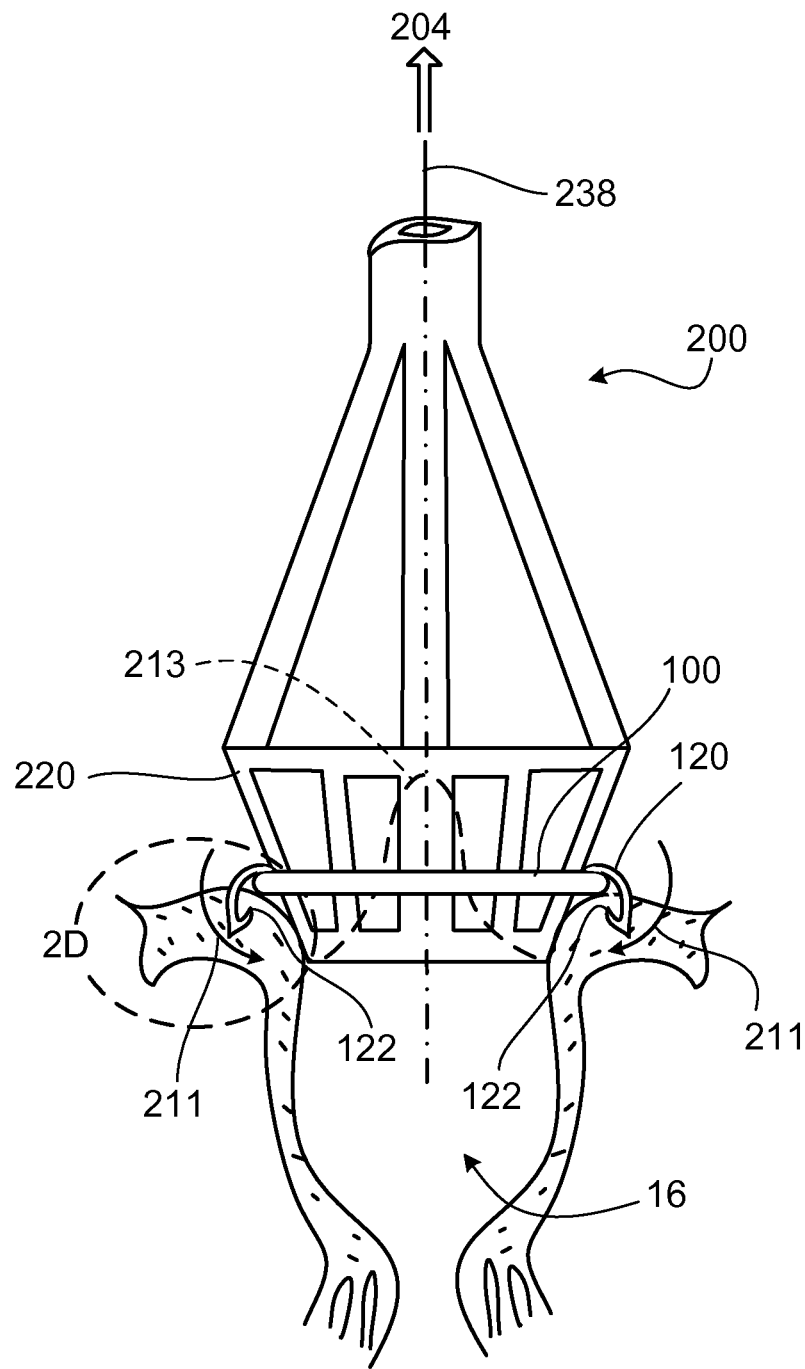
Figure 1D:
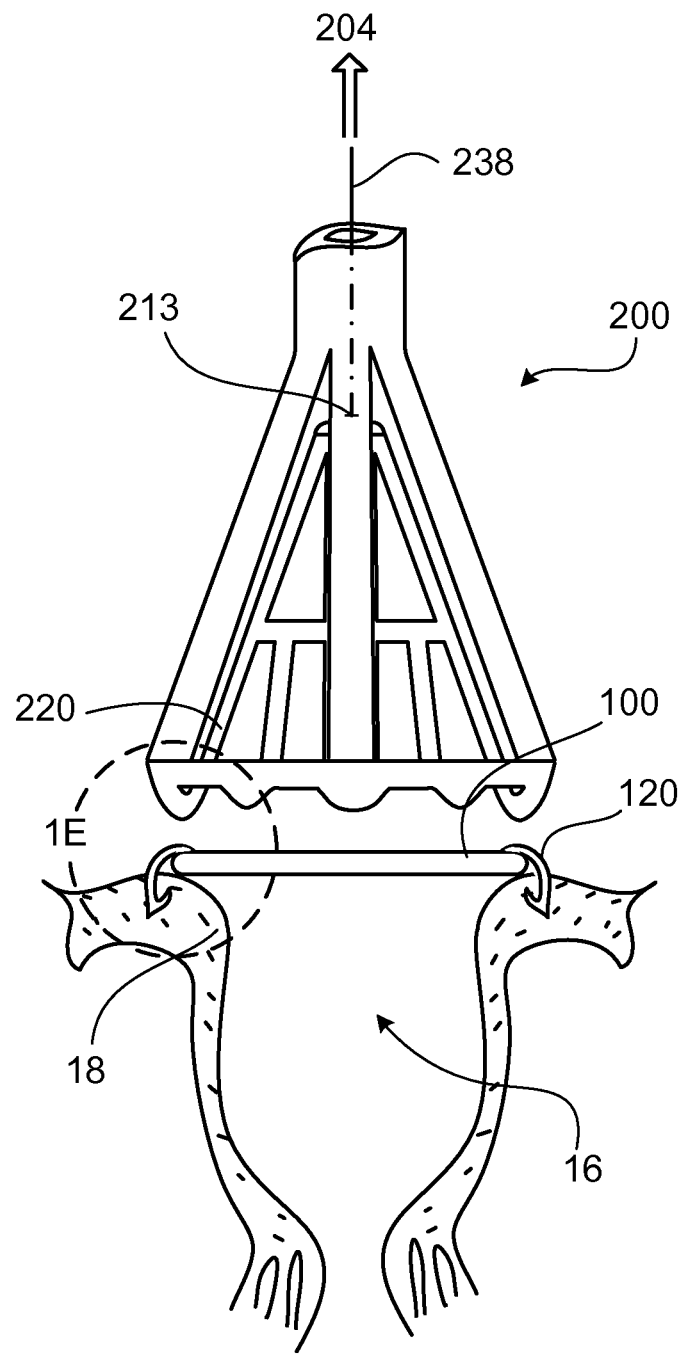
Figure 1E:
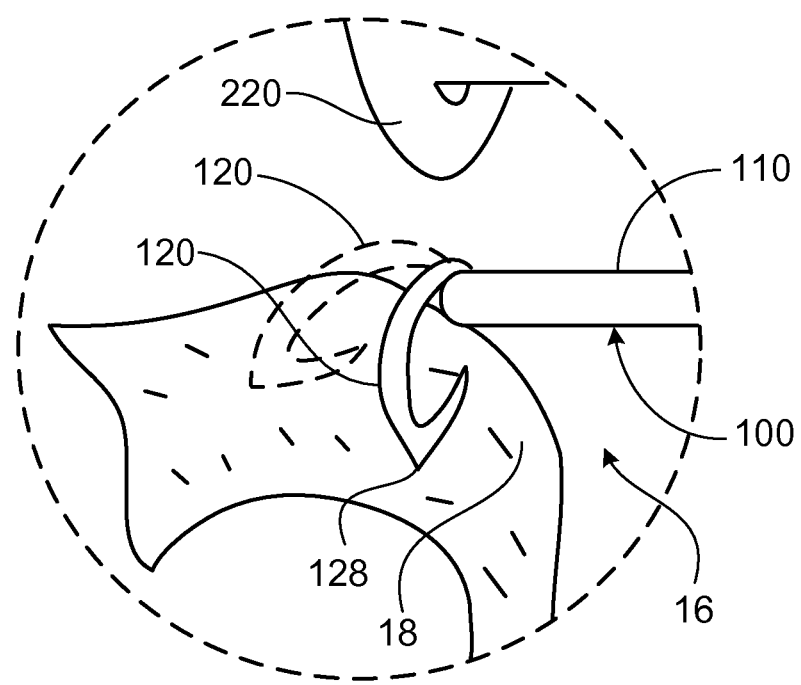
Figure 1F:
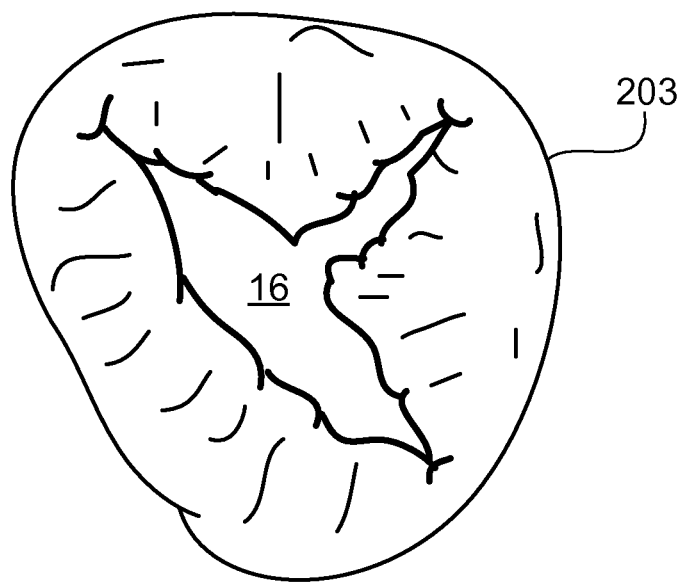
FIGS. 1F through 1H show contracting a support to its final size and shape and leaving the support permanently in place to maintain the annulus in the desired final configuration and size.
Figure 1G:
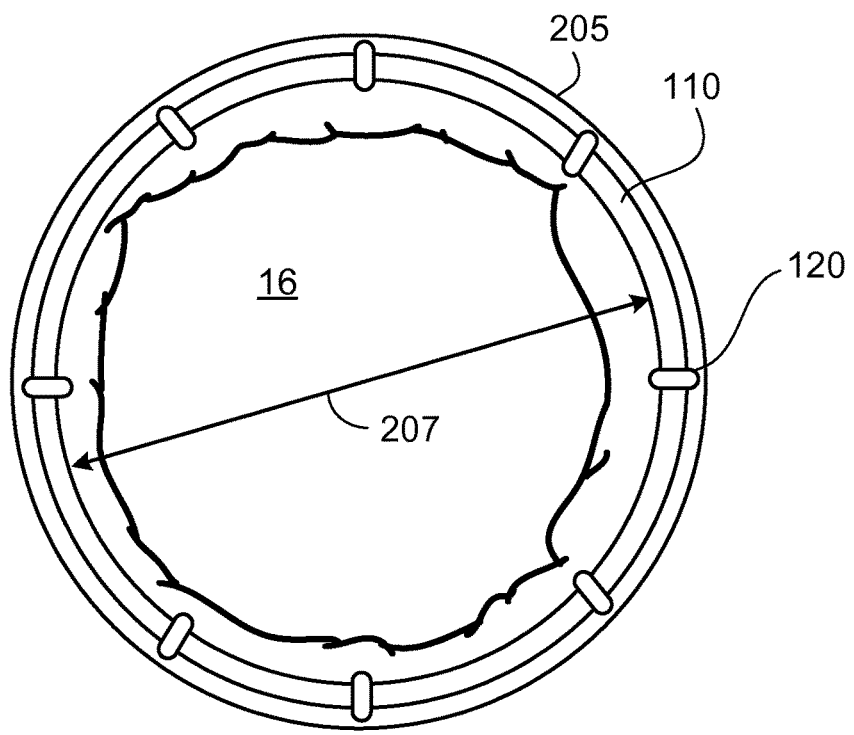
Figure 1H:
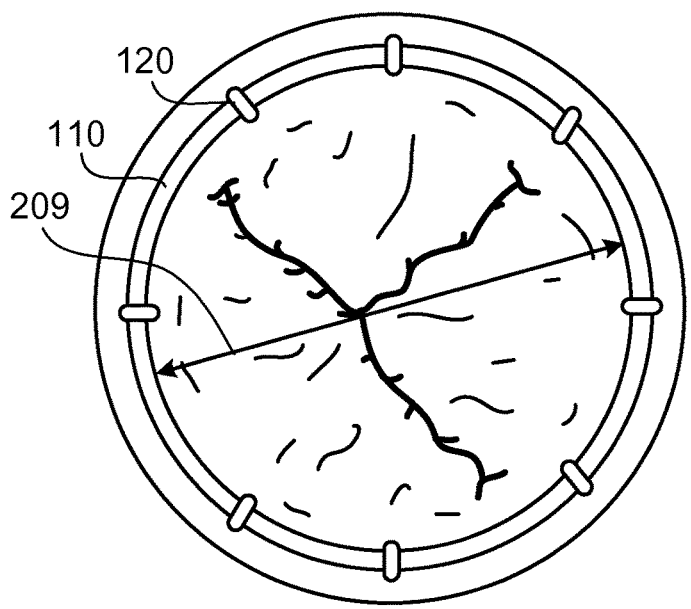

This application is related to U.S. patent application Ser. No. 12/794,235, filed on Jun. 4, 2010, International application PCT/US2010/027943, filed on Mar. 19, 2010, U.S. patent application Ser. No. 12/563,293, filed on Sep. 21, 2009, U.S. patent application Ser. No. 12/407,656, filed on Mar. 19, 2009, and U.S. patent application Ser. No. 11/620,955, filed on Jan. 8, 2007, all of which are incorporated here in their entirety by reference.

As shown in the examples of FIGS. 1A through 1G distortion of an annulus 18 of a heart valve 16 can be corrected simply and quickly by the following steps:

A. Push 201 (FIG. 1 A) a conical head-end basket 220 of a delivery tool 200 into the valve to force the distorted annulus (203, FIG. 1 F) to conform to a desired configuration (e.g., a circle 205, FIG. 1 G) and to a size that is larger (e.g., in diameter 207) than a desired final diameter 209 of the annulus (FIG. 1 H). (The tool including the basket are shown in side view and the valve and annulus are shown in sectional side view.)

B. Continue to push 201 the delivery tool to drive an expanded heart valve support 100 (which has the desired configuration and the larger size and is temporarily held in its expanded configuration on the basket of the tool) towards the annulus to seat multiple (for example, eight, as shown, or a larger or smaller number of) recurved hooks 120 located along the periphery of the support simultaneously into the valve tissue at multiple locations along the periphery 121 of the annulus (FIG. 1 B).

C. After the hooks are seated, pull 204 (FIG. 1 C) on and evert the tip 230 of the head end basket from the inside to cause the support to roll so that the tips 122 of the hooks rotate 211 and embed themselves more securely into the annulus tissue (FIG. 1 C).

D. After the hooks are further embedded, continue to pull 204 (FIG. 1 D) on the inside 213 of the tip of the head-end basket to break the tool away from the support (FIG. 1 E), allowing the support to contract to its final size and shape 215 (FIG. 1 H) and leaving the support permanently in place to maintain the annulus in the desired final configuration and size.

The entire procedure can be performed in less than a minute in many cases. By temporarily forcing the annulus of the valve to expand to the desired circular shape, it is possible to attach the support quickly, easily, and somewhat automatically by forcing multiple gripping elements into the tissue at one time. Hooks are used in this example, although other types of gripping elements may be used as well. The physician avoids the time consuming steps of having to attach individual sutures or clips one at a time along the periphery of a distorted annulus and then cinch them together to reform the supported annulus to a desired shape and size. Thus, the physician does not even need to be able to see the annulus clearly (or at all). Once attached, when the tool is removed, the support automatically springs back to its final shape and size.

As shown in FIGS. 2A and 2D, in some implementations the support includes a circular ring body 110 that bears the hooks 120. The body 110 can be expanded from (a) a minimal-diameter long-term configuration (FIG. 2A) to which it conforms after it has been attached to the annulus to (b) an expanded delivery configuration (FIG. 2D) to which it conforms when it is held on the head-end basket of the tool and while it is being attached in the steps shown in FIGS. 1A, 1B, and 1C. The long-term configuration is normally circular and has the diameter of a healthy annulus for a particular patient. When attached, the support maintains the healthy configuration of the annulus so that the valve will work properly.

In some examples, the body 110 has the same (e.g., circular) shape but different diameters in the delivery configuration and the long-term configuration. The body is constructed of a material or in a manner that biases the body to contract to the long-term configuration. For example, all or portions of the body 110 may be formed as a helical spring 110a such as a continuous helical spring connected at opposite ends to form a circular body or one or more interconnected helical spring segments (FIG. 2B). In some examples, the support body 110b may be a band of shape memory material such as Nitinol or a biologically compatible elastomer (or other material) that will return to the long-term configuration after being expanded to the delivery configuration (FIG. 2C).

The hooks 120 may number as few as three or as many as ten or twenty or more and may be arranged at equal intervals along the body or at unequal intervals as needed to make the body easy and quick to deliver, permanent in its placement, and effective in correcting distortion of the valve annulus. The hooks are configured and together mounted along the circular outer periphery so that they can be inserted simultaneously into the tissue along the periphery of the annulus and then firmly embedded when the tool is pulled away and the basket is everted.

In some examples, a portion or portions of the support body may not have hooks attached if, for example, a segment of the valve annulus shares a boundary with sensitive or delicate tissue, such as the atrioventricular (AV) node of the heart. This tissue should not be pierced by the hooks. A support body configured to avoid interfering with the AV node could have a section having no hooks attached or otherwise covered or protected to prevent penetration by hooks into the AV node. The support body should be positioned so that this special section of the support body is adjacent the sensitive or delicate tissue as the support body is put into place. The support body may have more than one special section lacking hooks, so that the operator has more than one option when placing the support body near the sensitive tissue. In some examples, the support body could have a section removed entirely, and would be shaped somewhat like the letter "C" instead of a complete ring. In any of these examples, the procedure described above could have an additional step preceding step A, in which the operator rotates the delivery head to position the section having no hooks or to position the gap in the support body to be adjacent to the sensitive tissue at the moment when the hooks are to be embedded in the other tissue. The support body may have radiopaque marks to help the operator view the positioning.

For this reason, as shown in FIG. 2E, for example, each of the hooks has two pointed features. One pointed feature is a sharp free end 122 pointing away from the valve leaflets during delivery. The other pointed feature is a barb 128 formed at a bend between the sharp free end 122 and an opposite connection end 124 where the hook is attached, e.g., welded or glued, to the body 110. The barb points toward the valve leaflets during delivery. Thus, the barb is arranged to penetrate the tissue when the tool is pushed toward the valve, and the sharp free end is arranged to embed the hook into the tissue when the tool is pulled away from the valve.

Each hook 120 can be formed of biologically compatible materials such as platinum, gold, palladium, rhenium, tantalum, tungsten, molybdenum, nickel, cobalt, stainless steel, Nitinol, and alloys, polymers, or other materials. During delivery the barbs of the hooks are together (and more or less simultaneously) forced into the tissue at a series of locations around the outer periphery of the temporarily expanded annulus. In a later step, the sharp free ends are forced to rotate somewhat away from the leaflets for secure (e.g., permanent) attachment.

Figure 3:
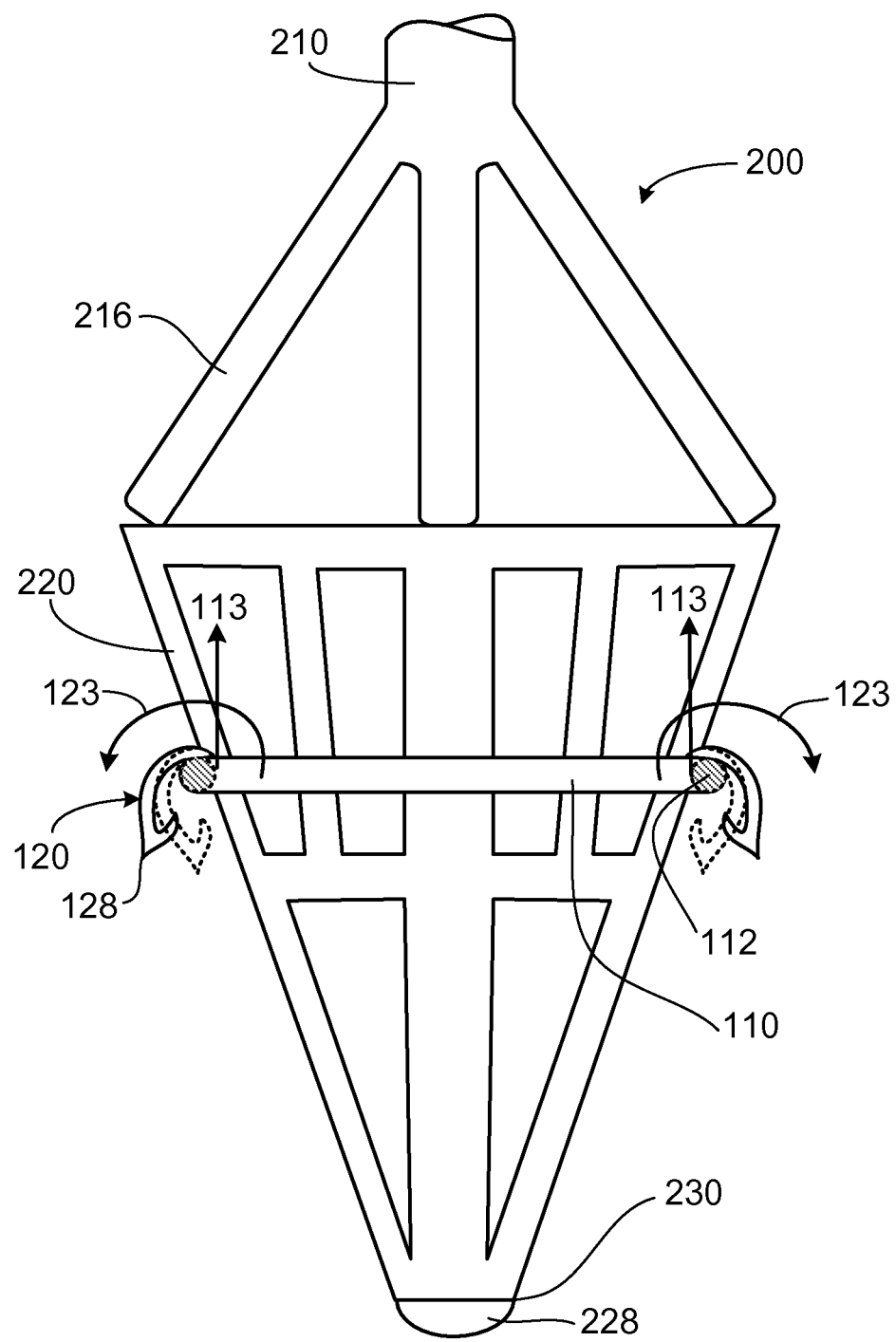
FIG. 3 is a section side view of a heart valve support showing the support body can be rolled about a central annular axis.

To cause the hooks to rotate during delivery, the hooks 120 are attached permanently to the support body 110 and the support body can be rolled 123 (FIG. 3) about a central annular axis 112 of the support body, as indicated. One way to cause the rolling of the support body and the associated rotation of the hooks is to enable the body to change its configuration by rotation of the entire body about an axis represented by the central circular axis 123, much as a rubber o-ring can be rolled about its central circular axis. The reconfiguration of the body to cause the rotation of the hooks can be achieved in other ways.

In some examples, applying an axial force (arrows 113) to the inner peripheral edge of the ring (we sometimes refer to the support broadly as a ring) will cause the ring to tend to roll and the hooks to embed themselves in the annulus as intended. By appropriately mounting the inner periphery of the ring on the outer periphery of the delivery tool, the axial force 113 can be applied by pulling the tool away from the leaflets of the valve, as explained earlier.

Figure 4A:
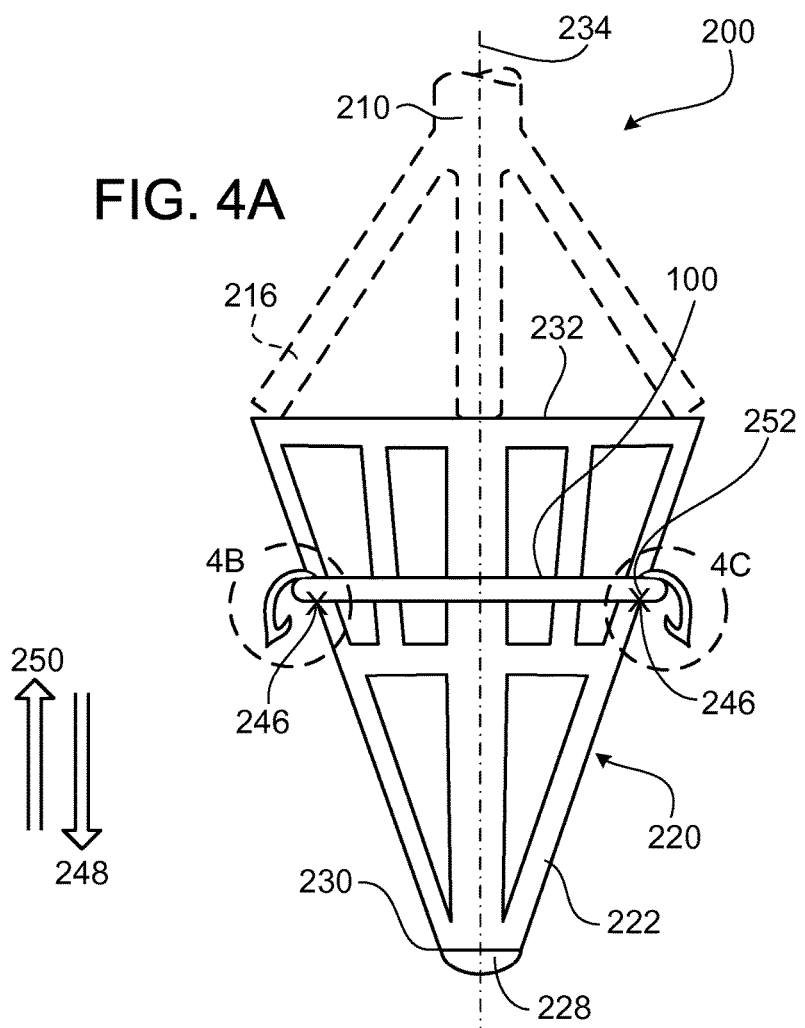
FIGS. 4A through 4C are side and detailed views of a delivery tool and heart valve support.

For delivery to the valve annulus, the valve support 100 is first expanded to its delivery configuration and temporarily mounted on a delivery head 220 of the tool 200 (FIG. 4A). The support could be expanded enough in its temporary mounting on the tool and mounted far enough away from the tip along the conical head-end basket so that when the head-end basket of the tool is pushed against the annulus to force it to expand to the size and shape of the expanded support, the annulus first has reached a circular, non-distorted shape before the support hook barbs begin to penetrate the tissue. The tapered profile of the head-end basket of the delivery tool allows the tool to accommodate supports of various sizes. In some implementations, different shapes and sizes of baskets could be used for supports of different sizes.

The heart valve support 100 is held in place on the delivery head 220 using one or more releasable connections 246. The connections 246 are arranged to translate forces from the tool 200 to the support 100 in each of two opposite directions 248 and 250, toward or away from the leaflets of the valve. When the support has been embedded in the annulus and the tool is pulled in the direction 250 to release it from the support, the force on the connections 246 exceeds a predetermined threshold, and the connections break, releasing the tool from the support at the end of the delivery process. The connections 246 may be, in some examples, breakable sutures 252 (FIG. 4A), or some other breakaway structure such as clips or adhesive or a structure that can be manipulated from the tool by unscrewing or other manipulation.

Figure 4B:
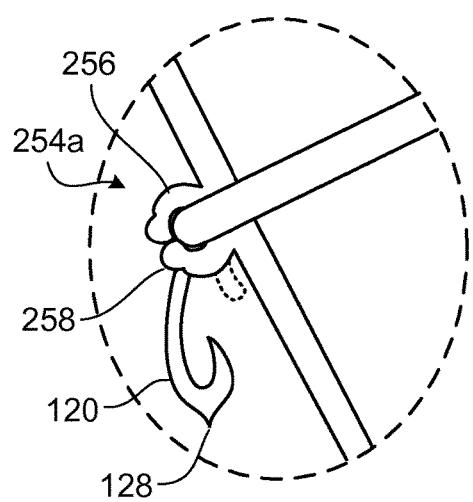
Figure 4C:
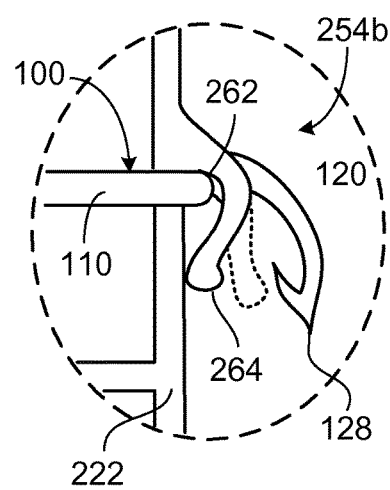

In some examples, the connections 246 include retainers that can take, e.g., the configurations shown as 254a or 254b (FIGS. 4B & 4C, respectively). In the example shown in FIG. 4B, the retaining element 254a has one rigid finger 256 to translate forces from the tool 200 to the support 100 when the tool is moved in direction 248 while the support is attached to the tool and being pushed into the heart tissue. A second deformable finger 258 aids in maintaining the connection between the support 100 and the tool 200 when the tool is moved in direction 250 and is deformable (dashed lines) to release the valve support 100 from the tool 200 when the force in direction 250 relative to the embedded support exceeds a predetermined threshold.

In the example shown in FIG. 4C, the retaining element 254b includes a finger 260 having a crook 262 to receive the support 100 and to translate forces from the tool 200 to the support 100 when the tool is moved in direction 248. The finger has a resiliently deformable tip 264 that is biased towards the tapered body 222 and helps to maintain the connection between the support 100 and the tool 200 and is deformable (shown in hidden lines) to release the valve support 100 from the tool 200 when the tool is moved in the second axial direction 250 against an embedded support and the force exceeds a predetermined threshold.

Figure 5:
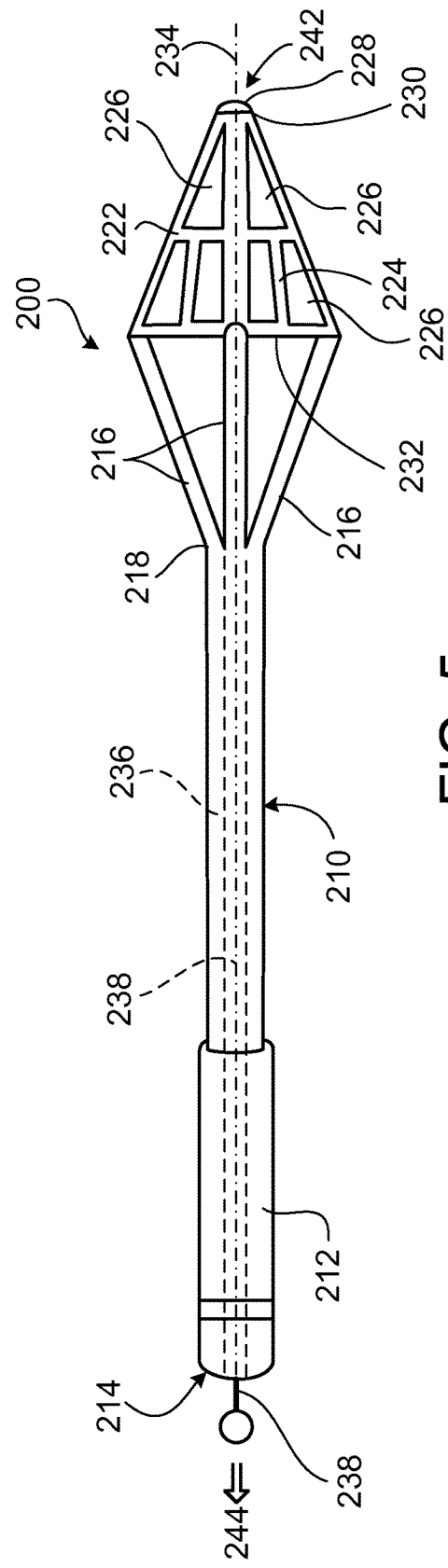
FIG. 5 is a side view of a delivery tool.

As shown in FIG. 5, in an example of a tool 200 that can be used for delivery of the support during open heart surgery, a basket 220 is connected at its broad end to a set of stiff wires or other rigid projections 216 that are splayed from a long shaft 210 having a handle 212 at the operator's end 214. Thus the projections 216 connect the shaft 210 to the basket 220 and transfer pulling or pushing force between the shaft and the basket (and in turn to the support).

The example of the basket shown in FIG. 5 includes a tapered body 222 having a network of interconnected struts 224 defining an array of openings 226 together forming a tapered semi-rigid net. In this example, the basket (which we also sometimes refer to as a delivery head) 220 has a rounded tip 228. The head 222 tapers radially outwardly with distance along a longitudinal axis 234 of the head 220 from the tip 228 towards the operator. The broad end 232 of the tapered body 222 is firmly attached to the projections 216, which taper in the opposite direction from the taper of the basket. The net formed by the struts 224 is semi-rigid in the sense of having enough stiffness to permit the operator to force the valve support against the heart tissue to cause the barbs of the hooks of the support to penetrate the tissue, and enough flexibility to permit the head-end basket to be everted when the operator pulls on the handle to evert the basket and release the support from the basket.

In some implementations, the shaft 210 defines a lumen 236 extending between the heart valve end 218 of the shaft 210 and the handle 212. A wire 238 is arranged to move freely back and forth within the lumen 236. The wire 238 has one end 240 that extends from the handle 212 and an opposite end 242 that is connected to the inside of tip 228. The wire 238 can be pulled (arrow 244) to cause the delivery head 220 to collapse (hidden lines) and evert radially inwardly starting at the tip 228 as mentioned earlier.

Returning to a more detailed discussion of FIGS. 1 A through 1E, the operator begins the delivery of the support by pushing the tapered end 230 of the head basket 220 into the valve 16 (e.g., the tricuspid valve) to cause the valve leaflets 14 to spread apart. The tip 230 is small and rounded which makes it relatively easy to insert into the valve without requiring very precise guidance. Because the head-end basket is tapered, by continuing to push, the operator can cause the annulus 18 of the tricuspid valve 16 to expand in size and to conform to a desired shape, typically circular. During insertion, because of its symmetrical taper, the head-end basket tends to be self-centering. The taper of the basket 220 translates the insertion force in direction 248 into a radial force that causes the annulus 18 to expand and temporarily assume a desired shape (and a larger than final diameter).

As the operator continues to push on the tool, the ring of barbs of the hooks touch and then enter (pierce) the heart tissue along a ring of insertion locations defined by the outer periphery of the annulus, and the sharp free ends of the hooks enter and seat themselves within the tissue, much like fish hooks. Depending on how the operator guides the tool, the basket can be oriented during insertion so that essentially all of the hooks enter the tissue at the same time. Or the tool could be tilted during insertion so that hooks on one side of the support enter the tissue first and then the tool delivery angle could be shifted to force other hooks into the tissue in sequence.

Generally, when the number of hooks is relatively small (say between 6 and 20, comparable to the number of sutures that the physician would use in conventional stitching of a ring onto an annulus), it is desirable to assure that all of the hooks penetrate the tissue and are seated properly.

Once the hooks are embedded in the tissue, the operator pulls on the near end 240 of wire 238 to cause the basket 220 to collapse, evert, and be drawn out of the valve 16. Eventually, the everted portion of the basket reaches the valve support 100. By further tugging, the operator causes the body 110 of the support 100 to roll about its central axis (as in the o-ring example mentioned earlier) which causes the hooks 120 to embed more firmly in the tissue of the annulus 18 of the valve 16.

Using a final tug, the operator breaks the connections between the tool 200 and the valve support 100 and removes the tool 200, leaving the valve support 100 in place. As the everting basket 220 passes the points of connection 246, the retaining forces exerted by the embedded hooks 120 of the support body 110, acting in direction 248, exceed the forces exerted by the withdrawing basket 220 on the support body 110 (through the connections 246), acting in direction 250, thereby causing the connections 246 to break or release, in turn releasing the support 100.

The tool 200 is then withdrawn, allowing the valve support 100, along with the annulus 18, to contract to the long-run configuration.

In implementations useful for delivery of the support percutaneously, as shown in FIG. 6A, the delivery head 220a can be made, for example, from a shape memory alloy, such as Nitinol, which will allow the body 222a to be collapsed radially toward the longitudinal axis 234a prior to and during delivery of the head from a percutaneous entry point (say the femoral vein) into the heart. The delivery head 220a is biased towards the expanded, tapered configuration shown in FIG. 6A. Thus, the delivery head 220a, in the form of a tapered semi-rigid net, is connected to a catheter shaft 210a through projections 216a that splay radially outwardly from the catheter shaft 210a and taper in a direction opposite the taper of the delivery head 220a. (Here we refer to the delivery head as the head-end basket.)

The projections 216a are resiliently mounted to the catheter shaft 210a and are biased towards the expanded, tapered orientation shown, for example, by spring biased projections 216b shown in FIG. 6B. The projections 216a include springs 278, e.g., torsion springs (as shown), mounted to the catheter shaft 210a and forming a resilient connection.

A wire 238a slides within a lumen 236a of the shaft 210a in a manner similar to the one described earlier.

The tool 200a also includes a sheath 280 in which the catheter shaft 210a can slide during placement of the support. The sheath 280, the catheter shaft 210a, and the wire 238a are all flexible along their lengths to allow the tool 200a to be deflected and articulated along a blood vessel to reach the heart and to permit manipulation of the delivery head once inside the heart.

To deliver the support percutaneously, as shown in FIG. 7A, when the delivery head is prepared for use, the sheath 280 is retracted beyond the projections 216a, allowing the delivery head 220a to expand. The valve support 100 is then expanded to the delivery configuration (either by hand or using an expansion tool) and mounted on the tapered body 222a. The valve support 100 is connected to the delivery head 220a using releasable connections, e.g., breakable sutures and/or retaining elements (as described earlier).

The sheath 280 is then moved along the catheter shaft 210a towards the delivery head 220, causing the projections 216a and the delivery head 220a to contract radially inwardly to fit within the sheath 280, as shown in FIG. 7B. In the contracted configuration, the tip 228a of the delivery head 220a bears against the end 282 of the sheath 280. The rounded tip 228a may, e.g., provide easier delivery and maneuverability in navigating the blood vessels to reach the heart.

Figure 8A:
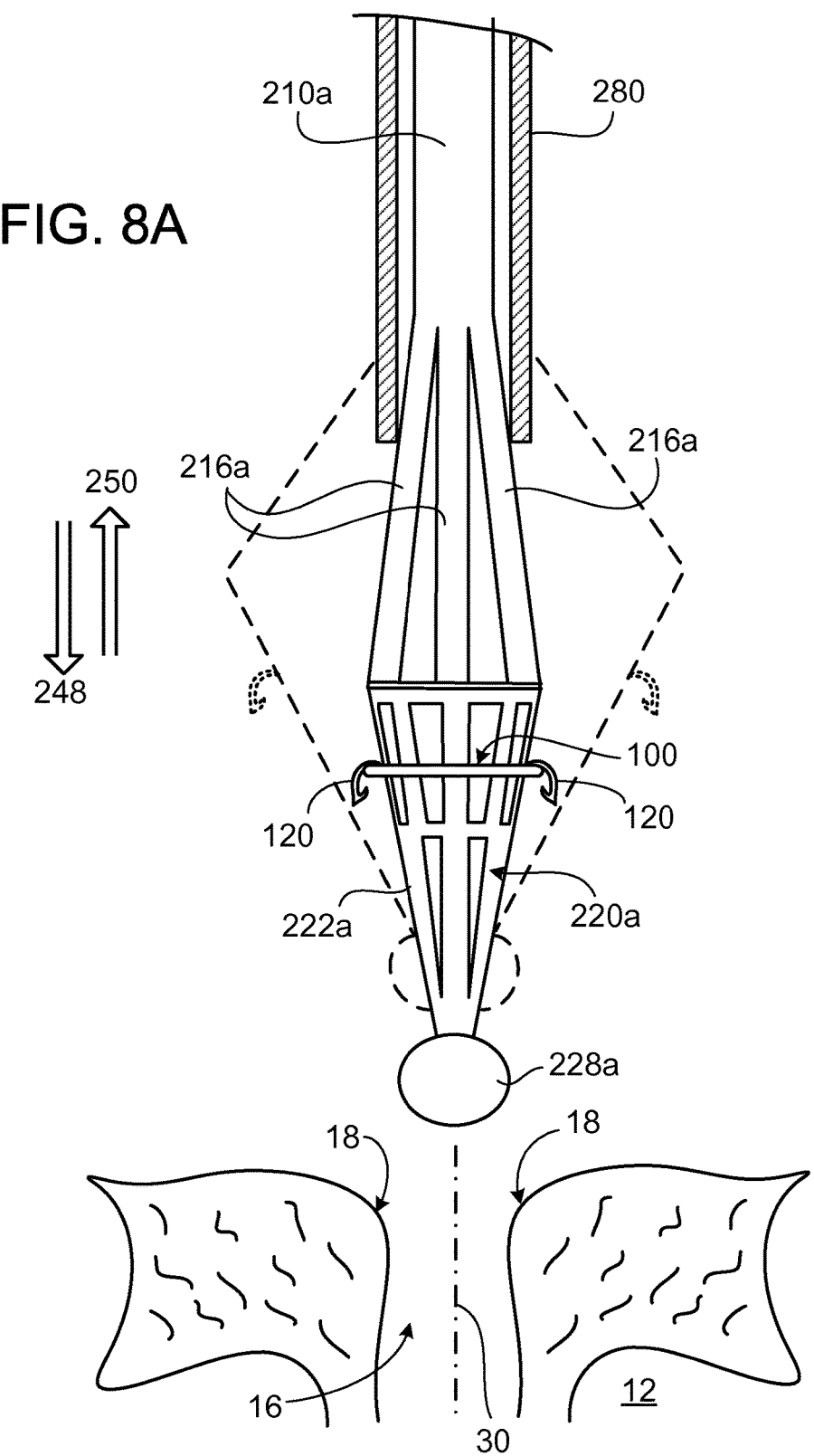
FIGS. 8A through 8I show delivery of a heart valve support where the delivery tool is fed percutaneously through blood vessels and into the right atrium. A sheath is then retracted, exposing the valve support, and allowing the projections, the delivery head, and the support to expand.

To deliver the support to the valve annulus, the end 230 of the tool 200a is fed percutaneously through blood vessels and into the right atrium 24 (FIG. 8A). The sheath 280 is then retracted, exposing the valve support 100 and allowing the projections 216a, the delivery head 220a, and the support 100 to expand, as shown in FIG. 8A.

Figure 8B:
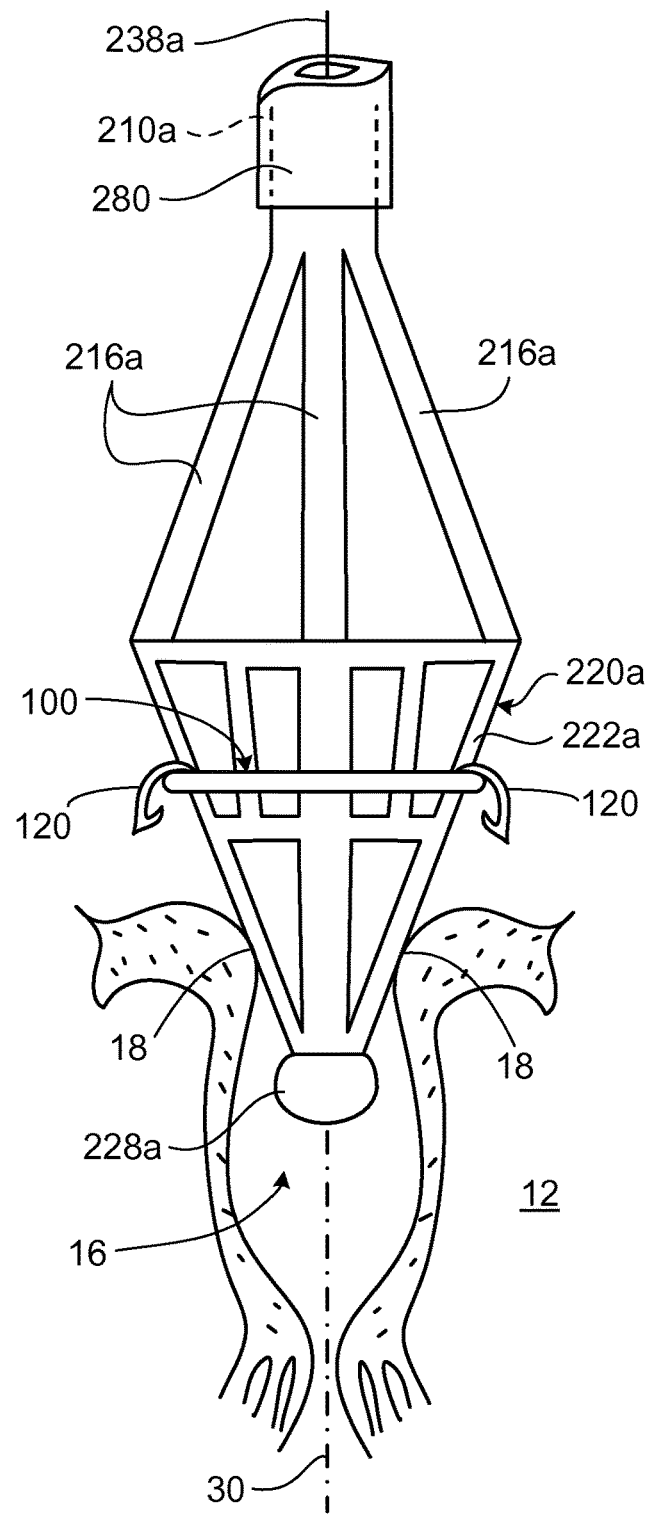

In steps that are somewhat similar to the open heart placement of the support, the catheter shaft 210a is then advanced, e.g., under image guidance, in the direction 248a along an axis 30 of the annulus 18. The operator forces the distal end 230a of the self-centering delivery head 220a into the valve 16 (FIG. 8B) using feel or image guidance, without actually seeing the valve 16.

Once the tip is in the valve 16, the operator pushes on the end 214a of the catheter shaft 210a to force the tool further into the valve 16. This causes the tapered body 222a of the delivery head 220a to restore the shape of the annulus 18 to a circle or other desired shape (such as the distinctive "D" shape of a healthy mitral valve). The tool 200a tends to be self-centering because of its shape. The net-like construction of the delivery head 220a (and the head used in open heart surgery, also) allows blood to flow through the valve even while the delivery head 220a is inserted.

Figure 8C:
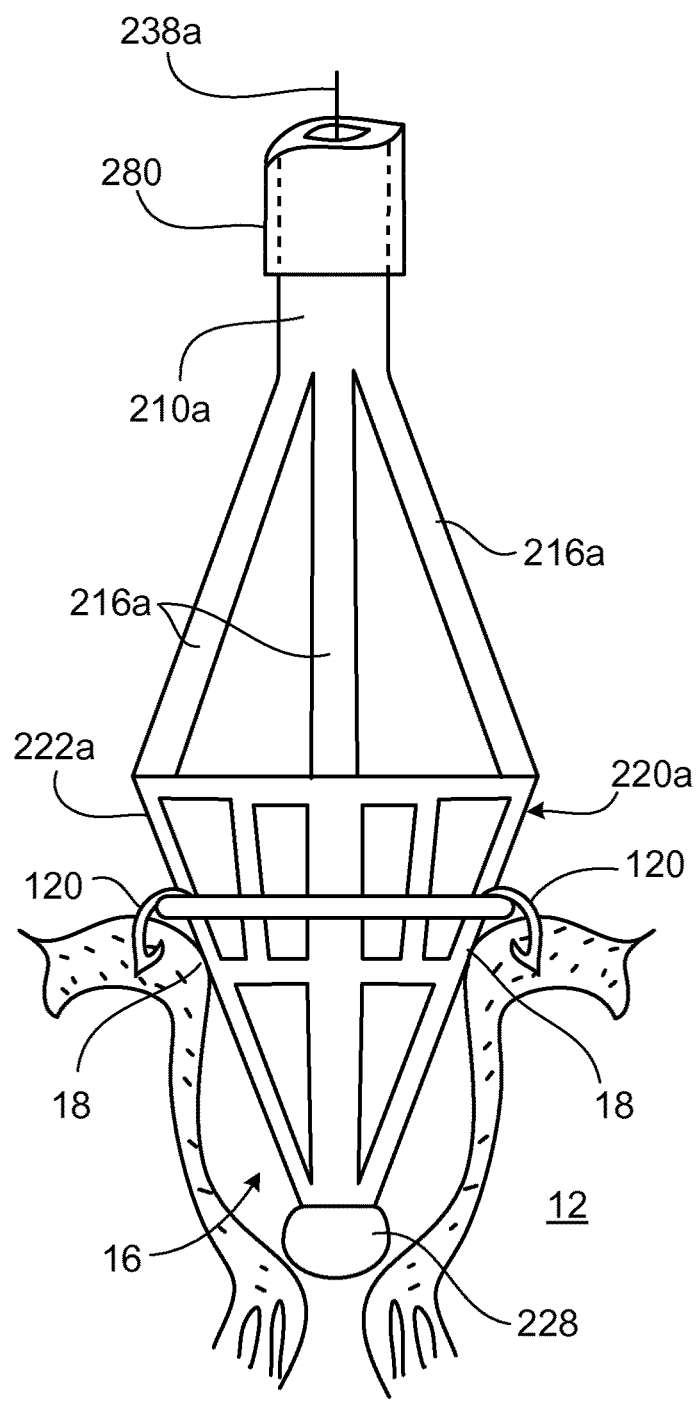

As tool 200a reaches the position at which the support hooks touch the annulus, by giving an additional push, the operator drives the hooks 120 of the valve support 100 together into all of the annular locations at which it is to be attached, as shown in FIG. 8C. In some examples, it may be possible for the operator to tilt the delivery head deliberately to cause some of the hooks to penetrate the tissue before other hooks. The configuration of the valve support 100 and the tool 200a and the manner of temporary attachment of the support 100 to the tool 200a tend to assure that the hooks 120 will penetrate the valve 16 at the correct positions, just along the outer edge of the annulus 18.

Figure 8D:
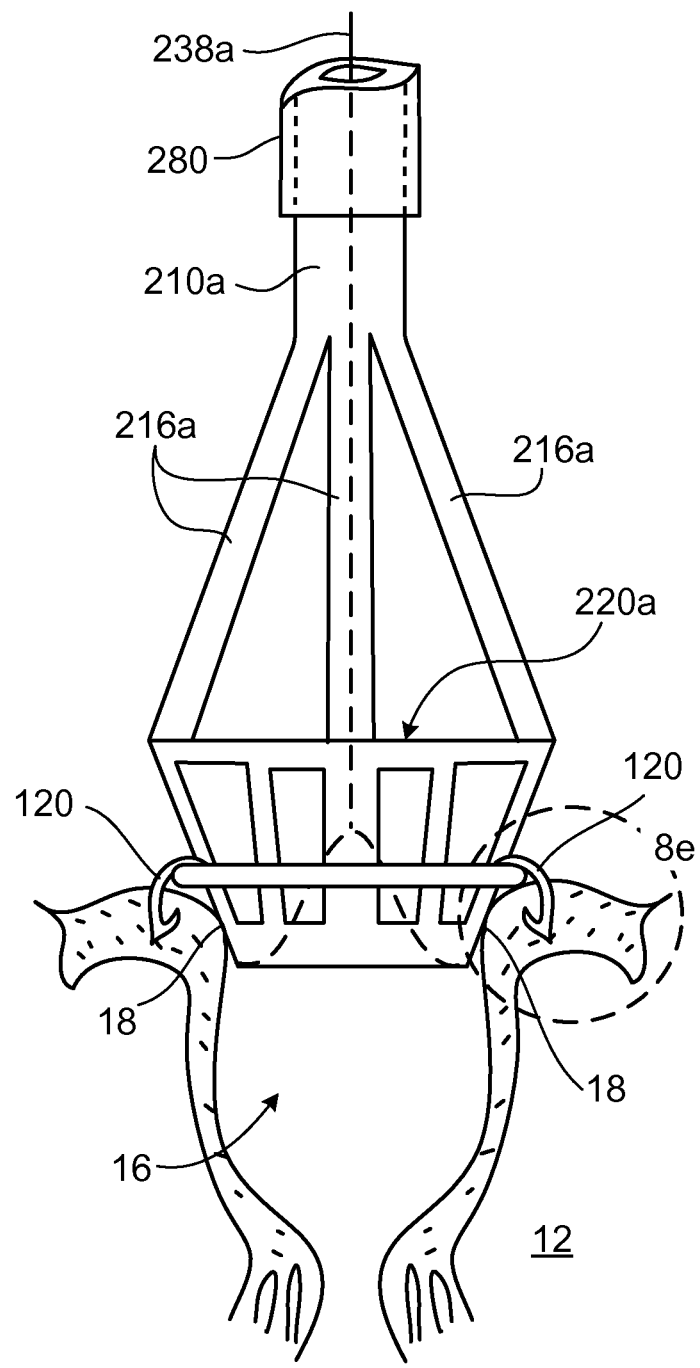
Figure 8E:
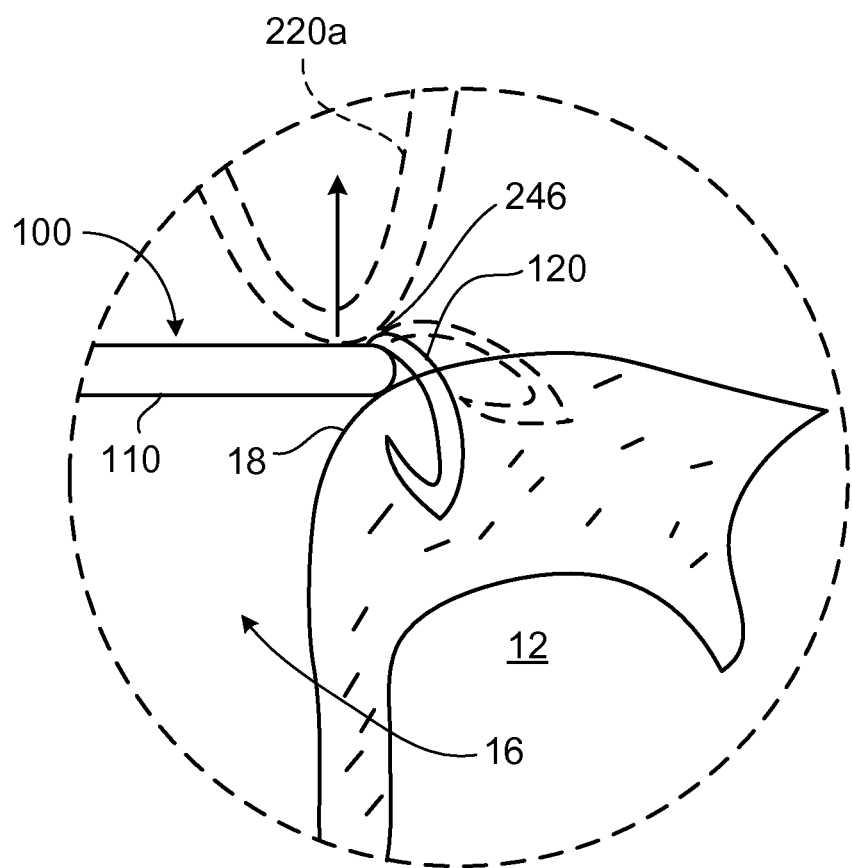

Once the valve support 100 has been attached to the valve 16, the operator pulls on the proximal end 240a causing the delivery head 220a to evert (hidden dashed lines) and be drawn out of the valve 16 (shown in FIG. 8D). Eventually the everted portion of the tool 200a reaches the valve support 100. By further tugging, the operator causes the torus of the support 100 to roll around its periphery which jams the free ends of the hooks 120 securely into the annulus 18 of the valve 16, as illustrated in FIG. 8E, seating the support permanently and permitting later growth of tissue around the support 100. The depth and radial extent of each of the placed hooks 120 can be essentially the same as a conventional suture so that their placement is likely to be as effective and familiar to the operator and others as conventional sutures.

Figure 8F:
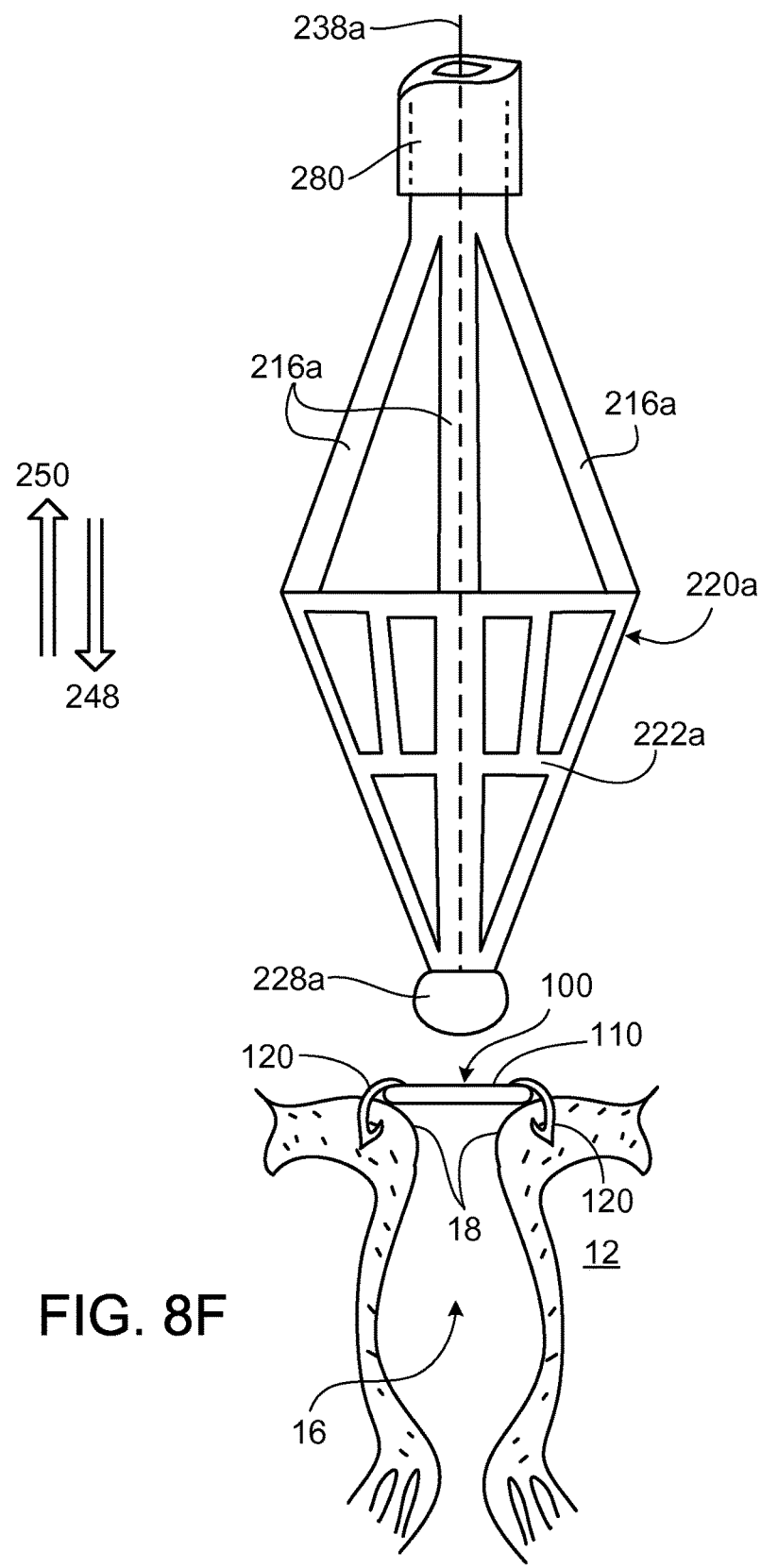
Figure 8G:
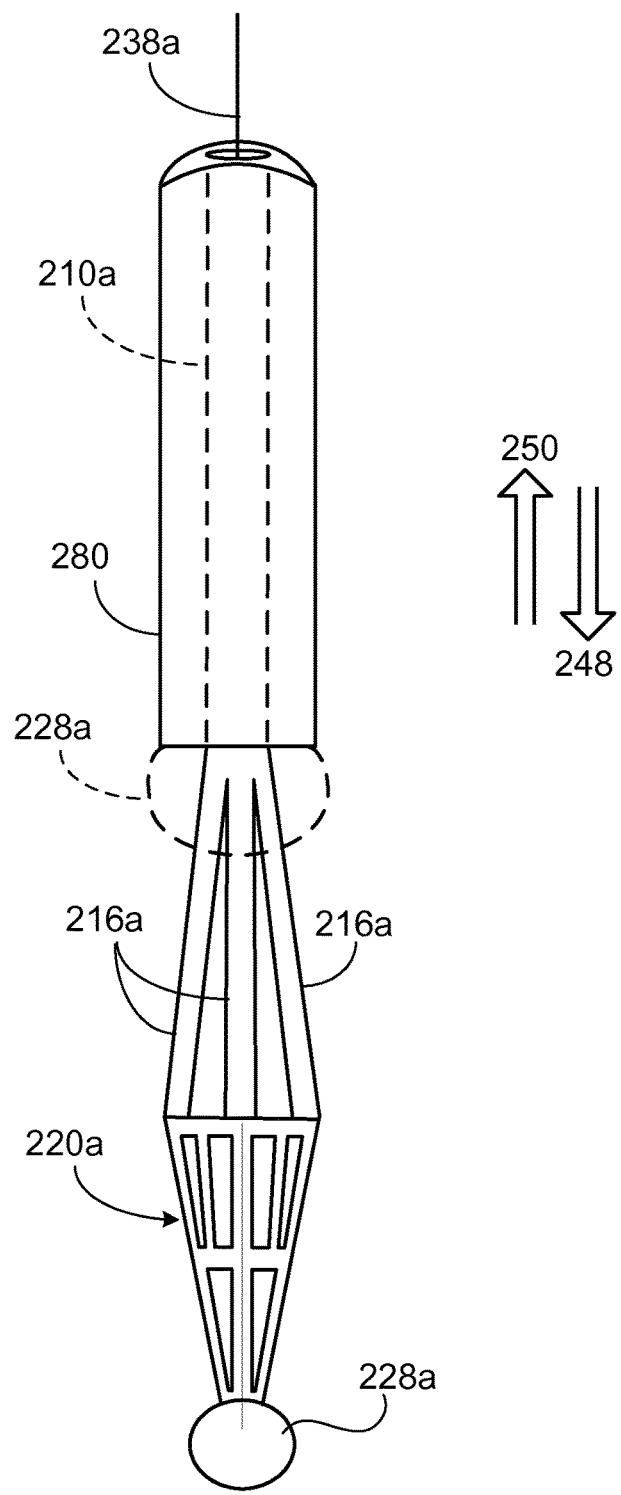

Using a final tug, the operator breaks the connections 246 between the tool 200a and the valve support 100 and retracts the catheter shaft 210, leaving the support 100 in place. The catheter shaft 210 is retracted to a position beyond the valve annulus 18 and the wire is advanced in the first direction allowing the delivery head 220a to assume its original tapered shape (FIG. 8F). The catheter shaft 210a is then retracted into the sheath 280 (FIG. 8G), and the tool 200a is withdrawn.

Figure 8H:
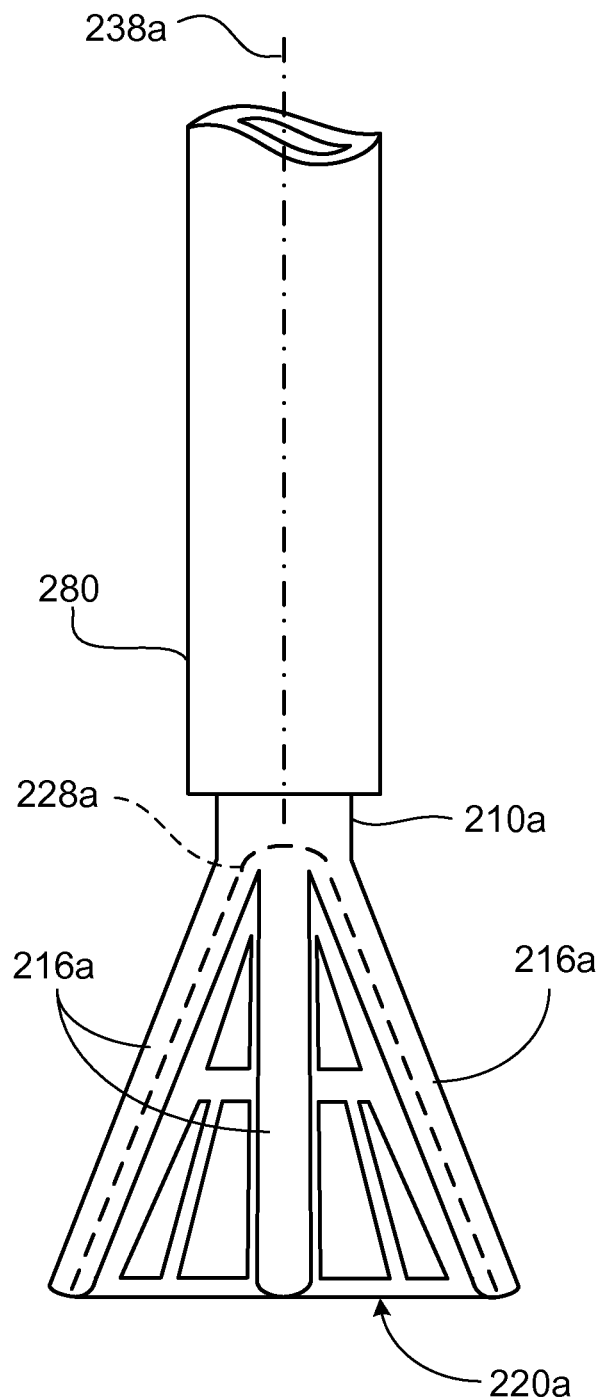
Figure 8I:
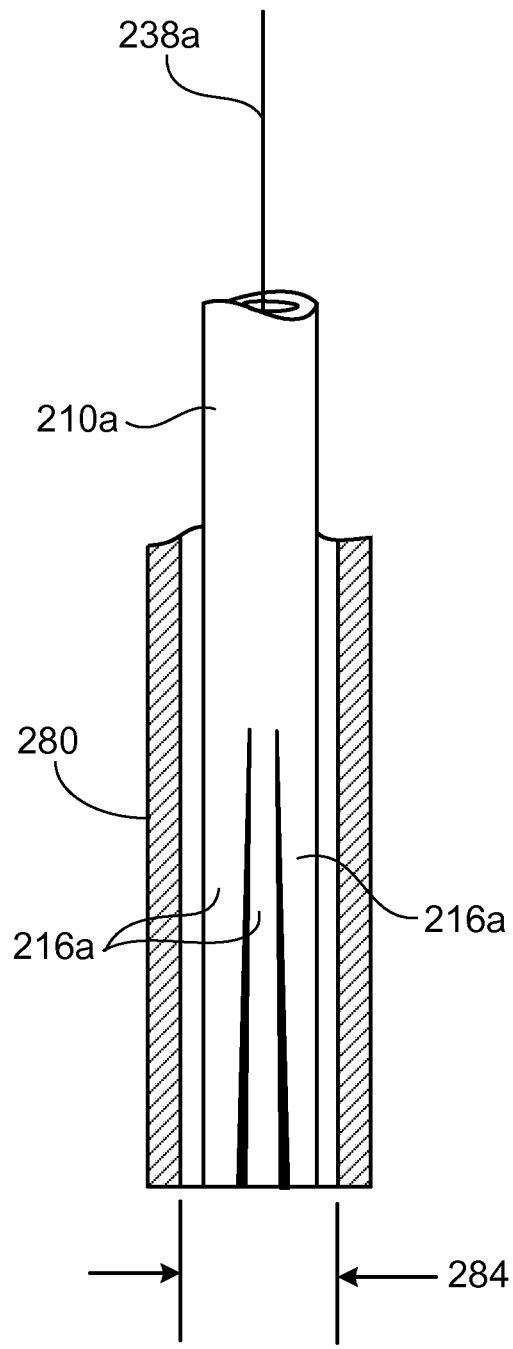

In some examples, as shown in FIGS. 8H and 8I, the tip 228a of the tool 200a, when everted, has a compressed dimension that is smaller than an internal diameter 284 of the sheath 280, permitting the catheter shaft 210a to be retracted directly into the sheath 280 after deployment, with the everted tip held within the collapsed delivery basket, as shown in FIG. 8I.

With the tool 200a withdrawn, the valve support 100 contracts, reshaping the annulus 18 such that the valve leaflets 14 coapt to prevent a backflow of blood during systole.

Other implementations are within the scope of the claims.

For example, distortion of either the tricuspid valve or mitral valve can be corrected. For tricuspid valve repair, the hooks can be arranged around only about three-quarters of the support and therefore the annulus. During the placement procedure, the operator will rotate the support to position the portion of the support having hooks. For mitral valve repair, the hooks can cover the entire periphery of the annulus. In this scenario, the hooks are arranged around the full circumference of the support. Alternatively, the hooks can cover only the posterior section of the annulus of the mitral valve. In this scenario, the hooks can be arranged around two-thirds of the support. Similarly to the tricuspid valve example, the operator will position the portion of the support having hooks against the posterior section of the mitral valve annulus. Further, for mitral valve repair, a back-up valve can be provided as part of the delivery tool to maintain heart function during the delivery procedure. Materials other than shape memory materials may be used as the material for the support body, and other ways can be used to force the support back to a desired size following expansion, including, for example, cross-bars that span the opening of the support.

In addition, the left atrial appendage of the heart can be closed by a similar technique. For example, the tool can be pushed into an opening of an atrial appendage causing the opening to assume a predetermined shape. The tool can continue to be pushed in order to embed the hooks of the expanded support into the periphery of the opening of the appendage. The tool can then be withdrawn, releasing the support, and allowing the support to contract. The support can have a relatively small contracted diameter such that, when the tool is withdrawn, releasing the support, the support can contract to a relatively small size, effectively closing off the appendage.

In addition to the open heart and percutaneous deployment procedures, the valve support can also be deployed through the chest.

The head-end of the tool need not be a basket, but can take any form, mechanical arrangement, and strength that enables the valve annulus to be forced open to a shape that corresponds to the shape of the support. The basket can be made of a wide variety of materials. The basket can be held and pushed using a wide variety of structural mechanisms that permit both pushing and pulling on the support both to seat and embed the support in the annulus tissue and disconnect the support from the tool.

The tool need not be conical.

The support could take a wide variety of configurations, sizes, and shapes, and be made of a wide variety of materials.

The hooks could be replaced by other devices to seat and embed the support using the pushing force of the tool.

The hooks of the support need not be embedded directly in the annulus but might be embedded in adjacent tissue, for example.

The support could take other forms and be attached in other ways.

Figure 9A:
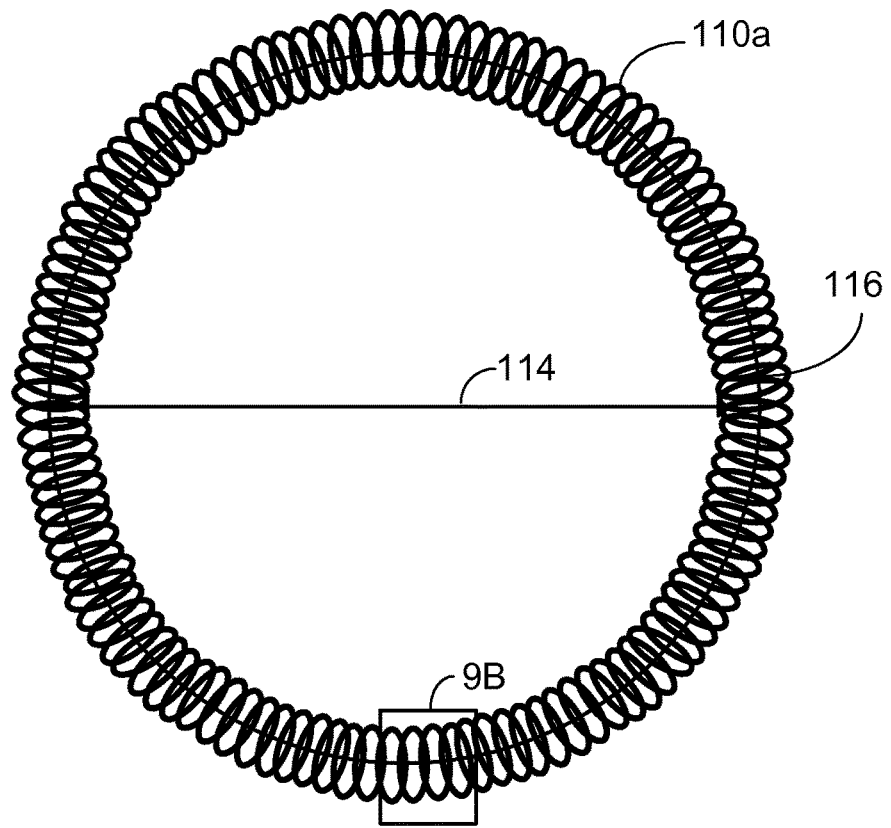
FIG. 9A is a plan view of a heart tissue support where the support body is a torus in the form of a helical spring.

In FIG. 9A, the support body 110a can be a torus in the form of a helical spring (as mentioned earlier). Such a support body can have a native circumference 116 on the order of ten centimeters in its contracted state, and a proportional native diameter 114. The circumference can be selected based on the physical requirements of a particular patient.

Figure 9B:
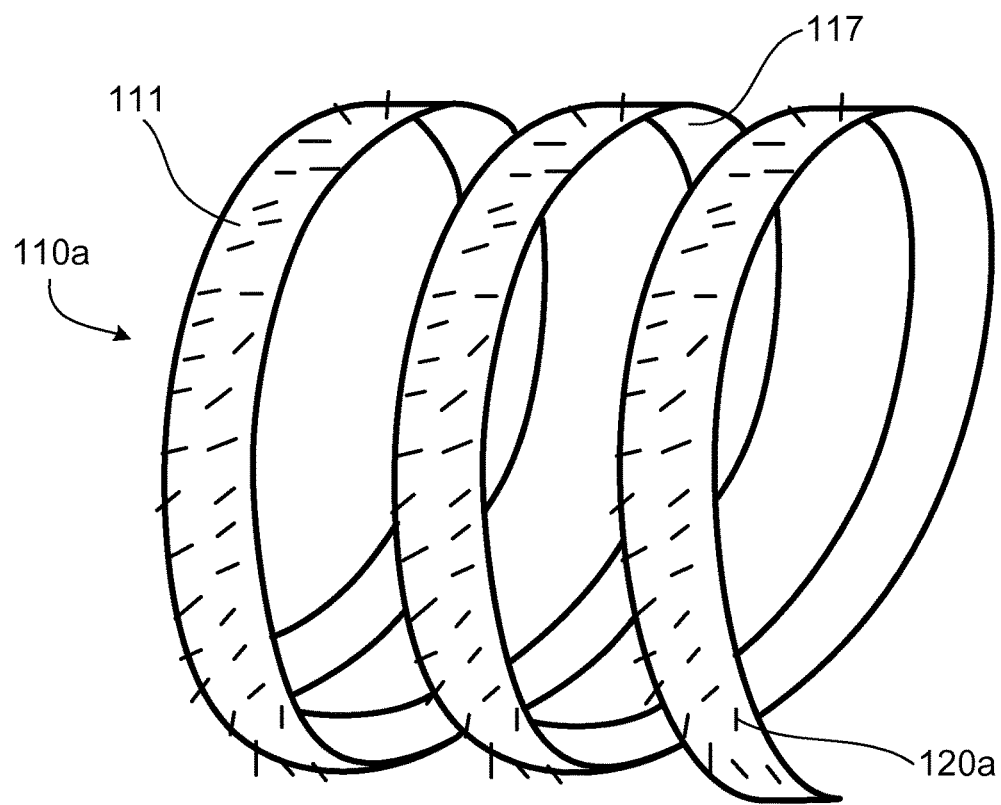
FIG. 9B is a perspective view of a fragment of a heart tissue support with burr hooks attached to the outside surface.

A close-up view of a fragment of this support body, FIG. 9B, shows that some implementations have a number (e.g., a large or very large number, for example, as few as say 15, or 100, and up to hundreds or even thousands) of burr hooks 120a attached to an outer surface 111 of the support body 110a. In the example shown in FIG. 9B, the helical support body is wound from a flat strip that has the outer surface 111 and an inner surface 117. Although FIG. 9B shows the burr hooks attached only to the outside surface, burr hooks could also be attached to the inner surface for manufacturing reasons or for other purposes.

The burr hooks, which are small relative to the body, are each configured to partially or fully pierce annular tissue when the part of the body to which the burr hook is attached is pushed against the tissue.

Figure 9C:
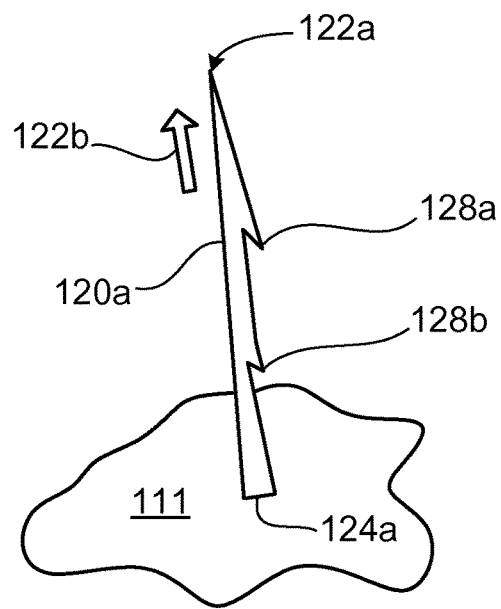
FIGS. 9C through 9E are side views of burr hooks.

As shown in FIG. 9C, in some examples, each burr hook 120a has a sharp free end 122a for piercing tissue and at least one barbed end 128a, 128b (two are shown in FIG. 9C) for keeping the burr hooks embedded in tissue. Each burr hook also has an end 124a that is attached to the surface of the support body. Once the support (we sometimes refer to the support structure simply as the support) is in contact with heart tissue, the embedded burr hooks hold the body in a proper position and configuration on the annulus. Burr hooks can be attached to the surface of the support body using glue, cement, or another type of adhesive, or formed from the support body as part of an industrial process, such as molding, etching, die cutting, welding, or another process, or can be attached by a combination of these techniques. Different burr hooks on a given support can be attached by different mechanisms.

Figure 9D:
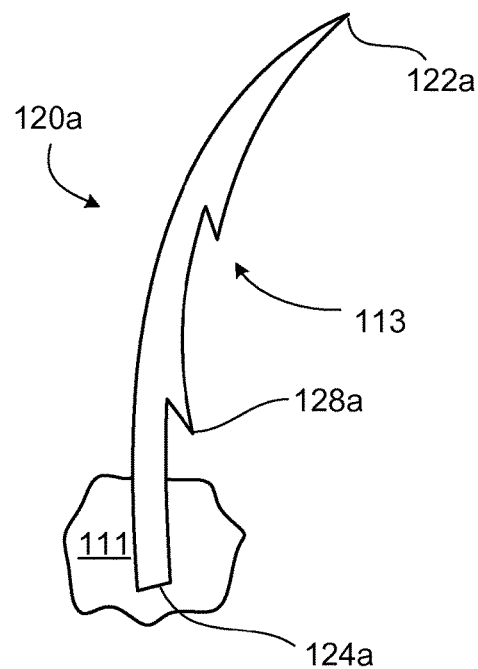
Figure 9E:
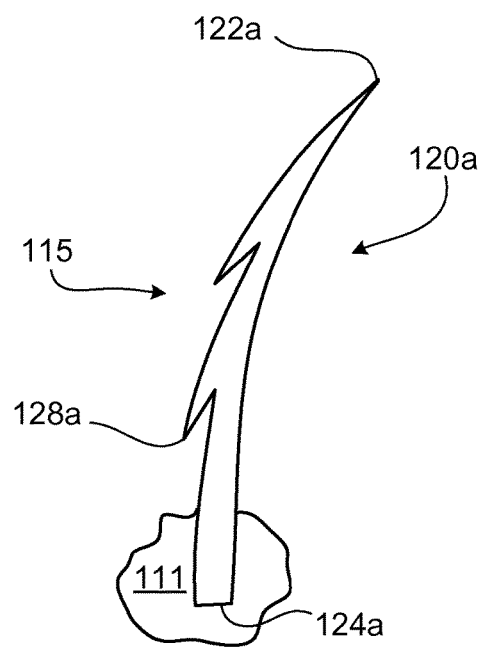

Each burr hook 120a can be structured and attached so that the free end 122a points in a direction 122b perpendicular (or some other selected effective direction, or deliberately in random directions) to the body surface 111. In some cases, the burr hook can be curved. A barbed end 128a could be located on a concave edge 113 (FIG. 9D) or a convex edge 115 (FIG. 9E) of a curved burr hook.

The burr hooks bear a resemblance to burr hooks on natural plant burrs. A different kind of attachment device could be used by analogy to metal tipped hunting arrows in which a sharp point has two broad and sharp shoulders that cut the tissue as the point enters. The tips of the two shoulders serve a similar function to the barbs, keeping the arrow embedded once it enters the tissue.

In some implementations, the burr hooks on a support body have two or more (in some cases, many) different shapes, sizes, orientations, materials, and configurations. By varying these features, for example, the orientations of the burr hooks, it may be more likely that at least some of the burr hooks will become embedded in the tissue, no matter how the support body is oriented at the moment that it comes into contact with the annulus. Varying the number, orientation, and curvature of the hooks may make it more likely that the support body will remain in place. For example, in such a support, a force applied to the support body in a particular direction may unseat or partially unseat some of the burr hooks by disengaging the barbed ends from the tissue, but the same force may not affect other burr hooks that have barbed ends oriented in a different direction or in a different configuration than the unseated burr hooks. The force applied to seat the support may cause some burr hooks to embed more securely than other burr hooks.

Figure 9F:
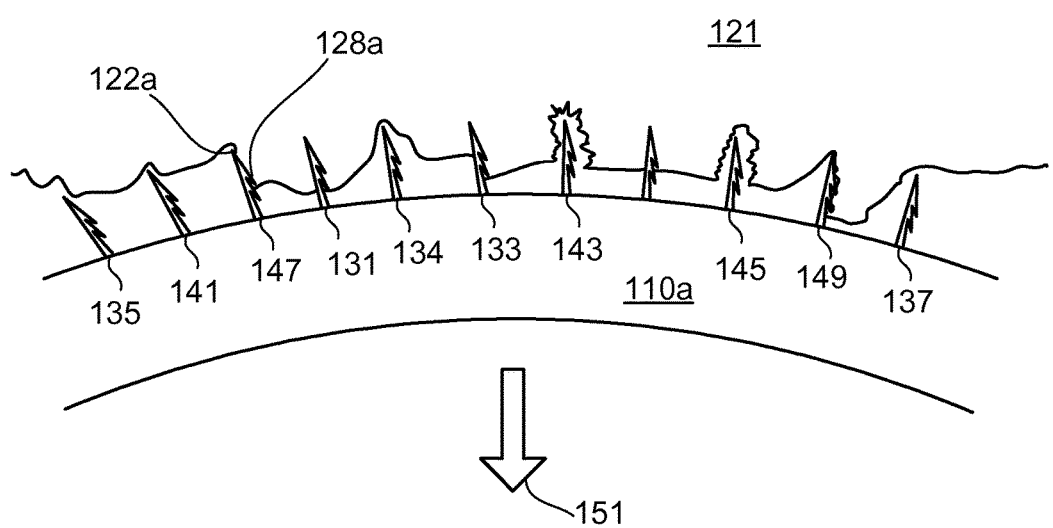
FIG. 9F is a schematic view of a heart tissue support attached to annular tissue.

In use, typically not all of (in some cases not even a large portion of) the burr hooks will embed themselves in the tissue when the support body is pushed against the tissue, or remain embedded after placement. As shown in FIG. 9F, there are enough burr hooks arranged in an appropriate way so only a fraction of the total hooks need be embedded in annular tissue (and in some cases only in certain regions) to create a physical bond to keep the support body properly in place. The proportion of burr hooks on a support that need to embed securely in the tissue could range from 1% to 10% or 40% or more. The averaging spacing of the successfully embedded burr hooks could range from, say, one burr hook per millimeter of support body length to one burr hook per two or three or more millimeters (or more) to secure the support appropriately. When burr hooks are grouped rather than arranged evenly on the support, the percentages of and distances between successfully embedded hooks may differ.

When the burr hooks come into contact with the annular tissue during delivery, some 131, 133, but not necessarily all, of the burr hooks pierce the tissue and (when a retracting force is applied to the delivery tool) their barbs grip the tissue. Of the remaining burr hooks, some 135, 137 may (because of the contours of the tissue, for example) not even come into contact with the tissue, and others 139, 141 may not come into contact with the tissue with sufficient force or in the right orientation to pierce the tissue and have their barbs seat securely in the tissue. Some of the burr hooks 143, 145 may penetrate the tissue but fail to grip the tissue. Some of the burr hooks 147, 149 may only penetrate the tissue at the barbed end 128a, and not with respect to the free end 122a, providing a physical bond that may be weaker than one in which the free end has been embedded in the tissue. For some or many or most of the burr hooks that enter the tissue, however, the barbed ends 128a seat properly and resist forces in the direction 151 that would otherwise unseat the burr hook. Even though a wrenching force applied to a particular burr hook in direction 151 could still be large enough to unseat the barbed end, overall the combination of many burr hooks embedded in tissue tends to keep the support body set in place and in the proper configuration. Over time, some of the burr hooks that were not embedded when the support was placed may become embedded, and some of the burr hooks that were embedded when the support was placed may become unseated.

The resistance provided by each of the barb or barbs to removal of a given burr hook from the tissue may be relatively small. However, the aggregate resistance of the burr hooks that successfully embed themselves will be higher and therefore can reliably keep the support body in place and the annulus of the valve in a desirable shape. In addition, because there are a number (potentially a very large number) of small burr hooks spread over a relatively large area, the stress on any part of the tissue of the annulus is quite small, which helps to keep the support body properly seated and the valve shape properly maintained along its entire periphery, all without damaging the tissue. The fact that a large number of burr hooks at close spacings may become embedded along the length of the support means that the support may become attached to the annulus more evenly and continuously than might be the case with the relatively smaller number of hooks described earlier, and therefore perform better.

With respect to the implementations described beginning with FIG. 1A, the implementations shown beginning at FIG. 9A tend to have more and smaller hooks not all of which need to become embedded successfully. A common concept between the two arrangements is that the hooks penetrate by being pushed into the tissue and have retaining elements that become securely embedded in the tissue when a pulling force is applied at the end of the placement process. The two concepts are not mutually exclusive. Supports like those shown in FIG. 1A could also have burr hooks and supports like those shown in FIG. 9A could also have hooks of the kind shown in FIG. 1 A. Placement of the support could rely on a combination of both kinds of hooks.

Figure 9G:
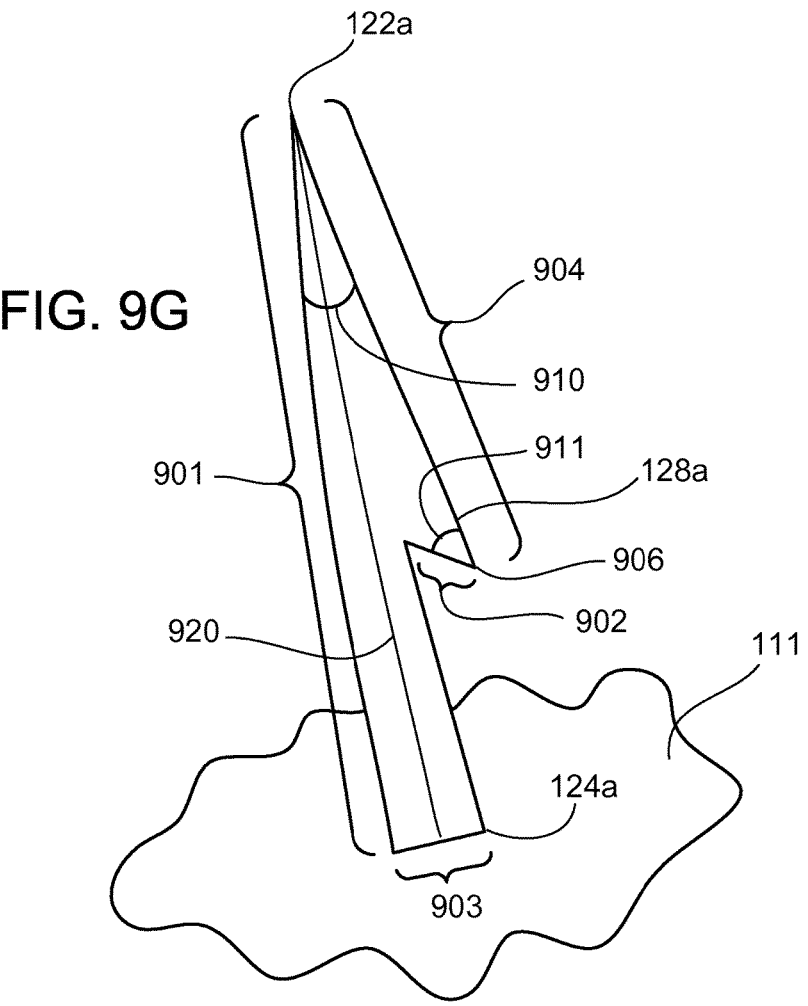
FIG. 9G is a side view of a burr hook that has one barbed end.

Each burr hook can be formed of a biologically compatible material such as platinum, gold, palladium, rhenium, tantalum, tungsten, molybdenum, nickel, cobalt, stainless steel, Nitinol, and alloys, polymers, or another material. As for the hooks shown beginning with FIG. 1 A, the hooks can also be formed of a combination of such materials. An individual support body may exhibit burr hooks having a range of compositions. Some of the burr hooks attached to a support body may be composed of one material or combination of materials, and some of the burr hooks may be composed another material or combination of materials. Each burr hook may be unique in composition. Further, some parts of a burr hook may be composed of one set of materials, and other parts may be composed of another set of materials. In some examples, the region of the burr hook at the barbed end is composed of one set of materials, alloys, polymers, or mixtures, and the region of the burr hook at the free end is composed of another set of materials, alloys, polymers, or mixtures, and the rest of the burr hook is composed of a further set of materials, alloys, polymers, or mixtures. FIG. 9G shows an example burr hook that only has one barbed end 128a. The burr hook extends from an attached end 124a to a free end 122a along the path of a principal axis 920 that (in this case) is perpendicular to the support body surface 111. The barbed end spans a length 904 from the burr hook's free end 122a to the barbed end's free end 906. This free end 906 forms a point spanning an acute angle 910 and the barbed end 128a spans an acute angle 911 to grab the tissue in response to any force that would otherwise pull an embedded burr hook away from tissue.

The length 901 of each burr hook could be between about 1 and 12 millimeters, as measured from the attached end 124a to the free end 122a along the principal axis. Each barbed end could extend a distance 902 from the burr hook lesser or greater than a principal width or diameter 903 of the burr hook as measured at the attached end. The cross-section of the body of the burr hook could be flat or cylindrical or ovoid or any other of a wide variety of shapes.

Figure 9H:
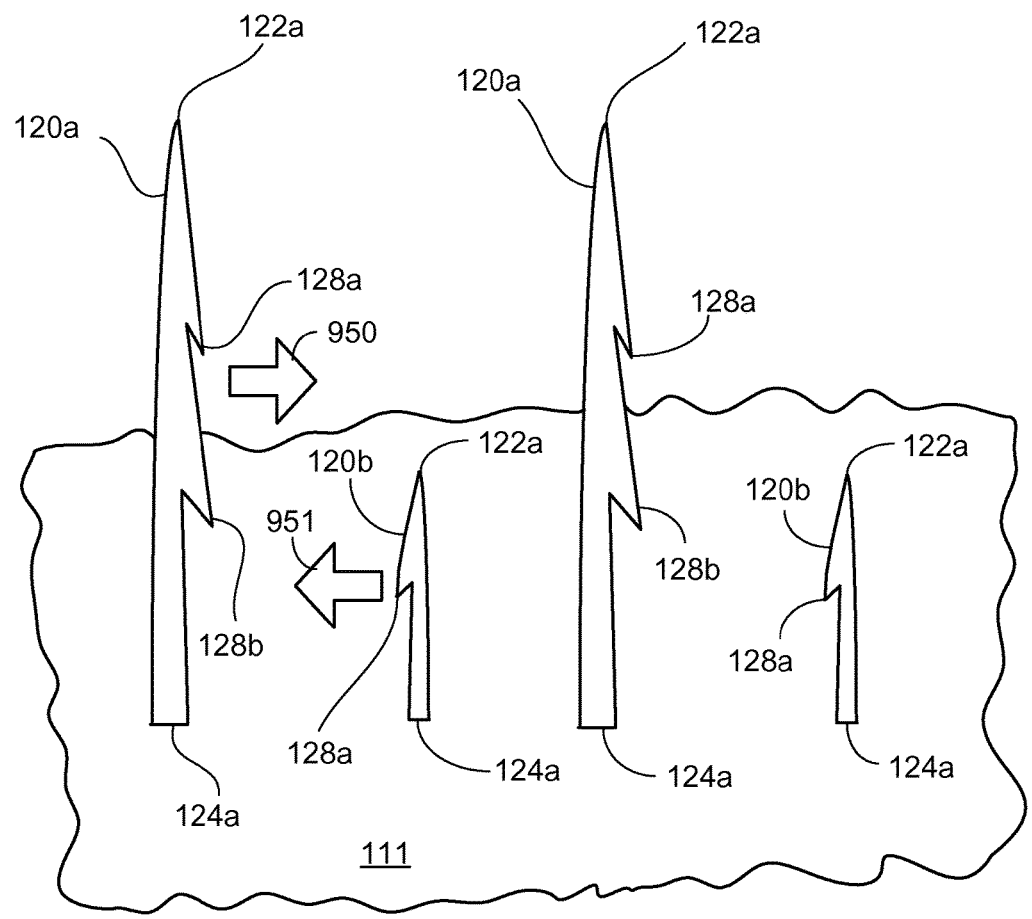
FIG. 9H is a side view of a portion of a support body surface containing burr hooks that each have two barbed ends facing in a first direction and shorter burr hooks each having one barbed end facing in a second direction.
Figure 9I:
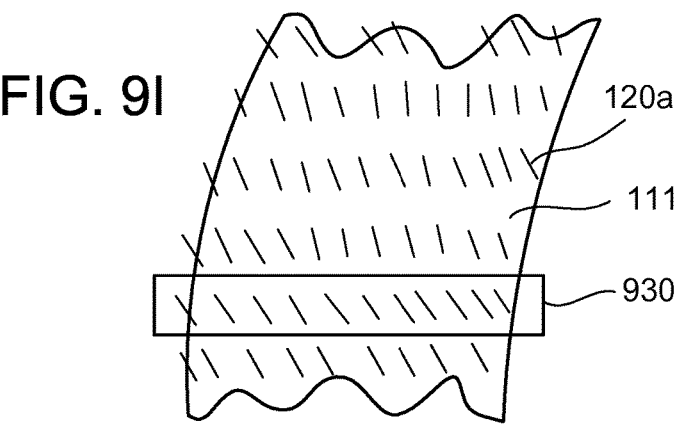
FIGS. 9I through 9M is a close-up view of portions of heart tissue support surfaces with burrs.
Figure 9J:
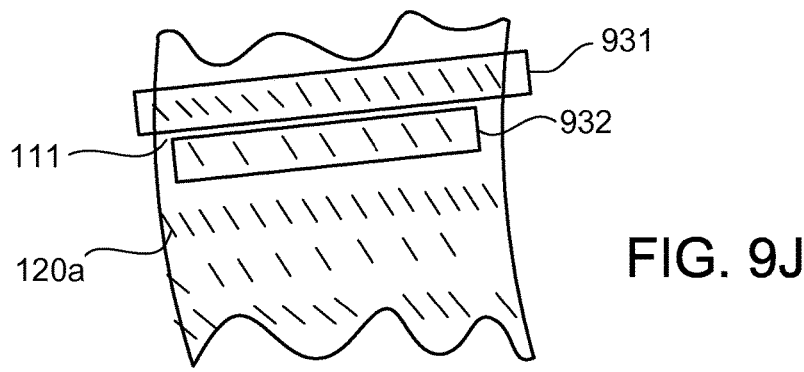
Figure 9K:
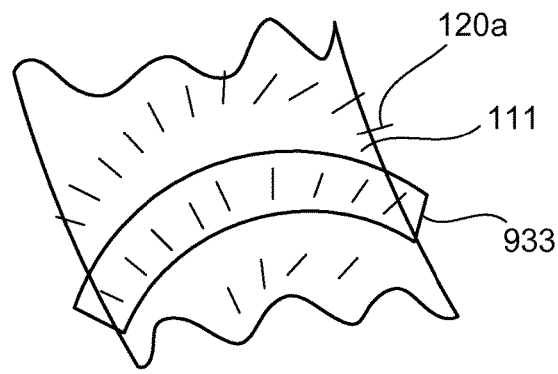
Figure 9L:
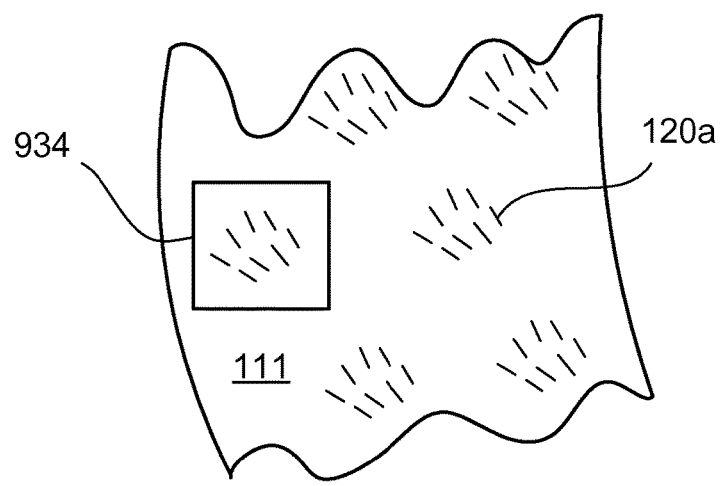
Figure 9M:
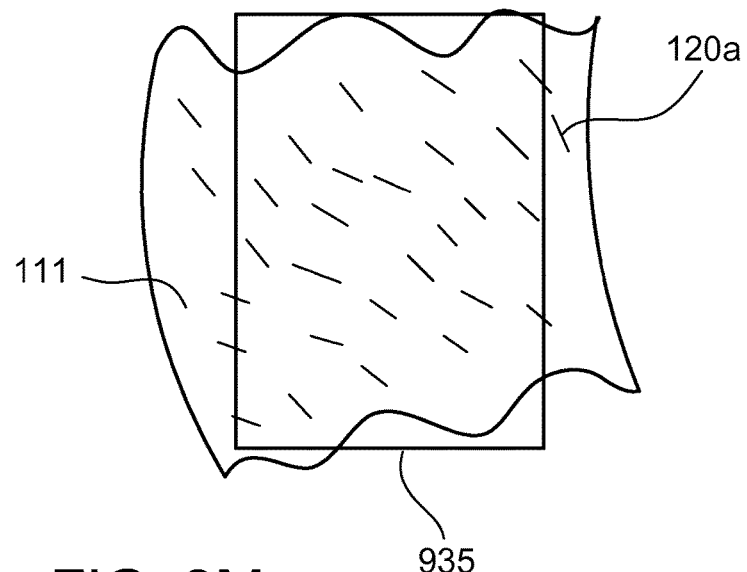

Different burr hooks may be placed on the support body surface in different sizes and configurations. For example, different burr hooks may have different lengths and different numbers and placement of barbed ends. As shown in FIG. 9H, for example, a portion of support body surface 111 contains burr hooks 120a that each have two barbed ends 128a, 128b facing in a first direction 950 and shorter burr hooks 120b each having one barbed end 128a facing in a second direction 951. Also, the burr hooks may be arranged on the body surface in various densities and patterns of distribution. For example, as shown in FIG. 9I, the burr hooks may be placed on the surface of the body in repeating rows 930. As shown in FIG. 9J, the burr hooks may be placed on the surface in rows of different lengths and densities 931, 932. As shown in FIG. 9K, the burr hooks may be placed on the surface along are formations 933. As shown in FIG. 9L, the burr hooks may be placed on the surface as cluster formations 934. As shown in FIG. 9M, the burr hooks may be distributed randomly 935. Other patterns may also be used.

A single support body can include a wide variety of patterns of burr hooks on its surface, because the physical characteristics of a particular heart valve may mean that the valve tissue is either more receptive or less receptive to a particular pattern of burr hook distribution. Some patterns may be more effective on some types of tissue, and other patterns may be more effective on other types of tissue.

Figure 9N:
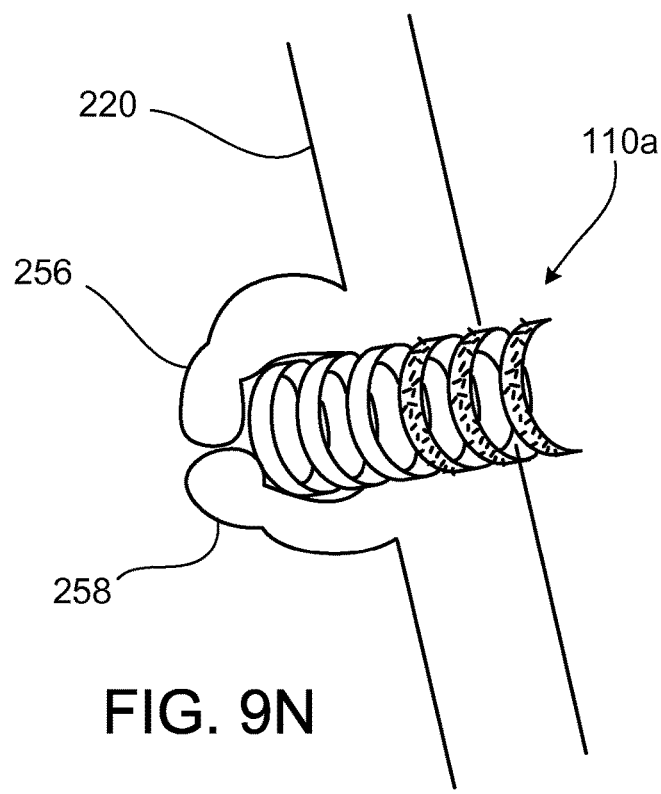
FIG. 9N is a view of a heart tissue support and a delivery tool.

In addition, as shown in FIG. 9N, the burr hooks need not be present at the points where the body 110a contacts the delivery tool 220, including in the area near the rigid fingers 256, 258. This tends to prevent the burr hooks from causing the support body to stick to the tool.

Figure 9O:
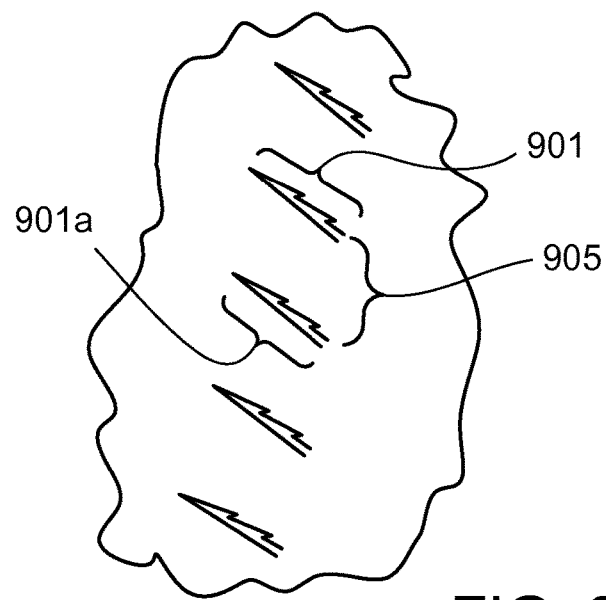
FIG. 9O is a close-up view of a portion of a heart tissue support surface with burrs.

As shown in FIG. 9O, any two burr hooks may be placed at a distance 905 from each other greater than or less than the length 901, 901a of either one.

Figure 9P:
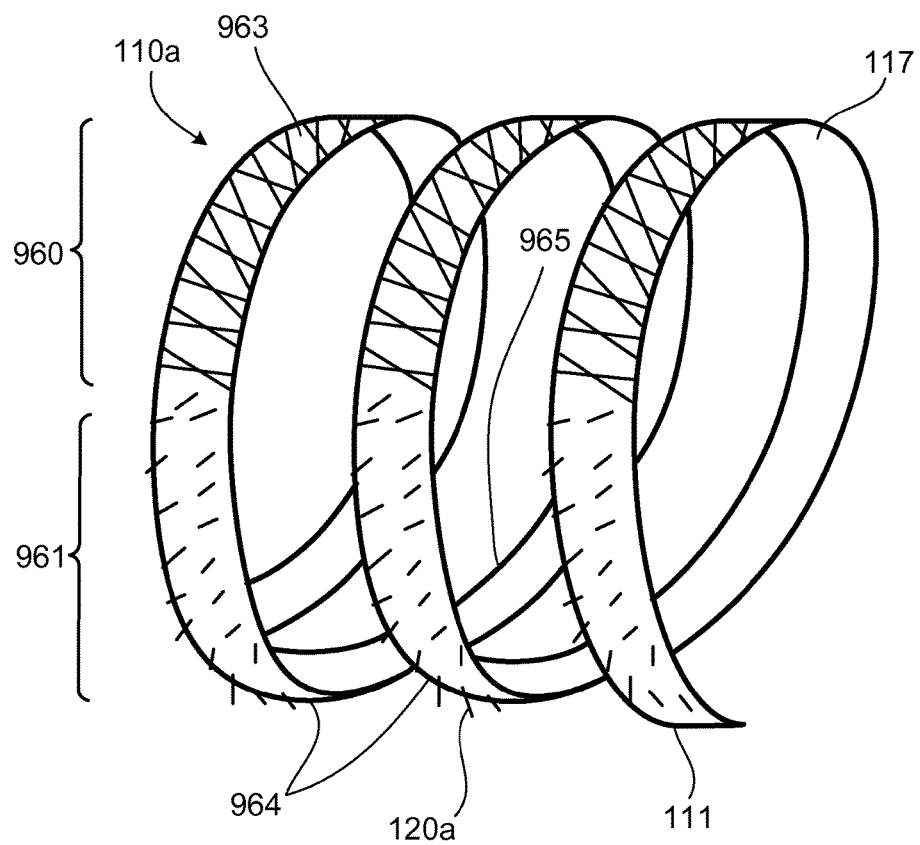
FIG. 9P is a perspective view of a helically formed support.

As shown in FIG. 9P, when a support is formed helically, the ring can be considered to have a front side 961 (which faces the valve when the support is delivered), and a back side 960 that faces away from the valve. In some examples, the support body 110a does not have burr hooks 120a on the back side 960. In these implementations of the support body, the back side 960 is covered by a sleeve 963. After the support body has been attached to the annulus, the sleeve assists in the long-term process of integration with valve tissue. Over a period of time, heart tissue will attach to the support body as part of the process of healing. The sleeve is made of a material that allows this process to occur faster than without the sleeve. For example, the sleeve may be composed of a porous material, which allows tissue to grow into the sleeve, thus securing the support to the tissue more effectively than without the sleeve. The sleeve material may be a thermoplastic polymer such as Dacron (polyethylene terephthalate). The sleeve material may alternatively be a metal or another type of material. The sleeve can be placed on the support body at a location other than the back side. For example, the sleeve could be placed on the inner side 965 of the body, with burr hooks remaining on the outer side 964.

The sleeve is formed as a half-torus in this example, but could have a wide variety of other configurations. Such a sleeve may be used with any kind of support, including the one shown beginning in FIG. 1 A, could cover all or only part of the support, and could cover portions of the support that include hooks or barb hooks or both. In the latter case, the hook may be arranged to penetrate the sleeve during setup and before the support is placed into the heart. The sleeve could also cover a portion of the support meant to contact delicate or sensitive tissue, such as the AV node. In this case, the sleeve is made of a material that is less likely to damage or interfere with the operation of the delicate or sensitive tissue, as compared to other materials that may be used in the support.

Using burr hooks may make attaching the support faster, simpler, more reliable, and easier than for the larger hooks described earlier. The delivery tool operator may not need to apply as much force as might be necessary to embed larger hooks in the annular tissue. In some cases, the barbs would not need to be rotated as described for the larger hooks in order to embed them securely. The operator need not be concerned whether all of the burr hooks have become embedded. Once the operator has determined that the support body has made contact with the tissue and by inference that many of the burr hooks have become attached, the operator can tug on the support to confirm that it has been seated and then release the support body from the delivery tool using one of the mechanisms described earlier. Because of the ease of positioning, the procedure could be performed easily in a non-surgical context, such as in a catheterization laboratory.

Figure 13A:
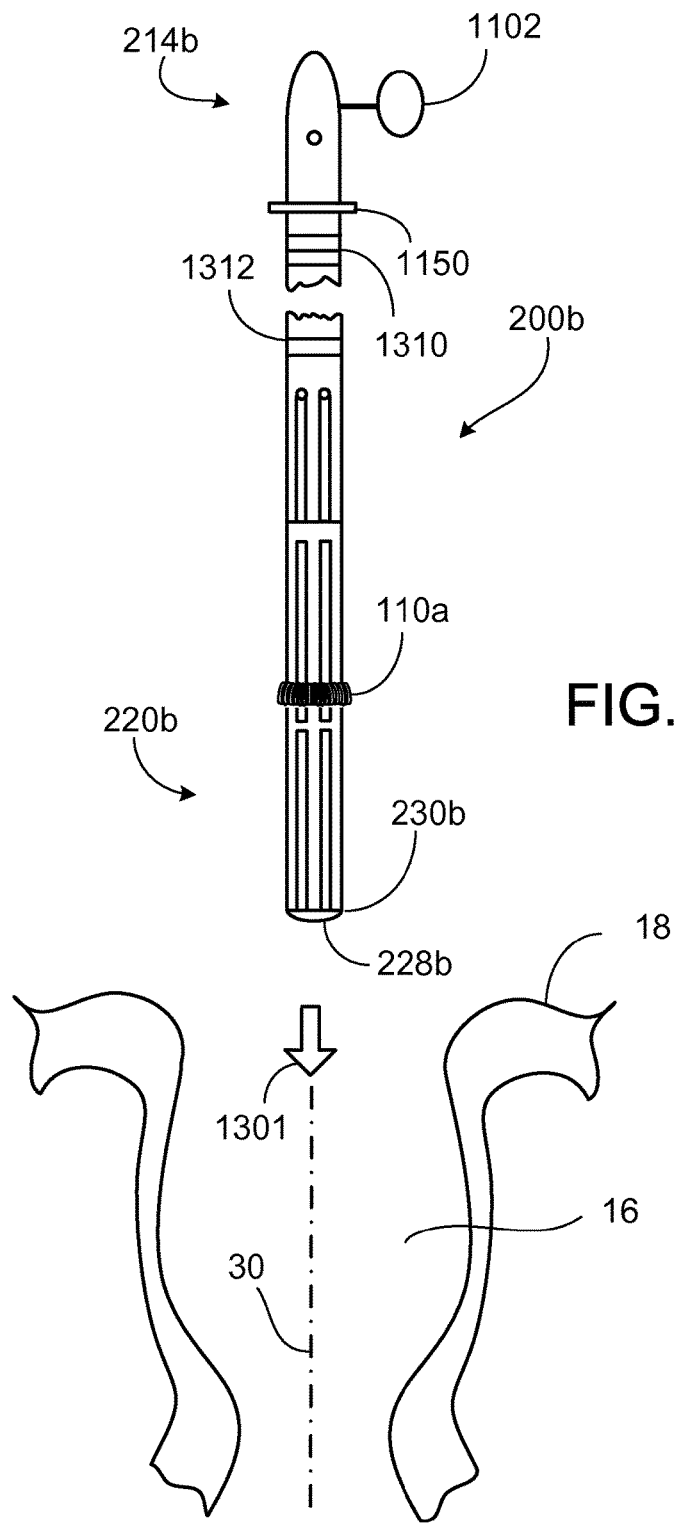
FIGS. 13A through 13D show delivery of a heart valve support and a delivery tool with a collapsed (closed) conical head-end basket.
Figure 13B:
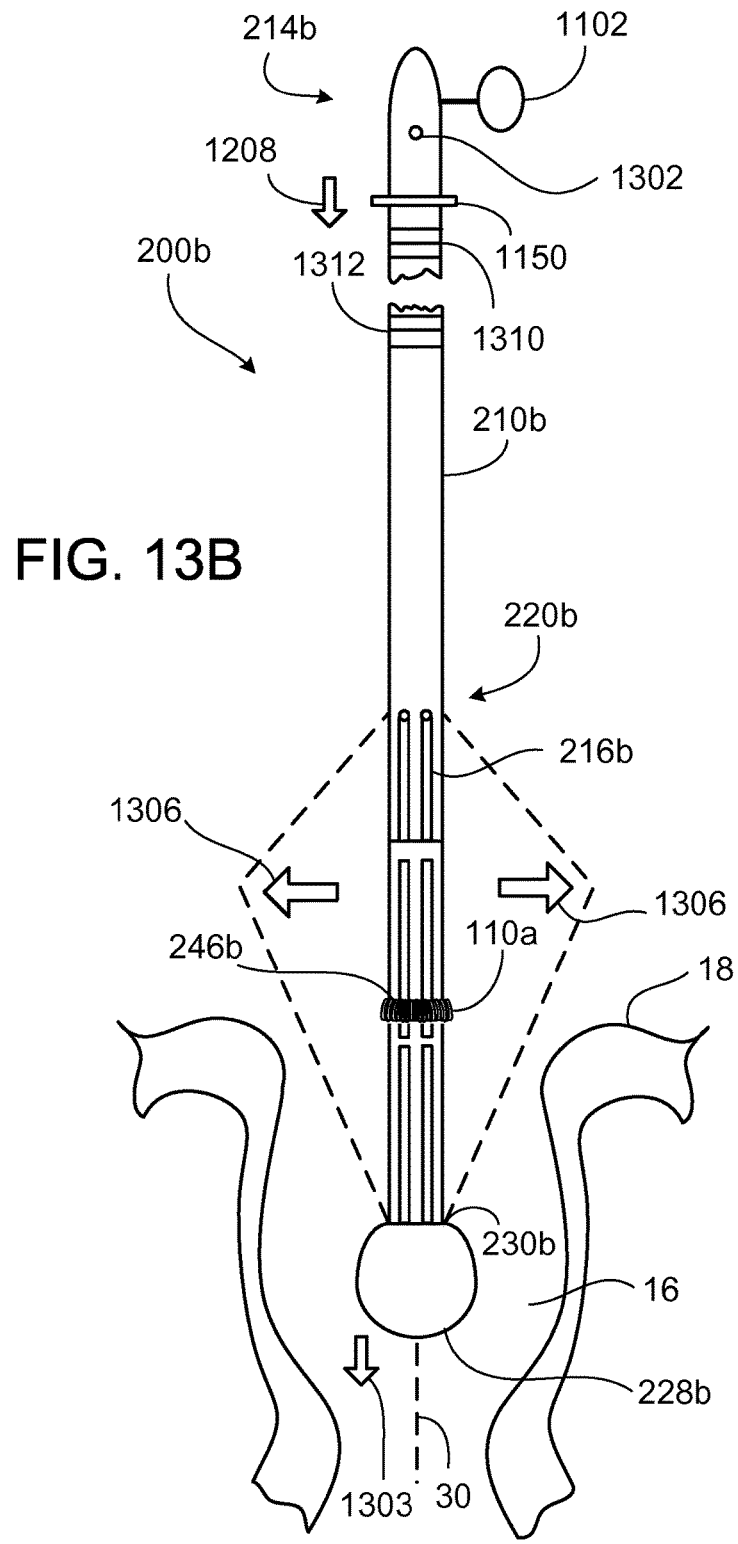
Figure 13C:
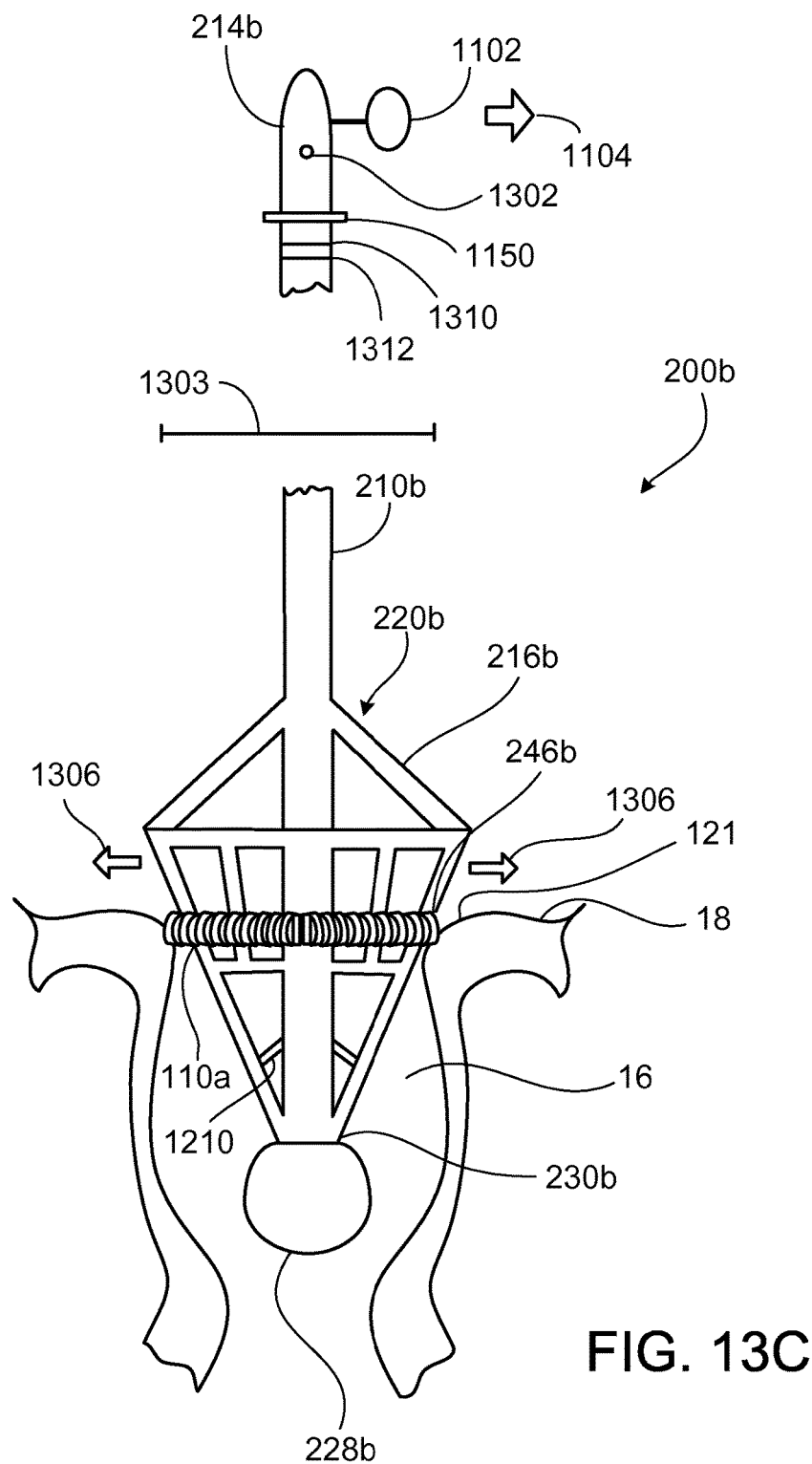

As shown in FIGS. 13A-13D, in the catheterization context, for a burr-hook support or any other kind of support being placed, the catheter may include a balloon 228b at the tip of the delivery tool. The balloon remains deflated as the catheter is passed through the patient's blood vessels into the heart, as in FIG. 13A. When the tip of the catheter reaches the heart, the balloon can be inflated, shown in FIG. 13B. The inflated balloon floats in the blood being pumped through the heart and (along with the delivery tool) is carried easily and to some extent automatically toward and into the valve that is to be repaired. The balloon can continue to move beyond the valve annulus, and, when located as shown in FIG. 13C, supports the distal end of the catheter while the operator supports the proximal end of the catheter. The shaft of the catheter then serves as a "rail" supported at both ends and along which operations involving the delivery tool and the support can be performed with confidence that the rail is being held generally on axis with the valve.

In some of the examples described earlier, the annulus of the heart valve is expanded to the desired shape by pushing a conical surface, such as the basket, along the axis of and into the heart valve. Whether the delivery is done in the context of open heart surgery or in a catheterization lab, or elsewhere, the pushing of the conical surface into the annulus can be supplemented by or replaced by a technique in which the expansion of the annulus is done after the delivery tool is inserted into the valve.

Figure 9Q:
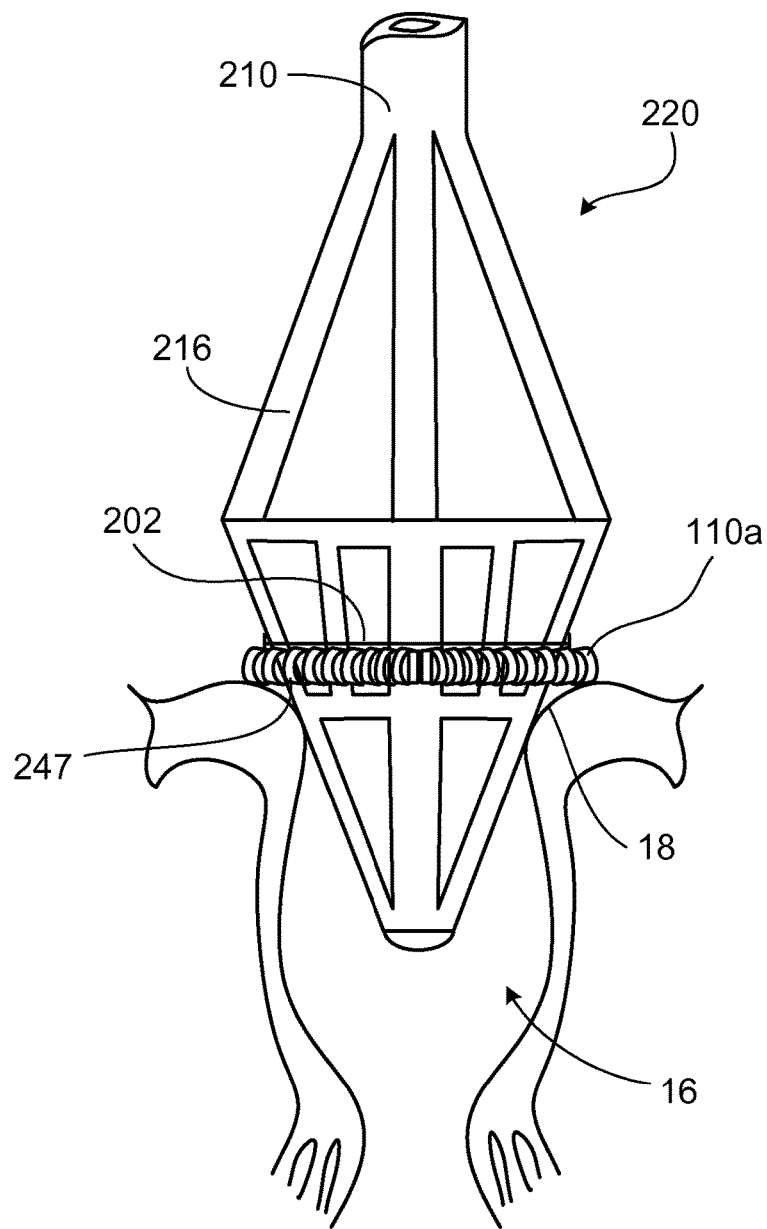
FIG. 9Q is a view of a heart tissue support and a delivery tool where the support body is placed on the delivery head and the coils of the helical spring stretch outward as the body expands to fit on the tool.

FIG. 9A shows one diameter of the support body, the native (long-term configuration) diameter 114. Recall that this diameter is different from the diameter in the delivery configuration. The former diameter 114 is, as shown in FIG. 9Q, smaller than the latter diameter 202 of the delivery tool at the point of support body attachment 247. When the support body is placed on the delivery head 220, the coils of the helical spring stretch outward as the body expands to fit on the tool.

Figure 13D:
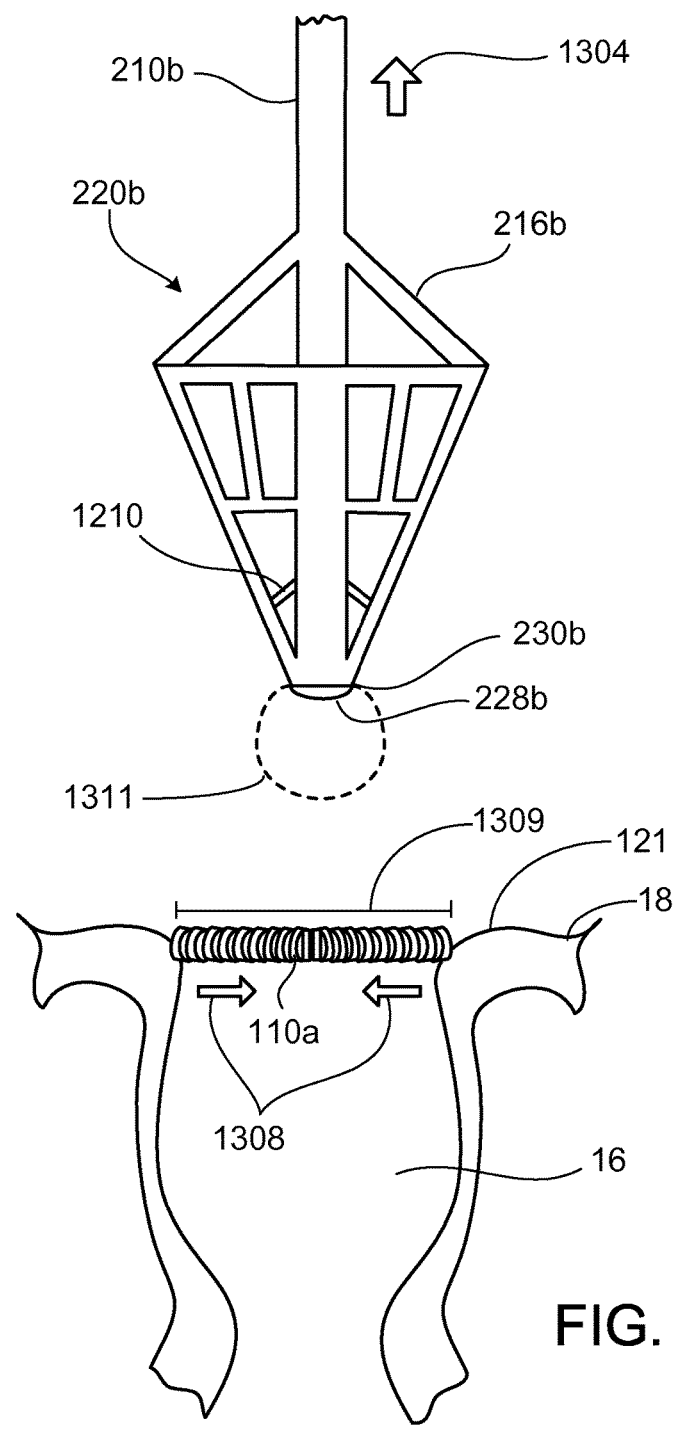

During delivery, shown in FIGS. 13A-13D, when the support body has been attached to the annulus 18, the operator releases the support from the delivery tool. FIG. 13D shows that, in the absence of the outward force previously applied by the delivery tool, the coils of the helical spring contract inwardly 1308 so that the support body returns to a final diameter 1309 of approximately its native diameter. Referring again to FIG. 1H, recall that because the annulus is attached to the support body, the support body will also pull the annulus inward, reforming the annulus to a desired smaller diameter 209.

If the support body is made of a material or alloy that is appropriately plastic, the support body may not fully contract to its original native diameter. However, if the support body is made of a shape memory alloy such as Nitinol, the memory effect of the alloy will tend to cause the support body to contract to a diameter nearly identical or identical to its original diameter.

Figure 9R:
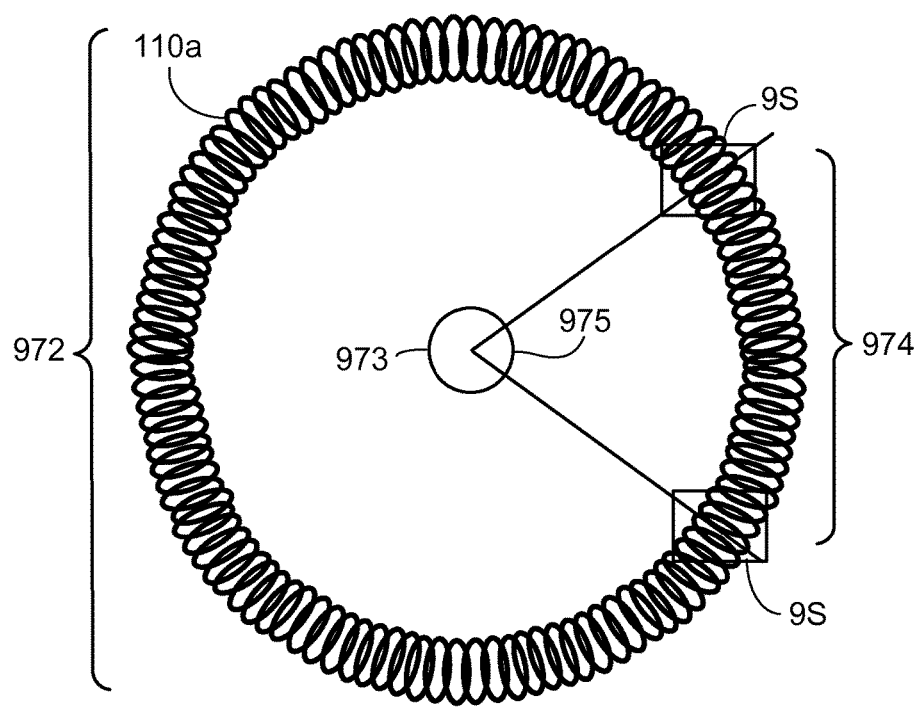
FIG. 9R is a plan view of a heart tissue support having a binding section having burr hooks and a non-binding section having no burr hooks.

As shown in FIG. 9R, the support body 110a may have other portions bearing no burr hooks. As mentioned earlier, sensitive or delicate tissue such as the AV node should not be punctured or bound to hooks. In some examples, the support body 110a can have a binding section 972 having burr hooks and a non-binding section 974 having no burr hooks. A non-binding section 974 of sufficient length to abut the AV node spans an angle 975 between about 40 and 60 degrees of the support body circumference. The binding section 972 will span an angle 973 of the remaining circumference. In some examples, a non-binding section 974 is covered in a sleeve made of a material suited to contact the AV node or other sensitive tissue.

Figure 9S:
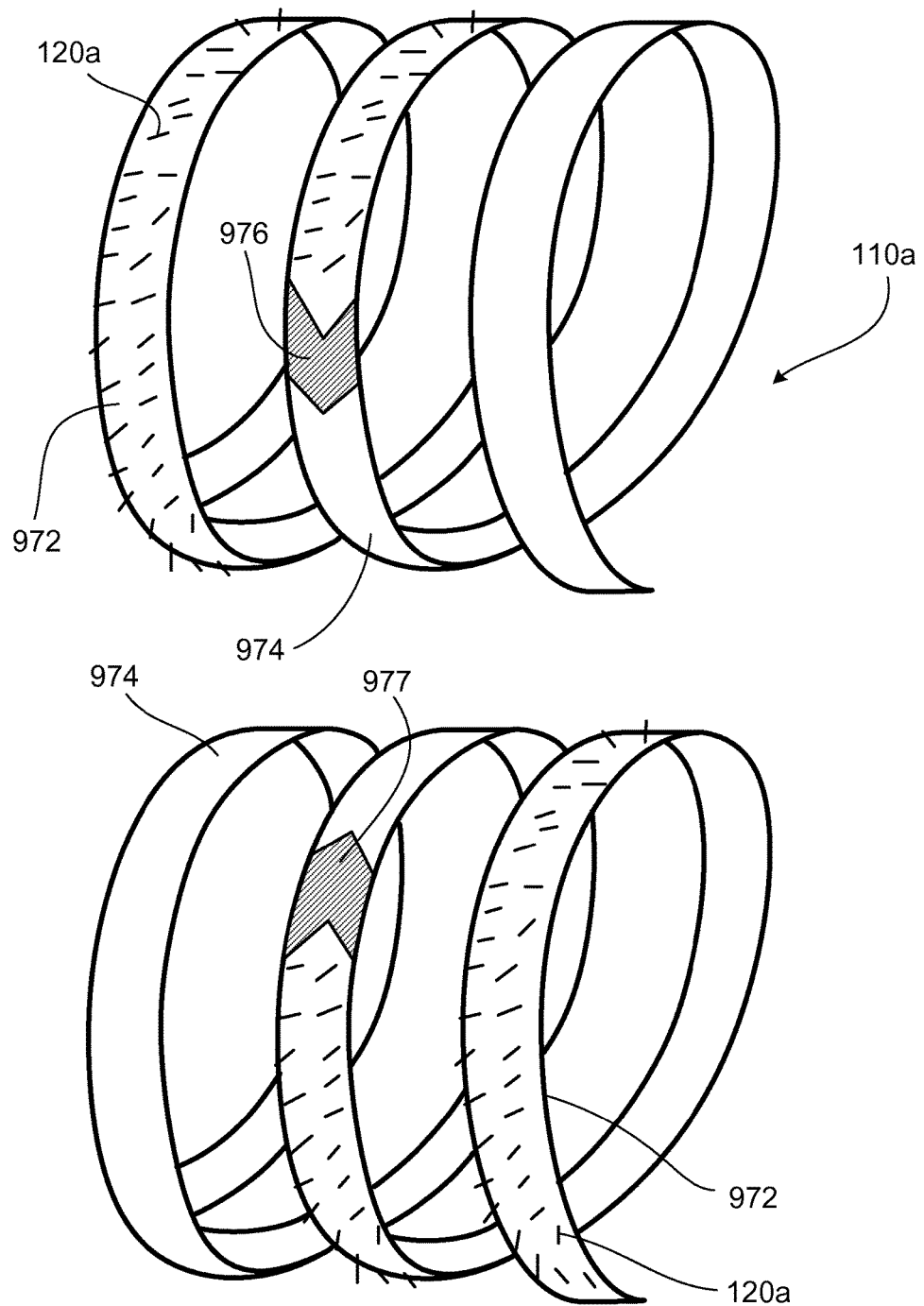
FIG. 9S is a perspective view of a fragment of a heart tissue support having radiopaque markers indicating the borders between a binding section having burr hooks and a non-binding section having no burr hooks.

As shown in FIG. 9S, the two sections 972, 974 can have radiopaque markers 976, 977 indicating the borders between the two sections. The markers 976, 977 are each in the shape of an arrow pointing to the non-binding section. During delivery, an operator can use the radiopaque markers 976, 977 to view the boundary of the non-binding section 974 and position the non-binding section 974 against the AV node or other sensitive tissue.

Figure 9T:
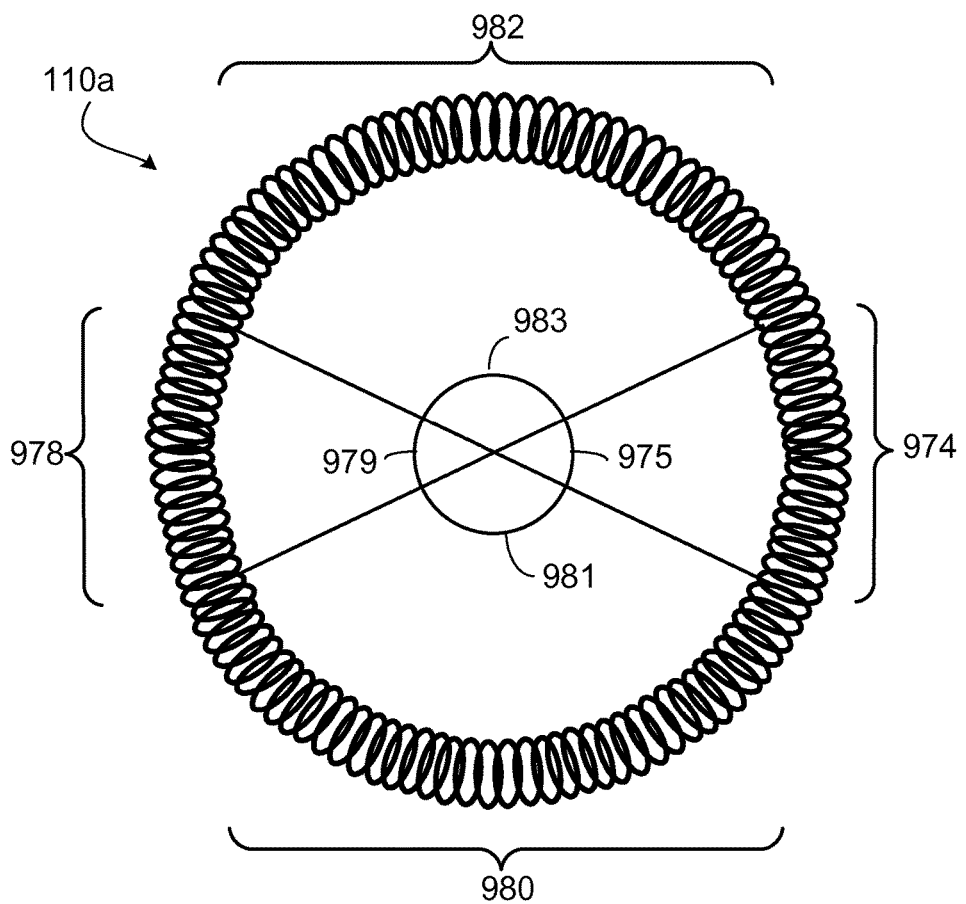
FIG. 9T is a plan view of a heart tissue support that can have multiple sections having no burr hooks.

As shown in FIG. 9T, the support body 110a can have multiple sections 974, 978 having no burr hooks. In some situations, the operator may be limited in the degree to which the delivery head can be rotated. In this example, the operator has multiple options for positioning the support body in order to avoid puncturing the AV node, and the operator would not have to rotate the delivery head more than about 90 degrees in any direction. Two non-binding sections are shown, but the support body can also have three or more of these sections. The non-binding sections 974, 978 span angles 975, 979 between about 40 and 60 degrees of the total circumference. In the example of two non-binding sections, there will also be two binding sections 980, 982 spanning angles 981, 983 of the remaining two lengths of circumference.

Figure 9U:
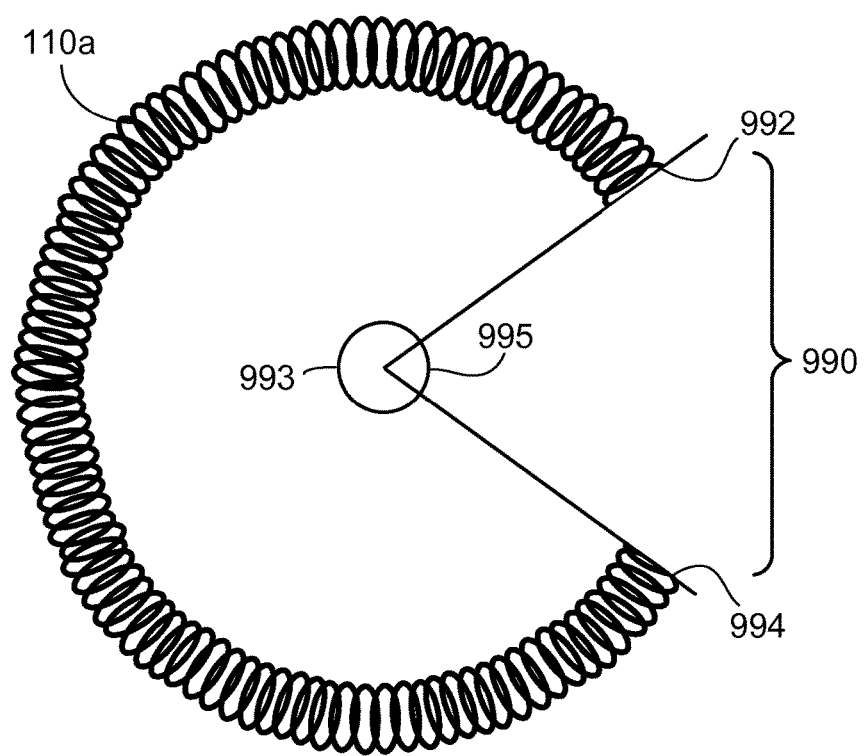
FIG. 9U is a plan view of a heart tissue support that has an open section.

As shown in FIG. 9U, the feature of the support body 110a that should abut the AV node can take the form of an open section 990. As with the non-binding section described above, the open section 990 may span an angle 995 between about 40 and 60 degrees of the circle defined by the support body 110a, while the support body spans the remaining angle 993. The open section 990 can also have radiopaque markers on the open ends 992, 994 of the support body 110a to assist an operator in positioning the open section 990 against the AV node or other sensitive tissue.

Figure 10A:
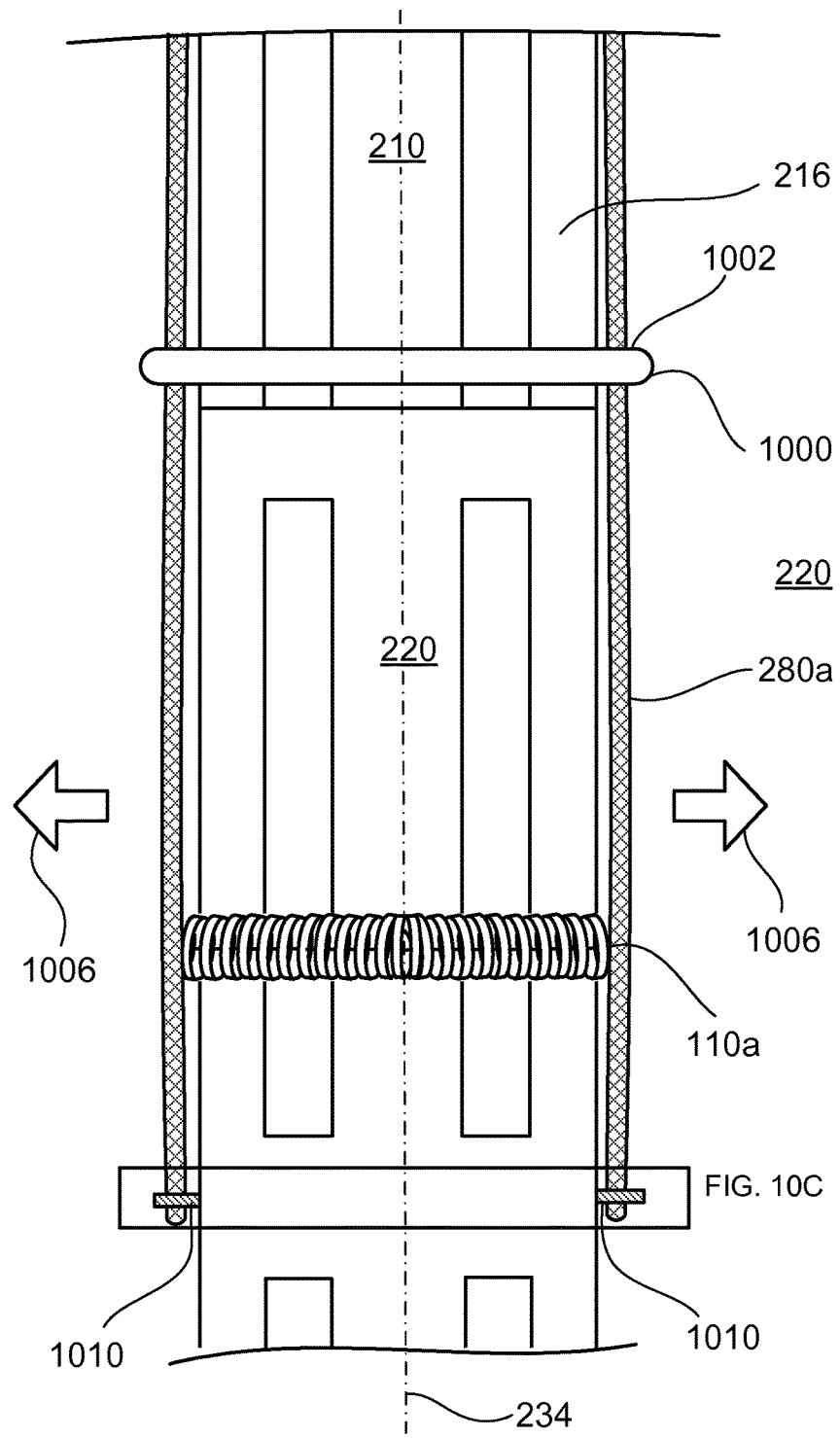
FIGS. 10A and 10B are side views of a delivery tool, and a cross-section of a sheath.
Figure 10B:
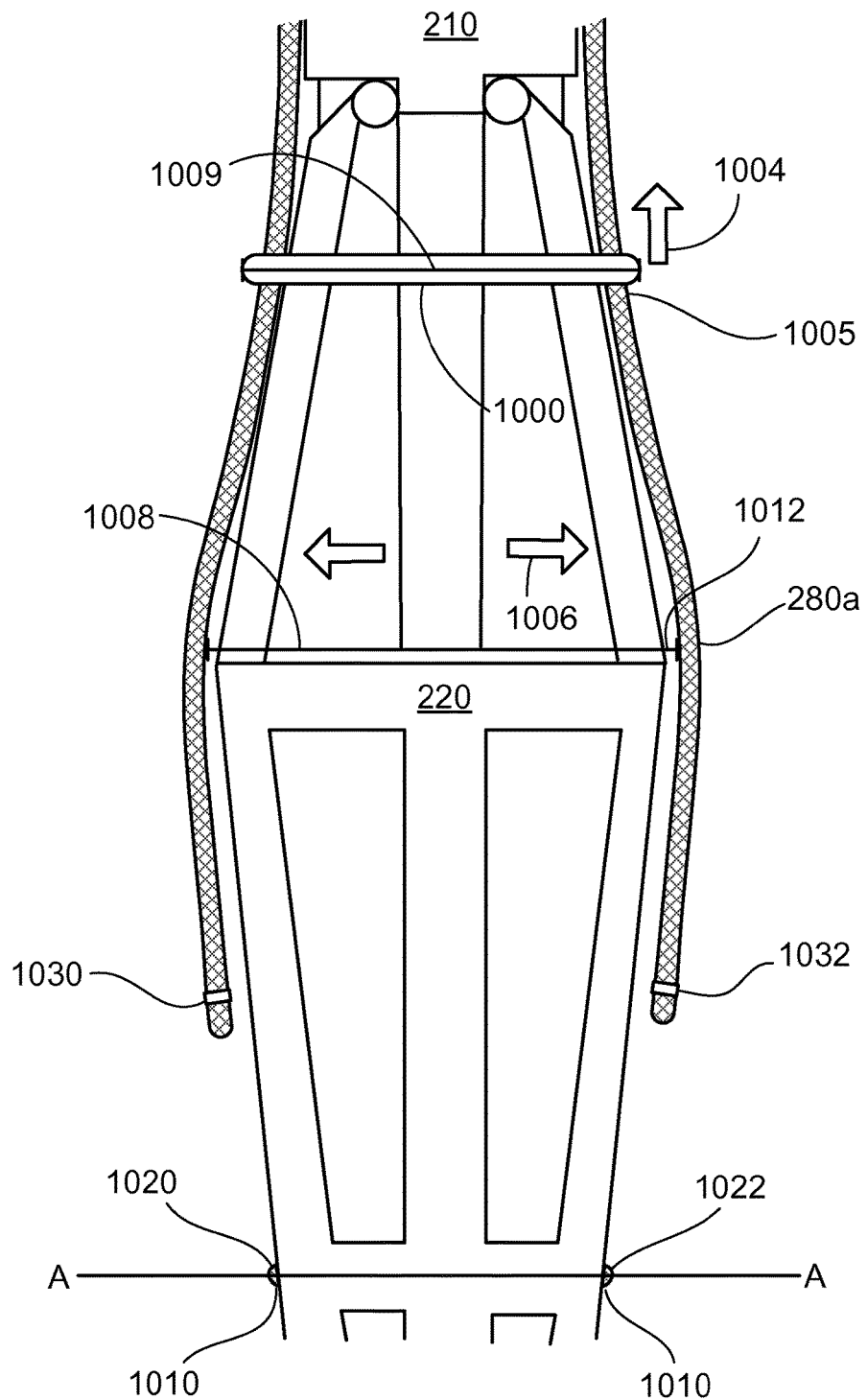
Figure 10C:
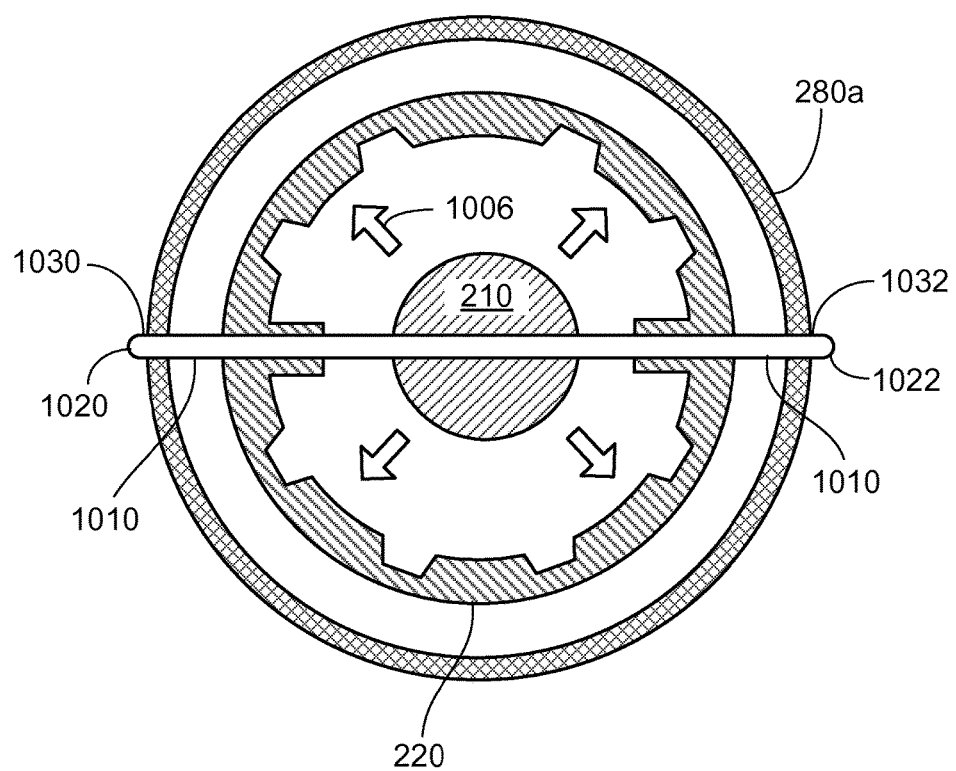
FIGS. 10C and 10D are cross-sectional views of a delivery tool and sheath.
Figure 10D:
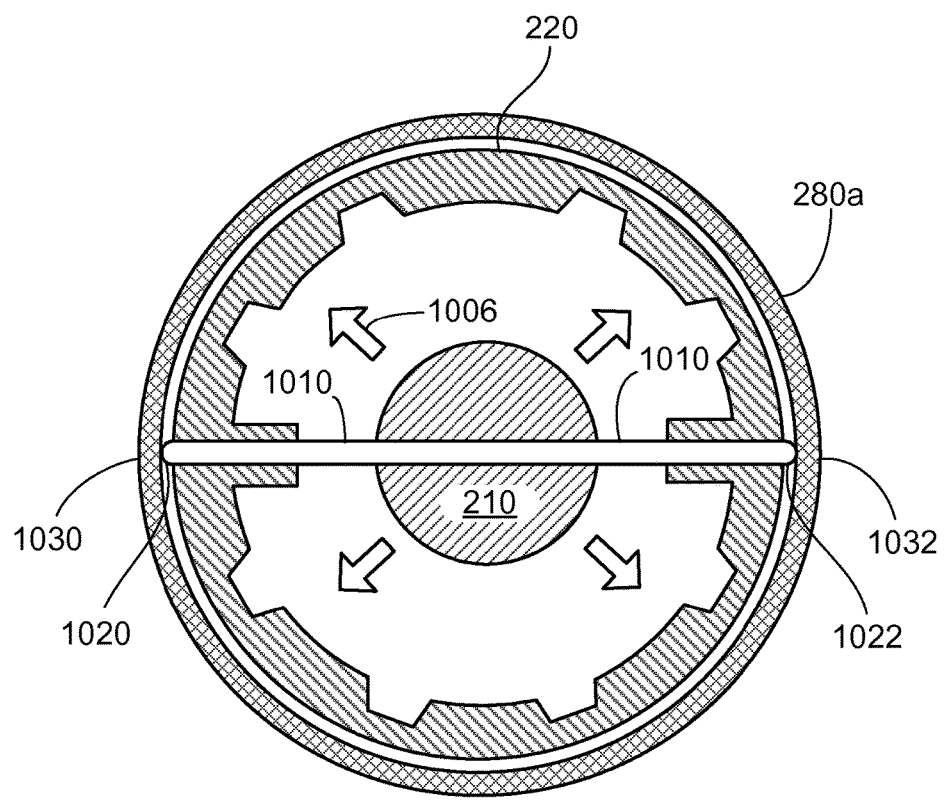

As shown in FIGS. 10A-10D, the delivery head 220 can include a sheath 280a for covering the support body during insertion. FIGS. 10A and 10B show the sheath in a side section, and FIGS. 10C-10D show the sheath as well as the delivery head in a cross-section at A-A in FIG. 10B. The sheath 280a wraps around the delivery head 220, including the support body 110a, so that the burr hooks do not accidentally puncture or attach to any other tissue or devices prior to reaching the annulus. The sheath is made of a flexible material, such as rubber, silicone rubber, latex, or another biologically compatible material or combination of materials. The sheath can also be made of the same material or materials as the catheter. Recall that one implementation of the sheath is shown in FIGS. 6A-6B and described in the corresponding text. Other implementations of the sheath are possible.

For example, the implementation of the sheath 280a shown in side section in FIG. 10A is kept in place by attachment to an elastic retainer ring 1000 and a crossbar 1010 permanently affixed through and extending outward from the catheter shaft 210 perpendicular to the longitudinal axis 234. The retainer ring 1000 is positioned closer to the operator and farther from the distal end than is the support body 110a, and the crossbar 1010 is positioned farther from the operator and closer to the distal end than is the support body. This sheath 280a is permanently attached 1002 to the retainer ring 1000. The sheath 280a is also attached to the crossbar temporarily at holes 1030, 1032 (visible in FIG. 10B) sized to fit the projecting tips 1020, 1022 of the crossbar 1010.

As shown in FIGS. 10B-10D, after insertion of the catheter into the valve and when the delivery head 220 is expanded in preparation for attaching the support body 110a, the combination of the retainer ring and crossbar allows the sheath to automatically detach from the crossbar and retract upward away from the support body as part of the expansion procedure. The process by which this happens is as follows.

Referring to FIG. 10B, when the delivery head expands outward 1006, the diameter 1008 of the delivery head at the original point of retainer ring attachment 1012 increases to a diameter greater than the diameter 1009 of the retainer ring 1000. As a result, the retainer ring rolls upward 1004 from a point 1012 to a point 1005 on the delivery head of smaller diameter. As the retainer ring rolls, it pulls the distal end of the sheath in the same upward direction 1004 along the delivery head 220 and away from the support body 110a.

Part of the sheath 280a wraps around the ring as part of the rolling process; in a sense, the retainer ring is "rolling up" the sheath, in the fashion of a scroll wrapping around a roller. The retainer ring 1000 is rubber or another biologically-compatible material with sufficient elasticity to allow the ring to roll up the expanding delivery head.

When the delivery head 220 expands, the sheath 280a is also released from the crossbar. A cross-section of the delivery head 220 including the crossbar 1010 is shown in FIG. 10C. When the delivery tool is in transit to a heart valve, the delivery head 220 is in the collapsed configuration. The sheath 280a has holes 1030, 1032 configured to allow the crossbar 1010 to pass through, holding the distal end of the sheath to the crossbar. Because the crossbar projects beyond the sheath, the ends 1020, 1022 of the crossbar are rounded and smooth to prevent the crossbar from piercing or tearing any tissue that it contacts before the delivery head reaches its destination. Once the delivery head is positioned near or inside a heart valve and begins expanding outward 1006 from the shaft 210, the delivery head pushes the sheath 280a outward.

During the expansion process, as shown in FIG. 10D, the crossbar remains in place and does not extend outward or change configuration, because the crossbar is permanently and securely attached to the shaft 210. As a result, the delivery head pushes the sheath beyond the tips 1020, 1022 of the crossbar, releasing the sheath from the crossbar. Thus, the sheath can move freely when the retainer ring rolls upward along the delivery head, as described above. The crossbar 1010 may be made of any of the materials used in the delivery tool, or another biologically-compatible material, provided that the crossbar is sufficiently rigid to keep the sheath 280a in place, as described.

Figure 11A:
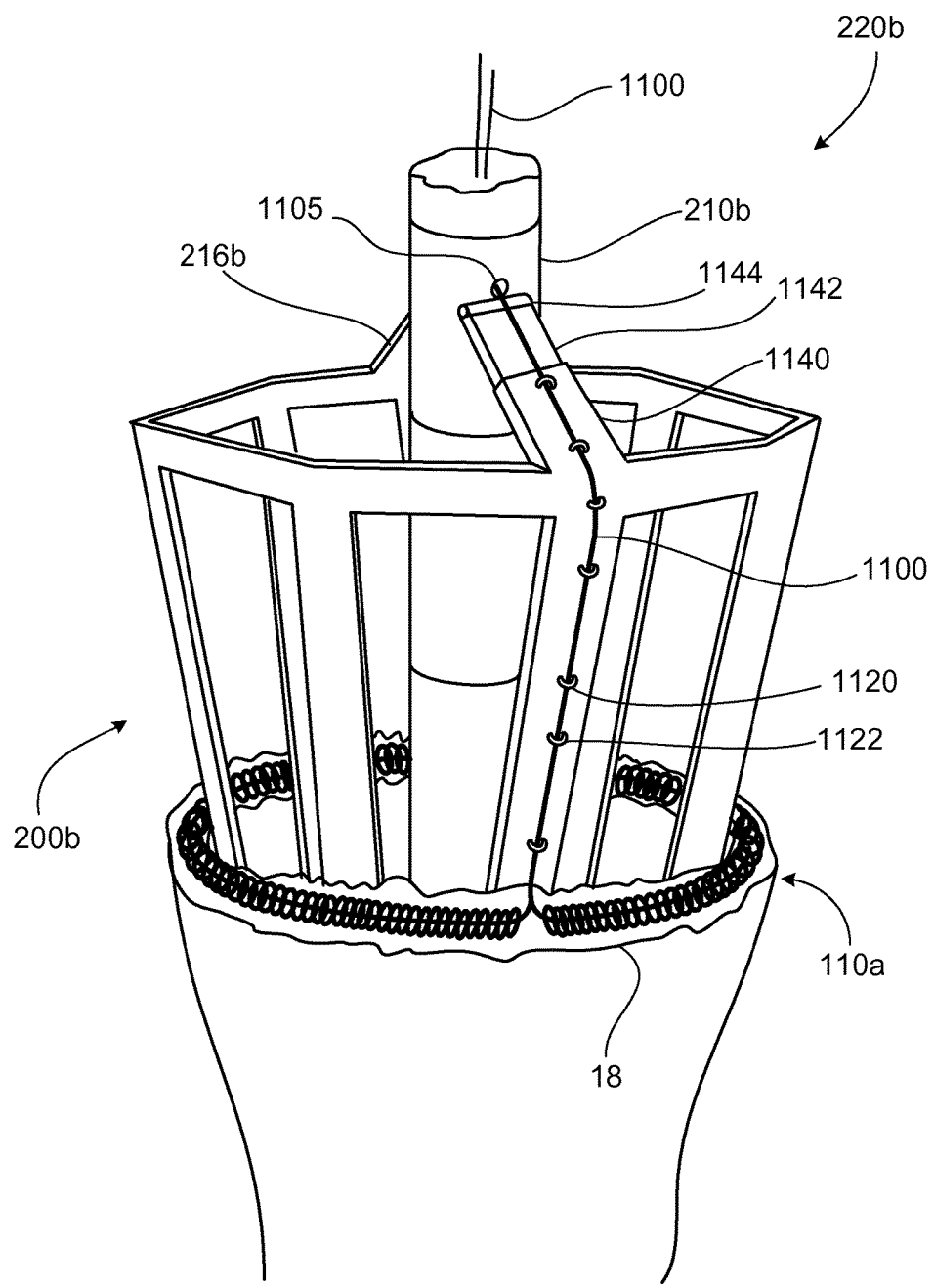
FIG. 11A is a perspective view of a delivery tool in a heart annulus.
Figure 11B:
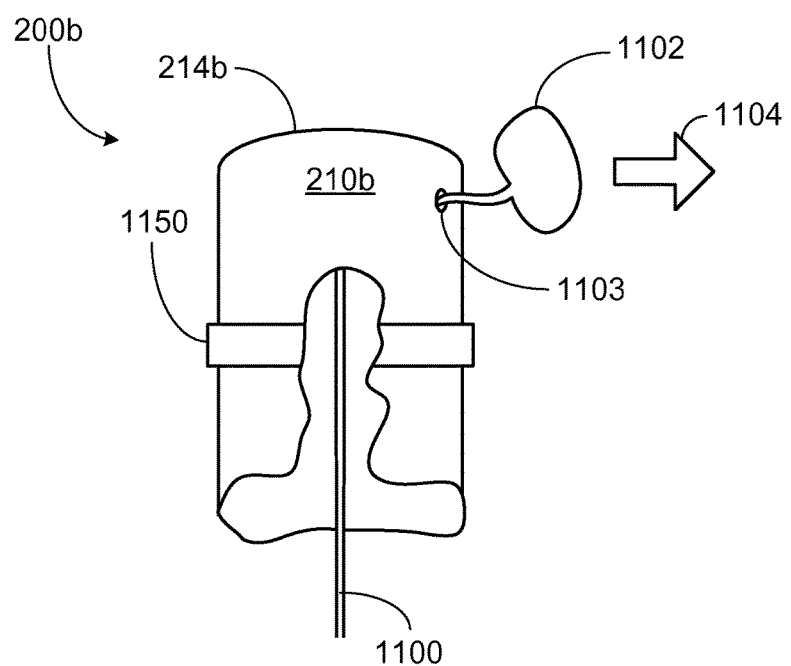
FIG. 11B is a view of the operator end of a delivery tool.

FIG. 11A shows another version of the delivery head 220b. This version differs slightly from the versions of the delivery head already shown. Specifically, in this version 220b, the rigid projections 216b are composed of an outer sleeve 1140 that encloses an inner arm 1142 attached to the shaft 210b by a hinge 1144. When this version of the delivery head expands, the sleeve 1140 extends from the inner portion 1142, and when the delivery head contracts, the sleeve withdraws along the length of the inner arm. This version of the delivery head is used in FIG. 11A to demonstrate the use of a tightening wire 1100, but this tightening wire can be used with other versions of the delivery head as well.

As shown in FIG. 11 B, this tightening wire 1100 is threaded into and back out of a hole 1103 at the operator end 214b of the delivery tool 200b. In doing so, the wire traverses the interior of the shaft 210b of the delivery tool 200b. The ends of the wire exterior to the operator end 214b form a loop 1102 to be manipulated by an operator. This wire 1100 can be used to activate a mechanism to adjust the shape of the support body 110a to a small degree, with the goal of contracting the final diameter 1309, an example of which is shown in FIG. 13B. Referring back to FIG. 11A, at the other end of the delivery tool 200b, the wire exits the shaft 210b at a hole 1105 placed at a point above the delivery head 220b. The wire extends down the side of the delivery head 220b, guided by hoops 1120, 1122. As shown in FIG. 11C, the wire is threaded along the interior of the helical coil 1150, 1152 of the support. At the position 1164 where the wire has completed a circumference of the support body 110a, the wire returns up the side of the delivery head and back into the shaft.

Figure 11C:
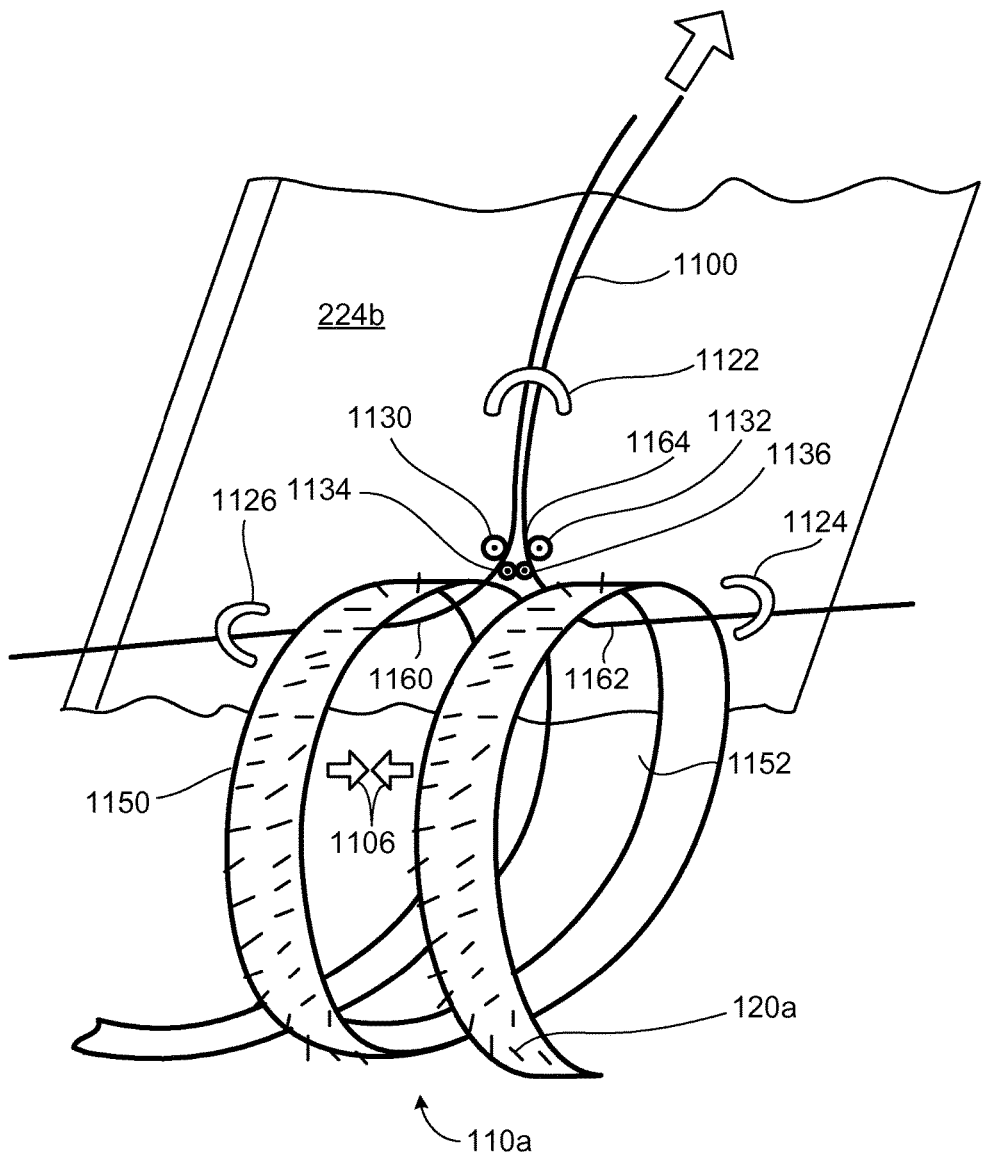
FIG. 11C is a close-up view of a heart tissue support attached to a delivery tool.

FIG. 11C also shows hoops 1124, 1126 that are placed on the struts 224b of the delivery head at regular intervals to keep the wire properly positioned. At the position 1164 where the wire meets itself and returns up the side of the delivery head, spools 1130, 1132, 1134, 1136 attached to the strut 224b guide the wire and prevent the wire from scraping against 1160, 1162 the helical loops 1150, 1152 at the wire exit region. The end of the wire that re-enters the hole 1105 (FIG. 11A) continues back up the shaft alongside itself, and exits the delivery tool (FIG. 11B) to form the loop 1102 by connecting with the other end.

When the support body 110a is firmly seated at the heart valve annulus 18 (for example, in the scenario shown in FIG. 13C), an operator can pull 1104 the loop 1102 (FIG. 11B) to reduce the final diameter of the support. When pulled, the wire tightens; as shown in FIG. 11C, this brings 1106 the coils 1150, 1152 of the support closer together.

Figure 11D:
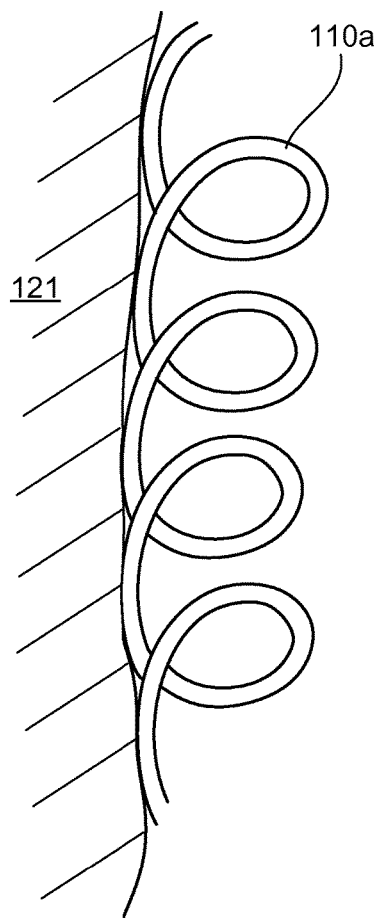
FIGS. 11D and 11E are close-up views of a portion of a heart tissue support attached to annular tissue.
Figure 11E:
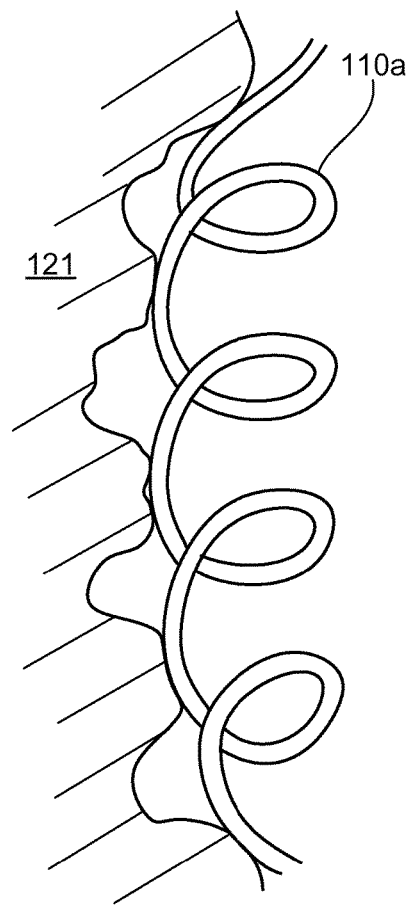

The adjusted circumference becomes permanent as the burr hooks of the support embed themselves in the annular tissue. Although some burr hooks will already have been embedded, the tightening procedure will pull out some of those burr hooks and embed other burr hooks in the tissue. This "bunches" annular tissue closer together. FIG. 11D shows an example of a portion of the support body 110a attached to the periphery 121 of an annulus before the support body is tightened. As shown in FIG. 11E, after tightening, the support body 110a pulls the tissue at the periphery 121 closer together. The final diameter of the annulus will be slightly smaller due to this bunching effect. Once the delivery head is removed, the support body, and thus the attached annulus, will contract to the desired size.

Figure 11F:
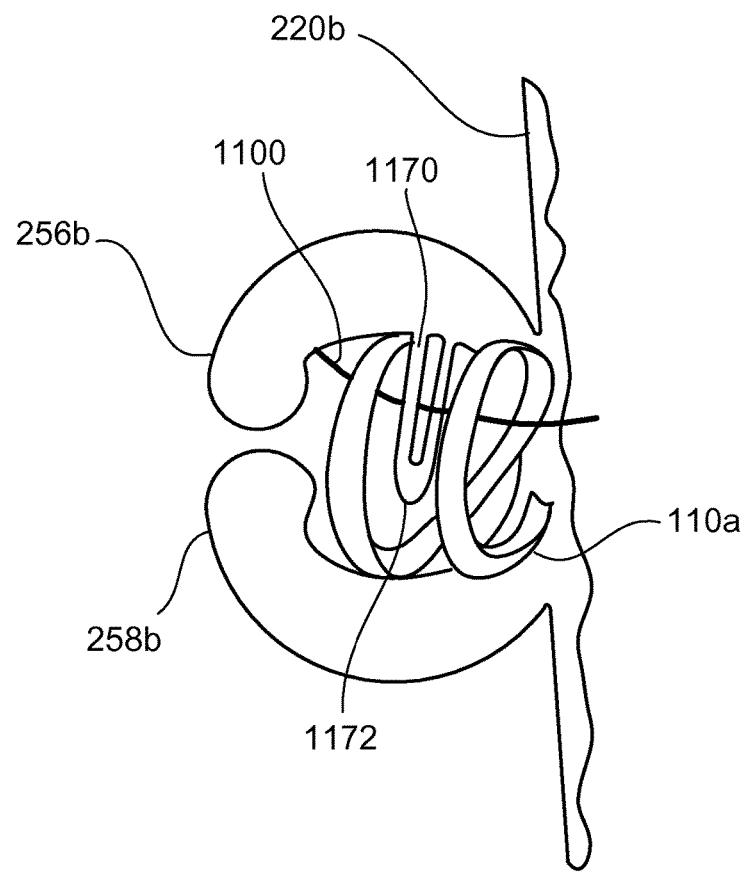
FIG. 11F is a close-up view of a heart tissue support and a delivery tool where the delivery head has a blade attached to one of the two rigid fingers that keep the support body in place.

Referring to FIG. 11F, to detach the wire from the support body 110a, the delivery head 220b has a blade 1170 attached to one of the two rigid fingers 256b, 258b that keep the support body in place. When the rigid finger 256b pulls away from the support body 110a after the support body is in place, the cutting segment 1172 of the blade structure severs the wire. The operator may pull the external loop after the wire has been severed to keep the stray ends of the wire from moving freely outside of the delivery tool when the tool is being removed from the annulus.

Figure 12A:
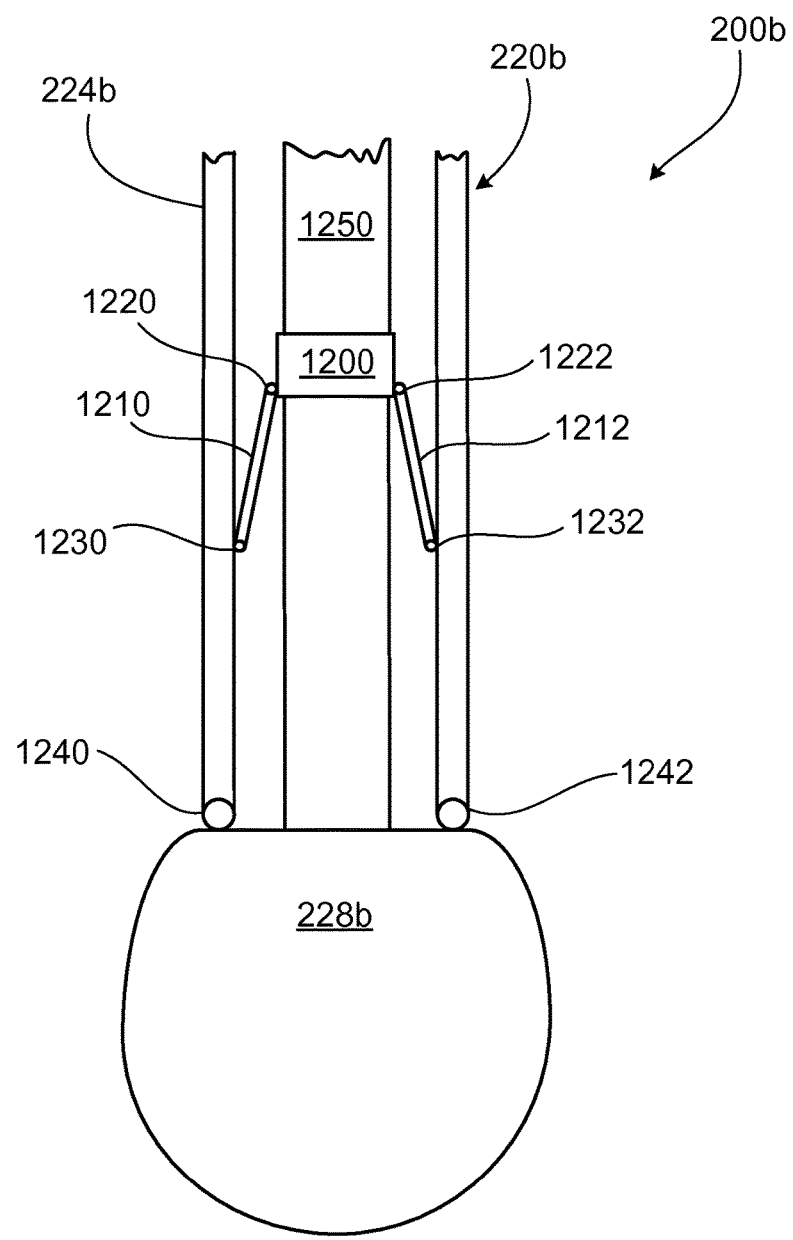
FIGS. 12A and 12B are views of a core of a delivery tool.
Figure 12B:
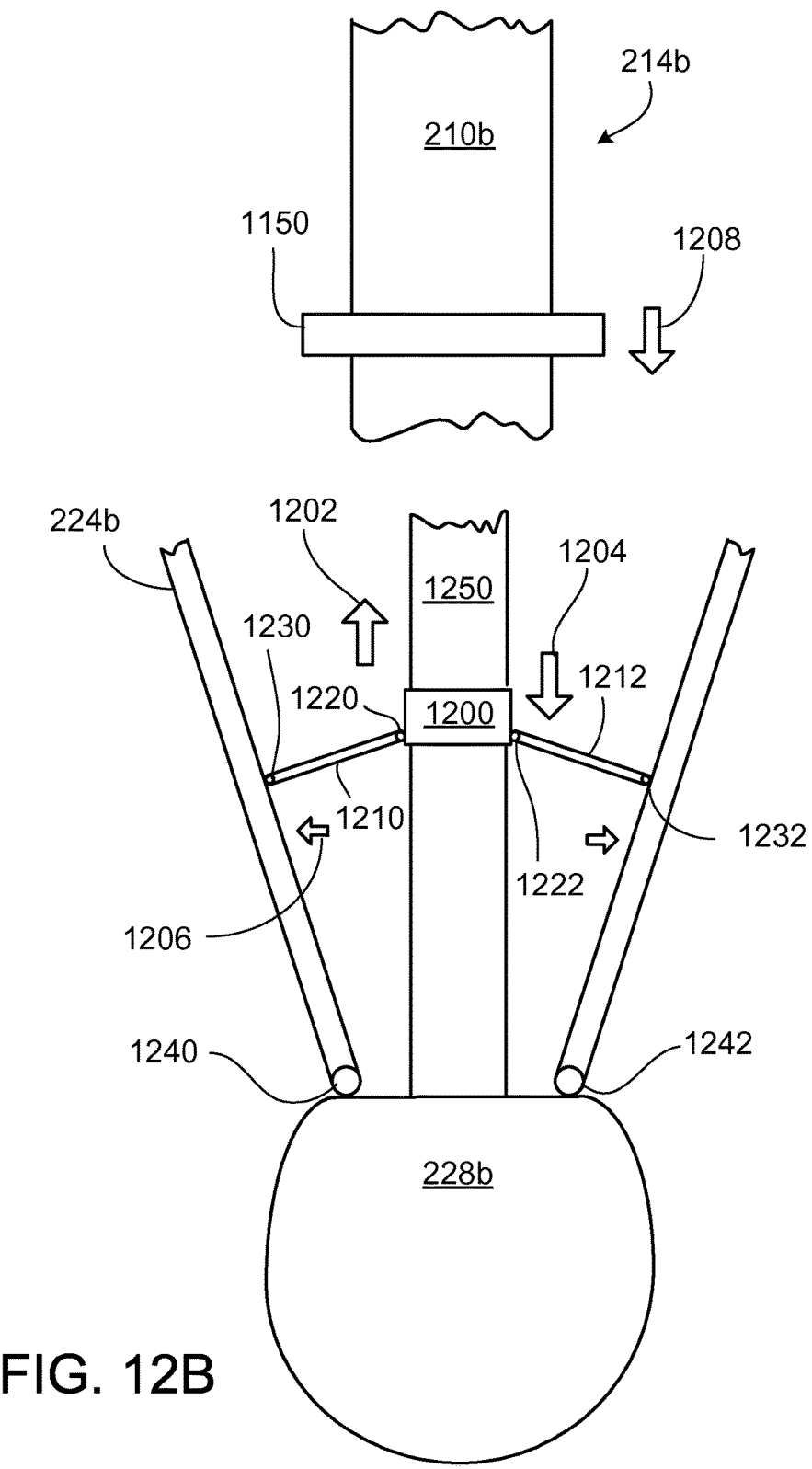
Figure 12C:
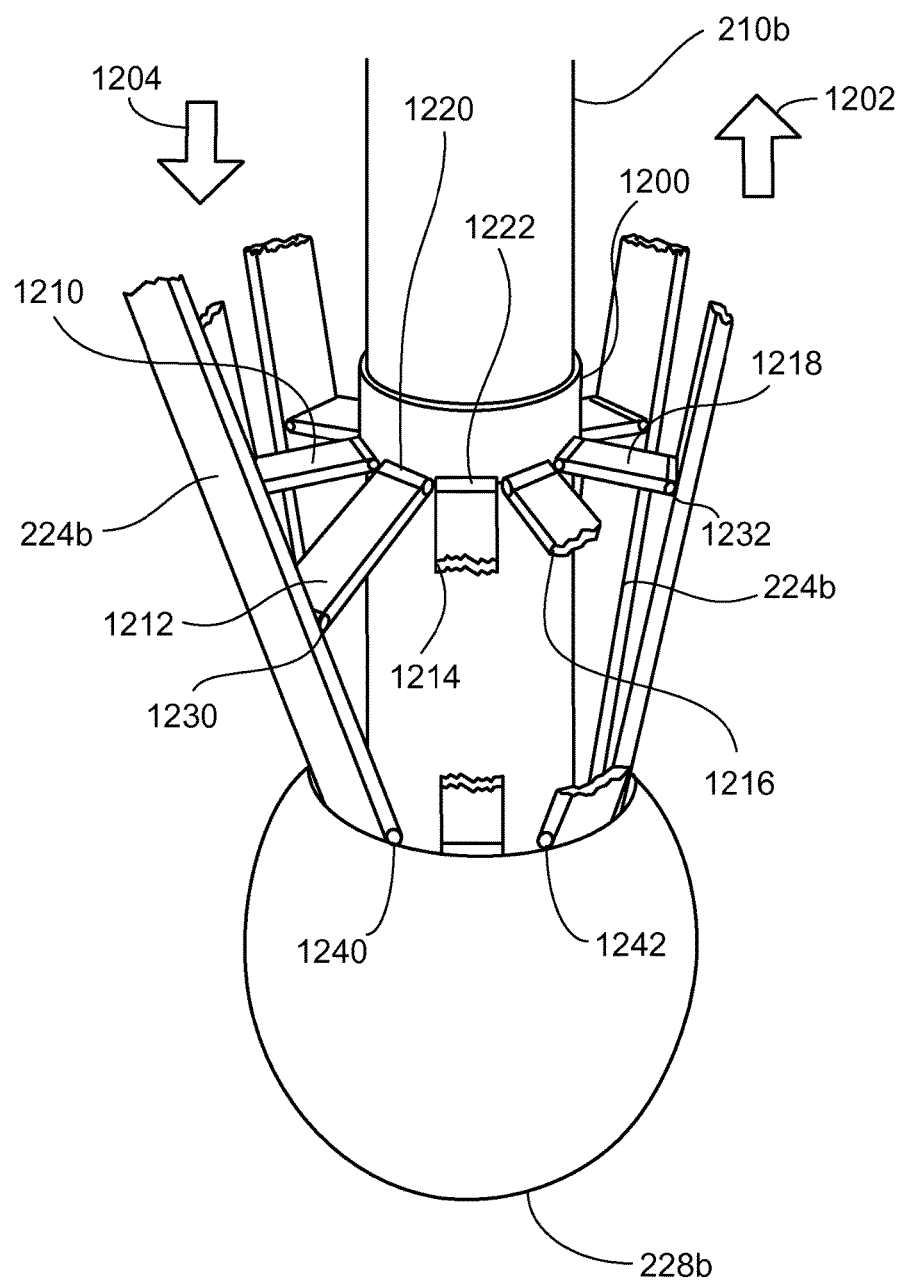
FIG. 12C is a perspective view of a core of a delivery tool.

As shown in FIGS. 12A through 12C, a delivery tool 200b for use in (but not only in) a catheterization context shares elements in common with the delivery tools discussed earlier, including the shaft 210b, collapsible conical head end basket 220b, set of struts 224b, and operator end 214b. This delivery tool 200b allows the operator to expand or contract the collapsible conical head-end basket 220b radially from a collapsed (closed) configuration (shown in FIG. 12A) to an expanded (open) configuration (shown in FIG. 12B), much in the way that an umbrella can be opened. For this purpose the basket can include a set of spars 1210, 1212, 1214, 1216, 1218 arranged about the axis, as shown in FIG. 12C. Referring back to FIG. 12B, each spar has one hinged end 1220, 1222 connected to a central collar 1200 that can ride up 1202 and down 1204 along a central shaft 1250 of the basket. Its other hinged end 1230, 1232 is connected to the hinged 1240, 1242 struts 224b of the basket in such a way that when the opening and closing mechanism is manipulated 1208 by the user to cause the collar 1200 to move back and forth along the shaft 1250, the spars 1210, 1220 force 1206 the basket open or closed, akin to the mechanism of an umbrella. The operator end 214b of the delivery tool has a twist or slide control 1150 that enables the operator to control the collar. In FIG. 12B, the control is a slide control, and can be slid downward, for example. In this way, the annulus can be expanded to the desired shape by radial forces 1206 that are not imposed by moving the entire basket linearly along the valve axis. Instead the basket is moved into the desired position linearly along the valve axis and then the annulus is expanded to its desired shape. The radial forces could also be imposed by a combination or sequence of moving the entire basket axially and expanding the basket laterally.

As shown in FIG. 13A, radiopaque measurement marks 1310, 1312 can be placed on the shaft or basket at regular spacings according to a standard measurement unit (e.g., one mark per centimeter). The marks can be used to determine the distance that the delivery tool has traversed inside the heart and the location of the basket as it is inserted into the valve, allowing the operator to place the basket at a good position along the axis of the valve.

The placement of the support from the basket onto the annulus can be done either as part of the operation of opening the basket or following the opening of the basket. In the former case, illustrated in FIGS. 13A through 13D, the basket would be inserted into the valve to a point where the basket is adjacent to the valve annulus. Simultaneously with the opening of the basket, burr hooks on the outer periphery of the support would be forced radially into the annulus tissue. In this method of placing the support, the porous sleeve described earlier and shown in FIG. 9P would be positioned on the inner periphery 965, away from the embedded hooks.

In the other approach, akin to the process shown in FIGS. 1A through 1 D, the basket would be inserted into the valve so that the support on the basket was positioned slightly upstream of the location of the annulus. The basket would then be opened to force the annulus into the desired shape, then the tool and basket would be pushed slightly to force the support into place, embedding the hooks.

In either approach, once the support is placed, the basket would be at least partially closed, releasing the basket from the support, and the tool would be withdrawn from the valve.

Further, in some implementations, a combination of the approaches could be used. For example, the basket could be partially opened, inserted into the annulus, and then fully opened.

The approach of FIGS. 13A through 13D follows these steps:

A. Position 1301 (FIG. 13A) the collapsed (closed) conical head-end basket 220b of the delivery tool 200b at the medial axis 30 of the valve with the support adjacent the annulus. (The tool and basket are shown in side view and the valve and annulus are shown in sectional side view.)

B. Press a button 1302 on the operator end 214b to inflate a balloon 228b (FIG. 13B) on the distal end 230b of the delivery tool, allowing the delivery head 220b to float into the correct position in the heart valve 16. If necessary, rotate the delivery head to align any section of the support body not bearing burr hooks, or any gap in the support body, or any portion that is sheathed, with any section of the annulus abutting delicate or sensitive tissue.

C. Slide 1208 or twist the control 1150 to expand 1306 the basket bringing the support body 110a into contact with the distorted annulus 18. The support bears burr hooks that embed themselves in valve tissue at the periphery 121 of the annulus 18 upon contact, thus attaching the support to the tissue (FIG. 13C).

D. When the basket 220b has reached a desired diameter 1303, the expanded heart valve support 110a forces the annulus 18 to conform to a desired configuration (e.g., a circle) and to a size that is larger (e.g., in diameter) than a desired final diameter of the annulus. Optionally, pull 1104 the wire loop 1102 to tighten the coils of the support body 110a to achieve a smaller final diameter.

E. When the heart valve support is in its final position, to break the tool away from the support attachments 246*b*, pull 1304 (FIG. 13D), allowing the support to contract 1308 to its final size (including final diameter 1309) and shape and leaving the support permanently in place to maintain the annulus in the desired final configuration and size. Deflate 1311 the balloon 228*b* by pressing the button on the operator end.

In some implementations, as shown in FIGS. 14A through 14D, the support is constructed from several pieces including an elastic multiple-loop circular coil 302 of strip material 304. The coil is encased in a tubular toroidal sheath 306. A large number of burrs or hooks 308 (the number could be, for example, between 20 and 60, but could also be much larger in number, even orders of magnitude larger, or in some cases smaller) are mounted at regular small intervals 310 around the circumference of the toroidal sheath.

In some implementations, the multiple-loop circular coil is made of Nitinol strip, approximately ⅛ inch wide and approximately 10/1000-15/1000 inch thick. During fabrication, the Nitinol strip is shape set into a coil with final desired implant diameter. For purposes of insertion, the Nitinol coil would be expanded, as explained later. During expansion the ends 312, 314 of the strap would move circumferentially around the coil (in the directions indicated by arrows 316 and 318) to accommodate the increase in diameter of the ring. In FIGS. 14A through 14D, the ring is shown in its native, unstressed diameter corresponding to the final desired implant diameter. The numbers of loops can be varied depending on the material used, the thickness, and other considerations. In some implementations the number of loops can be 3.5, or 5 or 8, or other numbers ranging from 1 to 10 or more.

In some implementations, other materials and combinations of them can be used to form the resilient coil. These could include, for example, plastics, metals, and coils of these and other materials.

Figure 14A:
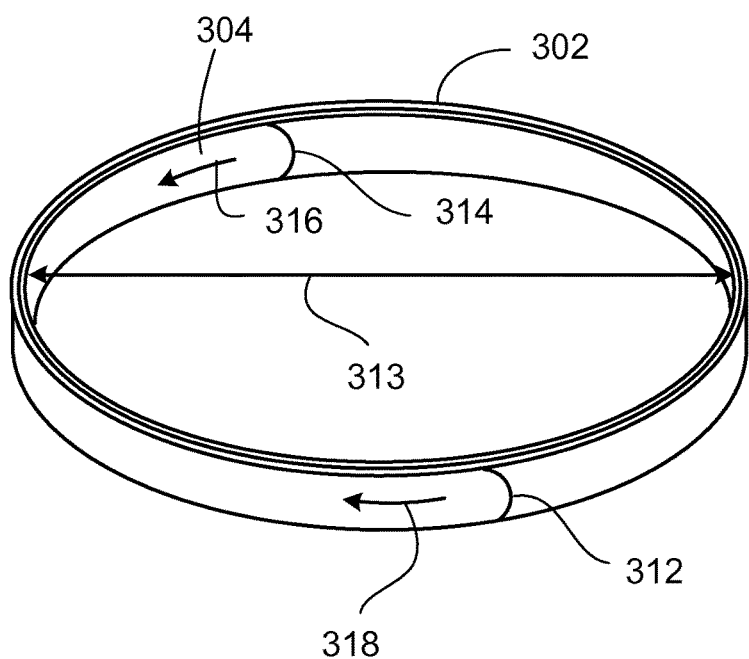
FIGS. 14A through 14D are perspective views of portions of supports, where the support is constructed from several pieces including an elastic multiple-loop circular coil of strip material.
Figure 14B:
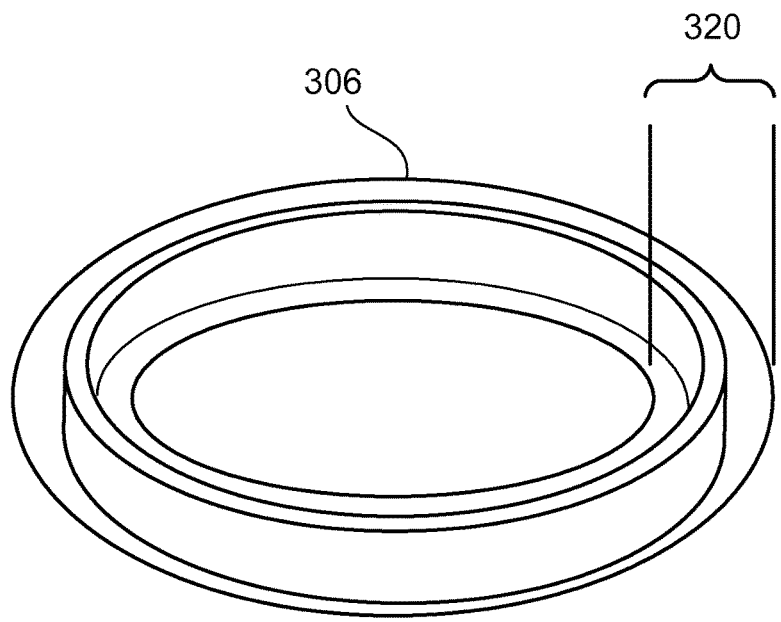
Figure 14C:
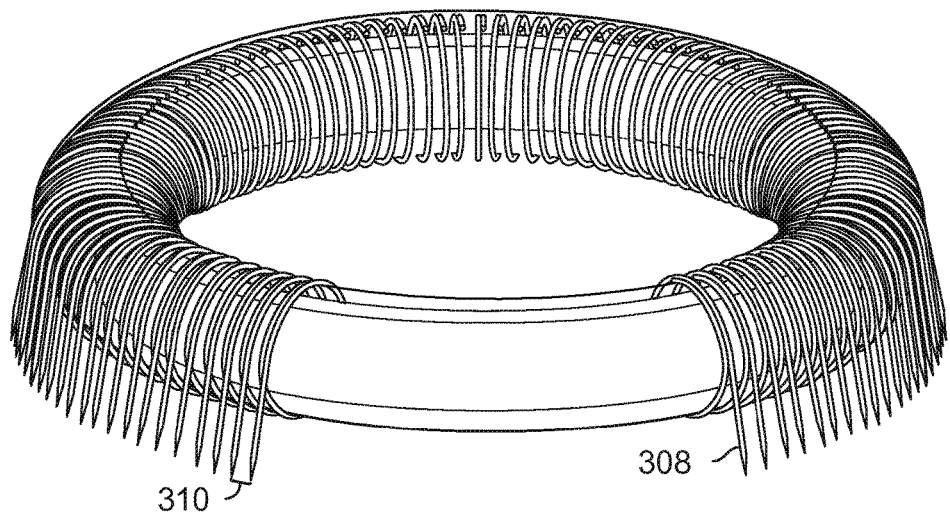

In some implementations, the overall shape of the coil could be different from the one shown in FIG. 14A, including non-circular and non-planar shapes.

The coil (or other resilient core ring) needs to have enough strength and durability to be expandable to fit on the delivery tool, to be forced onto the heart valve annulus, to contract to pull the annulus back into the desired shape, to tolerate the force incurred when the insertion tool is disconnected, and to form a long-lasting and strong support for the annulus. It also needs to have enough resiliency to be able to contract the support and the annulus to which it is attached to the desired shape and size after insertion and to retain the support in essentially that shape and size against forces in the heart that may act against the support.

In some implementations, if there is a chance of exposure of the materials of which the coil is made to the blood or tissue of a patient, biocompatible materials are used.

The coil is held within the sheath 306 in a way that permits the coil to slide within the inner lumen of the sheath, especially as the coil is expanding for insertion and contracting after insertion. The sheath has an elasticity that allows it to move radially with the coil during expansion and contraction. Because the burrs or hooks (we sometimes refer to burrs and hooks and a wide variety of other gripping devices as grippers) are mounted on the sheath, and not on the coil, the expansion and contraction of the coil can occur without disruption of the angular locations of the grippers relative to the central axis of the support.

In some implementations, the sheath can be formed of a simple tube. To embed the coil in such a tube the coil can be unwound and wrapped through the tube repeatedly until all turns of the coil have been embedded. Once the coil is completely embedded, in the tube, one end of the tube can be pulled over and glued to the other end to finish the assembly.

In some implementations, the sheath can be formed of a specially molded piece that has the toroidal shape formed during molding and includes a way to secure the two ends together.

In some implementations, the sheath is meant to be sealed to prevent fluids from passing into the chamber that contains the coil. In some cases, the sheath is not sealed and fluid can pass freely. In some implementations, a fluid is used to fill the space within the sheath to provide lubrication for the sliding of the coil within the sheath and to displace air which could cause problems when the support is used inside the heart. The fluid could be blood or saline solution, for example.

The sheath must be strong enough to enclose the coil without breaking even when the support is expanded and contracted prior to, during, and after placement in the valve. As the diameter of the support is expanded and contracted, the cross-sectional diameter will also tend to change, and the amount of that change must not be so great as to disrupt the attachment of the grippers to the valve tissue, to constrain the sliding of the coil within the sheath, or to allow the grippers to become dislodged or disoriented relative to the sheath, among other things. The sheath can be resilient so that when the support is contracted after being expanded, the sheath contracts along with the coil.

A wide variety of materials can be used for the sheath, including silicone, plastics, and fabrics, for example. Combinations of materials can also be used.

Figure 14D:
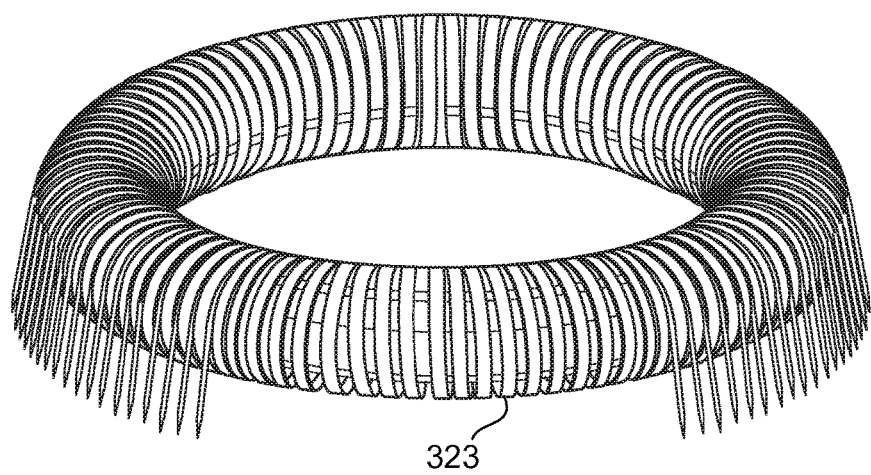

As shown in FIG. 14D, an outer surface 322 of the sheath can bear grooves 323 that accommodate (and hold in place) portions of the grippers, as explained below. In some implementations, the grooves can be parallel and lie at equal small intervals around the perimeter of the sheath.

The cross-sectional diameter of the sheath can be large enough so that the inner lumen accommodates the coil and allows it to slide, and the outer surface supports the grippers, and small enough that the support does not obstruct adequate flow of blood through the heart valve after installation.

Figure 15:
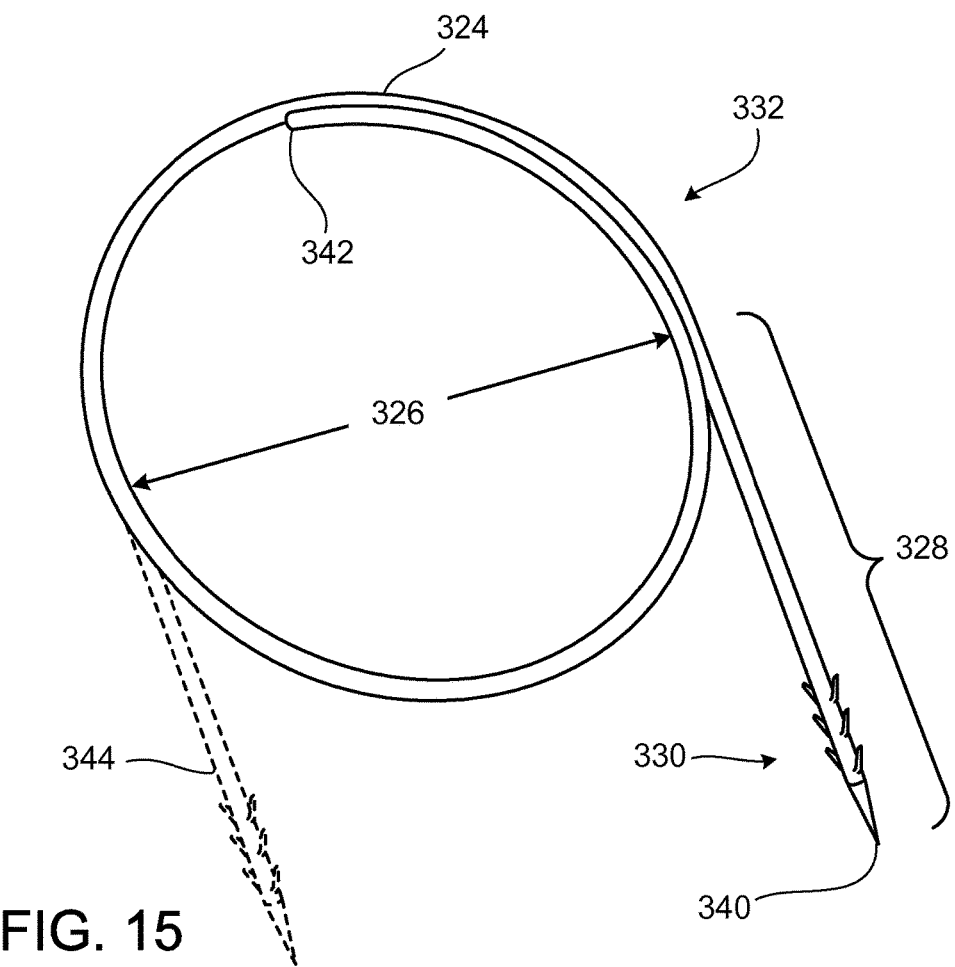
FIG. 15 is a perspective view of an anchor with grippers formed on a length of wire that includes a closed ring.

As shown in FIG. 15, in some implementations, each of the grippers can be formed on a length of wire that includes a closed ring 324 that has about the same diameter 326 as (or slightly smaller than) the diameter of the cross section of the sheath. A straight section 328 extends from the ring and has the gripper 330 formed on its free end.

We sometimes refer to the entire piece that includes the gripper, and a portion to attach the gripper to the support, as an anchor 332.

In some implementations, the anchor is prefabricated with the ring in its final shape and the gripper projecting from the ring. In some examples, the anchor is formed of stainless steel or another biocompatible material.

A wide variety of materials and combinations of them can be used to fabricate each of the anchors or groups of them, including metals and plastics. The cross-sectional shape of the anchors can vary and be, for example, round, oval, flat, or bent, or a variety of other shapes.

In some implementations, the anchors can be made from tiny fishhooks with the hook end serving as the gripper and the other end being bent to fit onto the support.

The thinner the anchors in the direction along the circumference of the sheath, the more anchors that can be fit onto the support. In some implementations, a larger number of thinner anchors would be useful in making the support easy to install and effective. In some cases, the arrangement of the anchors along the sheath can be other than regular and closely spaced. The spacing can be varied along the sheath or the number of anchors can be varied along the sheath, for example.

To install an anchor, its ring portion can be pulled open and slipped over the sheath, then released. In examples in which the outer surface of the sheath is molded to have grooves, the ring portions of the anchors can be seated in the grooves.

In some examples, the anchors can all be mounted to cause their grippers to point at a common angle 336 from a central axis 338 of the support as shown in FIG. 14D (in which some of the anchors have not yet been mounted). In some examples, the grippers can be pointed at different angles relative to the central axis.

In some examples, the anchors can be mounted in such a way that they do not tend to slip or rotate around the outer surface of the sheath, but rather maintain their installed orientations. In some implementations, when the supported is expanded and contracted prior to, during, and following insertion into the heart valve, the stretching and relaxing of the sheath may cause a change in its cross-sectional diameter and therefore an opening and closing of the rings and a corresponding reorientation of the angles of attack of the points of the grippers. This effect can be useful in installing and providing secure attachment of the grippers in the valve tissue.

In some cases, if the angle of attack of the points is shared in common by all of the grippers, then it may not be desirable to have the successive anchors along the perimeter be spaced too closely 310 because the adjacent gripper points could interfere with each other during insertion, and be less effective in gripping the valve tissue. For this reason, in some implementations, the angles of attack of the points of the grippers can be varied slightly from anchor to anchor which would permit a closer spacing while still allowing some clearance between successive grippers. In some cases the orientations of successive grippers could alternate back and forth around a central line. Other arrangements are also possible.

In FIGS. 14A through 14D and 15, the anchors are shown as each having a single free end bearing a point 340. In some implementations, each anchor could provide for an extension of the other end 342 of the wire (for example, a symmetrical extension), as implied in dashed line 344. A wide variety of other arrangements are also possible.

In FIG. 15, the gripper has three barbs on each side of the free end of the wire. In some implementations, there could be more or fewer barbs, and the barbs could have a wide variety of other configurations on the gripper.

Figure 16:
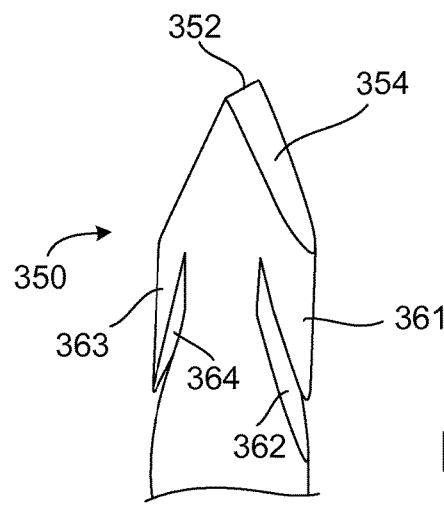
FIG. 16 is a perspective view of a gripper.
Figure 17:
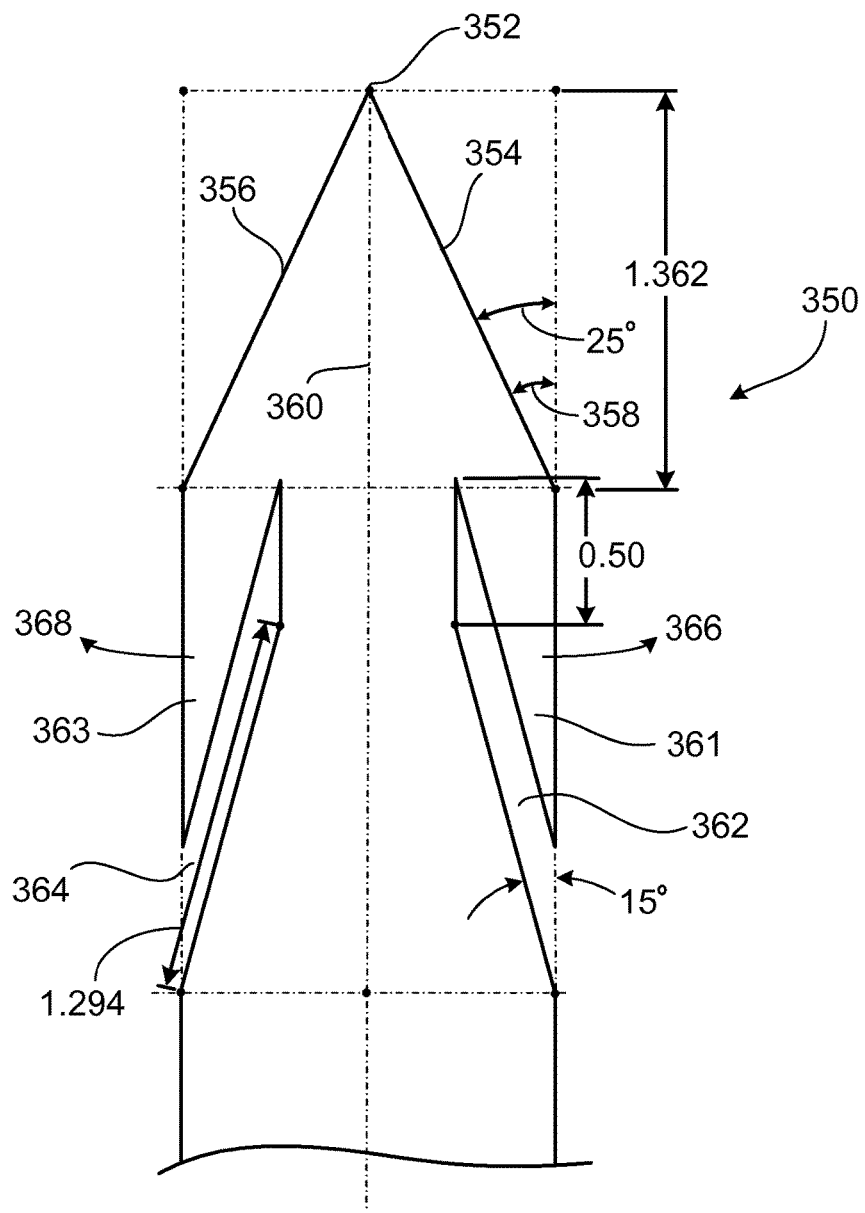
FIG. 17 is a side view of a gripper.

In some implementations, each of the grippers 350 can be formed of wire or other cylindrical material and can be formed, machined, or molded, for example, to have the configuration shown in FIGS. 16 and 17, including a point 352 having two symmetrical faces 354, 356 each at an angle 358 of, for example, 25 degrees relative to a central axis 360 of the gripper. Below the point are two barbs that are formed, by laser cutting, machining or otherwise imparting slots 362 and 364 at a common angle (15 degrees in this example) to the central axis.

Once the barbs are formed they can be bent away from the axis in the directions 366 and 368 to form the final barbs.

A wide variety of other configurations and forms of manufacture are possible for the barbs and the grippers. In the particular example shown in FIGS. 16 and 17, the grippers are formed of Nitinol wire that is 1.26 mm in diameter and the length of the gripper to the bottom edge of the slots is 22.87 mm.

As shown in FIG. 14D, in some examples, when installed each of the grippers extends from about 2 to about 4 millimeters (dimension 339) from the bottom of the sheath surface.

In some implementations, the support—which includes the coil, the sheath and portions of the anchors—is wrapped in a cloth covering as are many existing rings that are hand-sutured to the valve annulus by a surgeon. The cloth allows the heart tissue to attach itself securely to the support over time, making for a secure repair.

Figure 18:
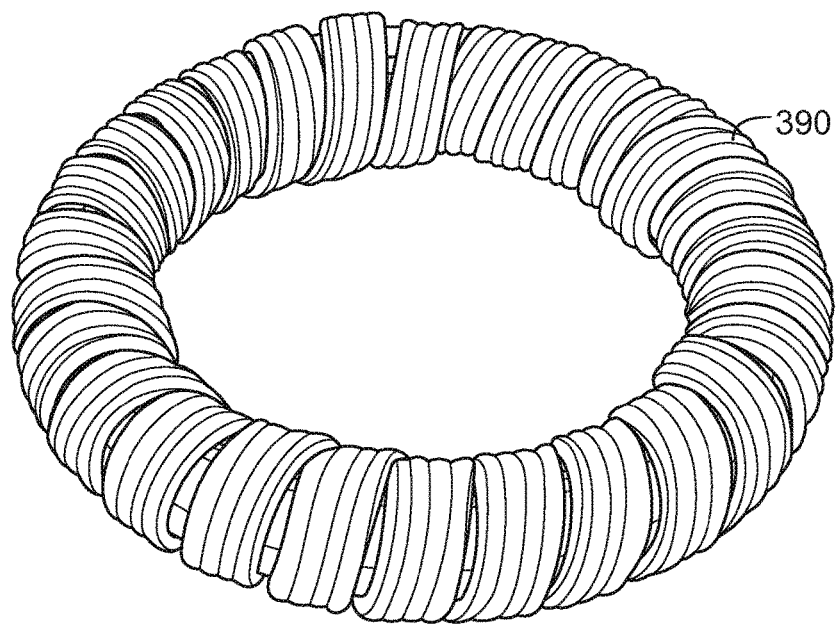
FIG. 18 is a perspective view of a covering wound around the other parts of a support.

As shown in FIG. 18, in some cases, the cloth covering can be a thin strip of material that is helically wound around the other parts of the support. The material may be attached to the support by suturing, gluing, or in other ways. The helical winding allows an inelastic material to be employed and still accommodate the circumferential expansion of the support. In some examples, the cloth covering may include a series of independent tubular cloth segments placed over the support. The segmented arrangement will allow inelastic cloth to be used without hindering circumferential expansion of the support.

As the cloth is placed on the support, it is pulled over the grippers, each of which penetrates the cloth and remains ready for insertion. A wide variety of covering materials or combinations of them could be used including metal, fabric, and plastic. The covering should be able to accommodate the expansion and contraction of the support without becoming distorted and should be biocompatible and porous enough to accept and encourage the growth of tissue through its structure, A wide variety of other configurations of parts and materials, and ways to assemble the parts of a support are possible. Different numbers of pieces can be used, and the functions described can be combined in different ways into different pieces of the support.

Figure 19:
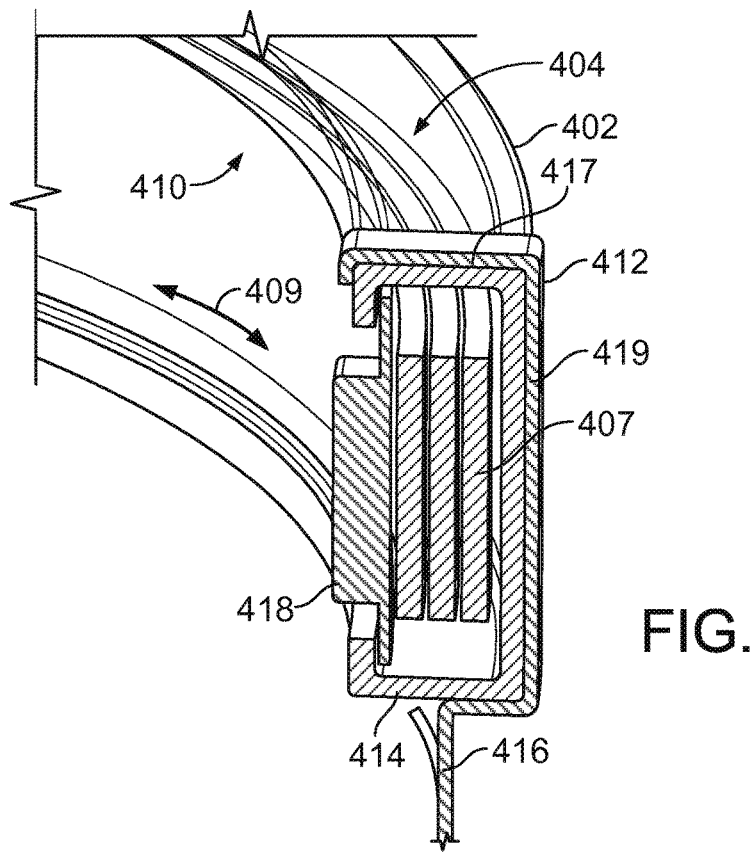
FIG. 19 is a cutaway perspective view of a support.
Figure 20:
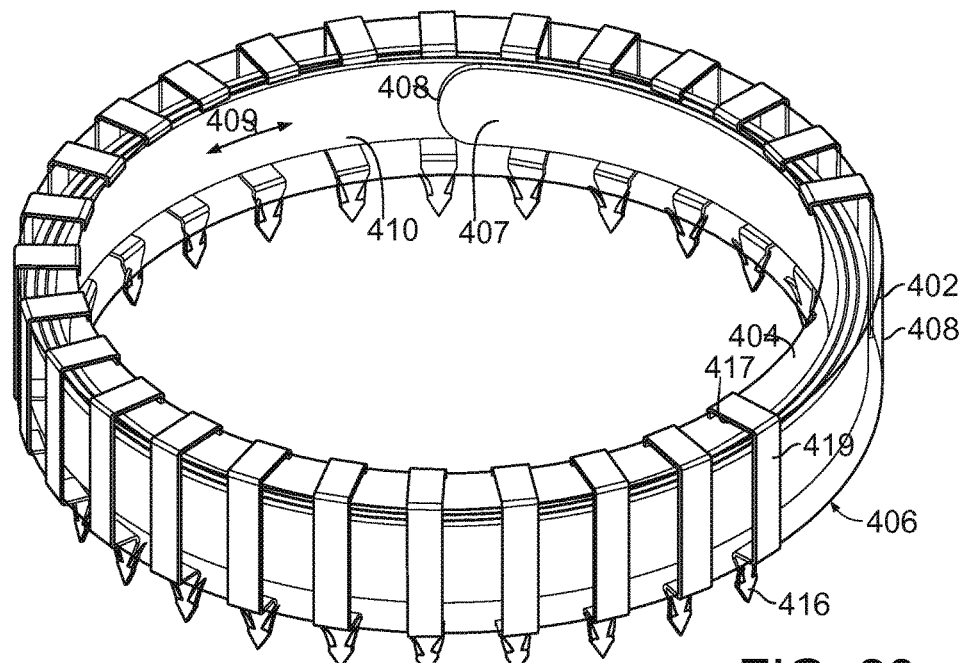
FIG. 20 is a perspective view of a support.
Figure 21:
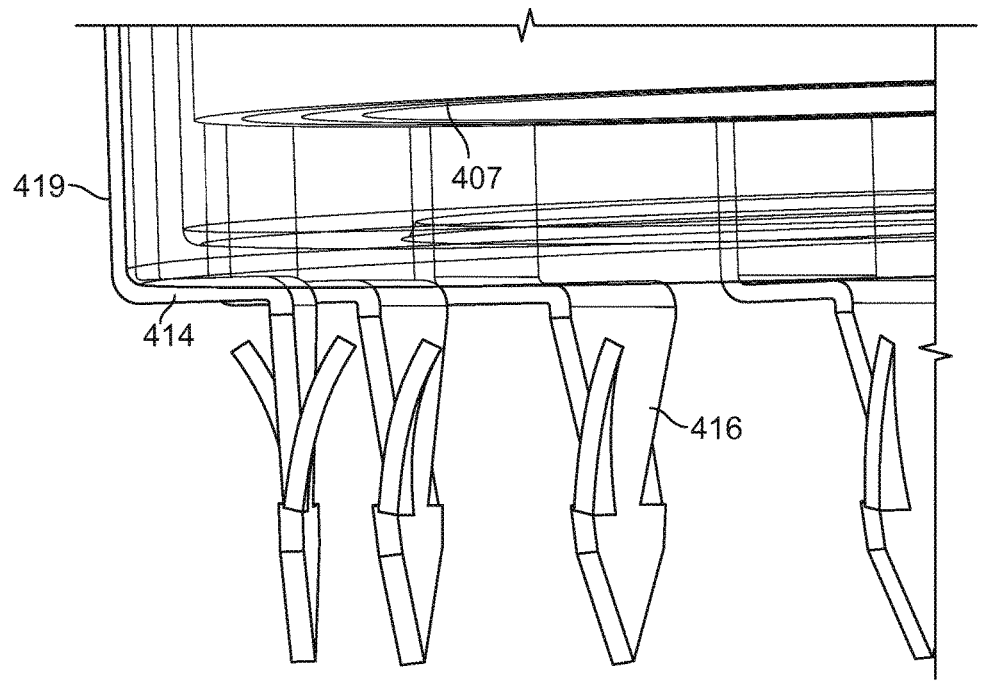
FIG. 21 is an enlarged perspective view of a portion of a support.
Figure 22:
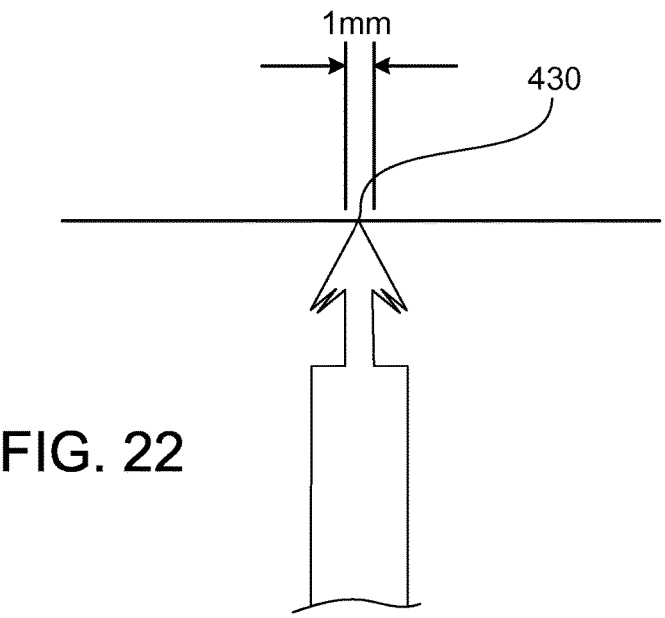
FIGS. 22 through 25 are top views of a gripper with a pointed end and on each side of the pointed end, a pair of barbs.
Figure 23:
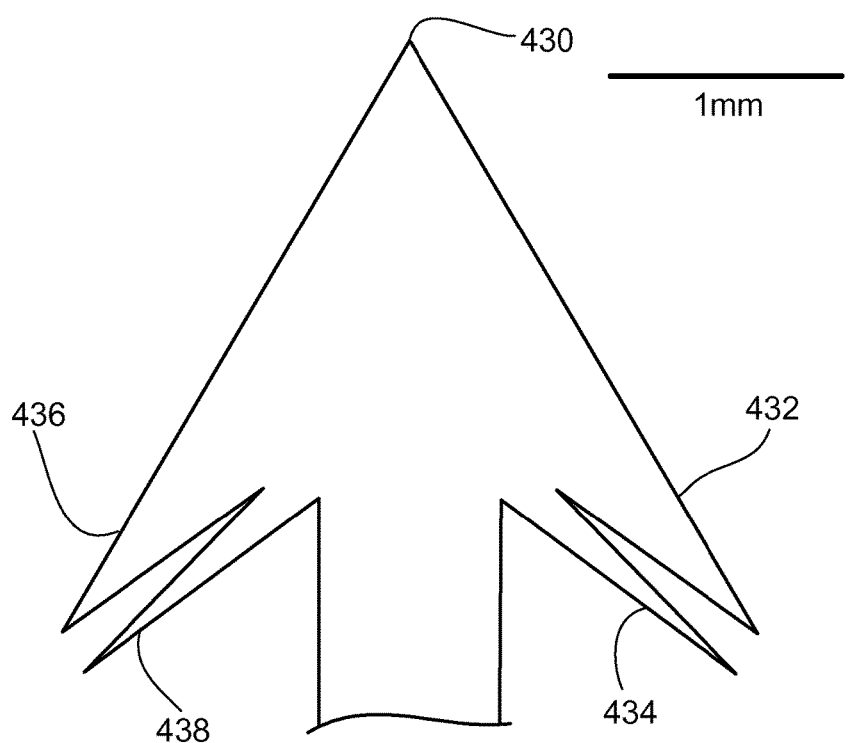

In some examples, shown in FIGS. 19, 20, and 21, the sheath can be made of two molded pieces that interlock. An outer annular housing 402 (sometimes called the outer piece) has upper and lower flat rings 404, 406 joined by an outer flat cylindrical wall 408. The coil 407 sits within the housing. The other, inner piece 410 of the sheath is a cylindrical wall that is captured between the upper and lower rings 404, 406 in a way that permits the inner end 408 of the coil to be tightened or loosened by sliding it circumferentially 409, causing the support to be expanded or contracted. During the sliding, the inner piece of the sheath slides circumferentially also.

In this example, the anchors 412 are formed from flat pieces of metal that are bent and then attached to the outer piece of the sheath. Each anchor includes an upper finger 417 that grasps the upper portion of the outer piece of the sheath, a vertical arm 419 and a lower finger 414 that grasps the bottom of the outer piece of the sheath. The gripper 416 extends downward from the lower finger. The inner piece of the sheath has a tab 418 that can be manipulated to pull or release the end of the coil to expand or contract the support. An opposite end of the inner piece of the sheath is attached to the end of the coil for this purpose. As a result, the support can be expanded or contracted without the anchors moving relative to the outer piece of the sheath. The tab 418 can be manipulated in a wide variety of ways, including by direct finger manipulation, use of an insertion tool in open heart surgery, or manipulation at the end of a catheter from a distant position in a catheter laboratory.

Figure 24:
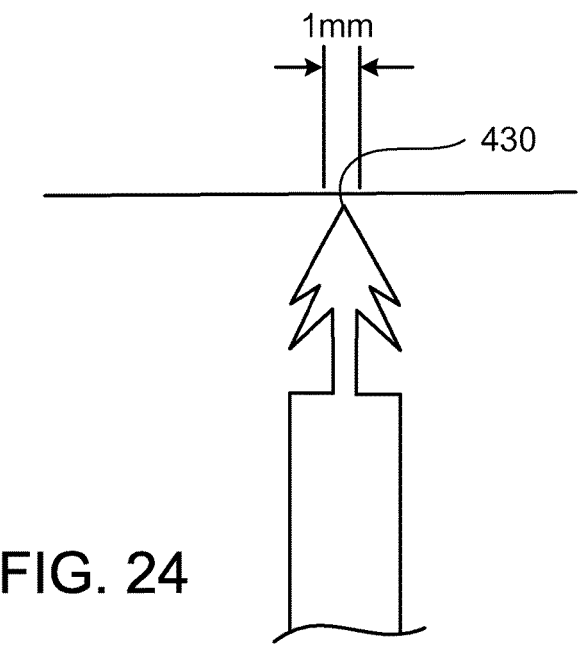
Figure 25:
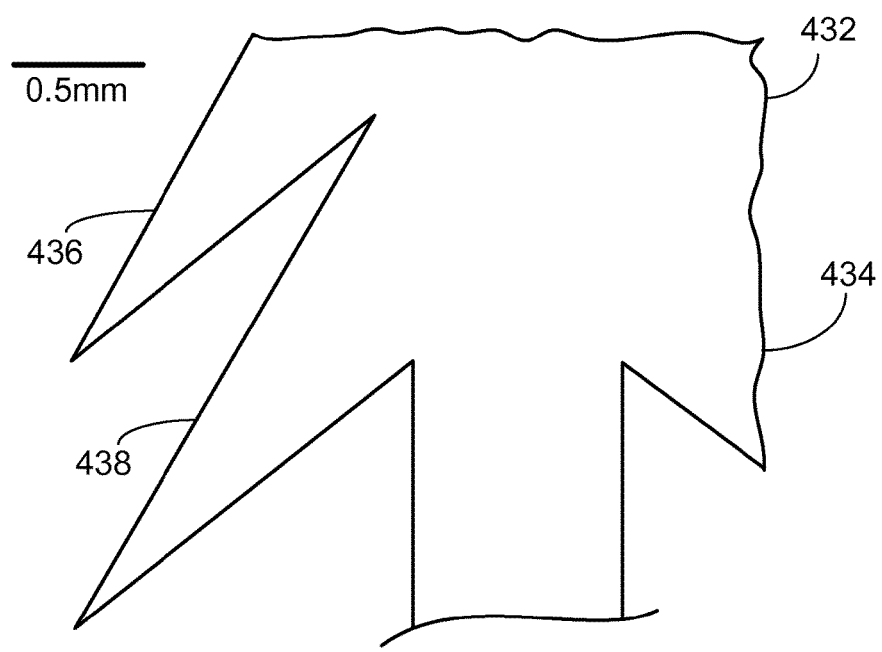

In some implementations of a gripper, as shown in FIGS. 22 through 27, there is a pointed end 430 and on each side of the pointed end, a pair of barbs 432, 434, 436, 438. In the example shown in FIGS. 22 and 23, the barbs 434 and 438 are smaller. In the example of FIGS. 24 and 25, the two barbs on each side of the point have a similar size and shape.

Figure 26:
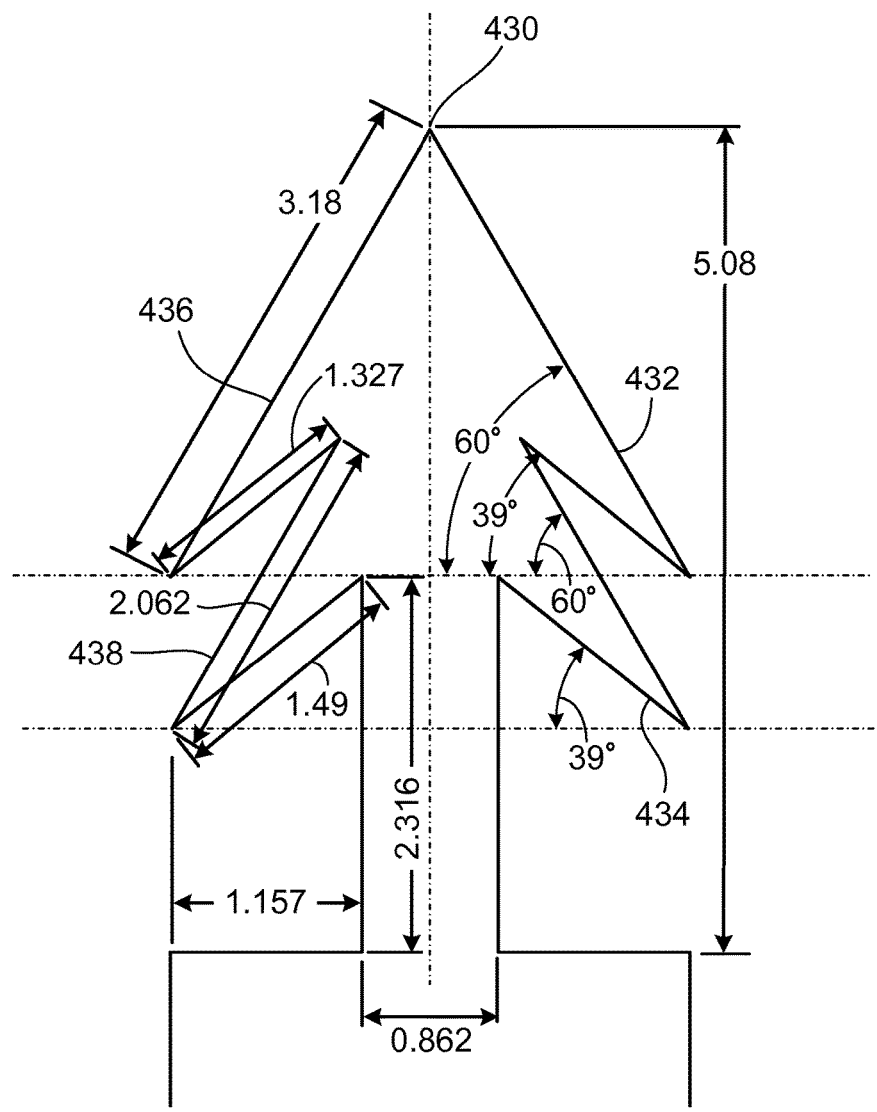
FIGS. 26 and 27 show the detailed configuration of a Nitinol strip that includes a point and barbs.
Figure 27:
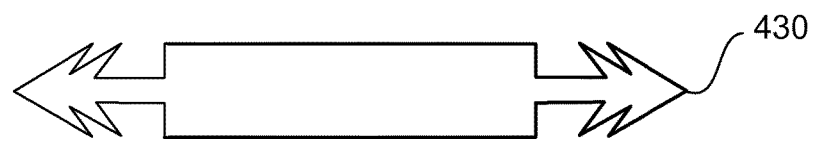
Figure 28:
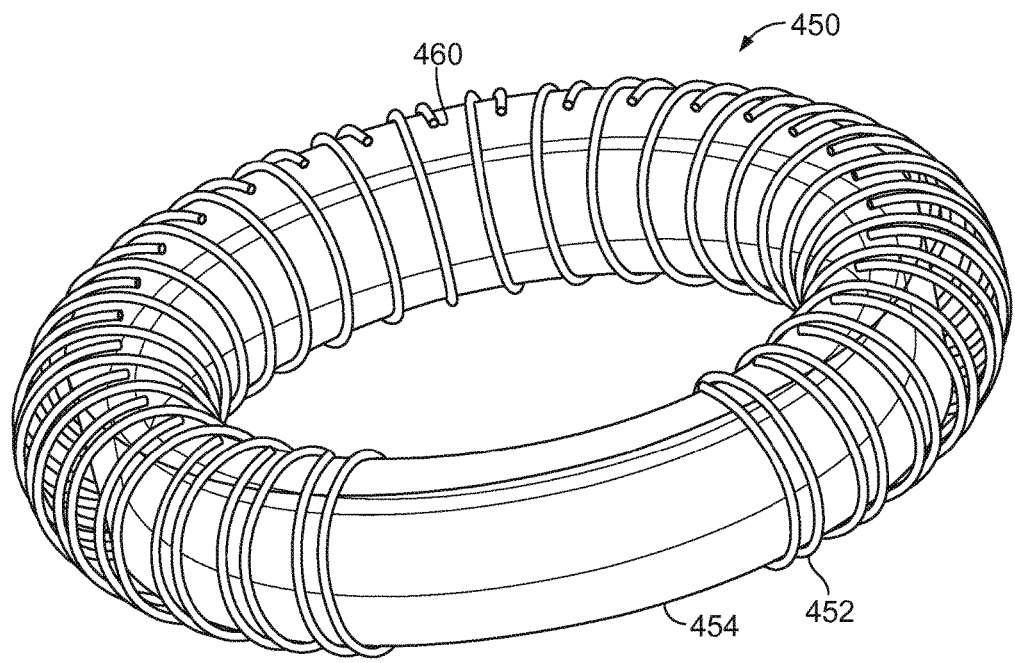
FIGS. 28, 29, 30, and 31 are a perspective view, a sectional perspective view, a perspective view, and a sectional perspective view, respectively, of a support including anchors in the form of loops.
Figure 29:
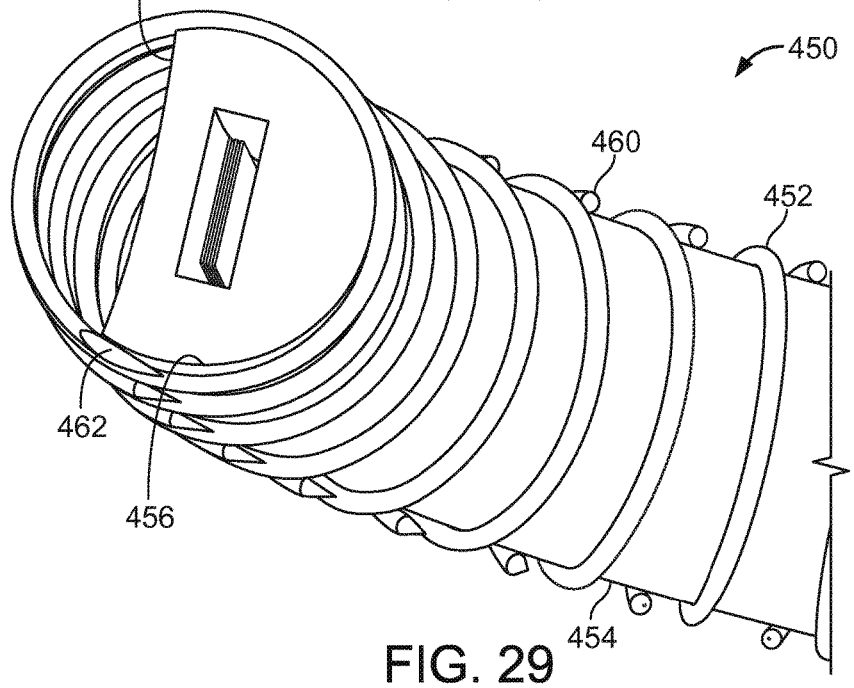

In some examples, as shown in FIGS. 26 and 27, the detailed configuration of a Nitinol strip includes the point and the barbs. As shown in FIG. 21, in some configurations, the barbs are bent out of the plane of the strip from which the gripper is formed in order to be more effective as barbs.

In general, in some examples, the support to be embedded in the valve tissue can be configured to achieve three related functions: (1) the ability to easily insert the grippers of the support into the tissue once the support has been correctly located at the annulus; (2) the ability to retain the support in the tissue securely in a way that maintains the correct shape for the annulus of the valve and is durable and long lasting, in part by providing a substantial resistance to forces that could cause detachment of all or part of the support after insertion; (3) the ability to deliberately withdraw all or a portion of the grippers during or after the insertion procedure in order to relocate or reorient the support relative to the valve annulus if doing so would be useful. These three functions require a careful and subtle design of the grippers, the anchors, and the other parts of the support, because some design factors that favor one of the functions can be a negative influence on another of the functions. These functions should also be implemented in a device that is simple, foolproof in its operation, and easy to use.

For example, easier insertion of the grippers into the tissue can be achieved by reducing the size and profile of barbs on the grippers and aiming the points of the grippers directly at the tissue. Removal of some or all of the grippers to reposition the support would also be aided. But those same features could reduce the stability and durability of the attachment of the support to the tissue. By giving the barbs a broader or more obstructive profile or aiming the points of the grippers off a direct path to the tissue, the gripping is made more secure, but inserting the grippers is more difficult as is repositioning.

Among the design features that can be adjusted and traded-off to achieve a desired mix of the needed functions are the number, shape, size, orientation, and method of mounting the anchors, the grippers, and the barbs, the shape, size, orientation and other configuration of the body of the support, the materials used for all of the parts of the support, and a wide variety of other factors.

In some cases, a mechanism or configuration can be provided that allows a deliberately reversible process for inserting and removing the grippers in the tissue for repositioning.

For example, as shown in FIGS. 28 through 31, a support 450 could include anchors in the form of, say, 30 loops 452 equally spaced around the body 454 of the support. A cross-section of the body 454 could include a circular segment 456 along the inner periphery of the body, and a flat or concave section 458 along the outer periphery of the body. Each of the loops could include two free ends 460, 462, one of which 460 is un-pointed and the other of which 462 has a sharp point. The loop does not have any barbed features.

Figure 31:
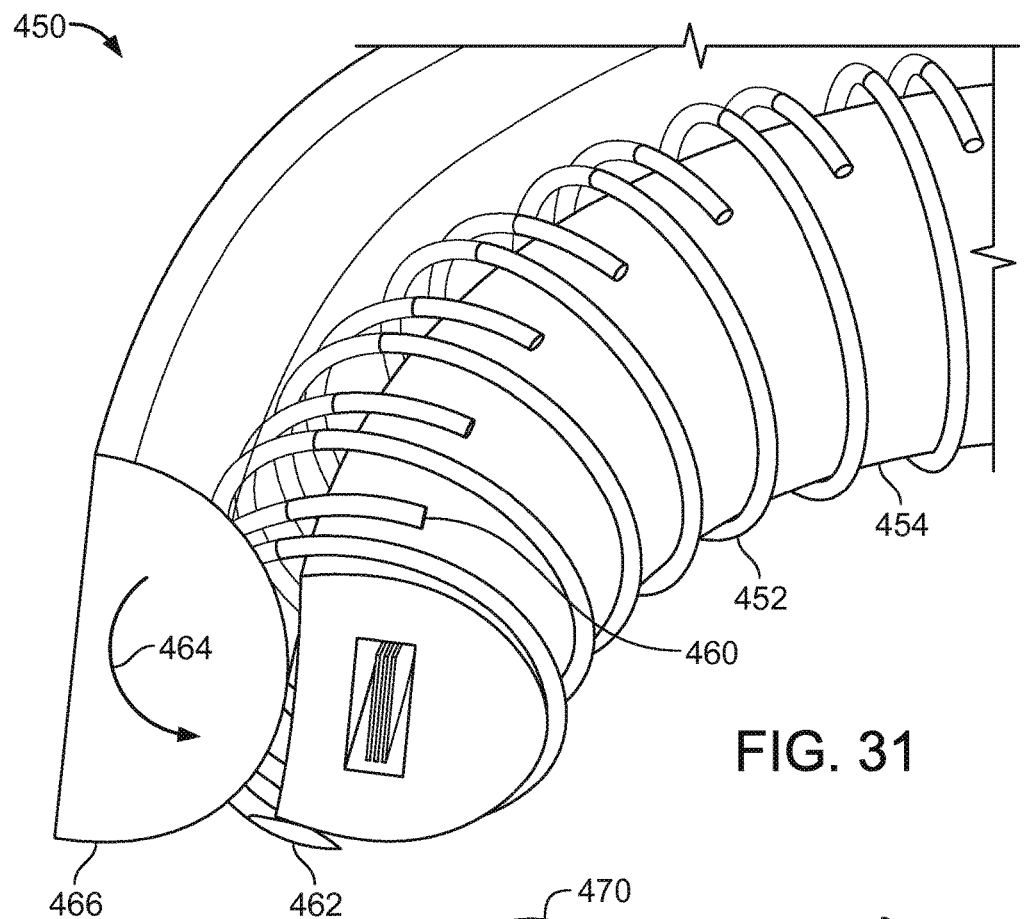
Figure 32:
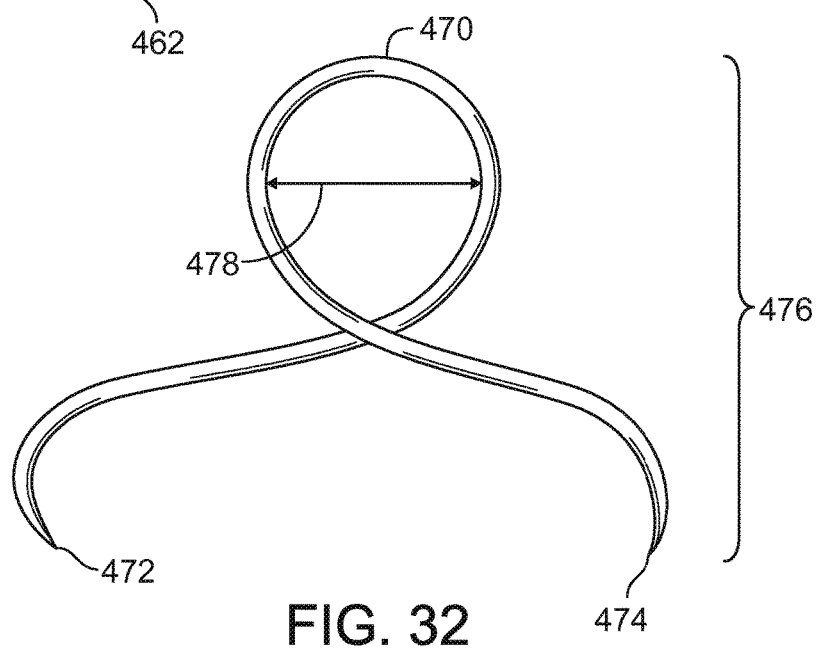
FIG. 32 is a top view of a gripper that allows a reversible process for installing and removing the grippers from the annulus tissue for repositioning.

In some modes of operation, prior to insertion, the curved sharp ends 462 of all of the grippers can be held away from body and aimed in the general direction of the annulus tissue. A sheath or other mechanism could be used to move them into and hold them in this temporary insertion position. During insertion, the insertion tool could be applied to force the grippers into the tissue. Once the pointed ends of the grippers are in the tissue, the sheath or mechanism could be manipulated to allow the anchors to assume their final shape, after following curved paths 464 through the tissue 466 and exiting from the tissue to lie next to the support body, as shown in FIG. 31.

Figure 30:
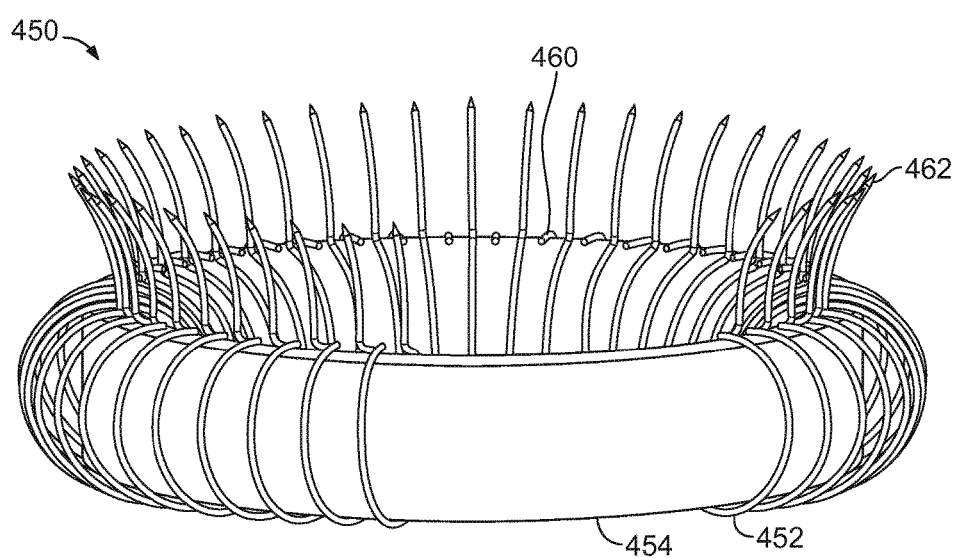

This configuration has the advantage that the process could be reversed using a similar sheath or mechanism to withdraw the grippers through the tissue and back to the configuration of FIG. 30. Because the gripping has been achieved by the curvature of the shafts of the anchors and not by barbs on the sharp tips, reversing the process is relatively easy. Gripping is also secure. However, insertion may be more difficult than in other implementations, and the reversibility requires an additional mechanism.

In some examples, the support could be provided with an adjustment and locking feature that would permit the size (e.g., the diameter) and possibly the shape of the support to be adjusted or locked or both, by the surgeon or operator at the time of insertion. In some cases, the support could be adjusted to different possible sizes at the time of insertion rather than requiring that it reach only a single non-selectable designed size.

Figure 45:
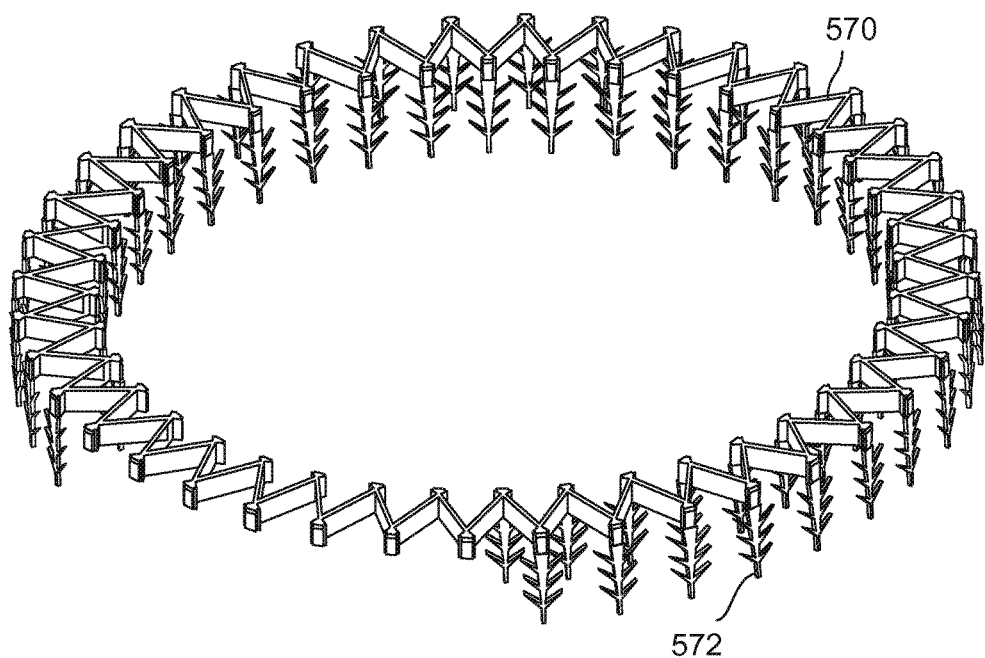
FIGS. 45 and 46 are perspective and enlarged perspective views of a portion of a support made of crimped stainless steel.

For example, as shown in FIG. 45, a core structural piece 570 of the support could be made of crimped stainless steel that is plastically deformed by an insertion tool (not shown). The tool could engage the top of the structural piece and force the piece temporarily to have a larger diameter for insertion. After pushing the support into the annulus to cause the grippers to attach to the tissue, the tool could collapse and allow the structural piece to collapse in diameter to its final size.

Figure 46:
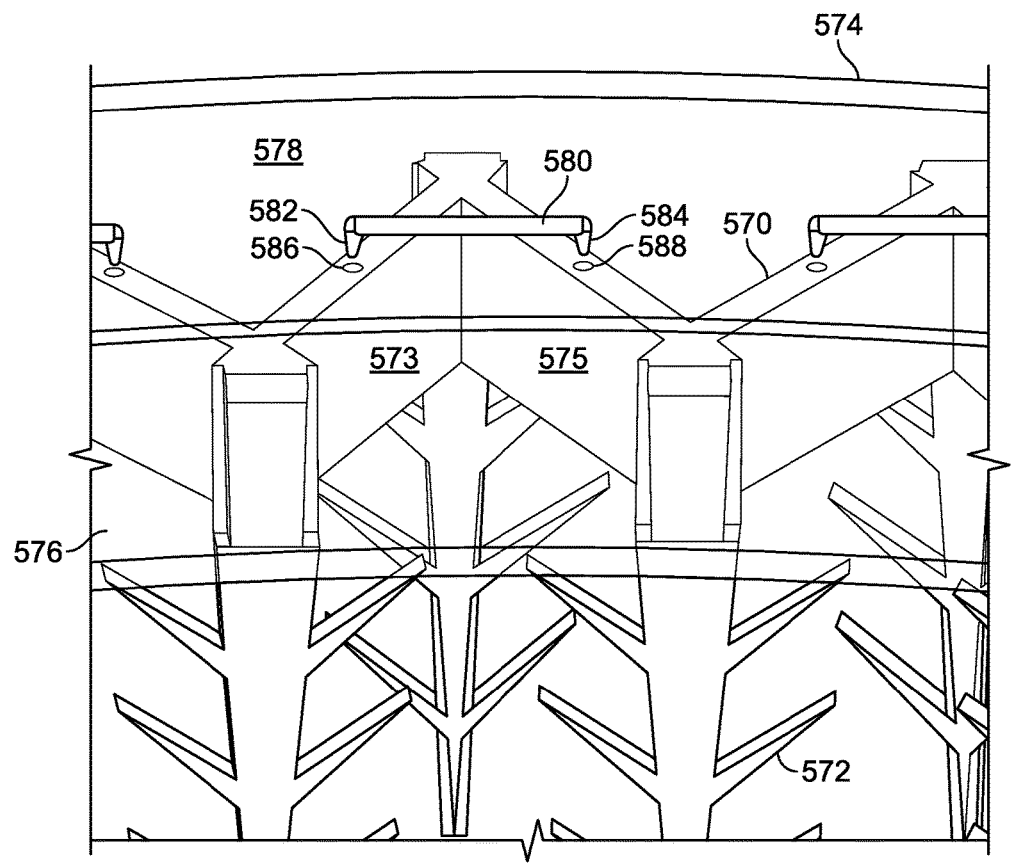
Figure 47:
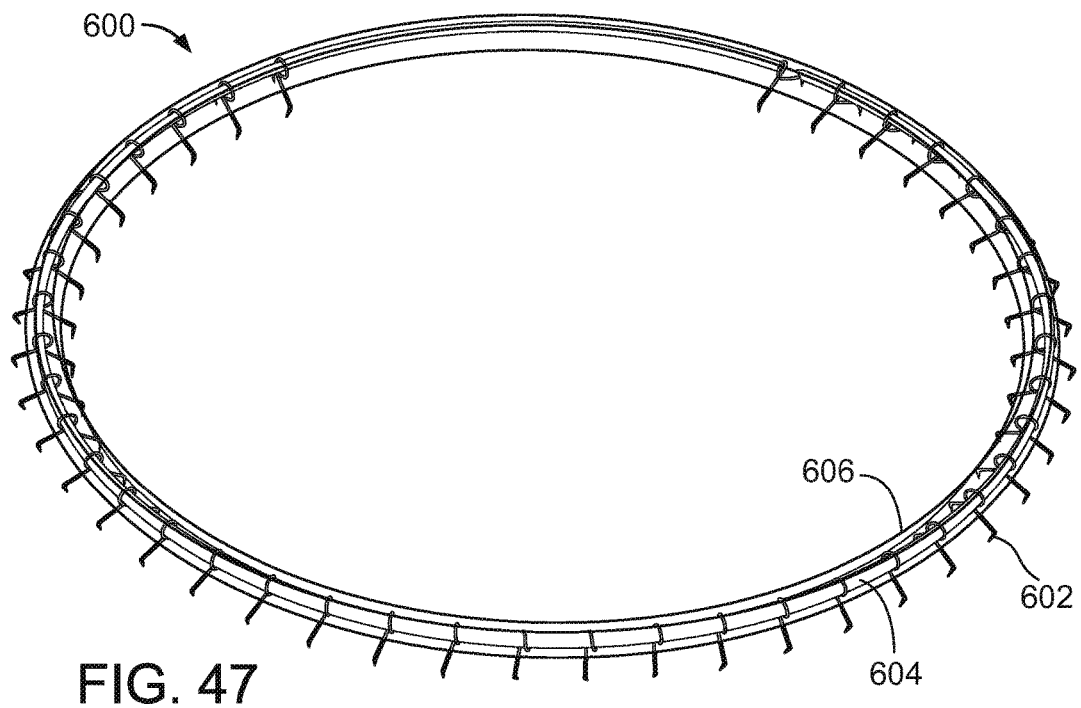
FIG. 47 is a perspective view of a support formed of three pieces.

As shown in FIG. 46, in some cases, individual expansion elements 573, 575 would bear holes 576, 578 that have locations and spacing to mate exactly with the locations and spacings of pins 582, 584 in rigid locking elements 580 once the structural piece has been expanded or contracted to exactly the desired dimension. The locking elements would be held at the proper places in an annular silicone support that has inner and outer peripheral walls 574, 576 joined by an upper annular wall 578. Pushing down on the silicone support when the support is properly sized will force the pins of the locking elements into the holes.

Referring to FIGS. 47 through 53, in some implementations, the support 600 could be formed of three pieces.

One of the pieces, an annular resilient (e.g., silicone) ring 606 has a cross-section that includes four linear segments defining a trapezoid, which provide stability to the shape of the ring. There are four corresponding faces of the ring. Pace 632 would have a configuration designed to match surfaces of a face of a dilator part of an insertion tool.

A second of the pieces is a metal ring 604 formed from a strip of, e.g., stainless steel having a curved cross-section and two overlapping ends 620, and 622. The curvature of the cross-section maintains the axial stability of the ring. Near one end 622, the ring has a series of slots that are meant to mate with corresponding tabs 623 formed near the other end 620. During fabrication and assembly the tabbed end of the ring is on the inside of the overlapping section 627 so that no mating and locking can occur. When finally installed, however, the tabbed end is on the outside of the overlapping section to permit locking. During manufacture, the silicone ring is molded around the metal ring. When the silicone ring is stretched and relaxed, the metal ring can expand and contract because the two ends are free to move relative to one another at the overlapping section. The support is essentially spring loaded.

The third piece of this example support is a double-pointed anchor 602, many copies of which are arranged around the ring (in this version, but not necessarily, at regular intervals). In some implementations, each of the anchors is made from a single loop 602 of wire that has a gripper (a barb or a fish hook, for example) at opposite free ends 616, 618. Each of the anchors is resilient and has a relaxed state shown in FIG. 53, with a distance 619 between the two grippers, and the points of the two grippers pointing generally towards each other. The loops of the anchors are placed on the metal ring and potted in the molded silicone ring.

Figure 51:
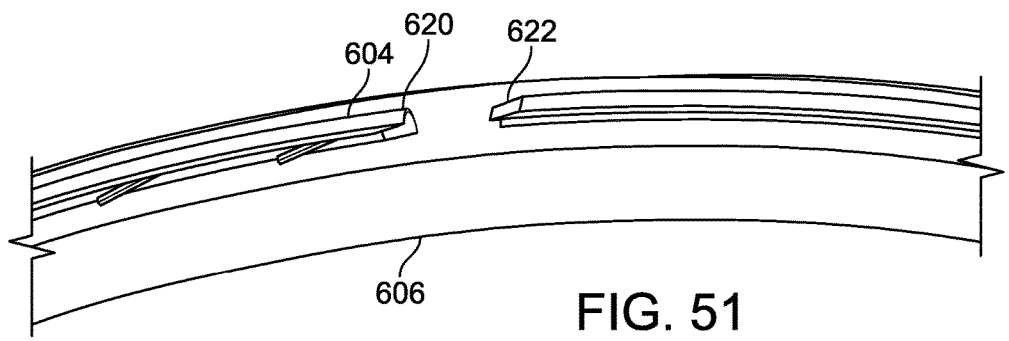
FIG. 51 is a perspective view of a ring and coil assembly.

After assembly, the support is stretched to a larger diameter and mounted on an insertion tool, not shown. The stretching has two effects. One, shown in FIG. 51, is that the two ends of the metal ring are pulled apart sufficiently to eliminate the overlap. The ends of the ring are biased so that the tabbed end moves to the outside relative to the slotted end. So when the two ends again form the overlap upon the later contraction of the ring, the tabs are positioned to mate with the slots. The ends of the metal ring are beveled to assist in achieving this arrangement as the ring contracts.

Figure 48:
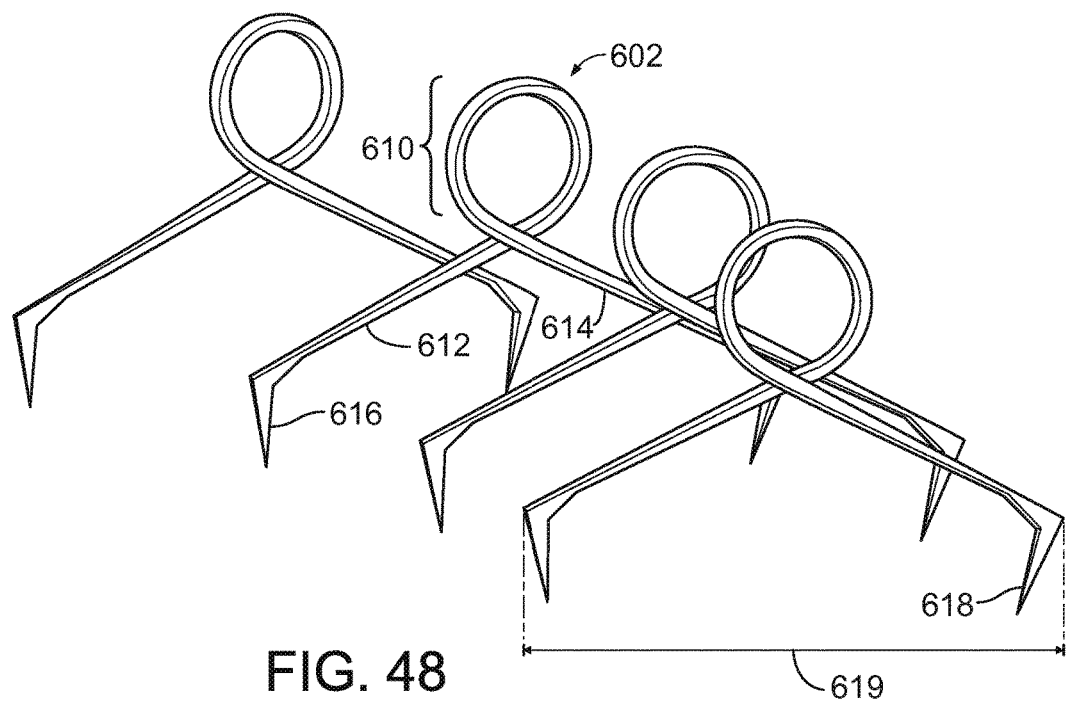
FIG. 48 is a perspective view of an anchors where the orientation of the points of the grippers have been rotated to face generally in the insertion direction.
Figure 49:
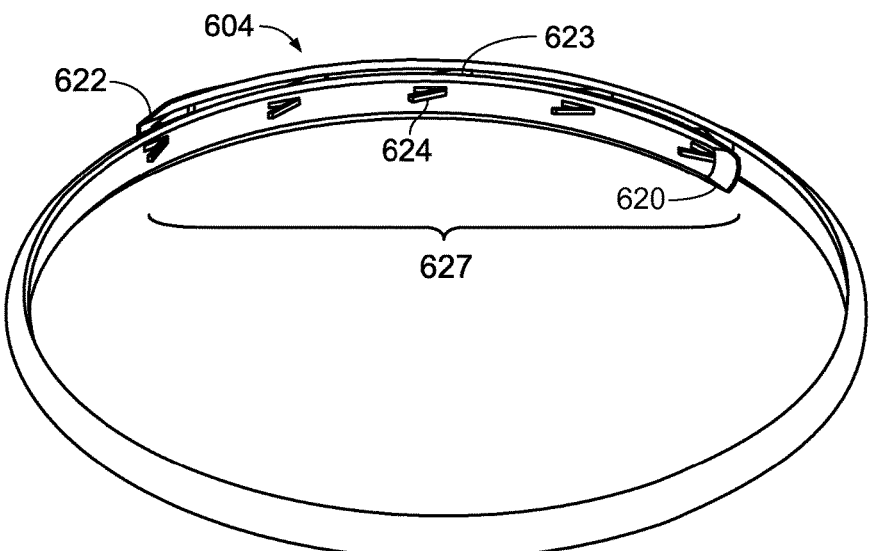
FIG. 49 is a perspective view of a coil.
Figure 50:
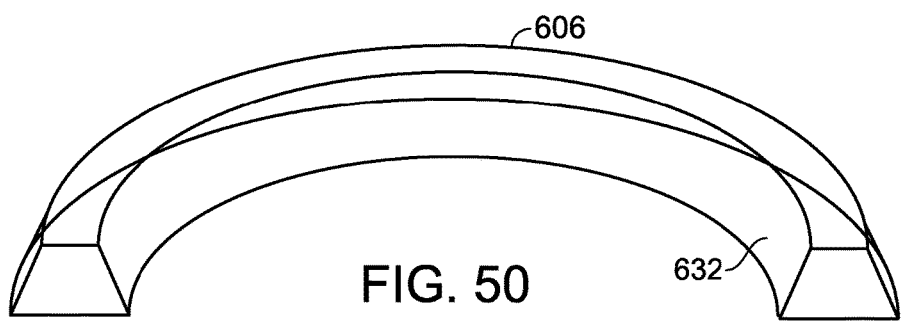
FIG. 50 is a perspective view of a resilient ring.

Also, as the silicone ring expands, the cross-sectional diameter of the silicone ring contracts; because the anchors are potted within the silicone ring, as the ring stretches in length and contracts in diameter, the matrix squeezes the loops 610 of the anchors and forces them into a temporary configuration shown in FIG. 48, in which the distance 619 has increased and the orientation of the points of the grippers has rotated to face generally in the insertion direction, ready for insertion.

Figure 52:
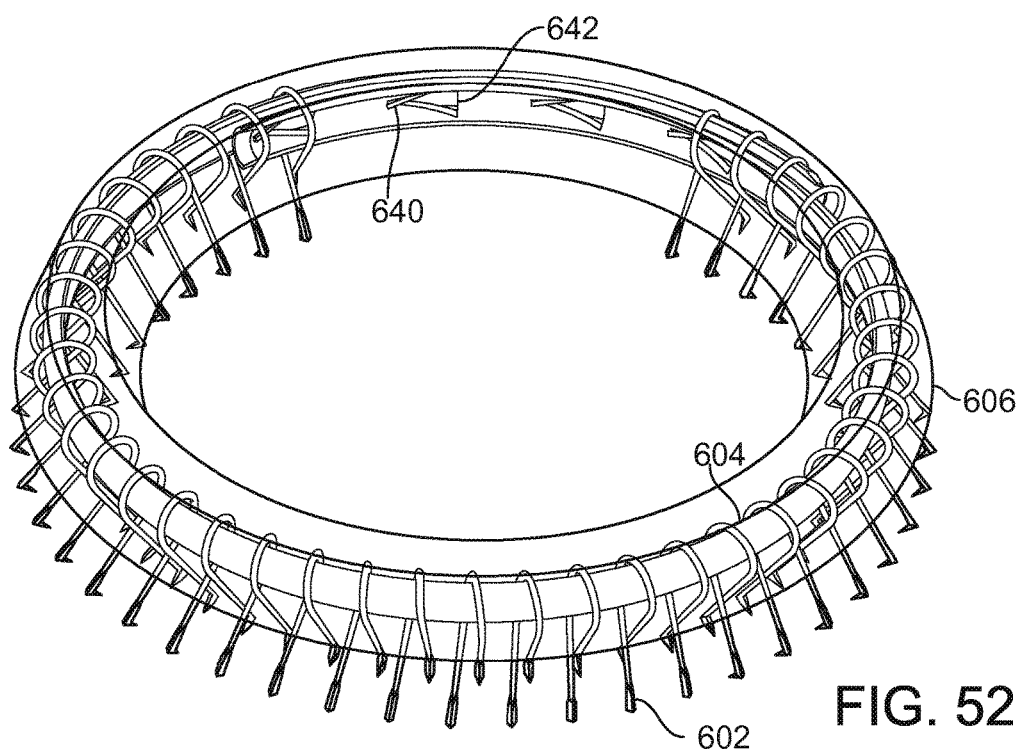
FIG. 52 is a perspective view of a support contracted in diameter when the insertion tool is removed from the support.
Figure 53:
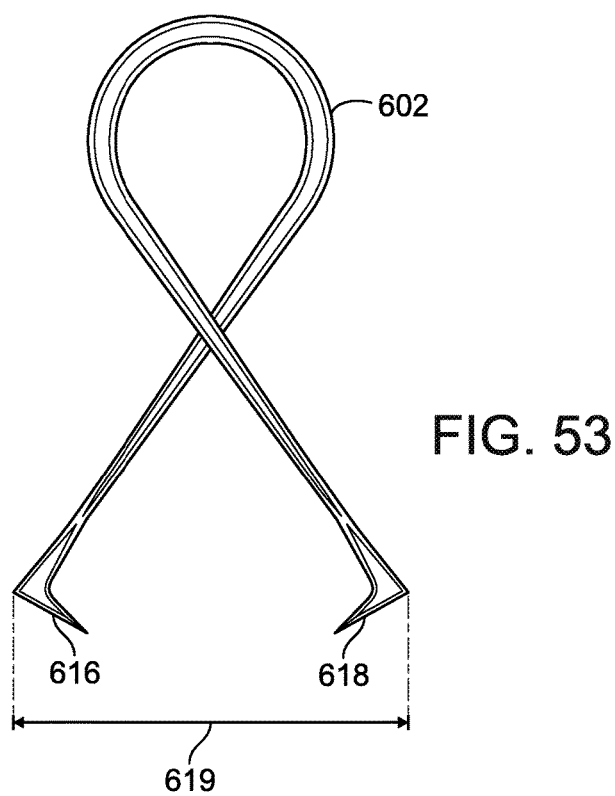
FIG. 53 shows relaxed anchors, driving the grippers to rotate and force the points towards each other, to hold onto the tissue securely.

As shown in FIG. 52, when the insertion tool is removed from the support, the support contracts in diameter, which reconfigures the annulus to the desired shape and size. And the silicone rings expands in cross-sectional diameter, which allows the anchors to relax (FIG. 53), driving the grippers to rotate and force the points towards each other, to hold onto the tissue securely. As the metal ring contracts, the tabs and slots cooperate in a ratchet action which permits the support to contract to its final shape and size, while prevent a reverse expansion from occurring again.

Figure 54:
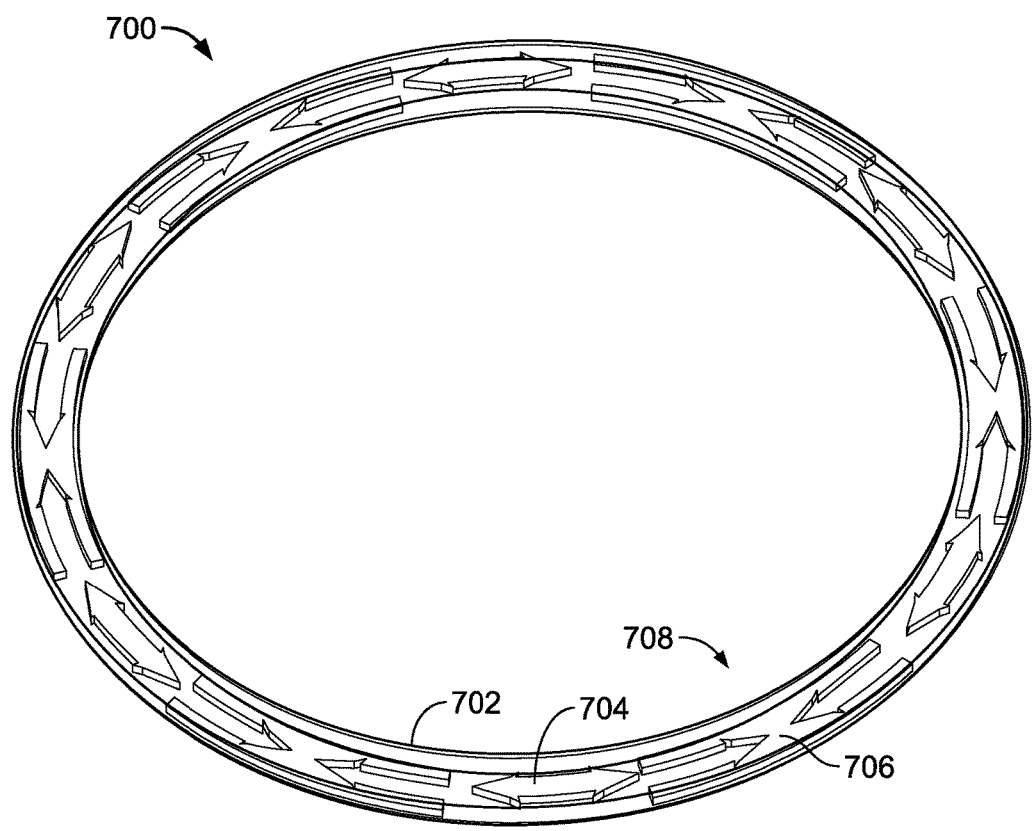
FIGS. 54 and 55 are a perspective and side view of an interlock with embedded mating elements in a resilient ring.
Figure 55:
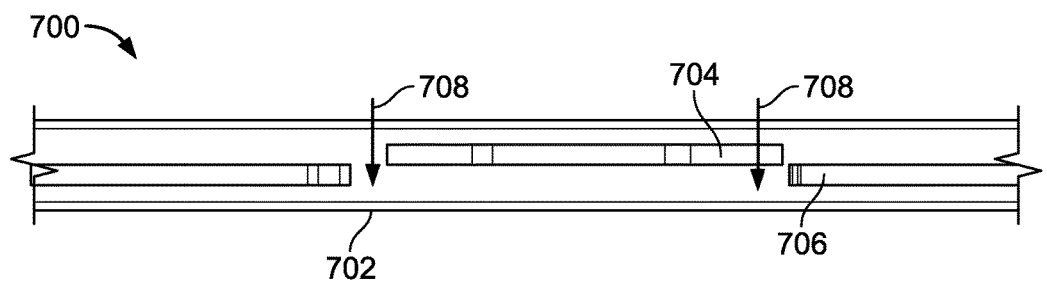
Figure 57:
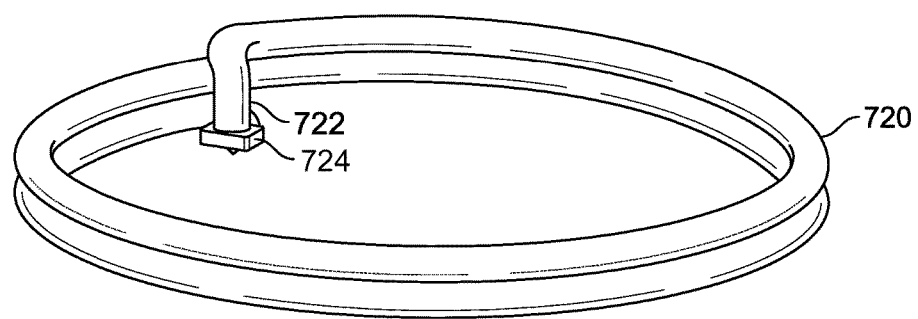
FIGS. 56 and 57 are perspective views of an interlock.
Figure 56:
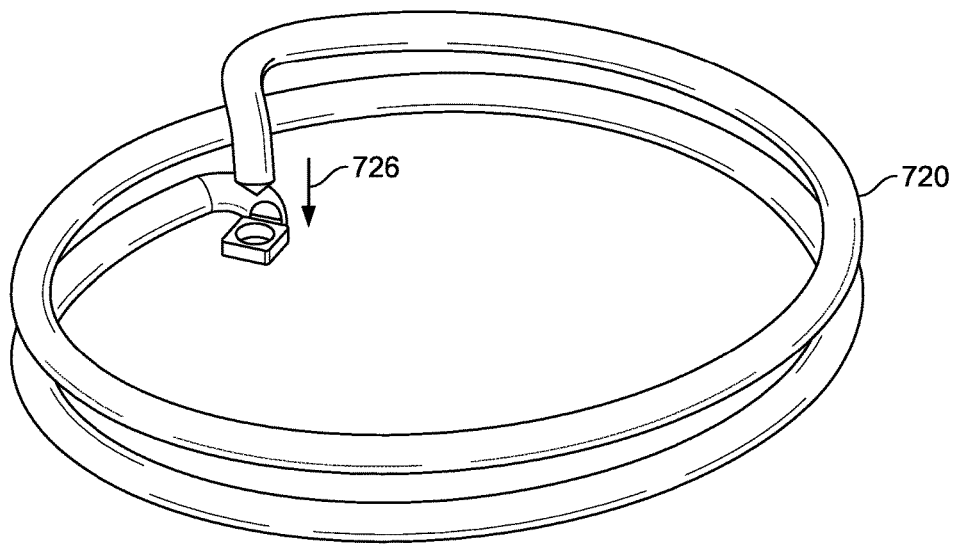

In some cases, shown in FIGS. 54 and 55, the locking of the final diameter of the support can be achieved by embedding mating elements in a resilient ring 700. One set of elements 704 can be embedded in one plane of the ring, and a corresponding set of elements 706 to be mated can be embedded in a second plane of the ring. The embedding is done in a way that permits the two different kinds of mating elements to slide relative to one another as the support is expanded and contracted prior to and during installation. When the proper diameter of the support has been reached, a tool can be used to press down on the silicone ring to cause the mating elements to occupy the same plane and be interlocked.

In some examples, two interlocking elements 722 and 724 can be formed at the ends of a resilient metal coil 720 that forms part of the support. Once installed and properly sized, the support can be locked by pushing down to cause the interlocking elements to mate.

In some cases, a support could have a central annular lumen filled with uncured polyurethane and arranged so that the diameter or shape or both of the support could be adjusted at the time of insertion. Once the desired diameter or shape or both have been reached, ultraviolet light, which could be delivered through a delivery tool or in other ways, would be used to cure and harden the polyurethane. Current curable materials and lighting can achieve curing in about 20 to 30 seconds.

FIGS. 32 through 35 show another example configuration that allows a reversible process for installing and removing the grippers from the annulus tissue for repositioning. Each of the anchors 470 incorporates a scissoring or pincering mechanism that has two pointed (but not barbed) grippers 472, 474 on opposite free ends of a 0.015 inch Nitinol wire loop. To form the each anchor, the wire is wound on a jig in the shape 476 shown in FIG. 32, which is the open configuration of the anchor. Then heat is used to memory set that open shape. The loop diameter 478 in this example could be about 0.20 inches for mounting on a toroidal resilient stretchable support body having a cross-sectional diameter 480 of about 0.25 inches.

Figure 33:
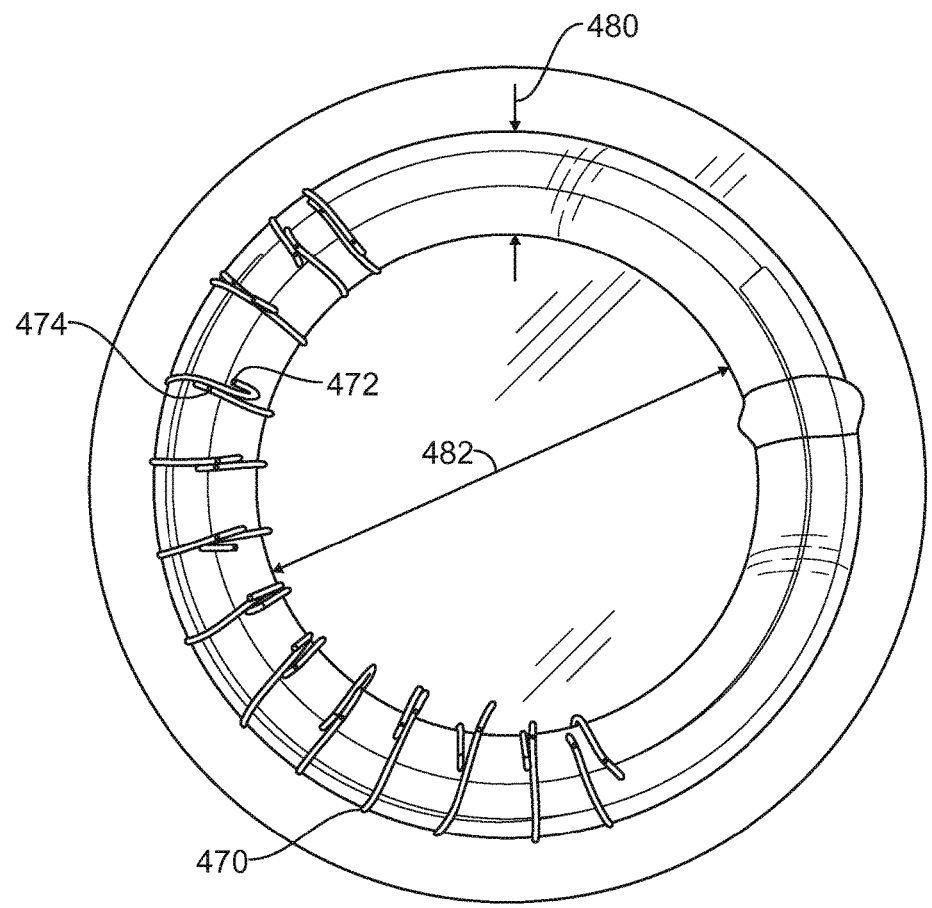
FIGS. 33 through 35 are a top view, a top view, and a perspective view of a support on a hypothetical insertion tool.
Figure 34:
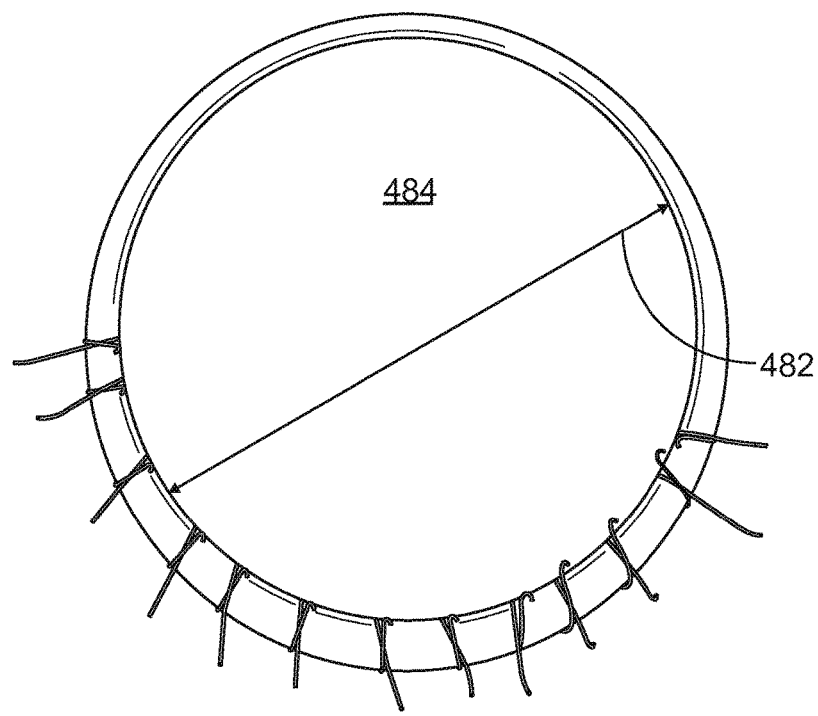
Figure 35:
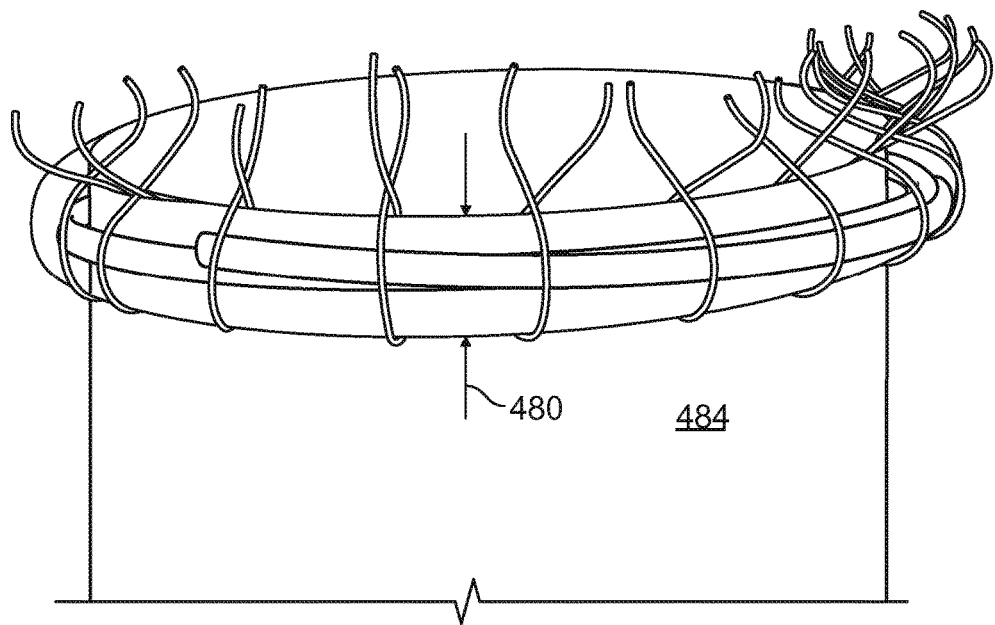

When the loop of each anchor is opened up to force it onto the larger diameter 480 support body, the configuration of the anchor automatically causes the two pointed free ends to close up into a gripping configuration as shown in FIG. 33. Prior to installation and before the support has been loaded onto the insertion tool, the support body is in its contracted installed shape as shown in FIG. 33, with all of the pincers closed. In FIGS. 34 and 35 the support has been stretched to its insertion configuration, in which the diameter 482 is larger to fit onto (here a simulated) insertion tool 484. Because of the shape and configuration of the support body (for example, a silicone tube), when the body is stretched, its cross-sectional diameter is reduced allowing the anchors to relax to their native, open shape, ready for insertion.

Insertion proceeds by pushing the support towards the opened and properly shaped annulus causing the sharp points of the grippers to penetrate the tissue. As the insertion tool is removed from the support, the support body contracts to the final desired shape and diameter of the valve annulus. As it contracts, the pincers are forced to grasp the tissue of the annulus and hold the support securely in place. Thus, the support is relatively easy to insert and can be removed and repositioned by reversing the process, that is by expanding the support body, which releases the pincers.

A wide variety of insertion tools (which we also sometimes call dilators) can be used to attach a support to the heart valve annulus tissue. Some have been described earlier and we describe others below.

An important principle of the configuration and operation of at least some examples of insertion tools is that they enable a surgeon or catheter operator to install the support reliably and easily in a wide range of patients having heart valves that are in a wide variety of conditions and have a wide variety of shapes and sizes. In other words, insertion can be achieved routinely and simply. This can be done by an insertion tool that automatically and easily temporarily expands and reconfigures any heart valve annulus to adopt a common expanded shape or size or both so that a support that has been pre-expanded to the common shape or size or both can be attached without concern for the upstretched context and configuration of the patient's valve annulus. The support is configured so that after insertion the support can be reconfigured automatically or by manipulation to a final secure stable desired shape and size, with the insertion tool removed.

FIGS. 36 through 39 illustrate an example of an insertion tool 500 that includes a dilator 502 formed of six arms 504 arranged at equal intervals around an insertion axis 506. Each of the arms is formed of a 0.125" wide spring steel metal strip that is bent at two places 508 and 510. Ends 512 of the arms are gathered together and held by a segment of plastic tubing 513 on the end of an aluminum inner tube 514 (0.28" outside diameter, 0.24" inside diameter). The opposite ends 516 of the arms are gathered together and held by a segment of tubing and a shaft collar 518 to an aluminum outer tube 520 (0.37" outer diameter, 0.30" inner diameter). The outer tube is connected to a handle 522. The inner tube, which slides within the outer tube along the insertion axis, is manipulated by a second handle 524.

Figure 38:
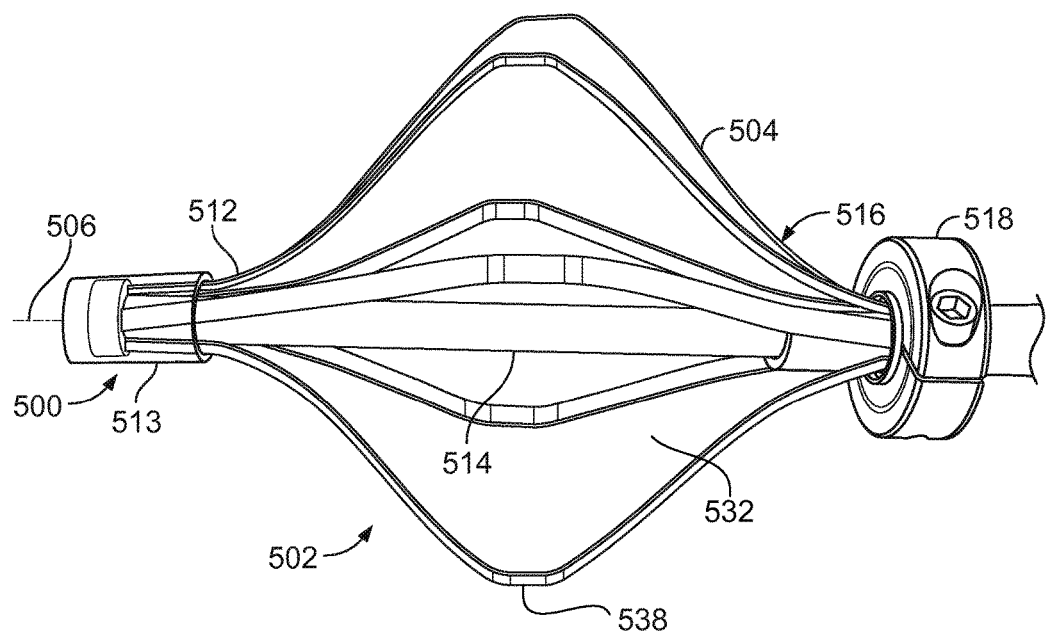
Figure 39:
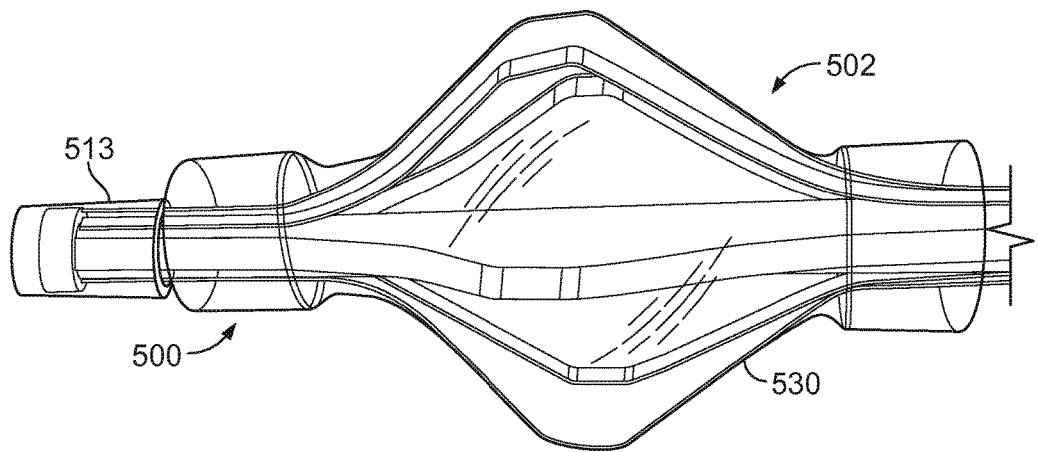
Figure 44:
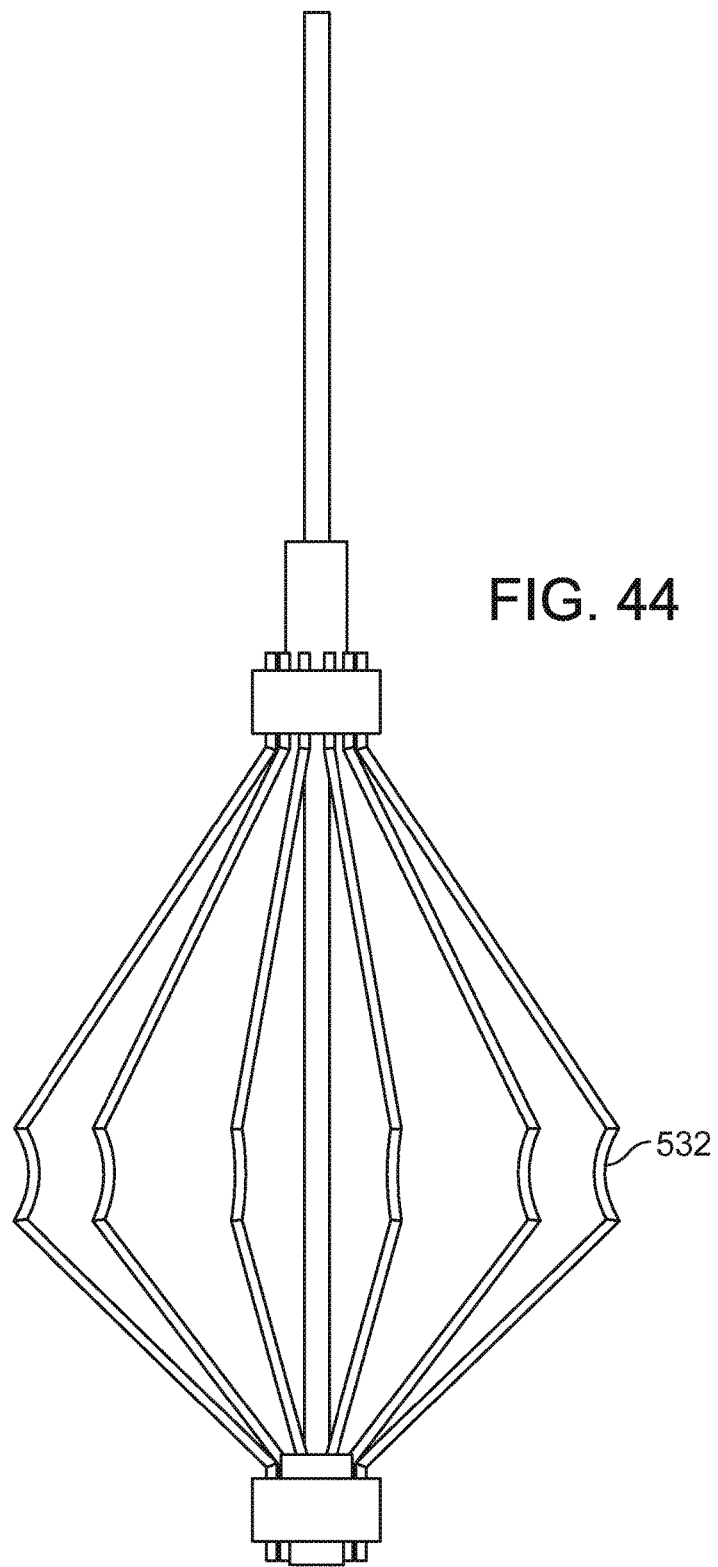
FIG. 44 is a side view of an insertion tool with a central ridge.

By pushing or pulling 526 on the second handle relative to the first handle, the inner tube is moved back and forth relative to the outer tube, which causes the arms to dilate as in FIG. 38 or contract as in FIG. 37. A thin molded sleeve of, e.g., silicone, 530 protects the mechanism and protects the heart tissue and the support from damage. Prior to installation of the support in the heart valve, the support is stretched and mounted on the dilator at the central ridge 532. It can be held in place by force and friction or can be lashed with sutures that are cut after installation, or the central ridge can be provided with a concavity in which the support is seated. Another view of the central ridge 532 is shown in FIG. 44.

As shown in FIGS. 42 and 43, in some examples, a dilator can include round wire arms 550 that are evenly spaced around the insertion axis and have each been shape set to the expanded configuration shown in FIG. 42. The ends 552, 554 of each wire are secured respectively to two circular hubs 556 558. The upper hub 556 has a central hole (not shown) that is threaded to receive a threaded rod 560 to which a handle 562 is clamped. The other end 559 of the threaded rod is fixed to the hub 558. Using the handle to turn 564 the threaded rod advances it or withdraws it (depending on the direction of rotation) through the upper hub, toward or away from the lower hub. The rod pushes or pulls on the lower hub, thereby increasing or decreasing the distance 566 between the two hubs and forcing the arms to contract or allowing them to expand to the shape set expanded configuration.

Figure 40:
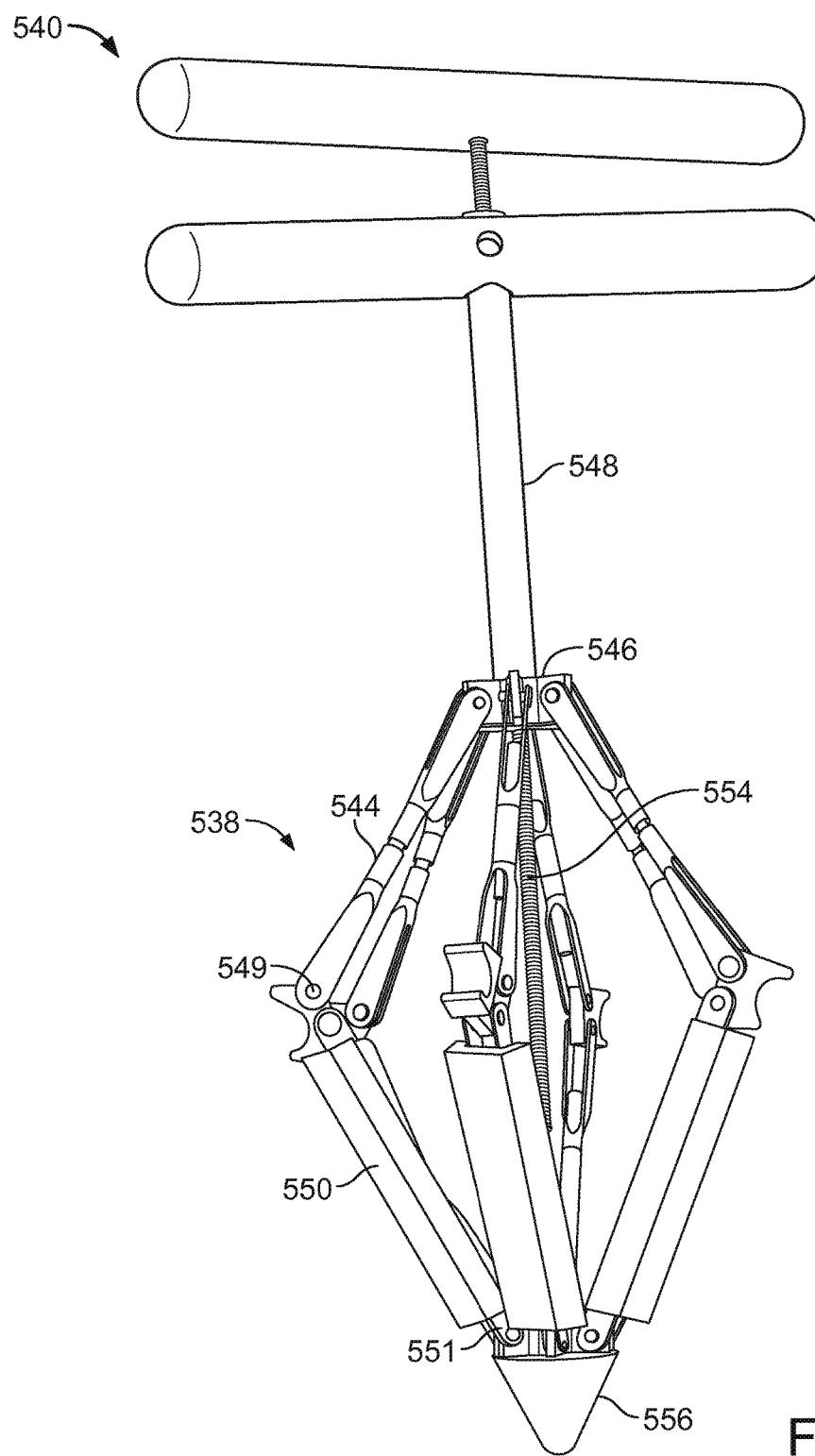
FIG. 40 is a side view of an insertion tool where each arm is formed of a stiff limb connected at one end to the outer tube, and at another end to a broader limb.

As shown in FIG. 40, in some implementations each arm 538 of an insertion tool 540 is formed of a stiff limb 544 connected at one end 546 to the outer tube 548, and at another end 549 to a broader limb 550. The other end 551 of the second limb is connected to the inner tube 554 at a tip 556. The limbs are joined by a hinged element that allows them to pivot relative to each other. On each of the arms, a clip 560 has a recess to capture the support at one location along its perimeter.

Figure 41:
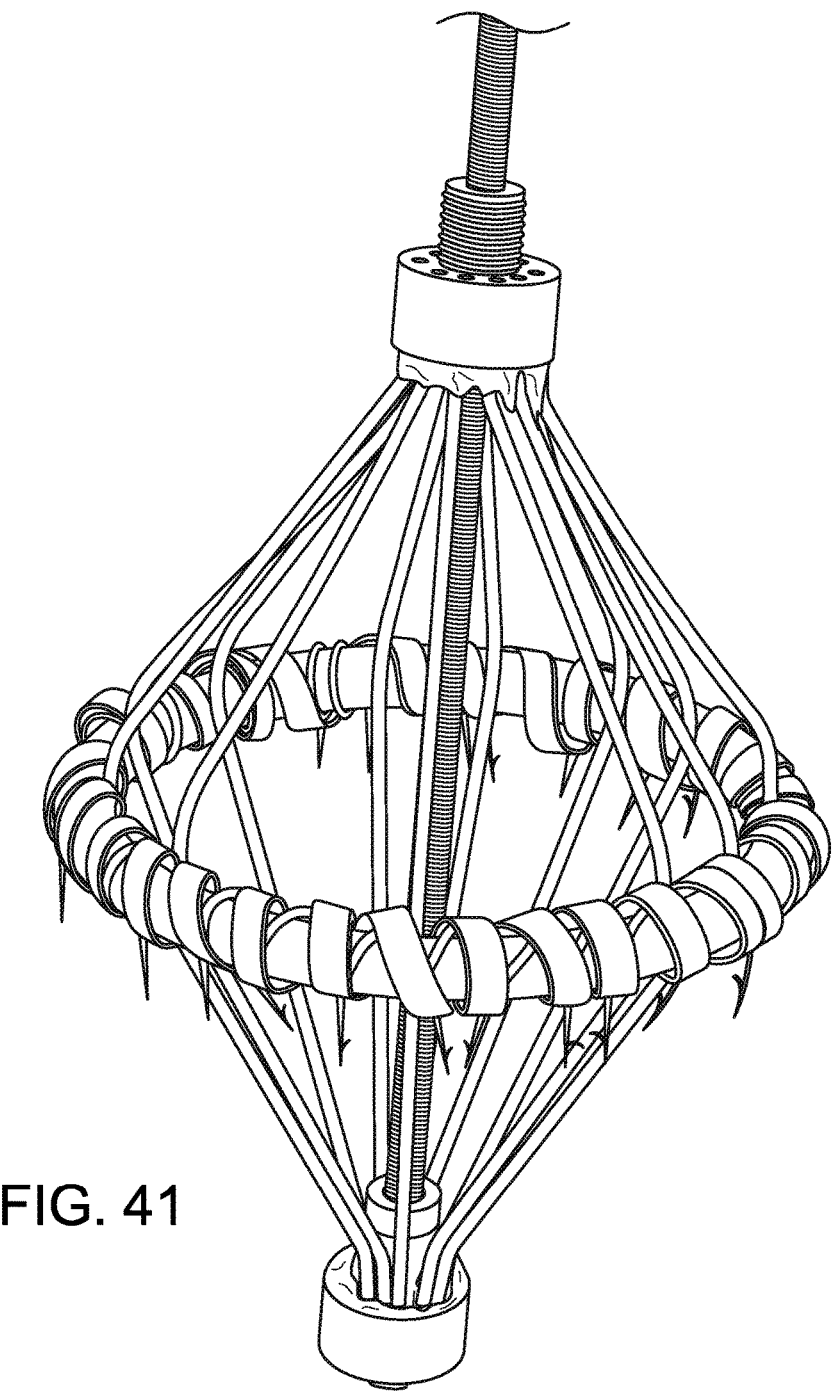
FIG. 41 shows a support mounted on an insertion tool ready for insertion.

FIG. 41 shows a support mounted on an insertion tool ready for insertion.

Figure 58:
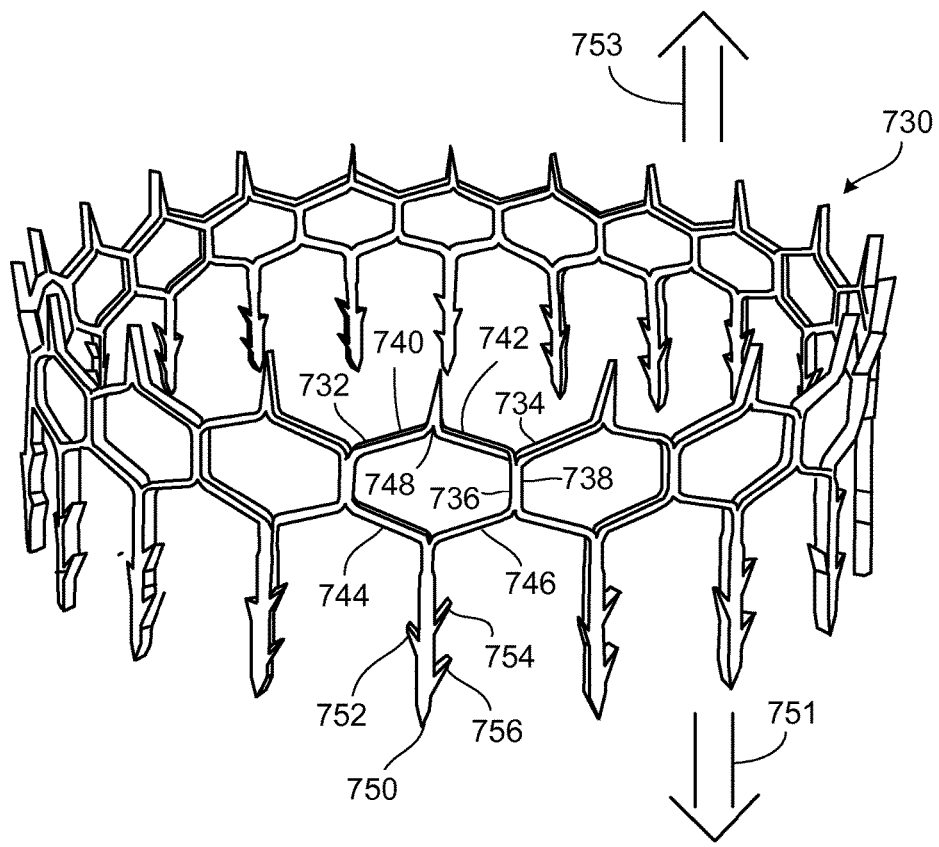
FIGS. 58 and 59 are perspective views of a support that has a ring of successive hexagonal sections.
Figure 59:
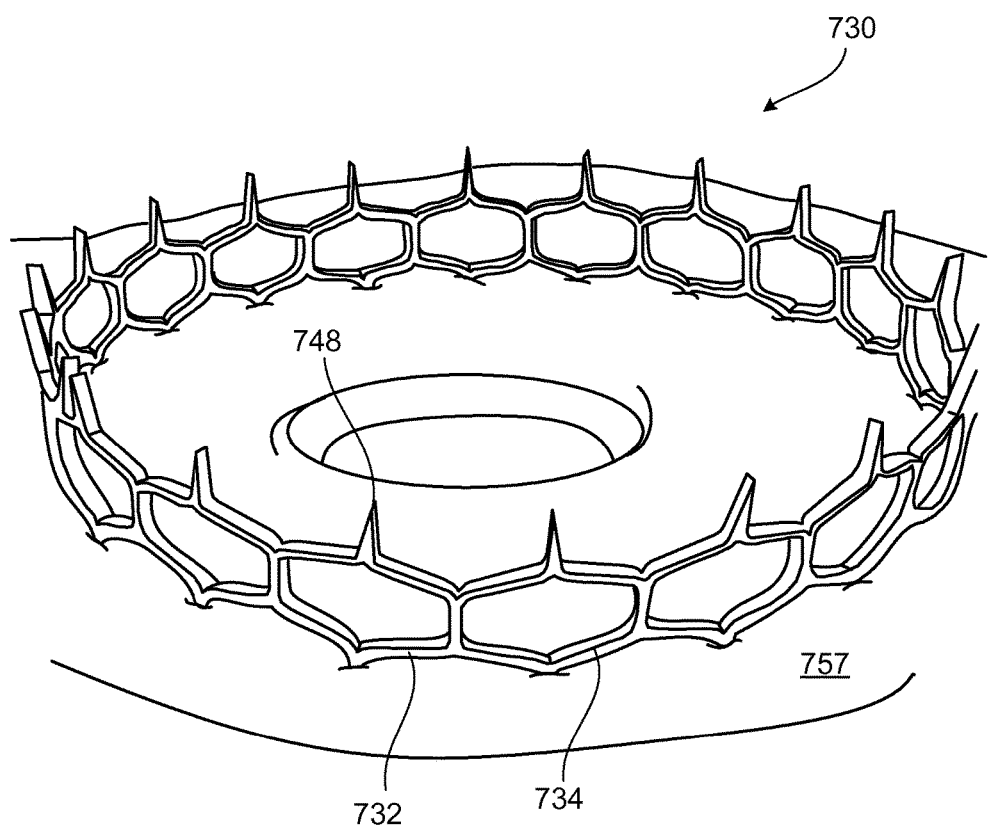

FIGS. 58 and 59 show a version 730 of the support. This version 730 has a ring of successive hexagonal sections 732, 734 touching at short edges 736, 738. At the junction of longer edges 740, 742, 744, 746 of the hexagonal sections are sharp free ends 748, 750, pointing in opposite directions. Further, on each hexagonal section, one sharp free end 750 is longer than the other sharp free end 748 and has barbs 752, 754, 756 for gripping tissue 757 that the barbed sharp free end 750 has pierced. All of the barbed sharp free ends 750 point in the same direction 751 on all of the hexagonal sections 732, 734. The other set of free ends 748 have no barbs and can further stabilize the support by piercing other adjacent tissue if any is present, lodging themselves inside and further securing the support to the tissue. All of the other free ends 748 point in the same direction 753 which is opposite the direction 751 that the barbed sharp free ends 750 point to.

This version 730 of the support is resilient and can be expanded to a delivery configuration and later will contract to a final configuration. As shown in FIGS. 60A and 61A, when the support is expanded 760 to a larger diameter 762 in a delivery configuration, e.g. by a delivery tool, each hexagonal section 732 increases in width 770 and decreases in height 772. As shown in FIGS. 60B and 61B, when the support contracts 764 to a smaller diameter 766 in a final configuration, each hexagonal section 732 decreases in width 770 and increases in height 772. In some implementations, this version 730 of the support can be made of a flexible shape memory material such as Nitinol or a biologically compatible elastomer (or other material) that is configured to contract 764 the support to the final configuration after insertion into tissue. For example, the support may be configured to contract upon a period of exposure to the temperature of the human body. In some implementations, this version 730 of the support can expand to 38.2 millimeters in diameter or more and contract to 6.5 millimeters in diameter or less.

Figure 62:
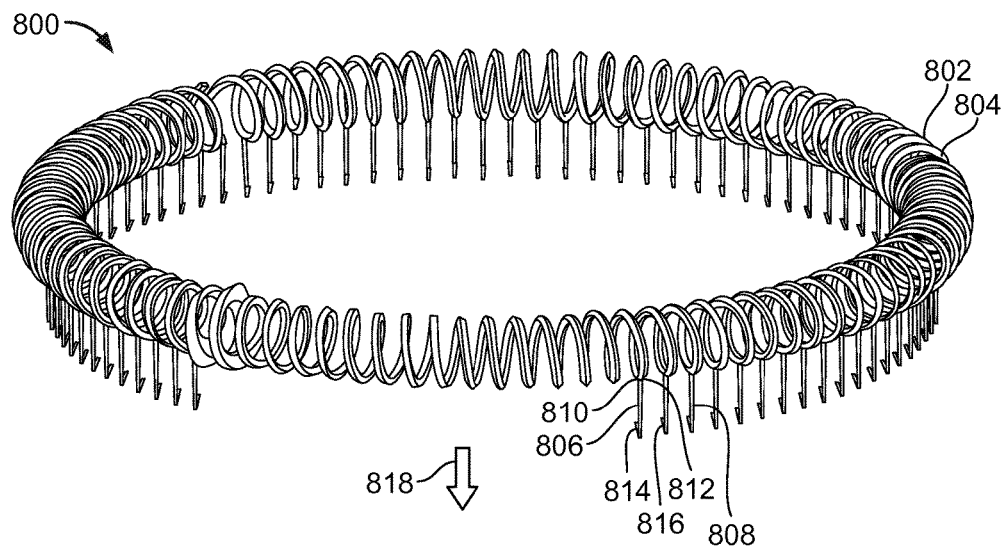
FIG. 62 shows a support that is a complete loop of round cross-section wire wrapped helically and with the helical winding looped in a torus in a configuration of successive windings.

FIG. 62 shows a support 800. Support 800 is a complete loop of round cross-section wire wrapped helically and with the helical winding looped in a torus in a configuration of successive windings 802, 804. The loop includes anchors 806, 808 each of which is bonded to a respective one of the windings 802, 804. The anchors 806, 808 are bonded at points of attachment 810, 812 such that sharp free ends 814, 816 of the anchors 806, 808 all point in the same direction 818 for piercing heart tissue and anchoring the support.

Figure 63:
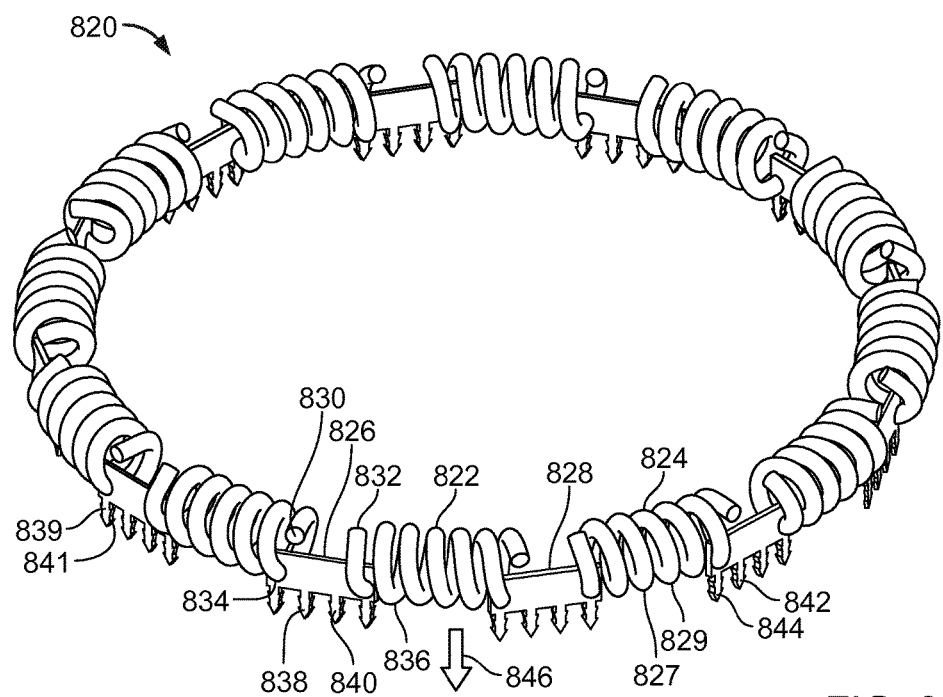
FIG. 63 shows a support having a series of helically coiled segments joined by intervening anchoring elements.

FIG. 63 shows a support 820 having a series of helically coiled segments 822, 824 joined by intervening anchoring elements 826, 828. The coiled segments 822, 824 and the anchoring elements 826, 828 alternate within the ring formation in such a way that every coiled segment joins with an anchoring element. The coiled segments 822, 824 are expandable and contractible and are made up of successive windings 827, 829 such that a single segment could have anywhere from one winding to a dozen windings or more. The anchoring elements 826, 828 can be rigid or semi-rigid relative to the coiled segments 822, 824. The ends 830, 832 of the coiled segments 822, 824 tightly fit through holes 834, 836 in the anchoring elements 826, 828 to form a secure connection between the coiled segments and the anchoring elements. The anchoring elements 826, 828 have anchors 838, 840 with sharp free ends 842, 844 all pointing in the same direction 846 for piercing heart tissue and anchoring the support. The anchors 838, 840 have two pairs of barbs 839, 841 for gripping pierced tissue. Each anchoring element 826, 828 could have as few as one anchor or as many as several dozen. The anchoring elements 826, 828 could be flat, round, or another shape, and are made of a biologically-compatible material such as a metal, a flexible or semi-flexible material such as Nitinol, or another material. Generally, a support may be easier and cheaper to manufacture if it uses dedicated anchoring elements as a platform to bear the anchors, rather than attaching anchors directly to other elements of the support such as the flexible coiled segments. For example, the anchors may be easier to attach to anchoring elements, or the anchoring elements could be manufactured separately from other elements like the coiled segments.

Figure 64A:
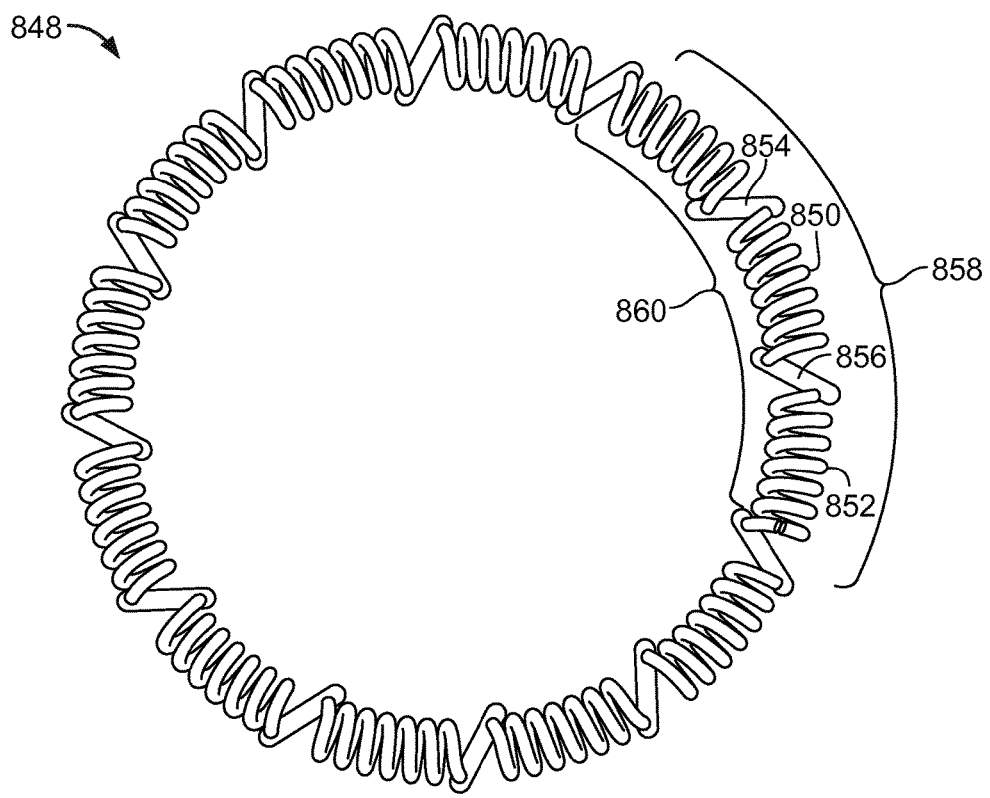
FIGS. 64A through 64D show a support having coiled segments joined in a ring formation by connecting elements.
Figure 64B:
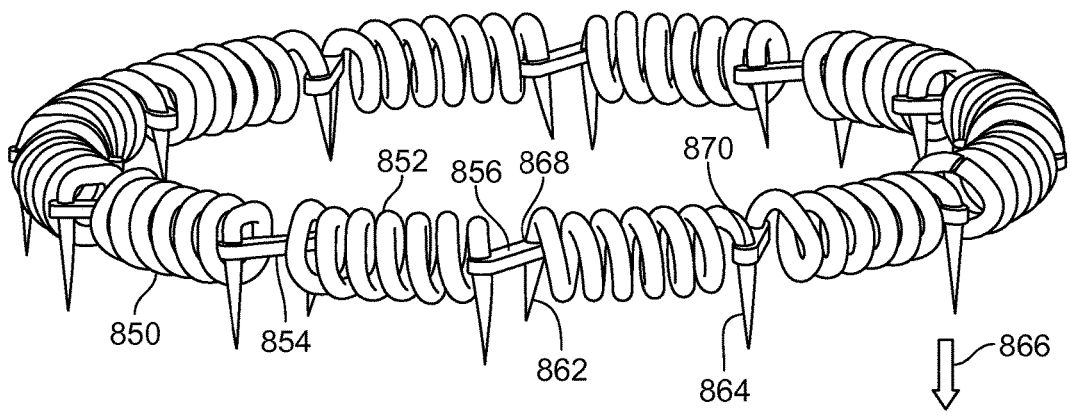

FIGS. 64A through 64D show a support 848 having coiled segments 850, 852 joined in a ring formation by connecting elements 854, 856. Both ends of each of the coiled segments 850, 852 terminate in sharp free ends 862, 864 all pointing in the same direction 866 for piercing heart tissue and anchoring the support. The free ends 862, 864 of the coiled segments fit tightly through holes 868, 870 in the connecting elements 854, 856 to form a secure connection between the coiled segments and the connecting elements. The coiled segments 850, 852 and the connecting elements 854, 856 alternate within the ring formation in such a way that every coiled segment joins with a connecting element. In some implementations, as shown in FIGS. 64A and 64B, each of the connecting elements 854, 856 joins a free end 864, of one of the coils. oriented at the outer edge 858 of the ring to a free end 862, of the next one of the coils, oriented at the inner edge 860 of the ring.

Figure 64C:
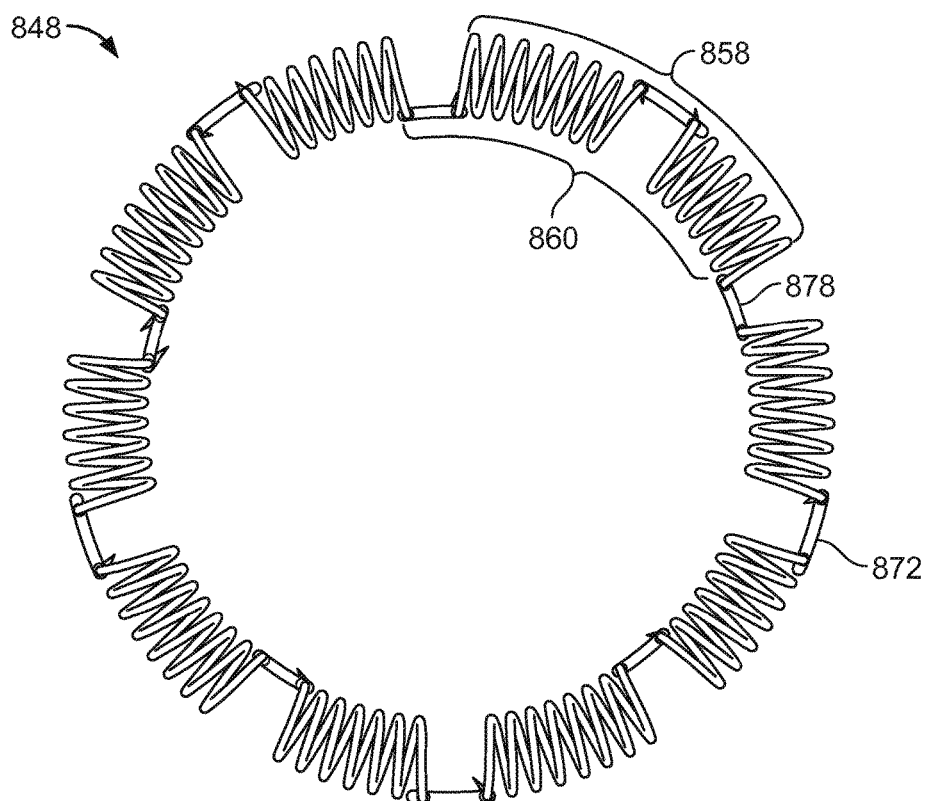
Figure 64D:
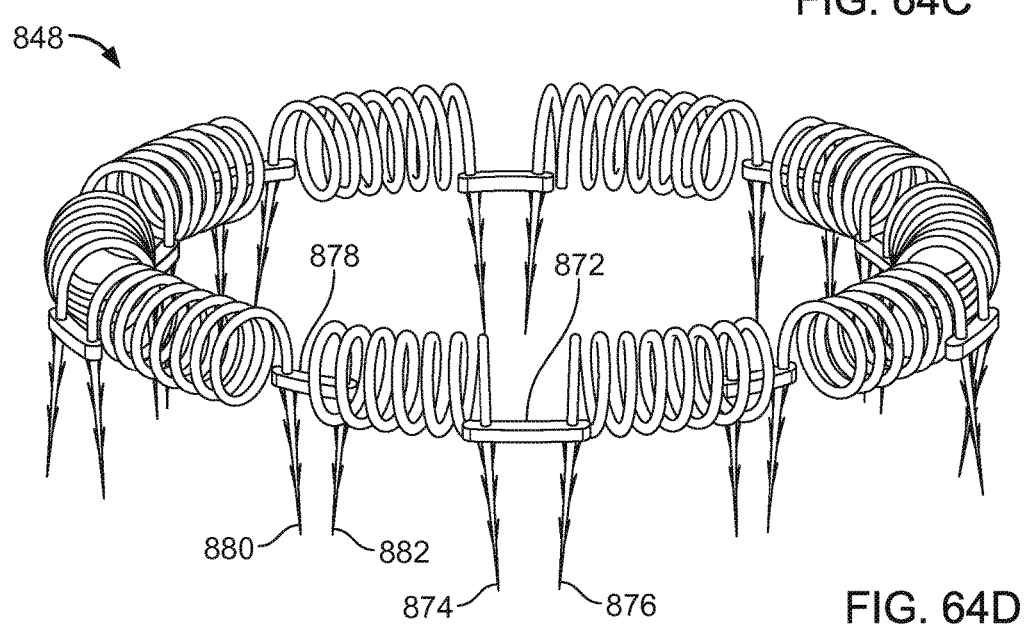

As shown in FIGS. 64C and 64D, in some implementations, some connecting elements 872 are arranged to join ends 874, 876 both oriented at the outer edge 858 of the ring and some connecting elements 878 arranged to join ends 880, 882 both oriented at the inner edge 860 of the ring. A combination of the arrangements of FIGS. 64A and 64C would also be possible.

Figure 65:
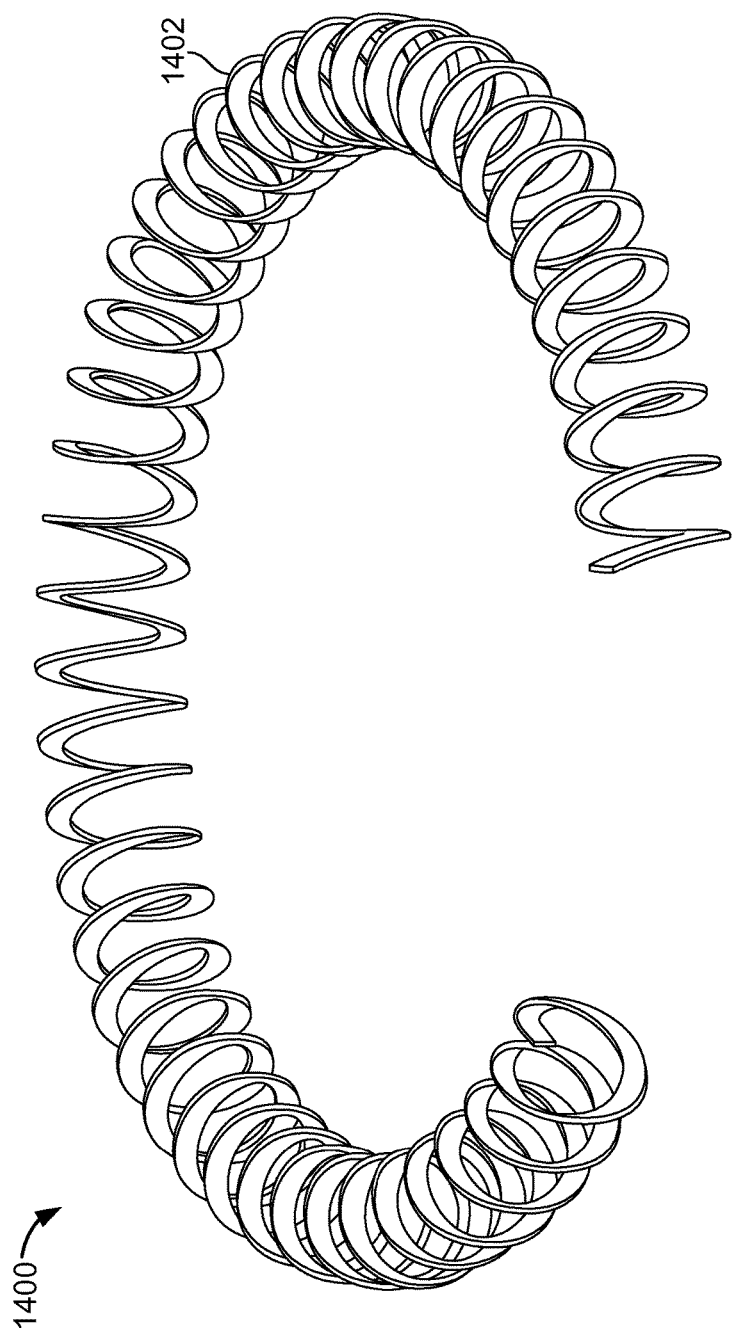
FIG. 65 shows a support made of a single continuous coil of flat wire.
Figure 66A:
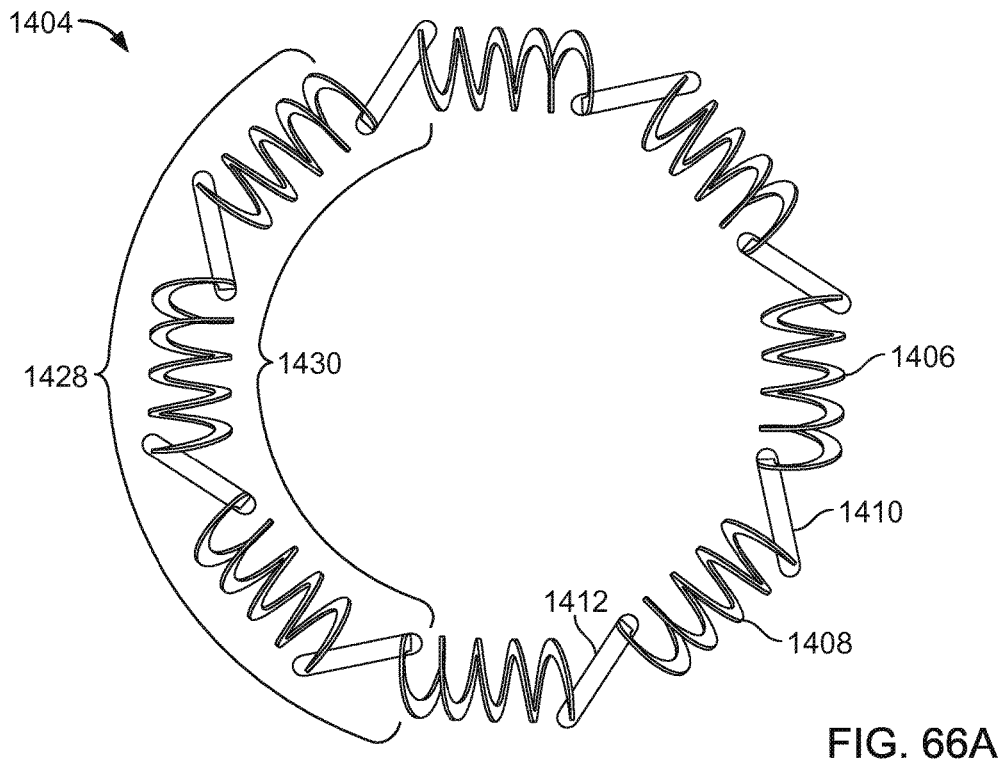
FIGS. 66A and 66B show a support having coiled segments made of flat wire joined in a ring formation by connecting elements.
Figure 66B:
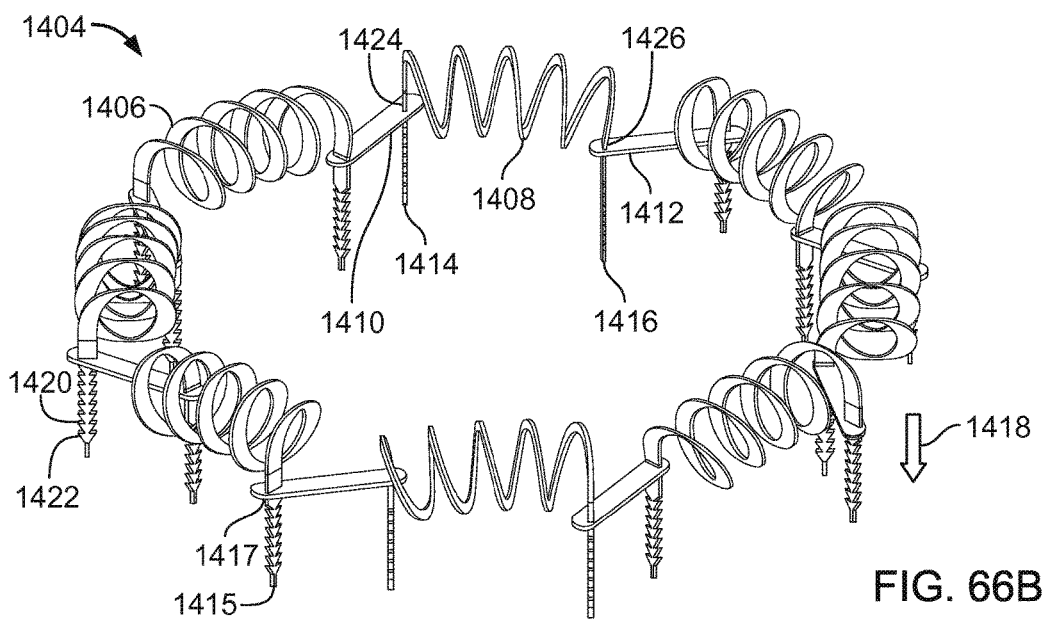

FIG. 65 shows a support 1400 made of a single continuous coil of flat wire 1402. Flat wire 1402 can be used in applications where other types of wire are not desirable or less desirable. For example, flat wire 1402 may provide advantages in manufacturing the support or attaching anchors or hooks. FIGS. 66A and 66B show a support 1404 having coiled segments 1406, 1408 made of flat wire joined in a ring formation by connecting elements 1410, 1412. The coiled segments 1406, 1408 terminate in sharp free ends 1414, 1416 all pointing in the same direction 1418 for piercing heart tissue and anchoring the support. The free ends 1414, 1416 have barbs 1420, 1422 for gripping pierced heart tissue. The barbs are in the form of multiple pairs that line the free ends 1414, 1416 from the tip 1415 to the point of attachment 1417 with the respective connecting element. The free ends 1414, 1416 of the coiled segments 1406, 1408 fit tightly through holes 1424, 1426 in the connecting elements 1410, 1412 to form a secure connection between the coiled segments and the connecting elements. In some implementations, the coiled segments 1406, 1408 and the connecting elements 1410, 1412 alternate within the ring formation in such a way that every coiled segment joins with a connecting element. For example, the connecting elements 1410, 1412 can be arranged to join a free end 1414 oriented at the outer edge 1428 of the ring to a free end 1416 oriented at the inner edge 1430 of the ring. Other arrangements of the coiled segments 1406, 1408 and connecting elements 1410, 1412 are possible.

Figure 67A:
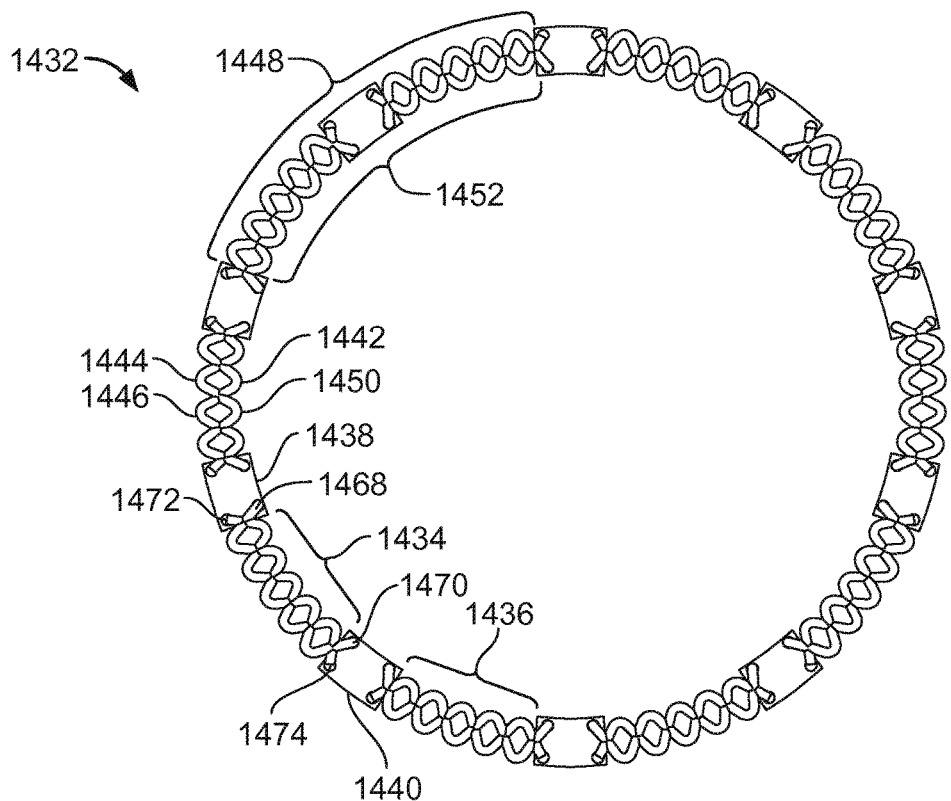
FIGS. 67A and 67B show a relatively flat support having doubled flat sinusoidal segments joined in a ring formation by connecting elements.
Figure 67B:
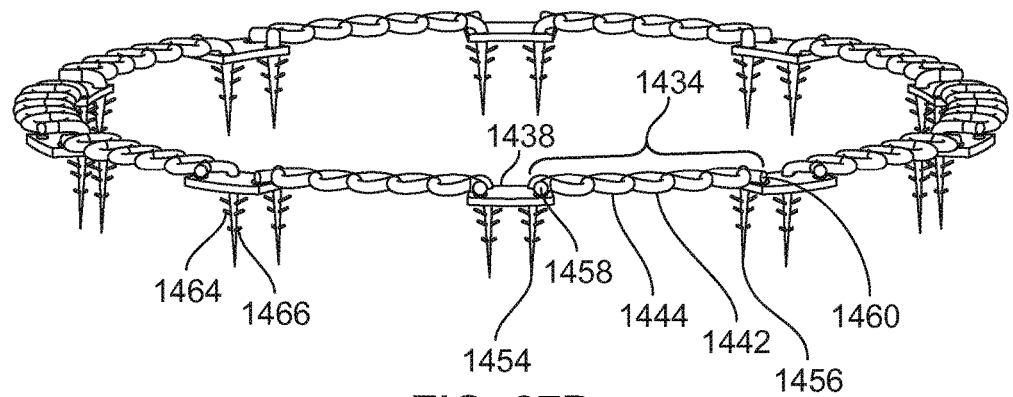

FIGS. 67A and 67B show a relatively flat support 1432 having doubled flat sinusoidal segments 1434, 1436 joined in a ring formation by connecting elements 1438, 1440. In use, this support 1432 sits flat against heart tissue. The doubled sinusoidal segments 1434, 1436 and the connecting elements 1438, 1440 alternate within the ring formation in such a way that every doubled sinusoidal segment joins with a connecting element. The connecting elements 1438, 1440 can be rigid or semi-rigid relative to the doubled sinusoidal segments 1434, 1436. The doubled sinusoidal segments 1434, 1436 are expandable and contractible and are each made of two sinusoidal wires 1442, 1444.

The peaks and valleys of the sinusoid of the first sinusoidal wire 1442 are inverted relative to the peaks and valleys for the second sinusoidal wire 1444 such that a peak 1446 of the first sinusoidal wire 1442 oriented toward the outer edge 1448 of the ring formation is positioned opposite a peak 1450 of the second sinusoidal wire 1444 oriented toward the inner edge 1452 of the ring formation. One sinusoidal wire 1442 in each double sinusoidal segment 1432 terminates in sharp free ends 1454, 1456 all pointing in the same direction 1462 for piercing heart tissue and anchoring the support. The sharp free ends 1454, 1456 have barbs 1464, 1466 for gripping pierced heart tissue. One sinusoidal wire 1444 in each double sinusoidal segment 1434 terminates in flat free ends 1458, 1460, which do not aid in piercing the heart tissue. In some configurations, both sinusoidal wires 1442, 1444 terminate in sharp free ends. The sharp free ends 1454, 1456 and flat free ends 1458, 1460 of the sinusoidal wires 1442, 1444 fit tightly through holes 1468, 1470, 1472, 1474 in the connecting elements 1438, 1440 to form a secure connection between the double sinusoidal segments 1434, 1436 and the connecting elements.

Figure 68:
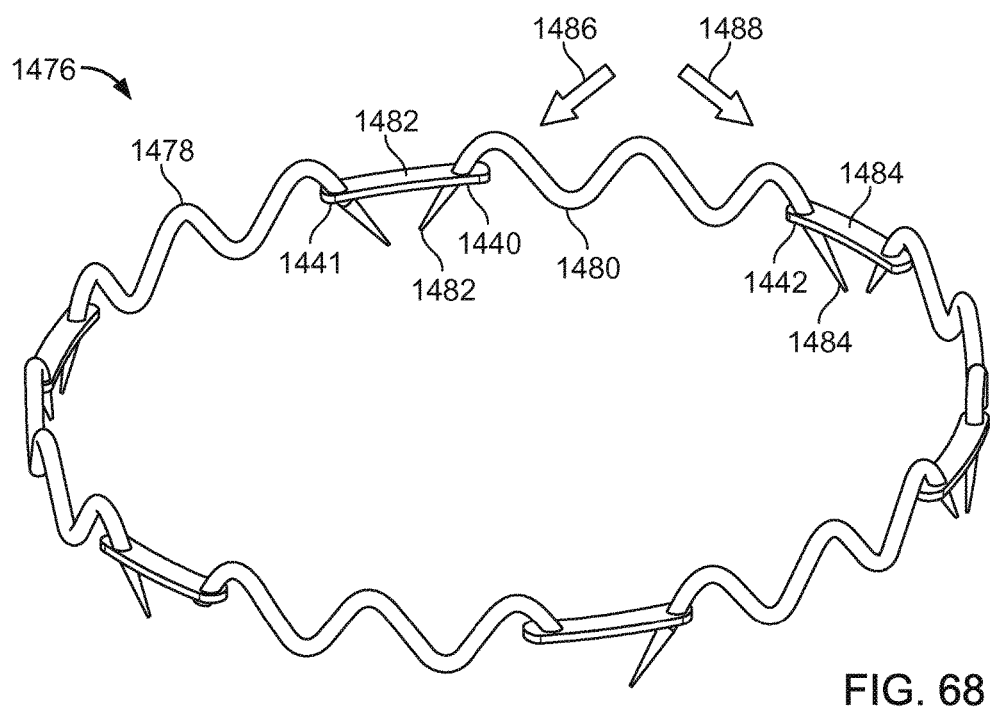
FIG. 68 shows a support having sinusoidal segments joined in a ring formation by connecting elements.

FIG. 68 shows a support 1476 having sinusoidal segments 1478, 1480 joined in a ring formation by connecting elements 1482, 1484. The sinusoidal segments 1478, 1480 and the connecting elements 1482, 1484 alternate within the ring formation in such a way that every pair of sinusoidal segments are joined by a connecting element. The connecting elements 1482, 1484 can be rigid or semi-rigid relative to the double sinusoidal segments 1478, 1480. The sinusoidal segments 1478, 1480 are expandable and contractible and terminate in sharp free ends 1482, 1484 for piercing heart tissue and anchoring the support. One sharp free end 1482 on each sinusoidal segment 1478, 1480 points in one direction 1486, and the other sharp free end 1484 points in another direction 1488. The sharp free ends 1482, 1484 fit tightly through holes 1490, 1492 in the connecting elements 1482, 1484 to form a secure connection 1491 between the sinusoidal segments and the connecting elements.

Figure 69A:
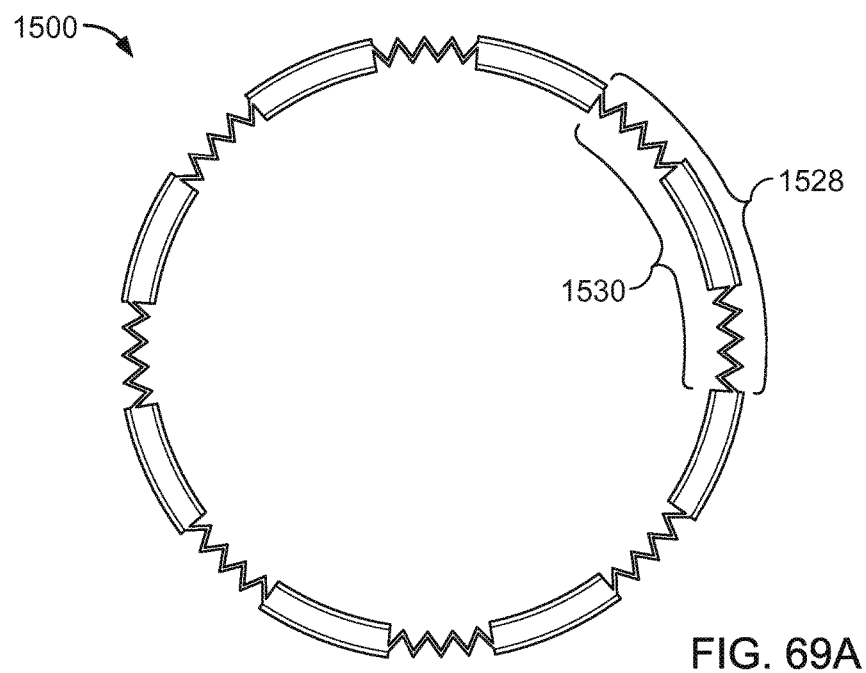
FIGS. 69A and 69B show a support having crimped segments joined in a ring formation by anchoring elements.
Figure 69B:
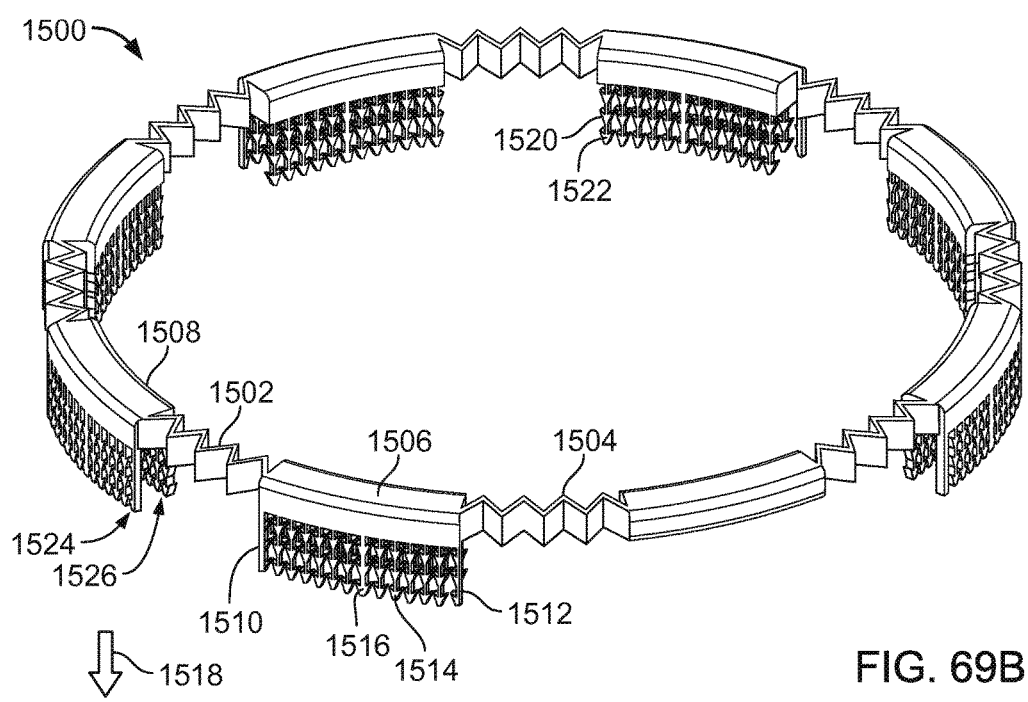

FIGS. 69A and 69B show a support 1500 having crimped segments 1502, 1504 joined in a ring formation by anchoring elements 1506, 1508. The accordion-crimped flat-metal segments 1502, 1504 and the anchoring elements 1506, 1508 alternate within the ring formation in such a way that successive crimped segments are joined by an anchoring element. The crimped segments 1502, 1504 and the anchoring elements 1506, 1508 can be joined by welding or bonding, for example, or the entire support could be formed from a single piece of material. The crimped segments 1502, 1504 can be made of a metal, e.g. stainless steel or another biologically compatible material, and can expand and collapse and the anchoring elements 1506, 1508 can be rigid or semi-rigid relative to the crimped segments 1502, 1504. The anchoring elements 1506, 1508 have two parallel rows of evenly spaced anchors 1510, 1512 with arrow-shaped free ends 1514, 1516 all pointing in the same direction 1518 for piercing heart tissue and anchoring the support. The anchors 1510, 1512 have barbs 1520, 1522 for gripping pierced heart tissue. Each anchoring element 1506, 1508 could have as few as one anchor or as many as several dozen. The anchors 1510, 1512 can be arranged in one or more rows 1524, 1526, for example, one row 1524 lined up along the outer edge 1528 of the ring formation and one row 1526 lined up along the inner edge 1530 of the ring formation.

Figure 70:
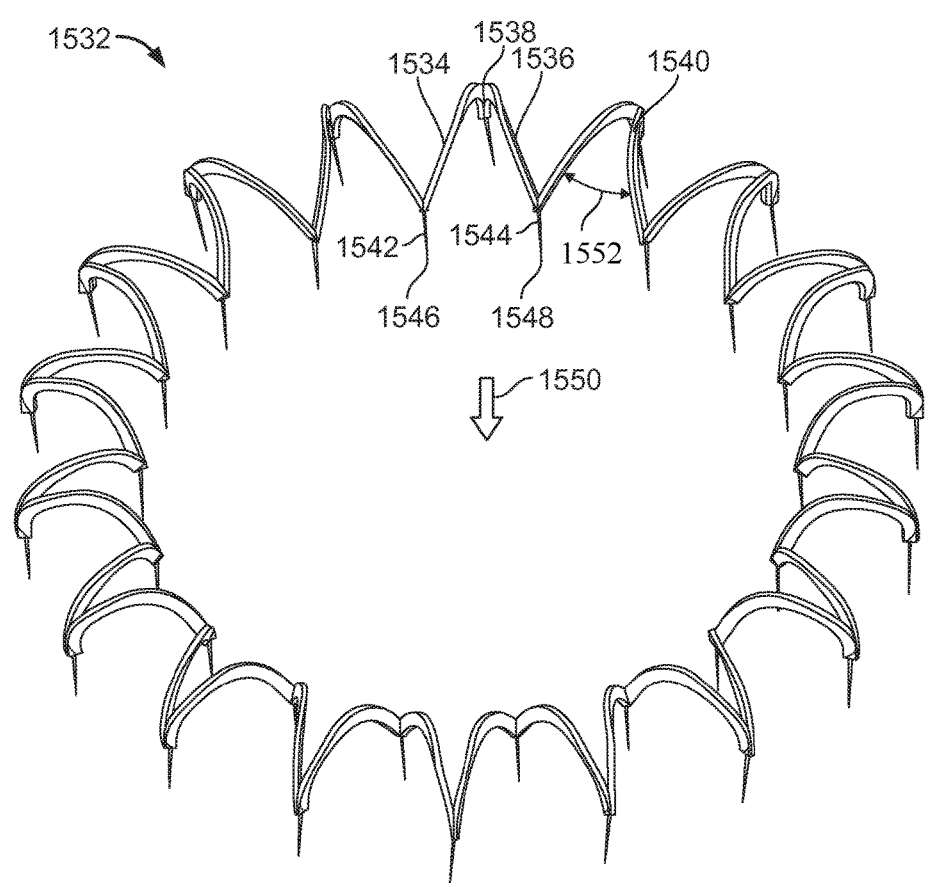
FIG. 70 shows a support having segments joined in a ring formation.

FIG. 70 shows a support 1532 having arc segments 1534, 1536 joined in a ring formation. The arc segments 1534, 1536 are welded or bonded at junctions 1538, 1540 bearing anchors 1542, 1544 with sharp free ends 1546, 1548 all pointing in the same direction 1550 for piercing heart tissue and anchoring the support. Further, the angle 1552 of the junctions 1538, 1540 between the arc segments 1534, 1536 is variable, allowing the support to expand and contract. For example, when the angle 1552 is reduced, the support contracts (e.g. by a delivery tool for a delivery configuration), and when the angle 1552 is increased, the support expands. The arc segments 1534, 1536 could be made of wire or cut from coils of a spring, for example.

Figure 71:
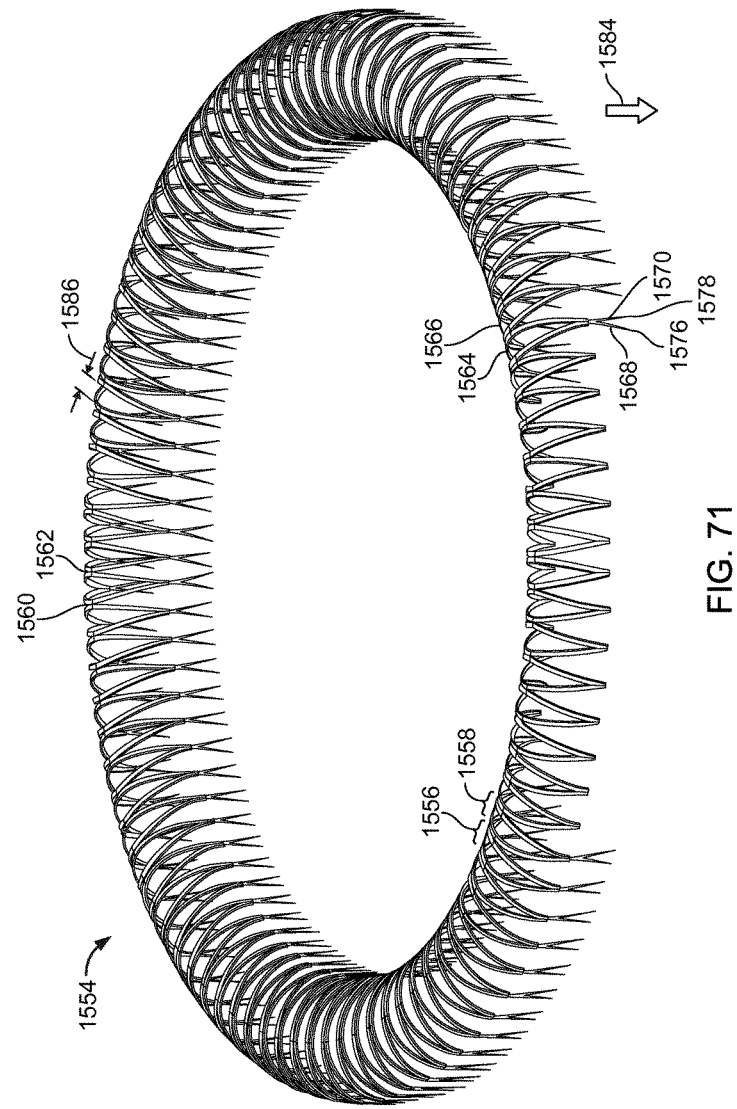
FIG. 71 shows a support having doubled segments joined at junctions in a ring formation.

FIG. 71 shows a support 1554 having doubled arc segments 1556, 1558 joined at junctions 1560, 1562 in a ring formation. The doubled arc segments 1556, 1558 have a pair of joined single are segments 1564, 1566 each terminating in anchors 1568, 1570 with sharp free ends 1576, 1578 all pointing in the same direction 1584 for piercing heart tissue and anchoring the support. Further, the separation distance 1586 of the single arc segments 1564, 1566 is variable, allowing the support to expand and contract. For example, when the separation distance 1586 is reduced, the support contracts (e.g. by a delivery tool for a delivery configuration), and when the separation distance 1586 is increased, the support expands. The single arc segments 1564, 1566 could be made of wire or cut from coils of a spring, for example.

Figure 72:
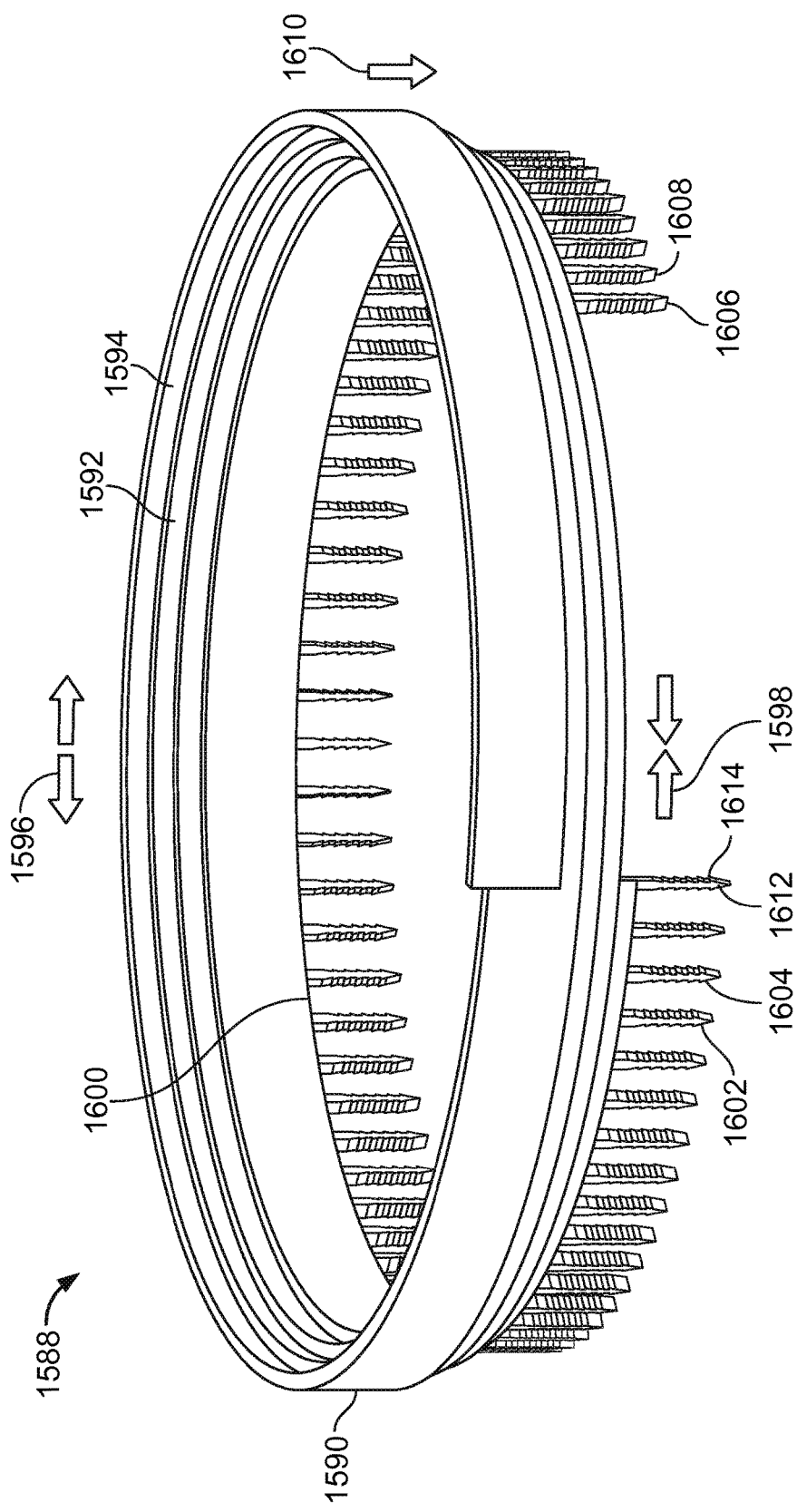
FIG. 72 shows a support having a metal ribbon coiled into a ring.

FIG. 72 shows a support 1588 having a metal ribbon 1590 coiled into a ring. The metal ribbon 1590 can be wrapped onto itself to form multiple overlapping layers 1592, 1594. When the support expands, the layers 1592, 1594 slide 1596 apart relative to each other, and when the support contracts, the overlaps 1592, 1594 slide 1598 together relative to each other. One edge 1600 of the metal ribbon 1590 bears anchors 1602, 1604 with sharp free ends 1606, 1608 all pointing in the same direction 1610 for piercing heart tissue and anchoring the support. The anchors 1602, 1604 also have barbs 1612, 1614 for gripping heart tissue. The anchors 1602, 1604 can be attached to the metal ribbon 1590 using one of several methods such as welding or bonding, for example, or they could be formed or cut directly from the metal ribbon 1590, for example.

Figure 73A:
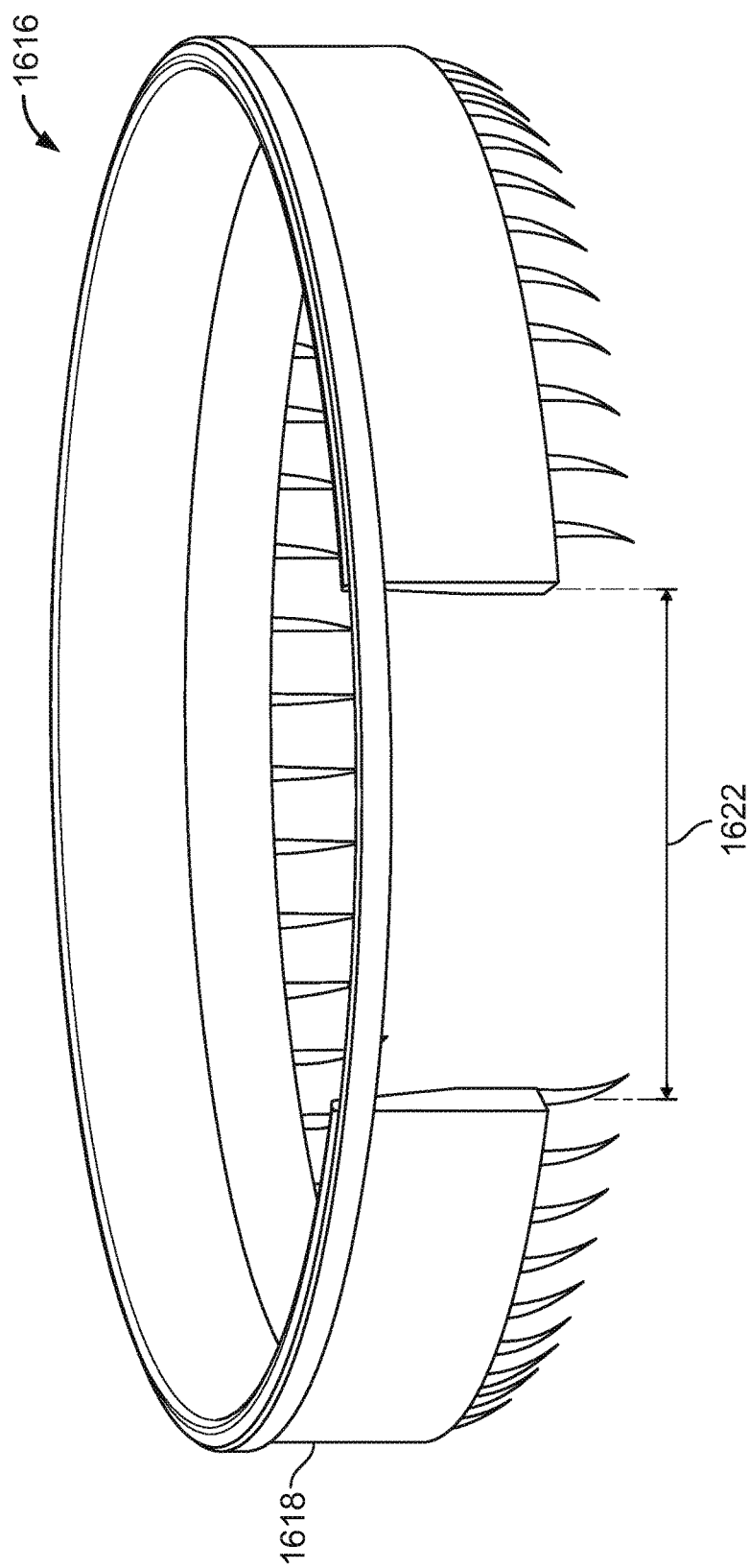
FIGS. 73A and 73B show a support having a c-shaped ring.
Figure 73B:
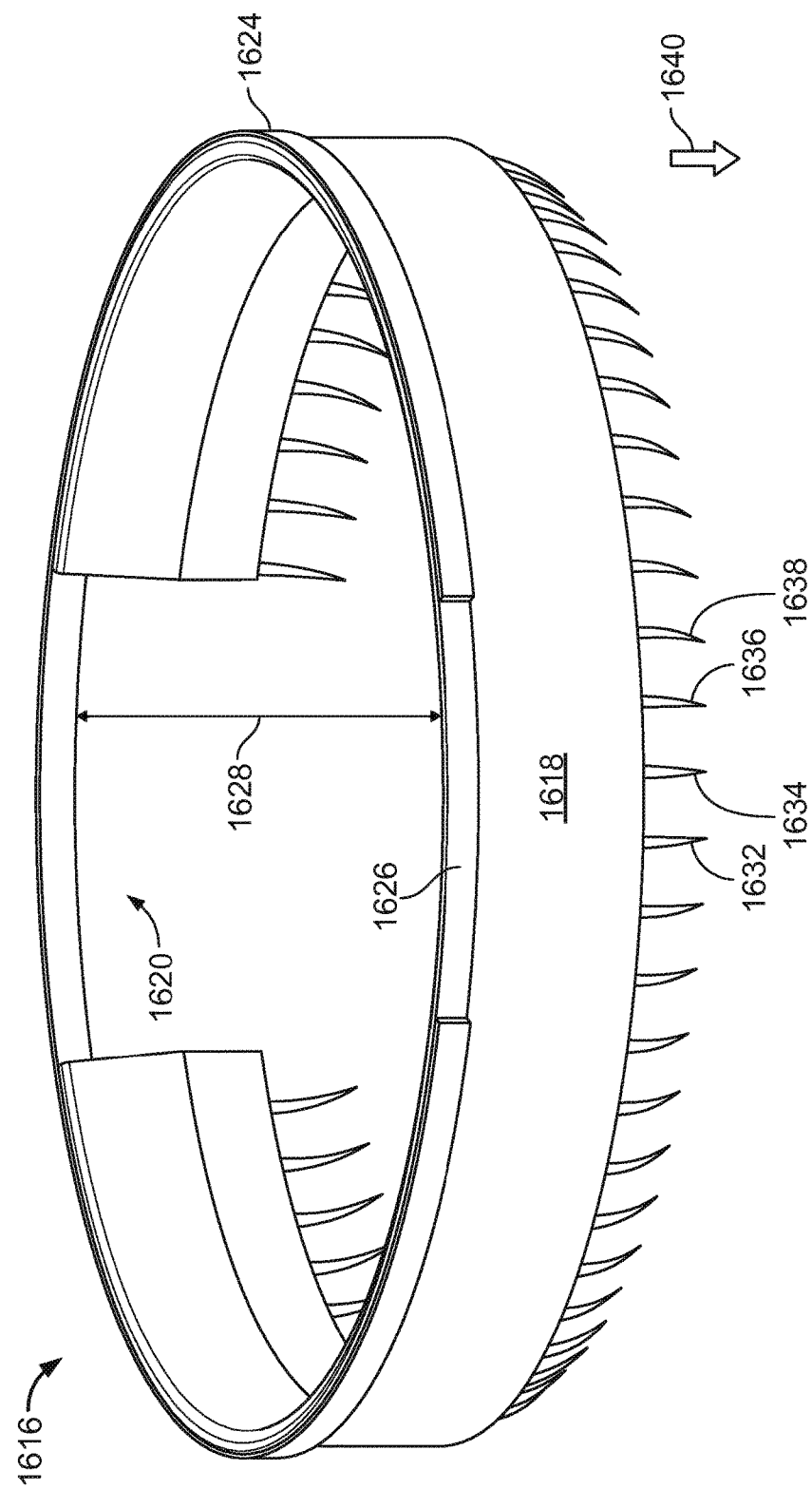

FIGS. 73A and 73B show a support 1616 having a c-shaped ring 1618. The c-shaped coil 1618 has a gap 1620 that allows the support to expand and contract. When the support expands, the gap 1620 increases in width 1622, and when the support contracts, the gap 1620 decreases in width 1622. The c-shaped coil 1618 is supported by an attached secondary ring 1624, which also has a gap 1626 positioned across the diameter 1628 from the gap 1620 of the c-shaped coil 1618. The secondary ring 1624 assists in maintaining the ring shape of the support by attenuating any physical distortion when the support expands and contracts. The c-shaped coil 1618 bears anchors 1632, 1634 all pointing in the same direction 1640 for piercing heart tissue and anchoring the support with sharp free ends 1636, 1638 curved slightly inward relative to the c-shaped coil 1618. The anchors 1632, 1634 can be attached to the c-shaped coil 1618 using one of several methods such as welding or bonding, for example, or they could be formed or cut directly from the c-shaped coil 1618, for example.

The slight curve of the free ends 1636, 1638 resists forces that pull on the support when the anchors 1632, 1634 are embedded in annular tissue. Some or all of the anchors 1632, 1634 could also have barbs, just as the barbed anchors shown on some of the other supports herein (e.g. the supports in FIGS. 62-72) could also have curved ends. If desired, any straight anchor could be bent to form a curve. Although the free ends 1636, 1638 shown in FIGS. 73A and 73B all curve inward, some or all of the free ends could also curve outward, to the side, have multiple curves, or have any combination of these curve configurations.

Figure 74:
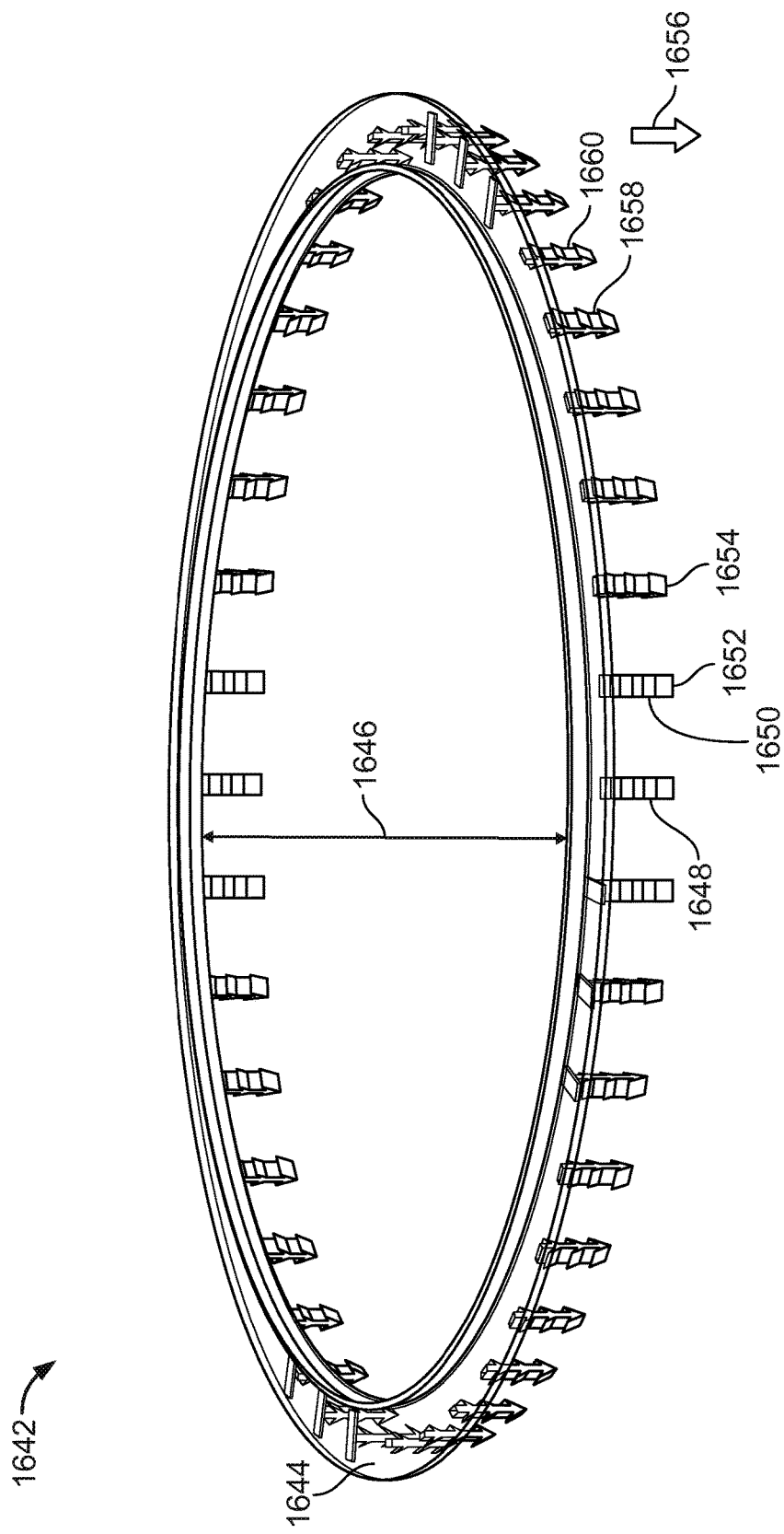
FIG. 74 shows a support having an elastic polymer flat ring.

FIG. 74 shows a support 1642 having an elastic polymer flat ring 1644. In use, this support 1642 sits flat against heart tissue. The elastic polymer flat ring 1644 is elastic enough to allow expansion during insertion (e.g. by an insertion tool) and is stiff enough to support a heart valve annulus after implantation. If desired, the support 1642 can also be folded during delivery, e.g., folded in half along the diameter 1646 of the support. The elastic polymer flat ring 1644 bears anchors 1648, 1650 with sharp free ends 1652, 1654 all pointing in the same direction 1656 for piercing heart tissue and anchoring the support. The anchors 1648, 1650 also have barbs 1658, 1660 for gripping heart tissue.

The supports shown in FIGS. 62-74 could be used with any of the implementations of the delivery tool shown throughout this description, including the delivery tool 200 shown in FIG. 1A, the delivery tool 200a shown in FIG. 6A, the delivery tool 200b shown in FIG. 11A, and the insertion tools shown in FIGS. 36-44, as well as other implementations of the delivery tool, for example. In general, the support chosen does not necessarily limit the choice of delivery tool. The variations of the support insertion process, such as the variations shown in FIGS. 1A-1D, FIGS. 8A-8I, and FIGS. 13A-13D, are not necessarily limited to any combination of support and delivery tool.

Figure 75B:
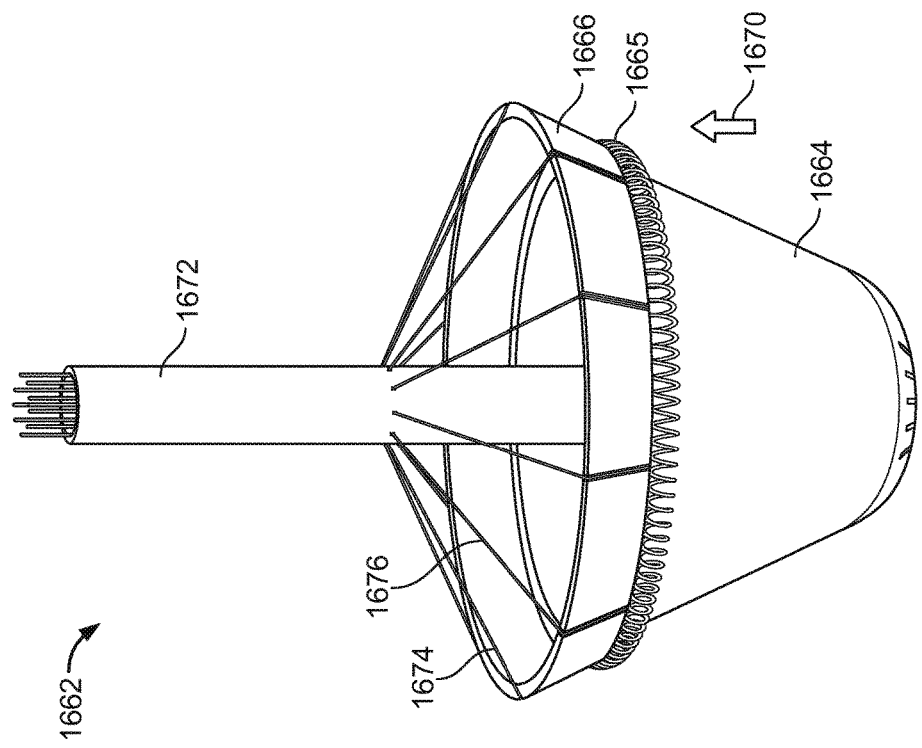
FIGS. 75A through 75D show a delivery tool having a continuous cone forming the portion of the tool for delivering a support.
Figure 75A:
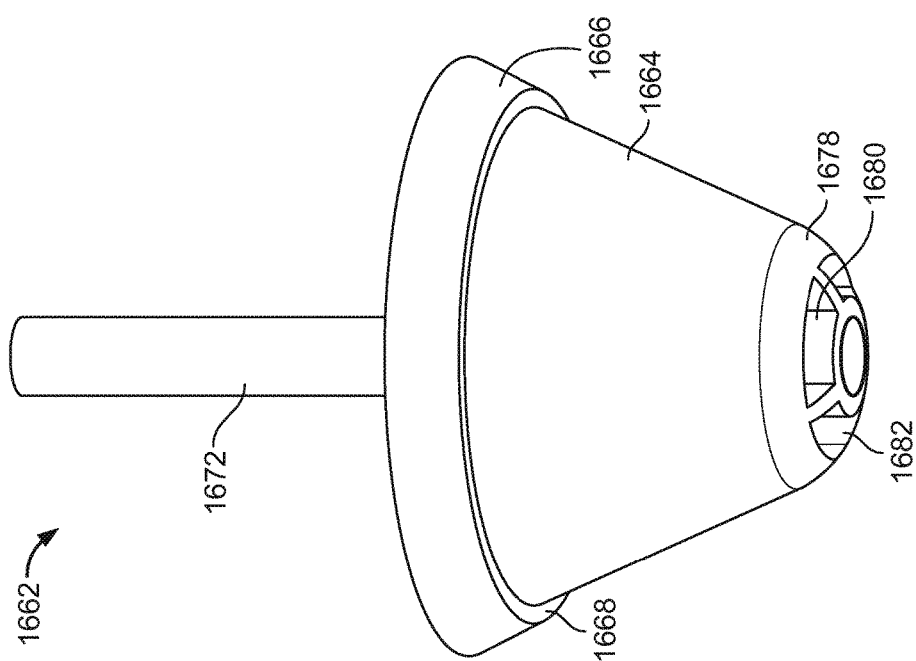
Figure 75D:
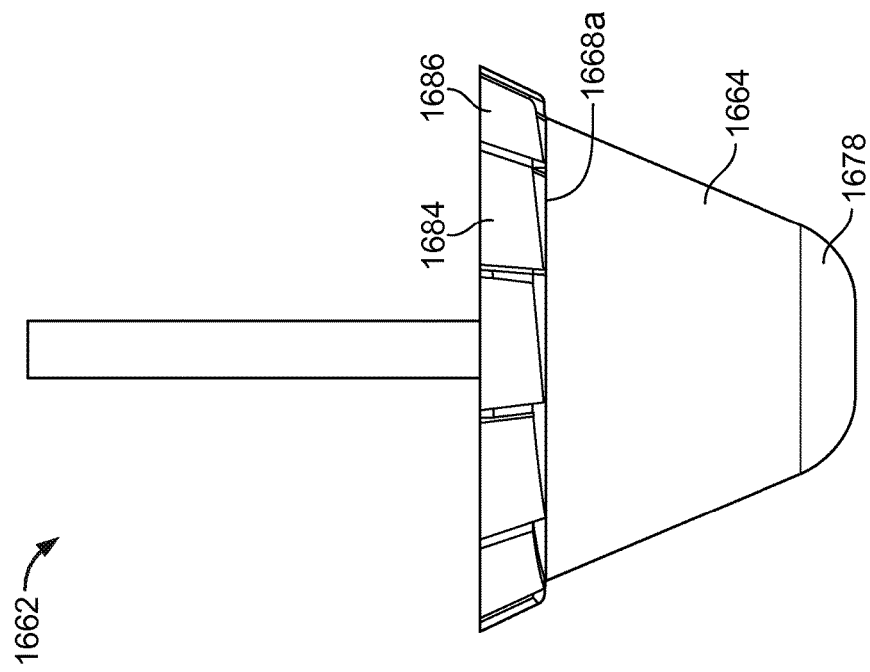
Figure 75C:
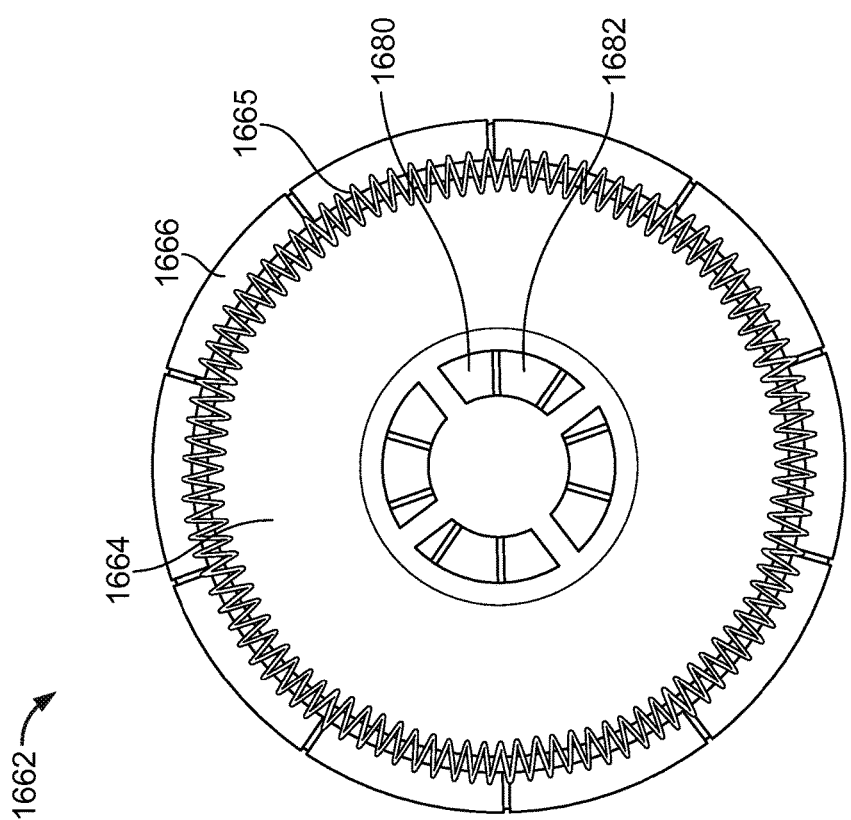

FIGS. 75A through 75D show a delivery tool 1662 having a continuous cone 1664 forming the portion of the tool for delivering a support 1665. The cone 1664 is made of a material such as rubber or a flexible polymer that allows it to expand and contract and slide smoothly against a heart valve annulus. The cone 1664 has an upper flange 1666 providing a shelf 1668 against which the support 1665 can securely rest. When the support 1665 is being delivered, the upward force 1670 upon the support by the annulus (not shown) is countered by the shelf 1668 of the upper flange 1666. This delivery tool 1662 also has a shaft 1672 that connects to the cone 1664 by several splaying projections 1674, 1676 that spread apart away from the shaft 1672 when the delivery tool expands and pull together toward the shaft 1672 when the delivery tool contracts. The head 1678 of this delivery tool 1662 has one or more openings 1680, 1682 allowing blood to flow past the delivery tool so as to not impede blood flow through the annulus. In some implementations of the delivery tool 1662, as shown in FIG. 75D, the upper flange 1666 is divided into angled or shaped segments 1684, 1686. The angled or shaped segments 1684, 1686 form a jagged shelf 1668a. The jagged configuration of the shelf 1668a allows portions of the support 1665 to shift slightly during delivery, which allows anchors, hooks, or grippers of the support to attach to heart tissue at slightly different angles relative to each other.

Figure 76C:
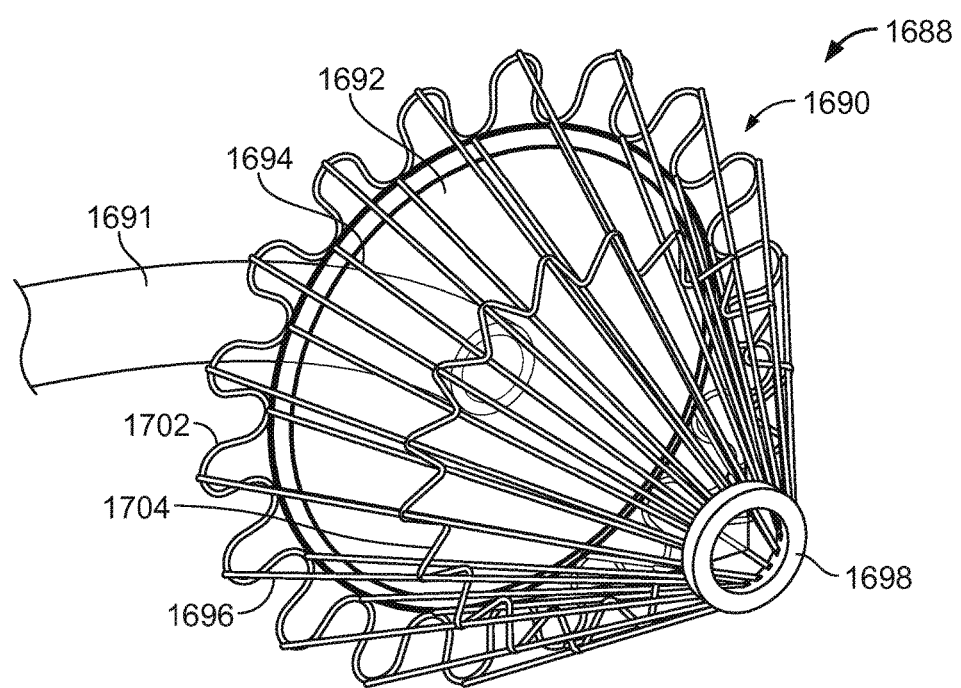

FIGS. 76A through 76C show a delivery tool 1688 having a cone-shaped wire cage 1690 enclosing a balloon 1692. The wire cage 1690 is expandable and contractible. When the balloon 1692 inflates with air, the force of the balloon against the wire cage 1690 causes the wire cage to expand. Air flows through a shaft 1691, which is surrounded by the balloon 1692. The wire cage 1690 has splaying projections 1694, 1696 extending from attachment points 1695, 1697 at a base ring 1698 up to attachment points 1699, 1701 at a top sinusoidal ring 1702. The splaying projections 1694, 1696 spread apart away from the balloon 1692 when the balloon expands and pull together toward the balloon when the balloon contracts. The splaying projections 1694, 1696 also attach to an intermediate sinusoidal ring 1704 located on the wire cage 1690 halfway between the base ring 1698 and the top sinusoidal ring 1702. Because the splaying projections 1694, 1696 attach at different points 1695, 1697 on the sinusoidal rings, some of the splaying projections 1694 are positioned to contact the balloon 1692, while the other splaying projections 1696 are positioned away from the balloon 1692 and are instead positioned to contact annular tissue (not shown) during a support ring delivery procedure.

The other, outer splaying projections 1696 form an outer edge 1706 of the delivery tool. The configuration provides a gap 1708 between the balloon 1692 and the outer edge 1706, and during a delivery procedure, blood can flow through the gap 1708 unimpeded by the balloon 1692. For example, in some implementations of the delivery tool 1668, the maximum diameter 1710 of the balloon 1692 is 28 millimeters, and the maximum diameter 1712 of the outer edge 1706 of the delivery tool is 35 millimeters. In this example, blood can flow through the gap 1708 at a rate similar to the rate of blood flow through a heart valve having a 21 millimeter flow area.

FIGS. 77A and 77B show another delivery tool 1714. This delivery tool 1714 has splaying projections 1722, 1724 spanning an upper ring 1716 and a base ring 1718 arranged around a shaft 1720. An annular support ring (not shown) can be placed over the splaying projections 1722, 1724 for delivery. The splaying projections 1722, 1724 each have a point of attachment 1726 at the upper ring 1716 and another point of attachment 1728 at the base ring 1718. The splaying projections 1722, 1724 spread apart away from the shaft 1720 in an expanded configuration and pull together toward the shaft 1720 in a contracted configuration. The upper ring 1716 and base ring 1718 have slots 1717, 1719 allowing the splaying projections 1722, 1724 to articulate at the points of attachment 1726, 1728. In a collapsed configuration, as shown in FIG. 77A, the splaying projections 1722, 1724 lie flat against the shaft 1720. In an expanded configuration for delivering an annular support ring, as shown in FIG. 77B, the upper ring 1716 slides 1730 down along the shaft 1720 toward the base ring 1718, causing the splaying projections 1722, 1724 to bend at an angle 1732. The angle 1732 begins at 180 degrees in the collapsed configuration and can decrease to less than 90 degrees in the expanded configuration. For example, in FIG. 77B, the angle 1732 is about 60 degrees.

Figure 78:
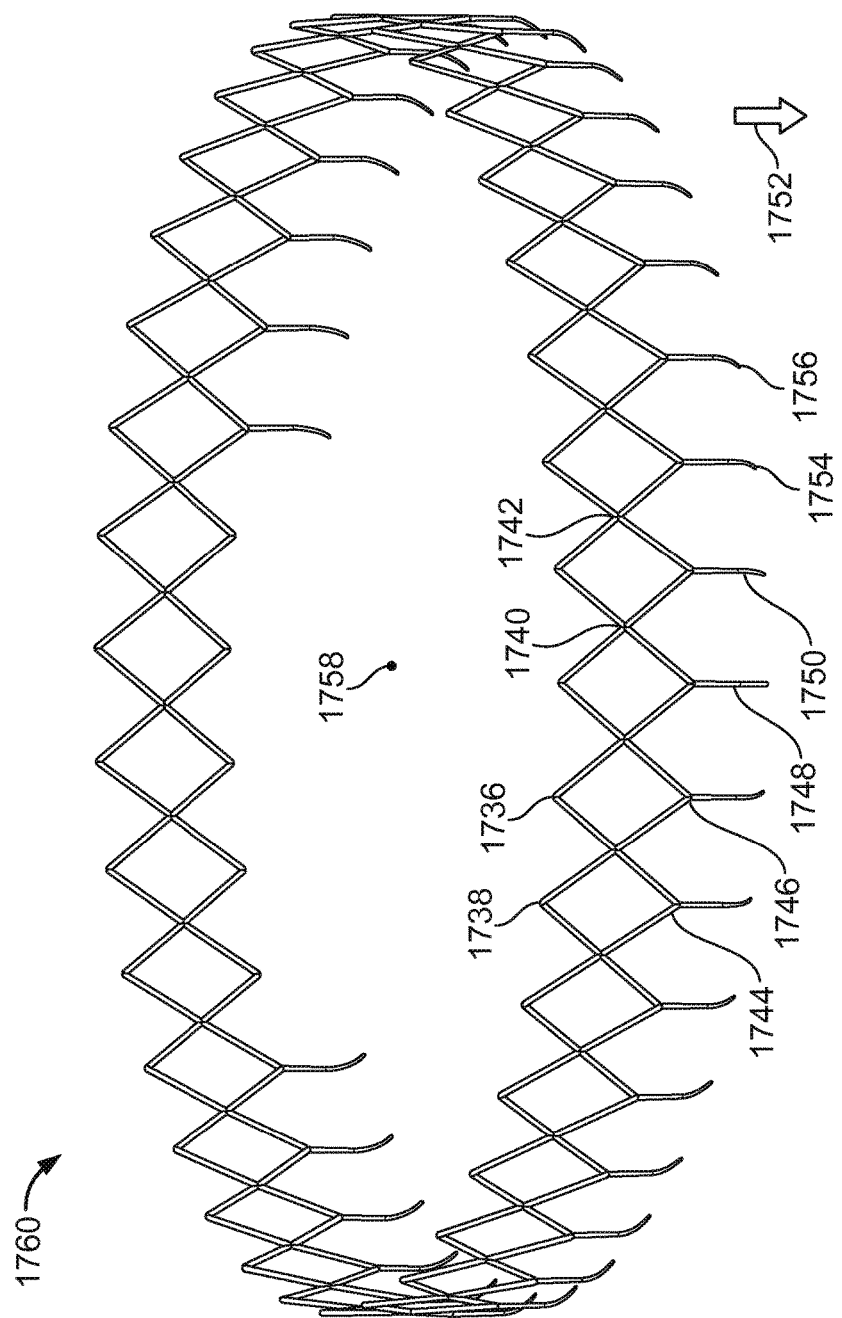
FIG. 78 shows a support having a ring of successive diamond sections touching at side corners.

FIG. 78 shows a support 1760 having a ring of successive diamond sections 1736, 1738 touching at side corners 1740, 1742. The bottom corners 1744, 1746 of the diamonds bear anchors 1748, 1750 all pointing in the same direction 1752 for piercing heart tissue and anchoring the support. The anchors 1748, 1750 have sharp free ends 1754, 1756 that curve slightly toward the geometric center 1758 of the ring formation. The slight curve of the free ends 1754, 1756 resists forces that pull on the support when the anchors 1748, 1750 are embedded in annular tissue. In some implementations, the anchors 1748, 1750 may have barbs for lodging in tissue, and in some implementations, the anchors 1748, 1750 may be replaced by hooks. The anchors 1748, 1750 can be attached to the diamond sections 1736, 1738 using one of several methods such as welding or bonding, for example, or they could be formed or cut directly from the same material from which the diamond sections 1736, 1738 are formed or cut, for example. The diamond sections 1736, 1738 and anchors 1748, 1750 could all be cut (for example, laser cut) as a single piece from tubing. The support 1760 could be used with any one of several implementations of the delivery tool, for example, the implementations shown in this description.

Generally, this support 1760 is similar in structure to a stent. The diamond sections 1736, 1738 could be different sizes, and other kinds of polygonal sections could be substituted for the diamond sections 1736, 1738. For example, hexagonal sections or zig-zag-shaped wire sections could be used, or a combination of different shapes and sizes could be used. While diamond sections 1736, 1738 may touch at side corners 1740, 1742, other types of polygons may touch at points other than corners.

The support 1760 is resilient and can be expanded to a delivery configuration and later will contract to a final configuration. The support can be made of a flexible shape memory material such as Nitinol or a biologically compatible elastomer (or other material) that is configured to contract the support to the final configuration after insertion into tissue. For example, the support may be configured to contract upon a period of exposure to the temperature of the human body.

Figure 79A:
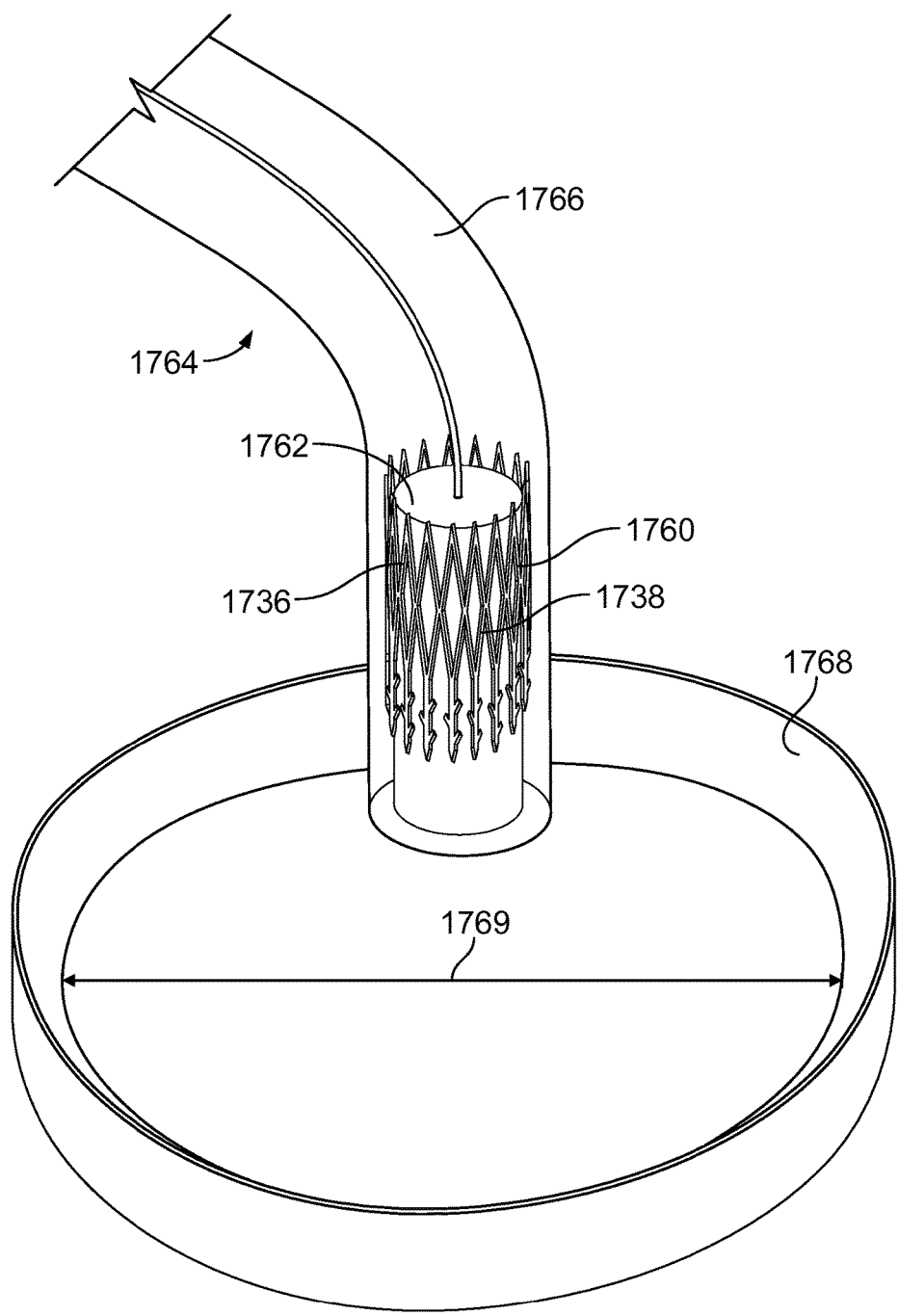
FIGS. 79A through 79C show delivery of a heart valve support.
Figure 79B:
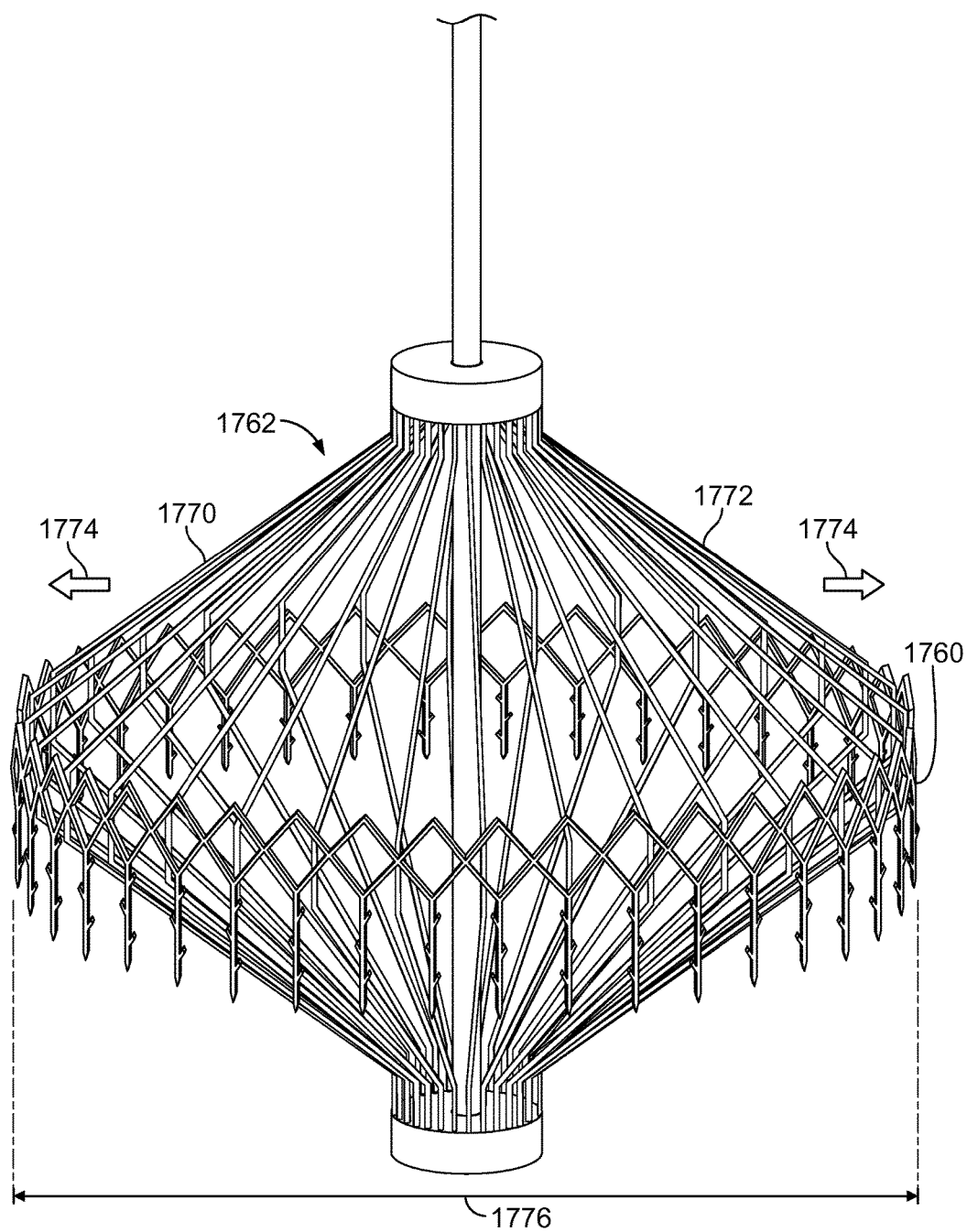
Figure 79C:
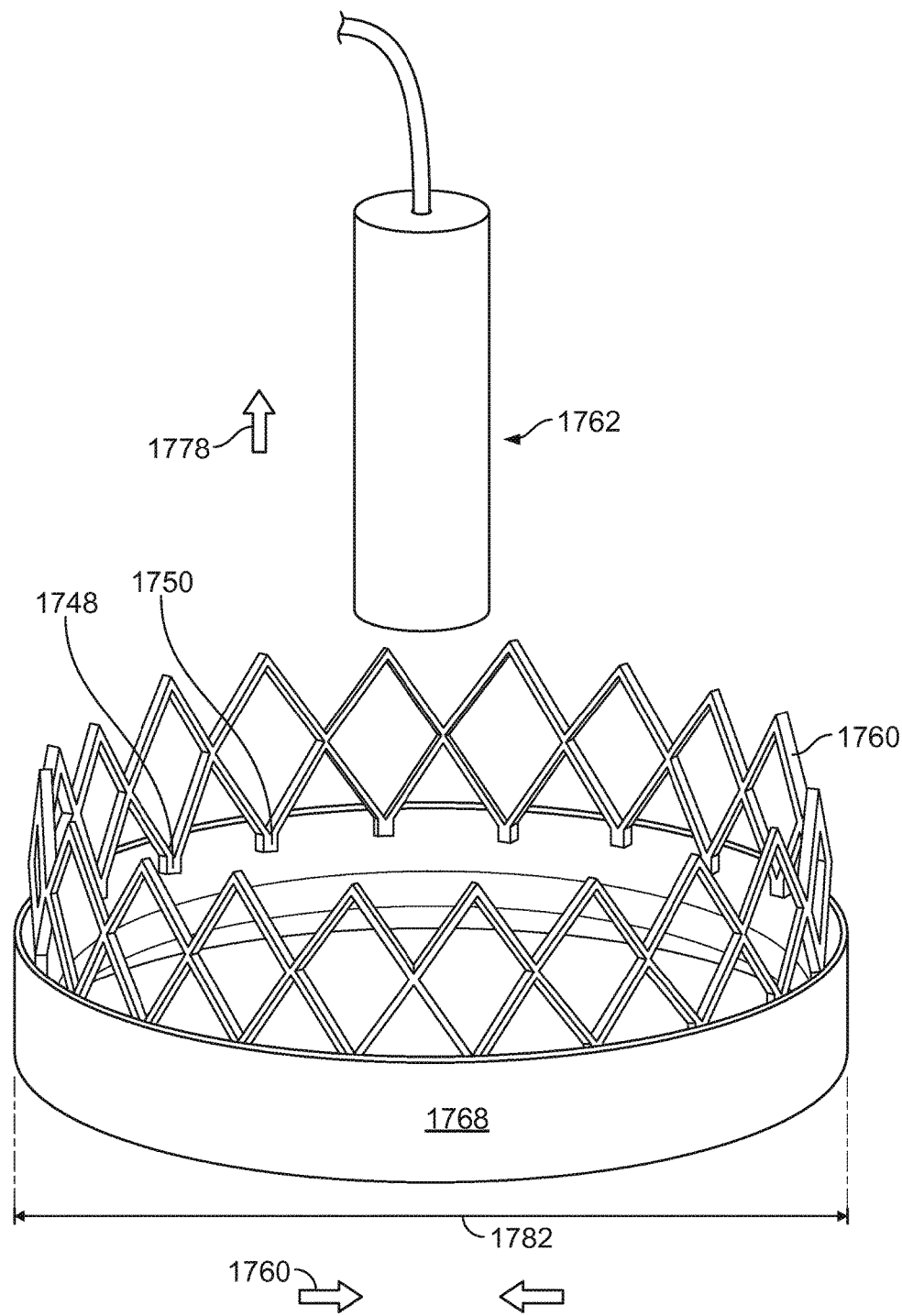

FIGS. 79A through 79C show one example of a delivery procedure for the support 1760. As shown in FIG. 79A, the support 1760 is placed in a collapsed configuration on the delivery head 1762 of a delivery tool 1764. The support 1760 and delivery head 1762 are covered in a sheath 1766 that can be removed when the delivery head 1762 arrives at a heart valve annulus 1768. In the collapsed configuration, the diamond sections 1736, 1738 are stretched vertically, reducing the diameter of the support 1760. As shown in FIG. 79B, splaying projections 1770, 1772 attached to the delivery head 1762 push 1774 outward on the support 1760, expanding the support to a diameter 1776 greater than the diameter 1769 of the heart valve annulus 1768 (FIG. 79A). As shown in FIG. 79C, the support 1760 is lowered onto the heart valve annulus 1768 and the anchors 1748, 1750 lodge inside the annular tissue. The delivery head 1762 is collapsed and pulled 1778 away from the support 1760, upon which the support 1760 contracts 1780, pulling the heart valve annulus 1768 to a smaller diameter 1782 than its original larger diameter 1769 (FIG. 79A).

In general, the delivery tool 1764 expands both the support 1760 and the heart valve annulus 1768 to the same diameter and brings the support anchors 1748, 1750 into radial alignment with the circumference of the annulus, thereby allowing attachment of the support to the annulus. Release or removal of the delivery tool 1764 allows the support 1760 to collapse to its preferred and predetermined size and retain the heart valve annulus at that size.

Figure 80A:
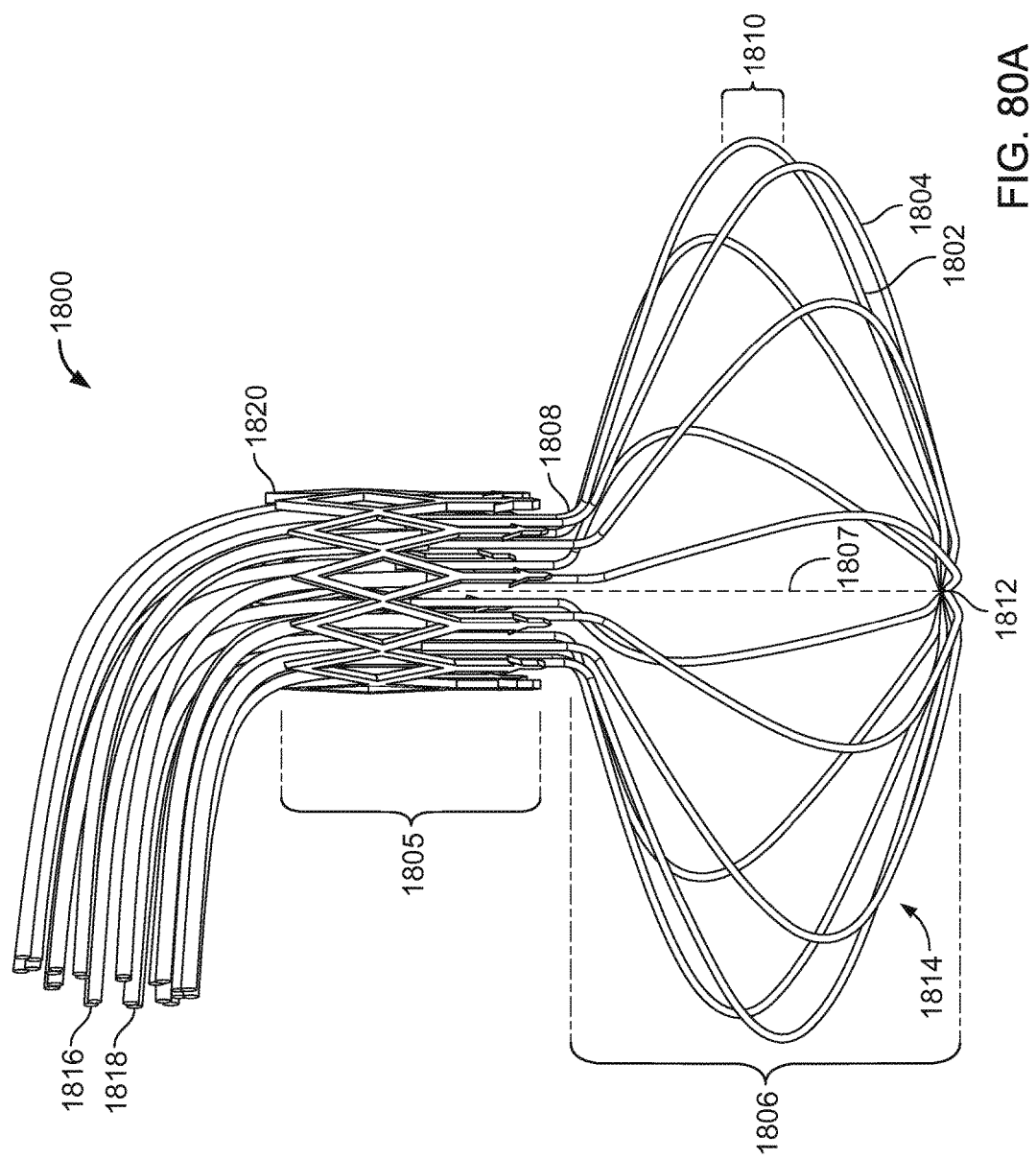
FIGS. 80A and 80B show a heart valve support attached to a delivery head.

FIG. 80A shows an example of a delivery head 1800 that includes of a cluster of pre-formed flexible wires 1802, 1804 arranged at equal intervals around a central axis 1801. In an upper portion 1805 of the delivery head, the upper ends 1803 of the wires 1802, 1804 are parallel and arranged around an imaginary cylinder. In a lower portion 1806, the wires 1802, 1804 each have an upper outward bend 1808 and a lower inward bend 1810, and meet at a junction 1812. This portion 1806 of the wires defines a pre-formed but flexible basket 1814. The wires 1802, 1804 can be made of any flexible material such as Nitinol or a biologically compatible elastomer (or other material). In some examples, opposite (with respect to the axis 1807) pairs of wires are coupled or joined continuously at the junction 1812, and in some examples the wires all end at the junction and a coupling is used to hold the ends in place.

Each of the upper ends of wires 1802, 1804 passes through one lumen of a corresponding tube 1816, 1818 that has multiple lumens. All of the multiple-lumen tubes 1816, 1818 attach to a heart valve support 1820 and hold the heart valve support during delivery to a heart valve annulus of a patient. The multiple-lumen tubes 1816, 1818 can be made of any flexible material such as Nitinol or a biologically compatible elastomer (or other material). Because the wires 1802, 1804 are held in position around the axis by the junction at the bottom of the basket, the upper free ends of the wires maintain their cylindrical arrangement and keep the ends of the multiple-lumen tubes in which they are held also in the preformed but flexible cylindrical arrangement. The wires 1802 can also be held in position during delivery by a support sheath or other support structure (not shown).

Figure 80B:
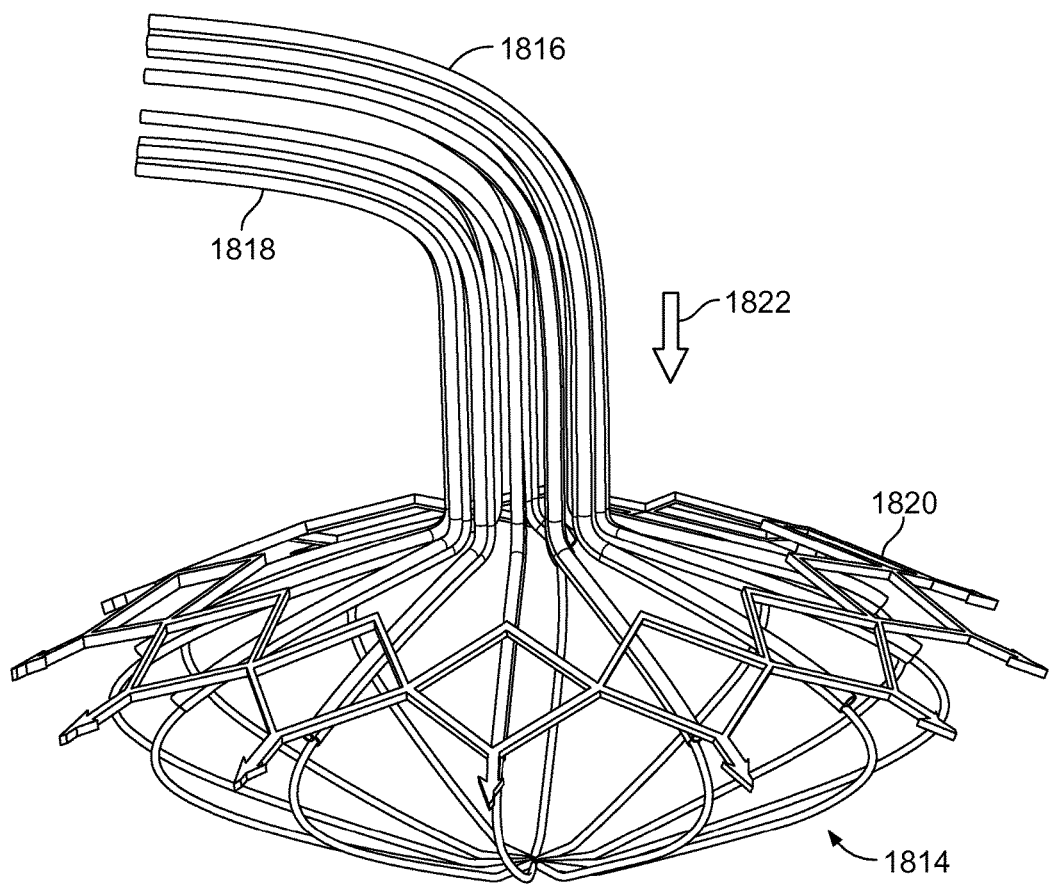

When initially deployed into the heart, the support can be located at the upper end of the basket as shown in FIG. 80A. As shown in FIG. 80B, for purposes of installing the support onto the annulus, the multiple-lumen tubes 1816, 1818 then can be pushed simultaneously 1822 downward which causes the one lumen of each of the multiple-lumen tubes to slip along the corresponding one of the wires 1802, 1804 to carry the heart valve support 1820 along the portion of the wires forming the basket 1814. Because of the shapes of the wires, this motion of the tubes also expands the heart valve support radially with respect to the axis, as the tubes progress to wider portions of the basket. The motion of the tubes and the shape of the basket wires also cause the shape of the support to become reconfigured as shown in FIG. 80B relative to FIG. 80A. If the basket is near to or in contact with a heart valve annulus, the motion of the multiple-lumen tubes 1816, 1818 puts the heart valve support 1820 in contact with annular tissue. The pushing action, as well as other actions of the delivery head, can be carried out by an operator using delivery controls (e.g. controls such as a loop 1102 or twist or slide control 1150 as shown in FIG. 13A).

Although the example shown uses multiple-lumen tubes arranged to surround wires, other structures could be used to bear the heart valve support. For example, the heart valve support could be affixed to a structure that travels along a delivery head along tracks, grooves, rails, or another kind of structure that guides the heart valve support along the delivery head to a heart valve annulus.

Figure 81A:
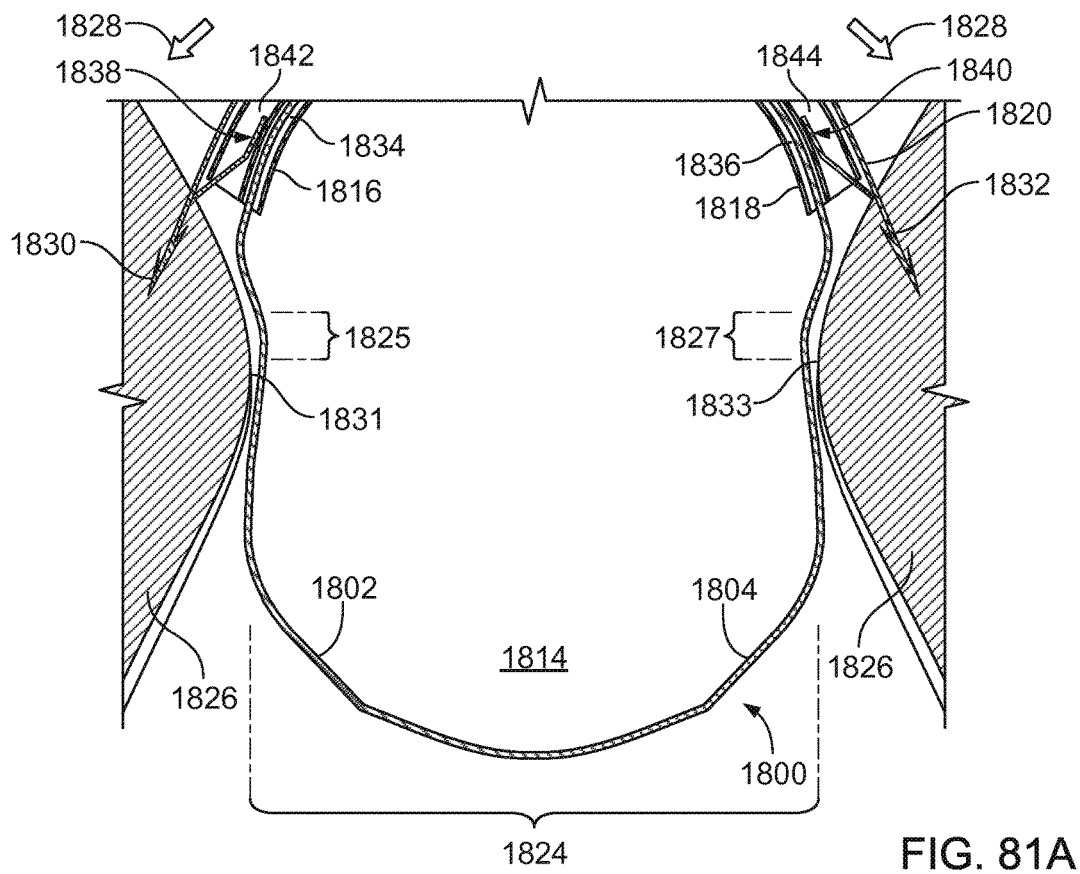
FIGS. 81A and 81B, show a delivery head basket and a heart valve annulus.

FIG. 81A shows a cross-section of the basket 1814 deployed within a heart valve annulus 1824. The wires 1802, 1804 are in contact with the inner peripheral edge of the annular tissue 1826, holding the delivery head 1800 in place axially and radially within the annulus. The forces applied by the wires against the inner peripheral edge of the annular tissue are small, sufficient to hold the head in place, but typically not enough to significantly deform the existing shape of the peripheral edge. The wires 1802, 1804, because of their flexibility, have slight bends 1825, 1827 at the points of contact 1831, 1833 with the annular tissue 1826. In some implementations, the wires may be pre-formed to have bends that correspond to and mate with the topography of the annulus. In other implementations, the wires have the form shown in FIG. 80A prior to deployment, and the wires become bent during insertion to a shape such as the one shown in FIG. 81A.

The wires 1802, 1804 pass through inner lumens 1834, 1836 of the multiple-lumen tubes 1816, 1818. Vertical struts 1838, 1840 of the heart valve support 1820, which are bent at common angles relative to the body of the support, are inserted in outer lumen 1842, 1844 of the multiple-lumen tubes 1816, 1818, keeping the heart valve support attached to the tubes as the basket is deployed.

In some implementations, the inner lumens 1834, 1836 can all slide along the corresponding wires in unison, and the outer lumens 1842, 1844 that carry the heart valve support therefore all move in unison.

In the view shown in FIG. 81A, the multiple-lumen tubes 1816, 1818 have traveled down along the wires 1802, 1804, and carried the heart valve support 1820. The motion 1828 of the multiple-lumen tubes 1816, 1818 and the heart valve support 1820 has caused anchors 1830, 1832 attached to the support to pierce the annular tissue 1826. The anchors 1830, 1832, are splayed outward in FIG. 81A relative to their axial direction in FIG. 80A, prior to deployment, because of the shapes of the wires. In some implementations, the curvature of the basket 1814 in the area where the anchors 1830, 1832 contact the annular tissue 1826 (for example, the inward bend 1810 as shown in FIG. 80A) causes curvature of the path of the anchors as the anchors approach the annular tissue. This may cause the anchors 1830, 1832 to pierce the annular tissue 1826 along a curved path 1835, which may provide further resistance to forces upon the anchors after the anchors are seated.

Figure 81B:
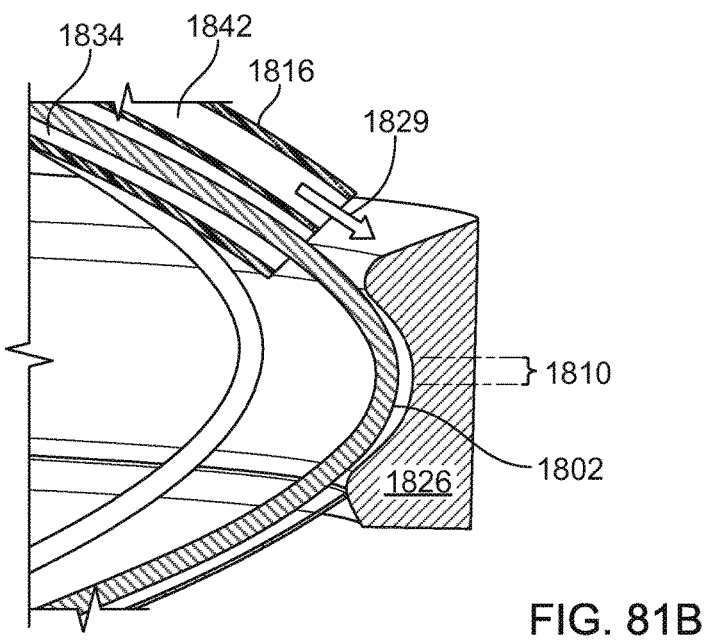

FIG. 81B shows a close-up view of one of the multiple-lumen tubes 1816 near annular tissue 1826. One of the wires 1802, at the location of its inward bend 1810, is shown in contact with the annular tissue 1826. The outer lumen 1842 for carrying a heart valve support (not shown) travels along the same path 1829 as the inner lumen 1834 through which the wire 1802 passes. As the inner lumen 1834 travels along the path 1829 toward the inward bend 1810 of the wire 1802, the outer lumen 1842 also travels along the same path 1829 directly to the annular tissue 1826. When the outer lumen 1842 carries a heart valve support, the heart valve support is also led directly to the annular tissue, in a direction that has a substantial radial component. The radial component can be, for example, more prominent than the axial component of motion.

Figure 82A:
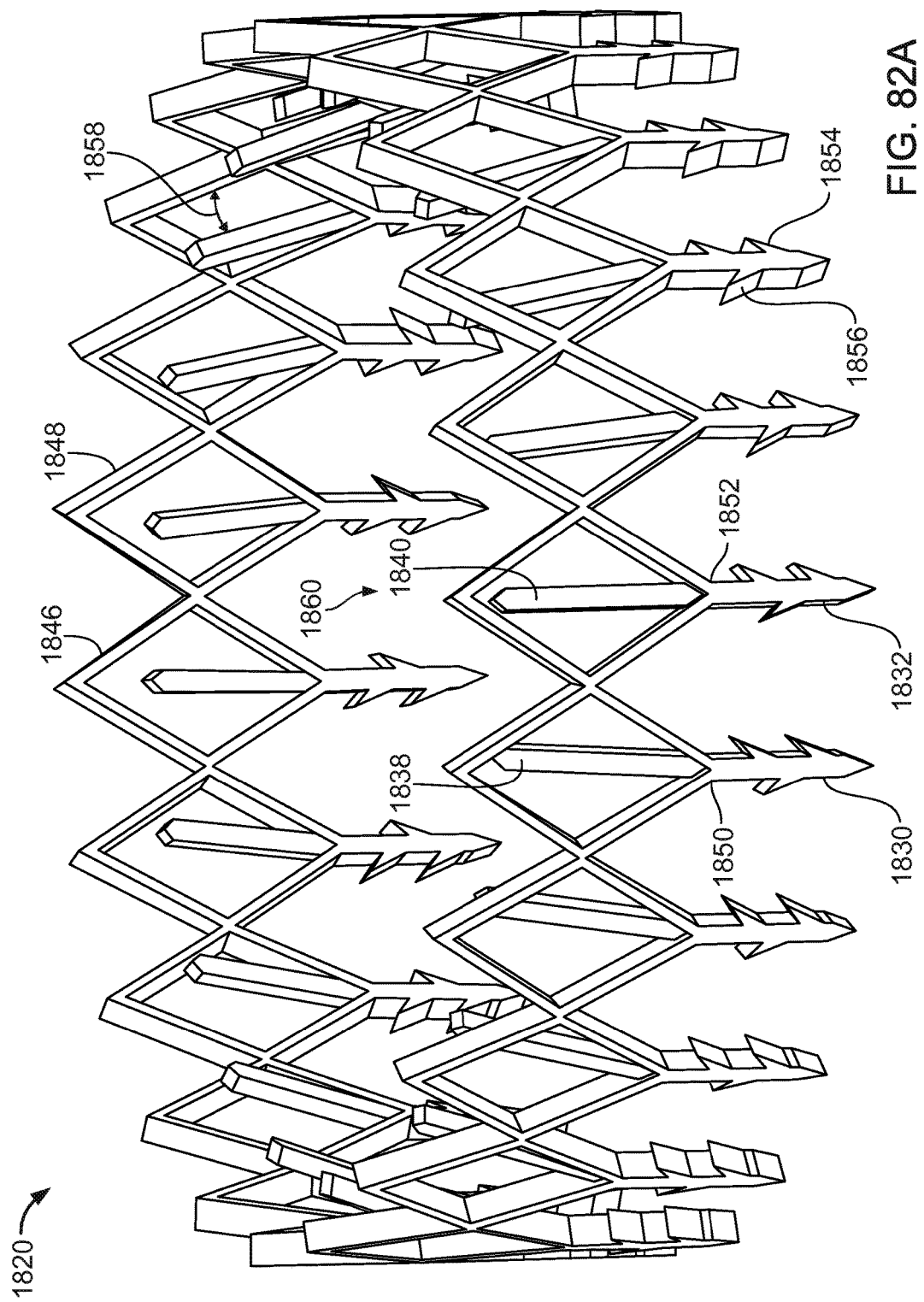
FIGS. 82A through 82F show a heart valve support including diamond sections and anchors extending downward from bottom corners of the diamond sections.

FIG. 82A shows an example heart valve support 1820. The heart valve support 1820 has substantially the same annular structure as the heart valve support 1760 as shown in FIG. 78 including diamond sections 1846, 1848 and anchors 1830, 1832 extending downward from bottom corners 1850, 1852 of the diamond sections. The anchors 1830, 1832 also have barbs 1854, 1856 for lodging in tissue and resisting removal. The vertical struts 1838, 1840 attached to the heart valve support 1820 extend upward from the bottom corners 1850, 1852 of the diamond sections 1846, 1848. Also, each of the vertical struts 1838, 1840 can be tilted at an angle 1858 toward (or, in some implementations, away) from the imaginary surface defined by the diamond section to which it is attached. The tilting can be done on a temporary basis, for example, by manipulating the vertical struts 1838, 1840 with a tool or, if the vertical struts are made of a shape memory material such as Nitinol, applying a stimulus such as heat or electricity. This tilted configuration provides adequate clearance for each of the vertical struts to be inserted into a corresponding lumen of the multiple-lumen tubes while the other lumen can slide along the corresponding wire. This arrangement also allows the support to be temporarily expandable. In some implementations, once the vertical struts 1838, 1840 are released from the multi-lumen tubes, the vertical struts spring back to become flush with the diamond sections 1846, 1848.

Figure 82B:
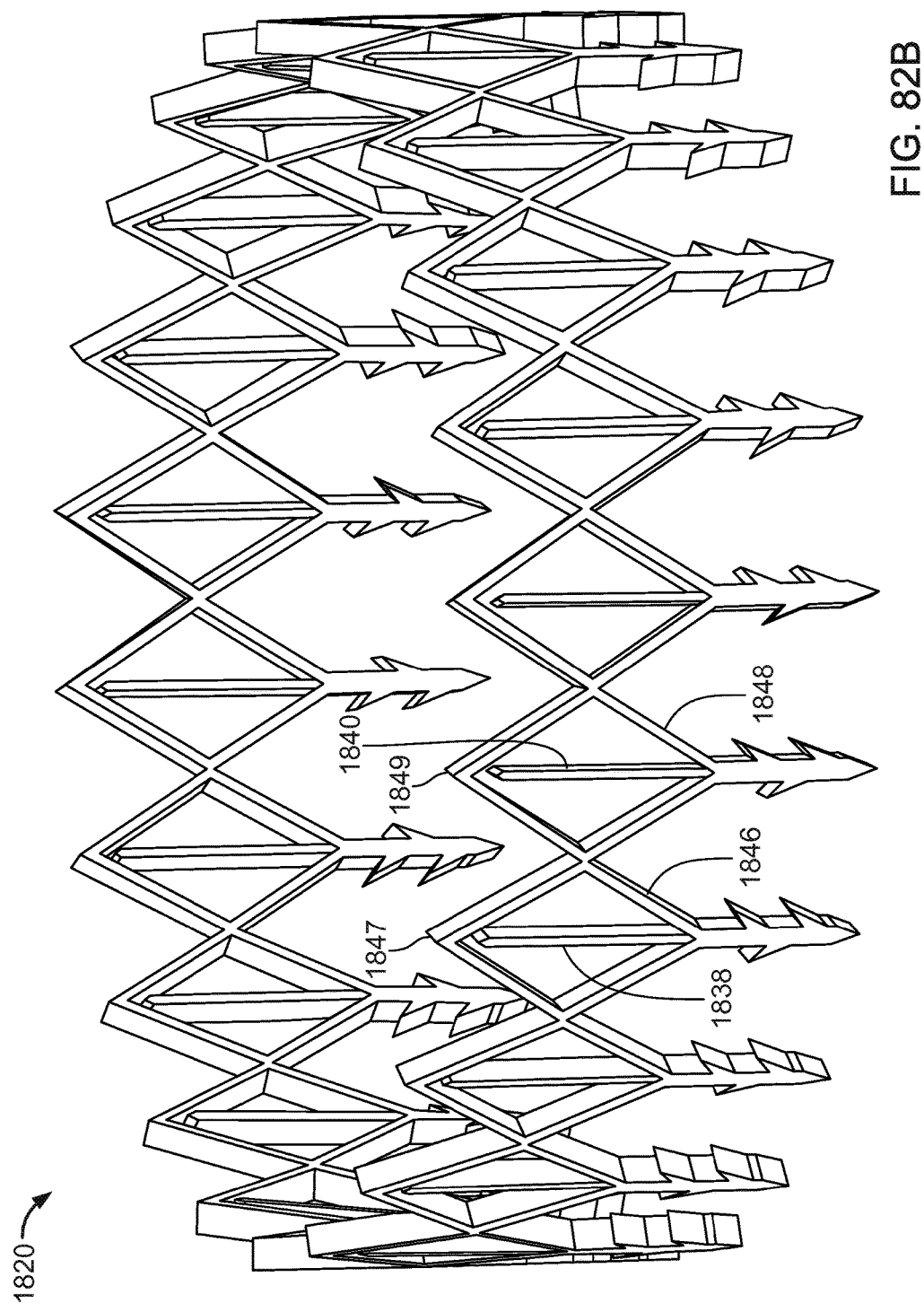

FIG. 82B shows the vertical struts 1838, 1840 positioned flush with the diamond sections 1846, 1848. In this configuration, the free ends of the vertical struts are positioned so if the support has forces on it tending to expand it radially or contract it axially, the forces are resisted by the vertical struts pushing against the rigid corners 1847, 1849 of the diamonds. In that way, the struts enable the support to resist contraction. Thus, the vertical struts act as support braces that resist vertical contraction and horizontal expansion of the diamond sections. For example, this configuration of the vertical struts can be used when the heart valve support 1820 has been placed in a static long-term configuration within a heart valve annulus. If the vertical struts 1838, 1840 are made of a shape memory material such as Nitinol, the vertical struts can be positioned by an appropriate shape memory stimulus such as heat or electricity. In some examples, the vertical struts 1838, 1840 can be manually positioned, for example, by a delivery head.

Figure 82C:
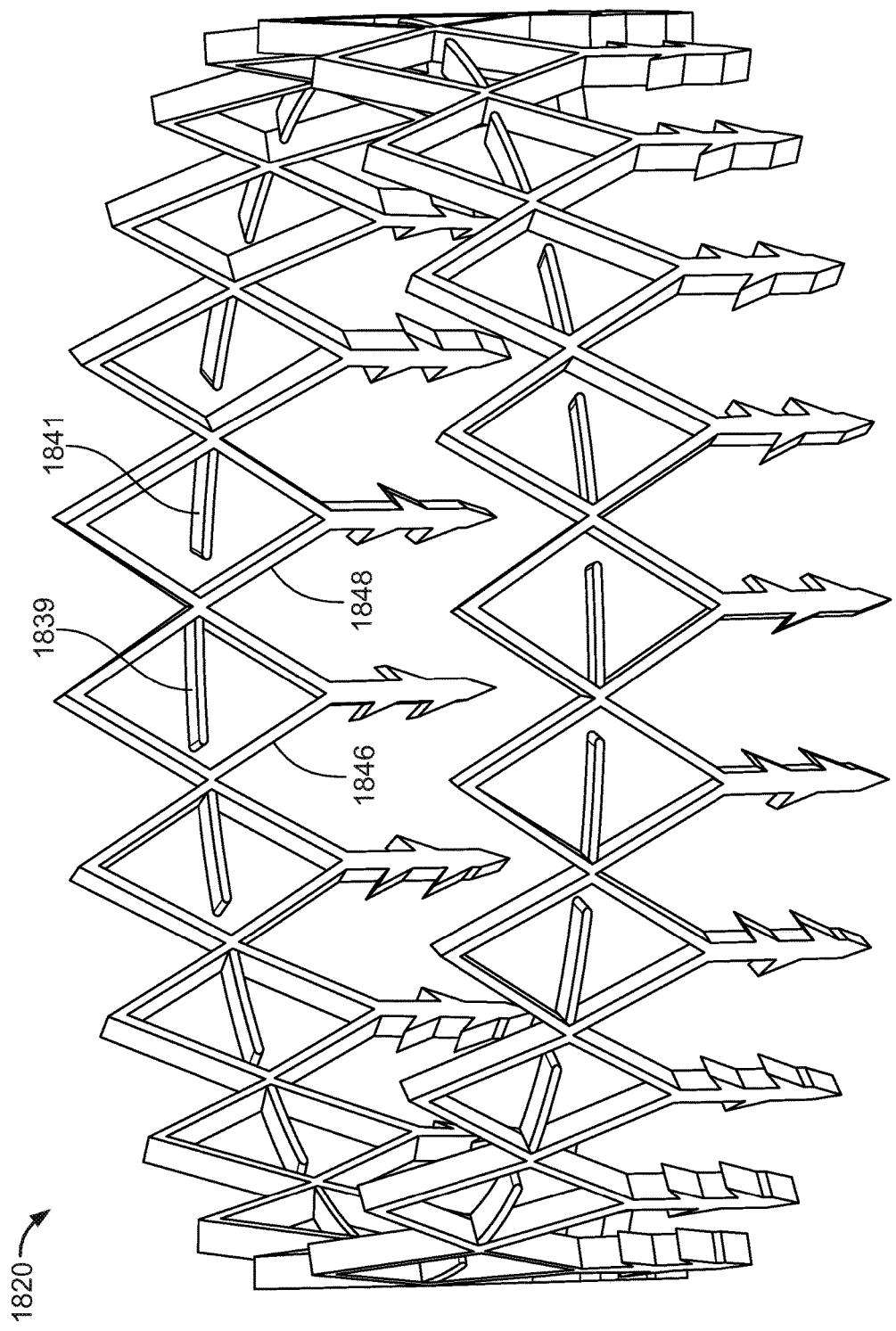

FIG. 82C shows a configuration of the heart valve support 1820 having horizontal struts 1839, 1841. The horizontal struts 1839, 1841, like the vertical struts, can be oriented flush with the diamond sections 1846, 1848 to prevent the diamond sections from horizontally contracting, although this arrangement may not be useful for an annuloplasty support in which contraction of the support may be useful.

Other arrangements of struts and other mechanical elements can be provided to achieve similar resistance to radial expansion of the support when in some configurations while permitting radial expansion while in other configurations.

Figure 82D:
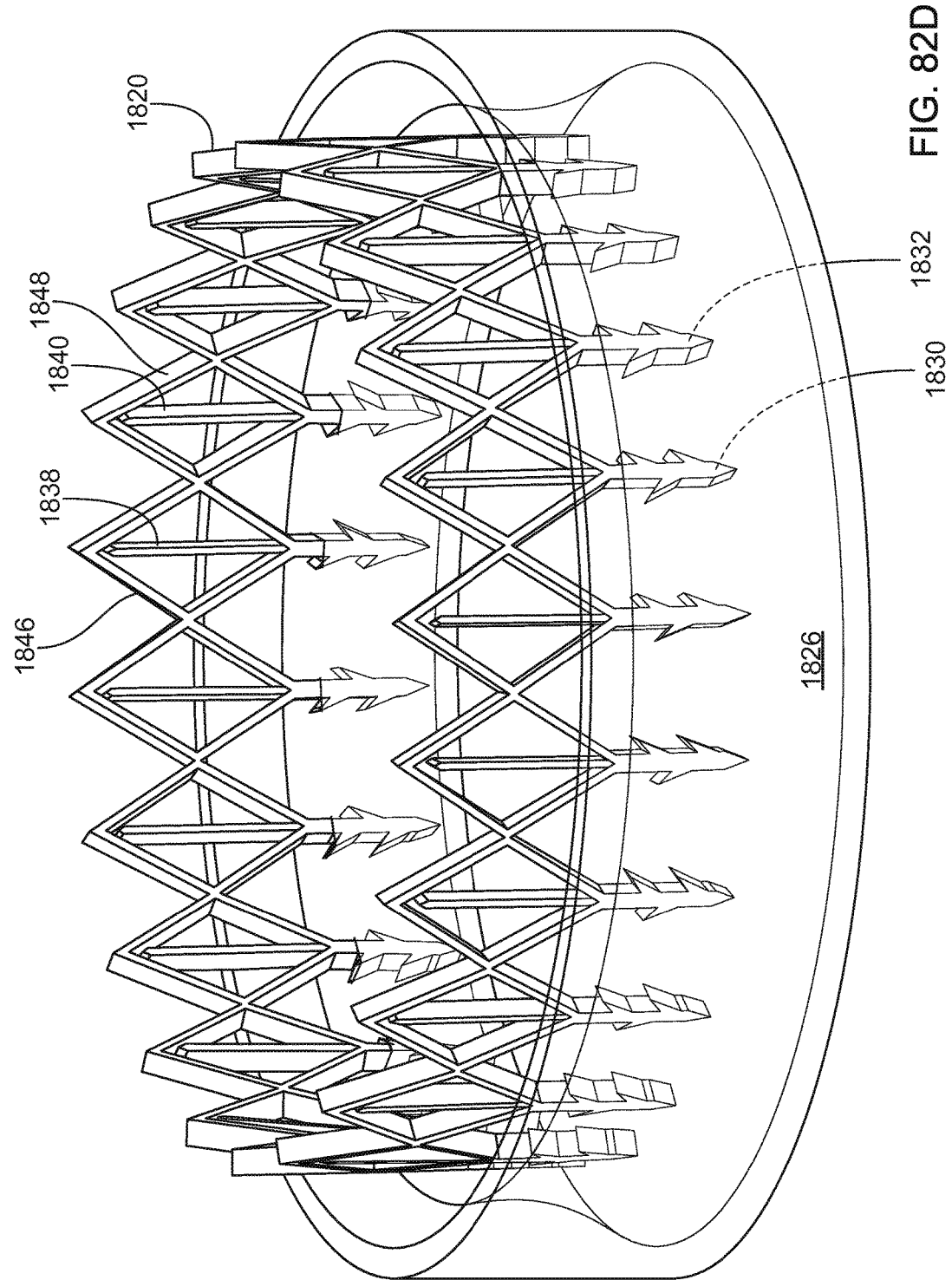

FIG. 82D shows the heart valve support 1820 attached to annular tissue 1826. The anchors 1830, 1832 are embedded within the tissue, and the vertical struts 1838, 1840 are flush with the diamond sections 1846, 1848 to limit the flexibility of the diamond sections and thereby prevent or reduce expansion of the support and heart valve annulus.

Figure 82E:
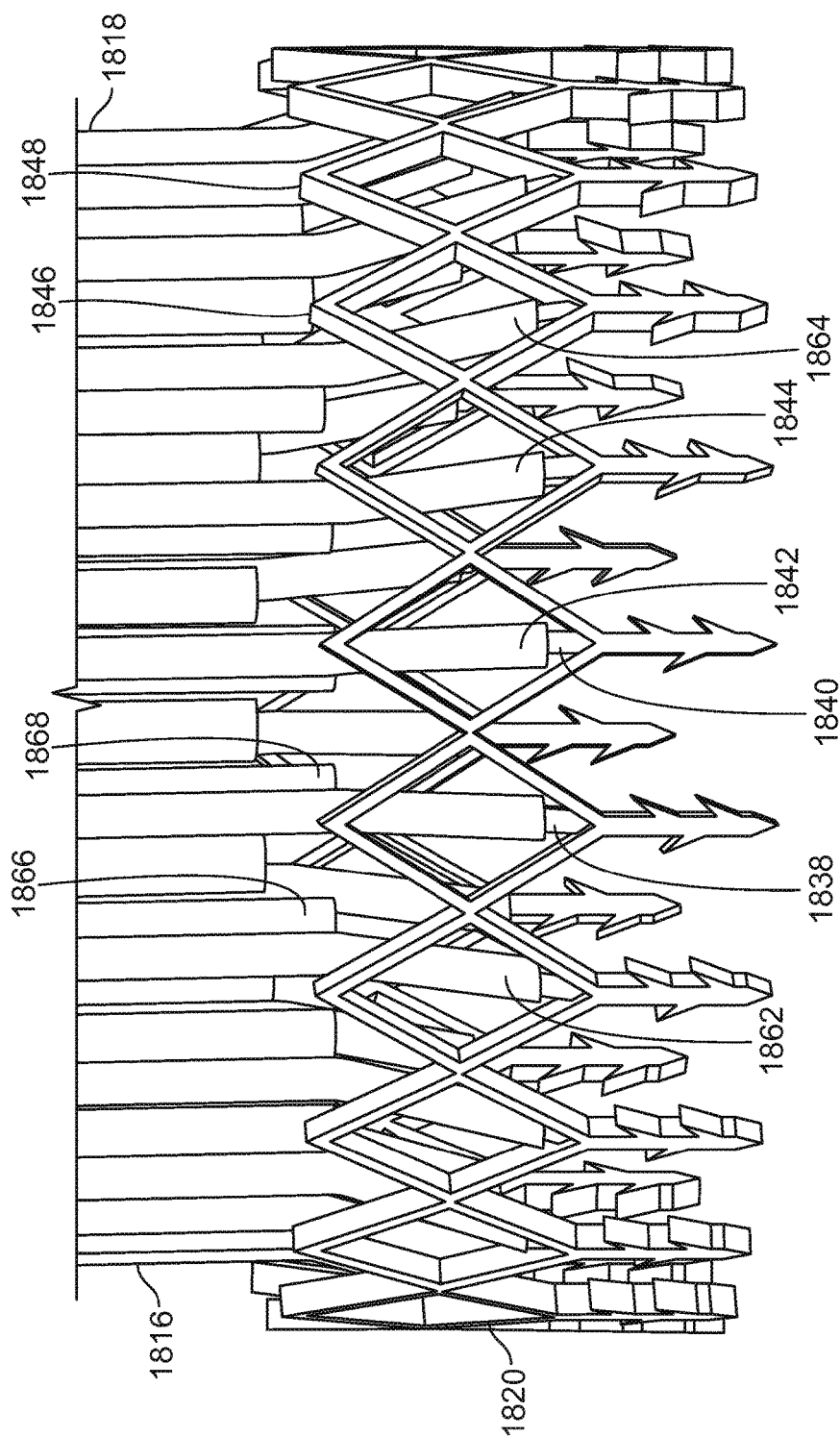

FIG. 82E shows the heart valve support 1820 attached to the multiple-lumen tubes 1816, 1818. The vertical struts 1838, 1840 are angled inward from the diamond sections 1846, 1848 and inserted inside the respective outer lumens 1842, 1844 of the multiple-lumen tubes 1816, 1818. In this example, the ends 1862, 1864 of the lumens 1842, 1844 containing the vertical struts 1838, 1840 extend beyond the ends 1866, 1868 of the lumens 1834, 1836 into which the flexible wires are inserted.

Figure 82F:
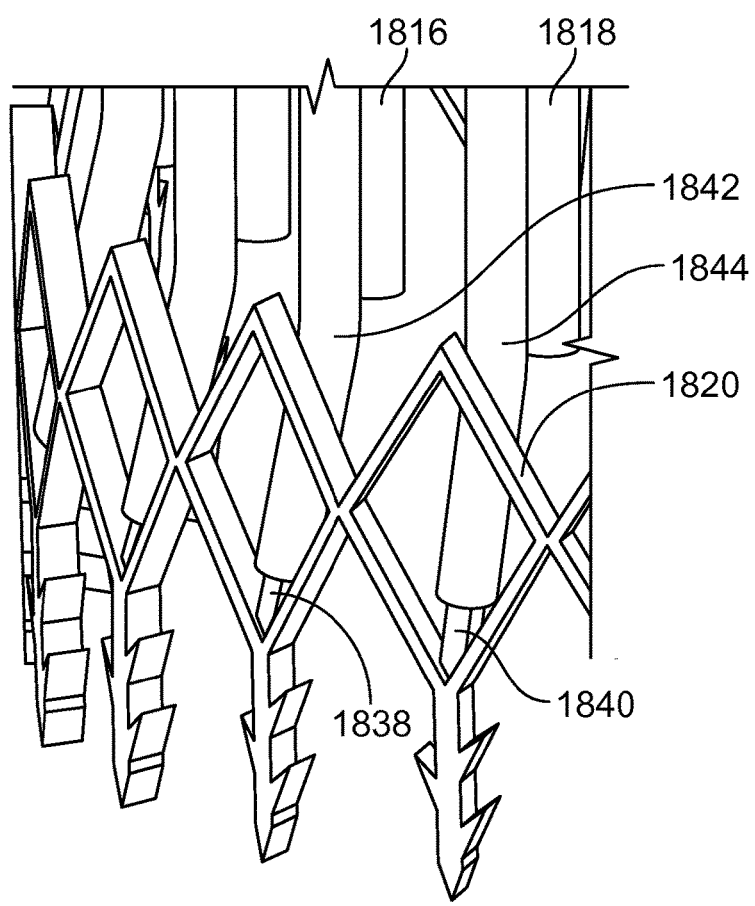

FIG. 82F is a close-up view of the heart valve support 1820 attached to the multiple-lumen tubes 1816, 1818, showing the vertical struts 1838, 1840 inserted inside lumens 1842, 1844 of the multiple-lumen tubes 1816, 1818.

Figure 83B:
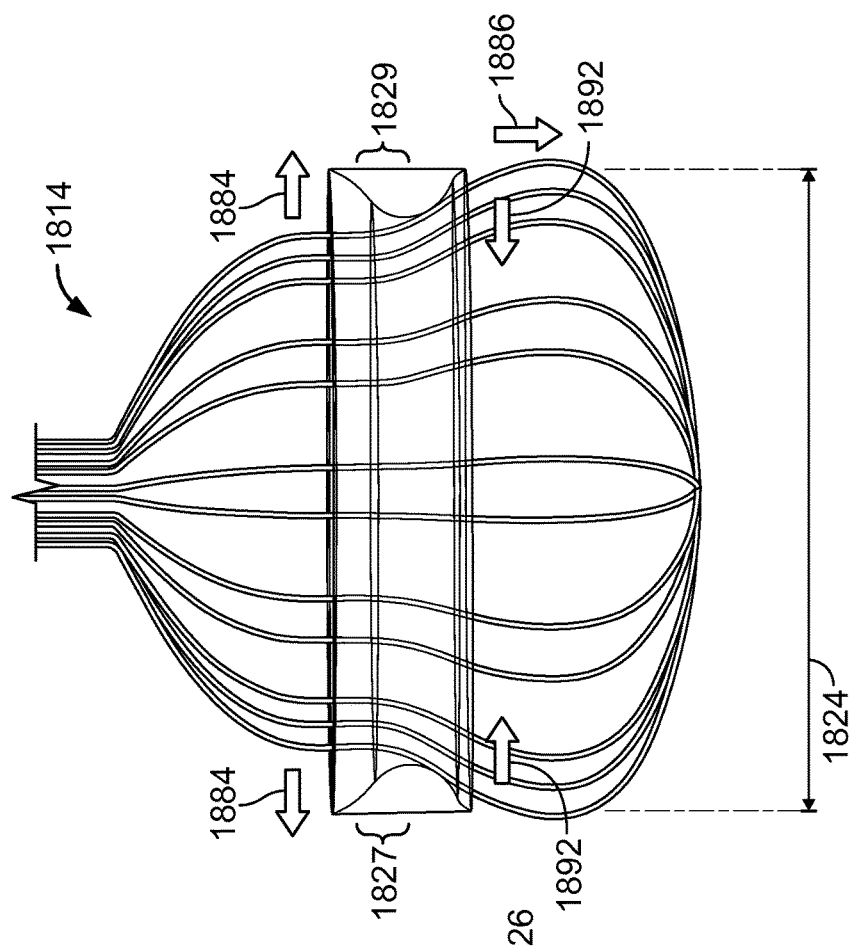
FIGS. 83A and 83B shows a basket structured to fill and conform to the annulus.
Figure 83A:
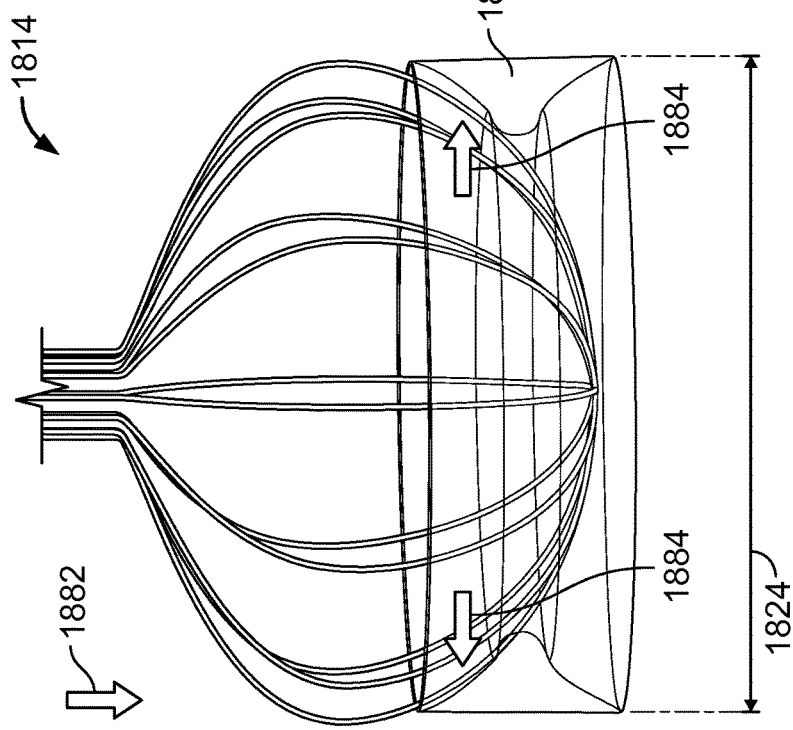

As shown in FIG. 83A, the basket 1814 is structured to fill and conform to the annulus 1824. When the basket is inserted 1882 into the annulus 1824 by pushing, the basket may apply slight pressure 1884 to the annular tissue 1826, allowing the basket to fit tightly against the annular tissue. FIG. 83B shows the basket advanced 1886 further into the annulus 1824. In reaction to the pressure 1884 applied to the annular tissue 1826, the annular tissue 1826 also applies pressure 1892 upon the wires 1802, 1804, causing a slight bend 1825, 1827 in the wires. In some configurations, the wires 1802, 1804 are pre-formed with one or more bends, allowing the basket 1814 to conform to the shape of the annulus and exert minimal pressure 1884, or none at all. In some configurations, the basket 1814 will take on an irregular (non-cylindrical) shape, and when the basket is used to deliver a heart valve support to the annulus (for example, as seen in FIG. 80B), the heart valve support will also take on an irregular shape as it tracks the shape of the wires forming the basket.

Figure 84A:
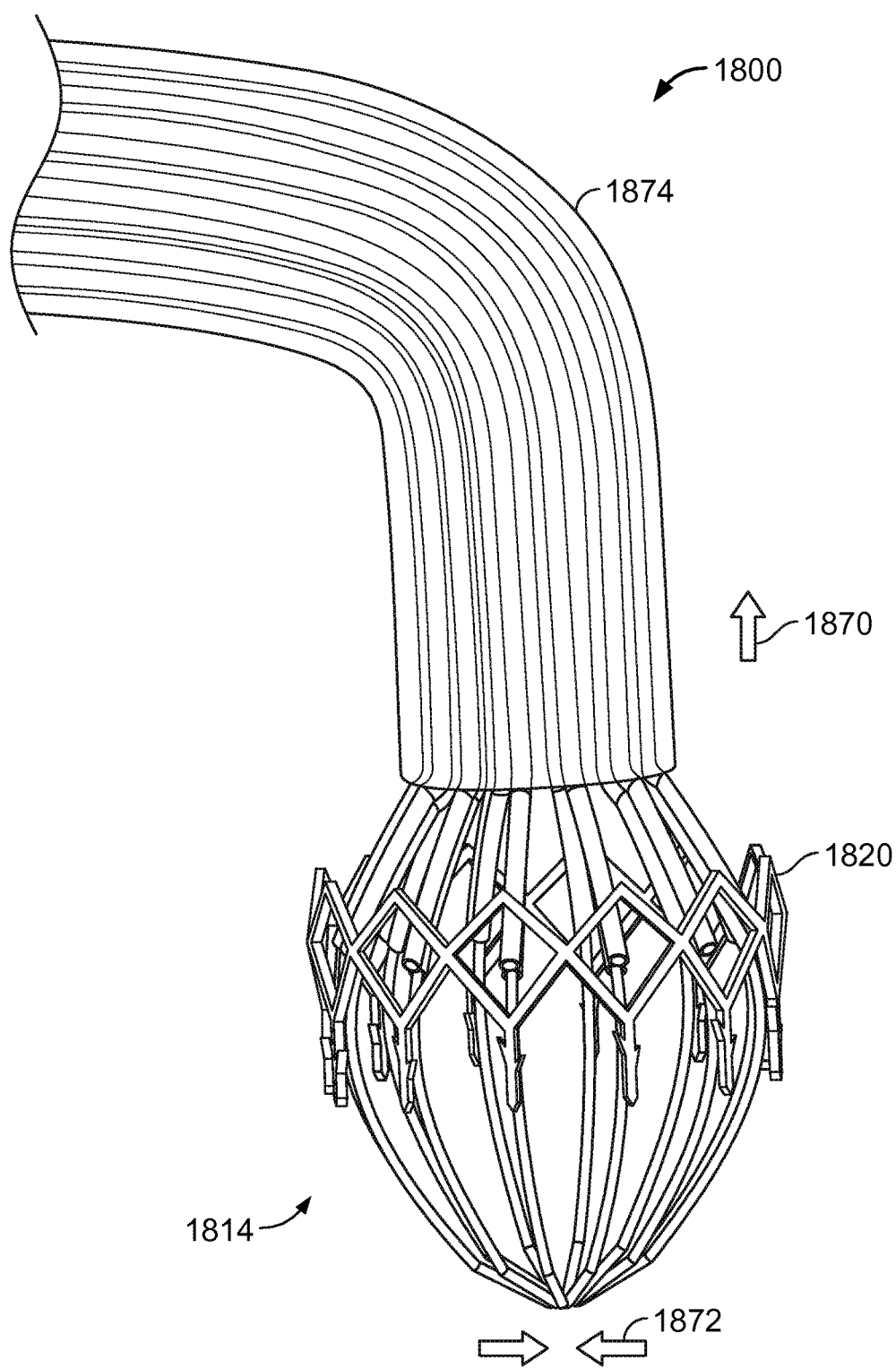
FIGS. 84A through 84C show a collapsible delivery head basket.
Figure 84B:
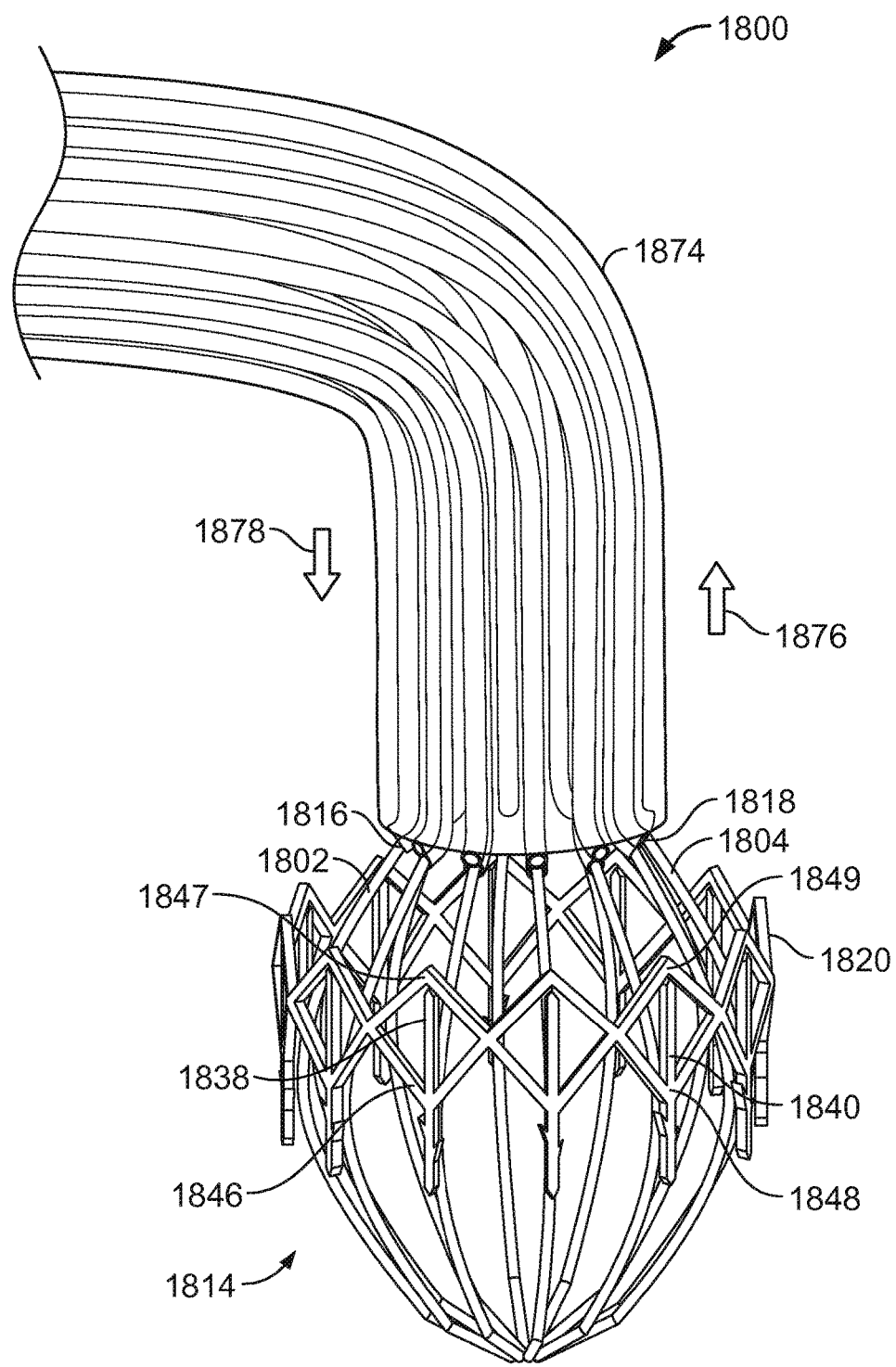
Figure 84C:
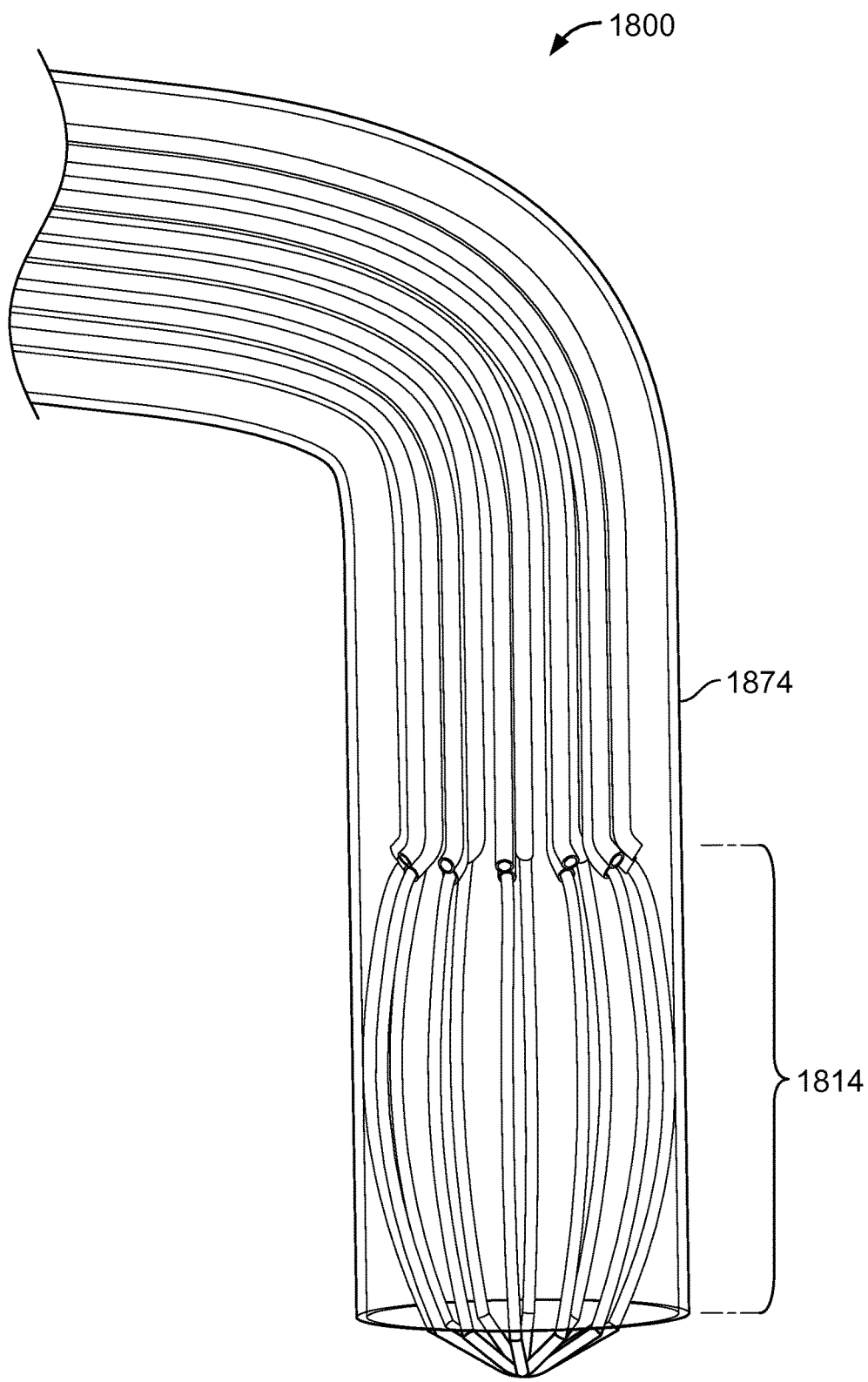

FIGS. 84A-84C show the removal of the delivery head 1800 after the heart valve support 1820 has been attached to annular tissue. As shown in FIG. 84A, a sheath 1874 can be used to cover the basket 1814 and protect the delivery head 1800. For example, if the delivery head 1800 travels through a patient as part of a catheterization procedure, then the sheath 1874 protects the delivery head during the delivery and removal of the delivery head from the patient. In some implementations, the sheath 1874 is made of a stiff material and the basket 1814 can be pulled 1870 up into the sheath to collapse 1872 the basket. In some implementations, the sheath 1874 can be advanced over the basket 1814 to collapse the basket, or the basket can be collapsed independent of the action of the sheath. As the basket collapses 1872, the heart valve support 1820 contracts.

As shown in FIG. 84B, the multiple-lumen tubes 1816, 1818 are pulled 1876 upward along the wires 1802, 1804 to detach them from the vertical struts 1838, 1840 of the heart valve support 1820. In some implementations, the vertical struts 1838, 1840 spring into place to line up with the diamond sections 1846, 1848 of the heart valve support 1820. Because the heart valve support 1820 has contracted, the diamond sections have increased in height, allowing the vertical struts to clear the upper corners 1847, 1849 of the diamond sections when the vertical struts move into a position flush with the diamond sections, as shown. In some implementations, the sheath 1874 is advanced 1878 over the basket 1814 to cover the basket in preparation for travel away from the annulus for removal from the patient.

In some configurations, the heart valve support 1820 is attached to annular tissue having an irregular shape (a shape other than a shape resembling a ring), for example, caused by disease or distortion. The heart valve support 1820 can be shaped to mimic the shape of the annular tissue (for example, during delivery as shown in FIG. 80B). When the heart valve support 1820 contracts, the heart valve support re-forms into the shape of a ring, also reconfiguring the distorted or diseased annulus into the shape of a ring.

FIG. 84C shows the basket 1814 fully collapsed and withdrawn into the sheath 1874. In this view, the delivery head 1800 is prepared for travel, for example, through the body of a patient in configurations in which the delivery head is part of a catheter.

Figure 85B:
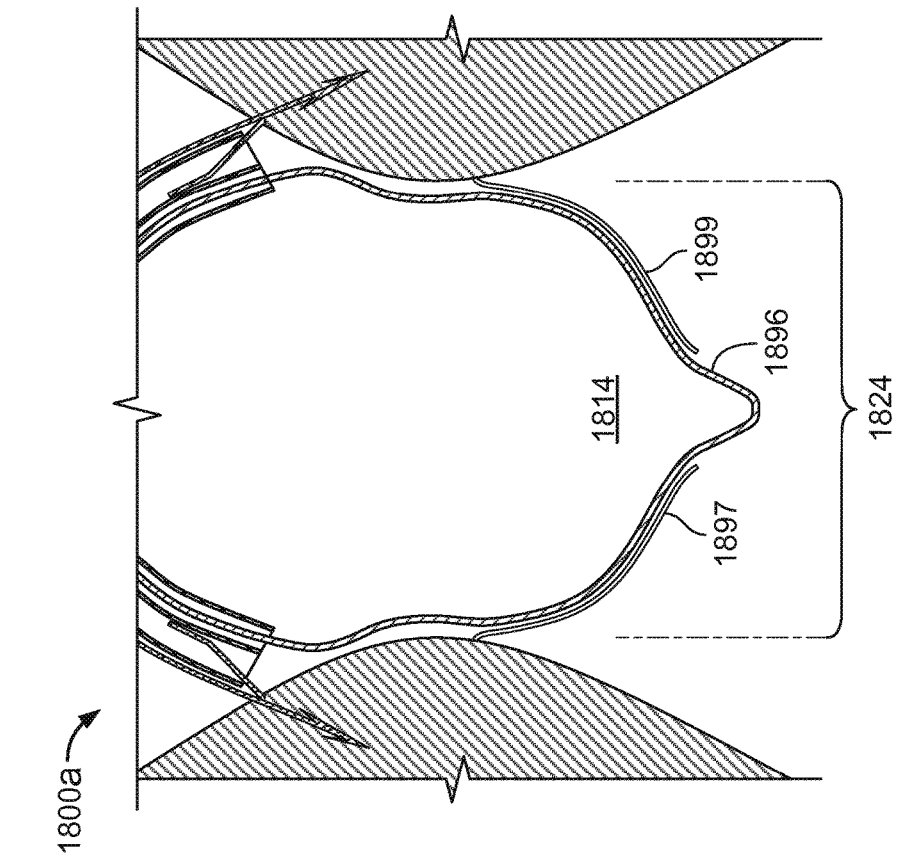
FIGS. 85A and 85B show a delivery head where each of the wires forming the basket has another bend near the junction that forms (with the other wires) a projection.
Figure 85A:
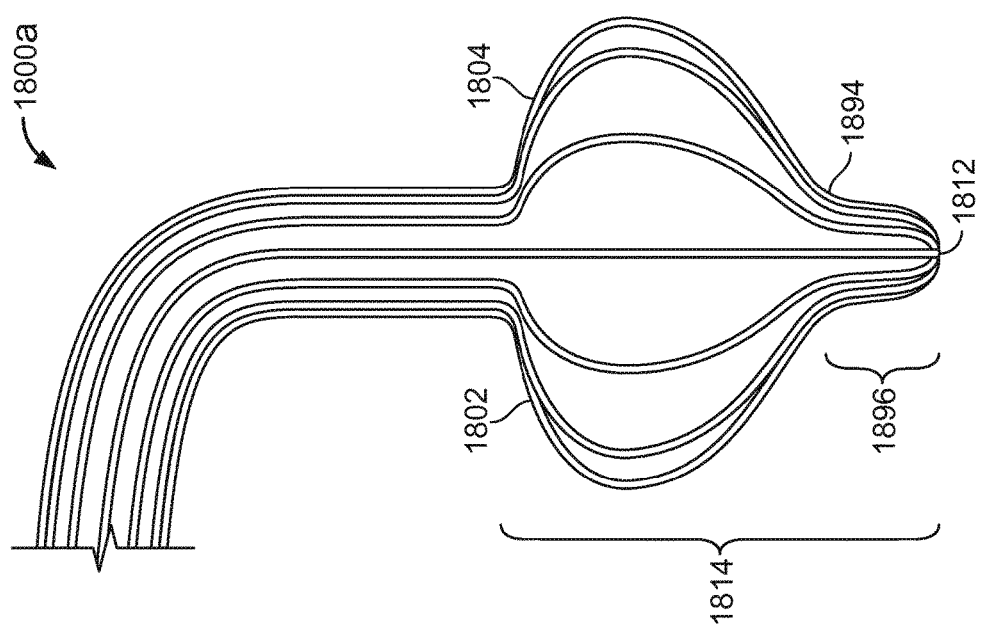

FIG. 85A shows a version of the delivery head 1800a in which each of the wires 1802, 1804 forming the basket 1814 has another bend 1894 near the junction 1812 that forms (with the other wires) a projection 1896. In some implementations, the projection 1896 extends into the heart valve farther than a basket 1814 would extend absent the projection. The effect of the projection 1896 extending into the heart valve may allow the basket 1814 to be more firmly seated within the heart valve. FIG. 85B shows a cross section of the basket 1814 of the delivery head 1800a within a heart valve annulus 1824 (similar to the cross section view shown in FIG. 81A). The basket 1814 allows leaflets 1897, 1899 of a heart valve (e.g. a mitral valve) to close and the shape of the basket supports the leaflets during closure.

Figure 86B:
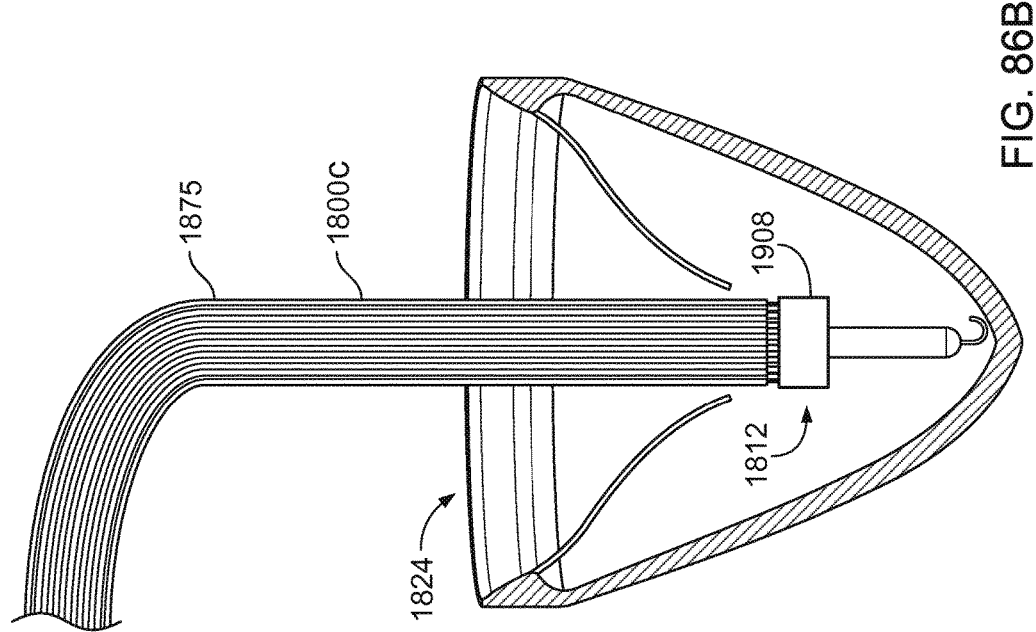
Figure 86A:
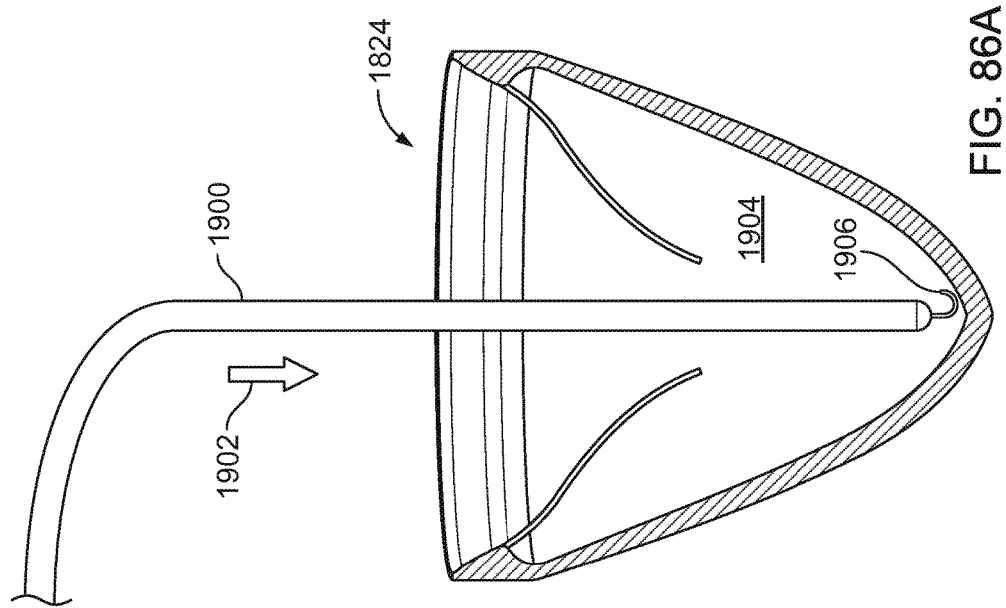

FIGS. 86A through 86J show the heart valve support being delivered by another version of the delivery head 1800c. As shown in FIG. 86A, this delivery process uses a guide catheter 1900, which is a narrow rod that can be used to stabilize the delivery tool within the heart valve annulus 1824. The guide catheter 1900 is inserted 1902 into the heart 1904 with enough depth to keep the guide catheter centered in place within the annulus. In some implementations, the guide catheter 1900 terminates in a j-wire 1906 which has a round and smooth shape that does not puncture heart tissue. The j-wire may touch the far end of the inner wall of the heart chamber that is downstream of the heart valve, which helps to stabilize the position and orientation of the delivery tool within the valve.

As shown in FIG. 86B, the collapsed delivery head 1800c is inserted into the annulus 1824. The delivery head 1800c surrounds the guide catheter 1900 and the guide catheter acts as a rail for centering the delivery head within the annulus. In some implementations, the delivery head 1800c has a collar 1908 at the junction 1812 of the wires of the delivery head. In some implementations, the wires are bonded to the collar 1908. The collar 1908 is a termination point of the wires and surrounds and contacts the guide catheter 1900 with a level of friction that allows the collar to slide up and down the guide catheter.

The delivery head 1800c is protected by a multiple-tube sheath 1875 that covers the wires. The multiple-tube sheath 1875 also holds the wires in a cylindrical formation until the multiple-tube sheath is retracted and removed.

Figure 86C:
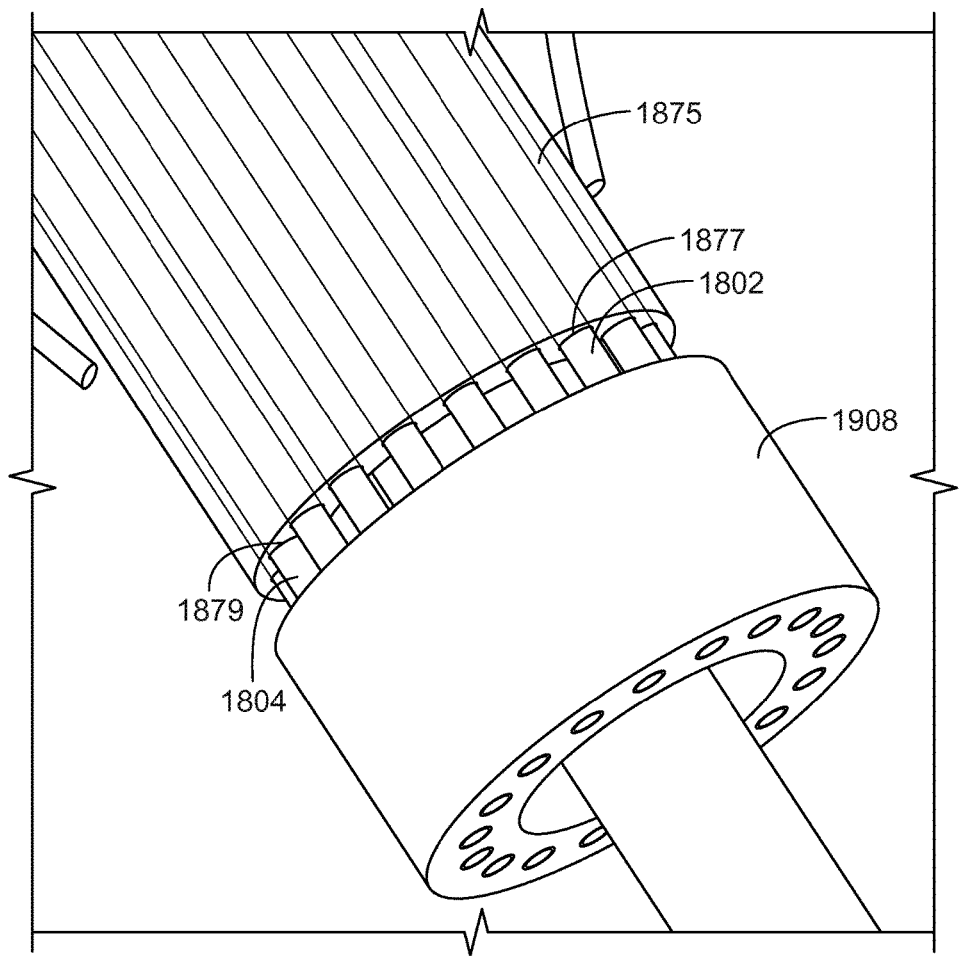

FIG. 86C shows a close-up of the multiple-tube sheath 1875, which has integrated tubes 1877, 1879. The individual wires 1802, 1804 pass through the tubes 1877, 1879 arranged in a ring formation within the multiple-tube sheath 1875. The multiple-tube sheath 1875 covers the wires 1802, 1804 up to the point at which the wires 1802, 1804 are bonded to the collar 1908.

Figure 86E:
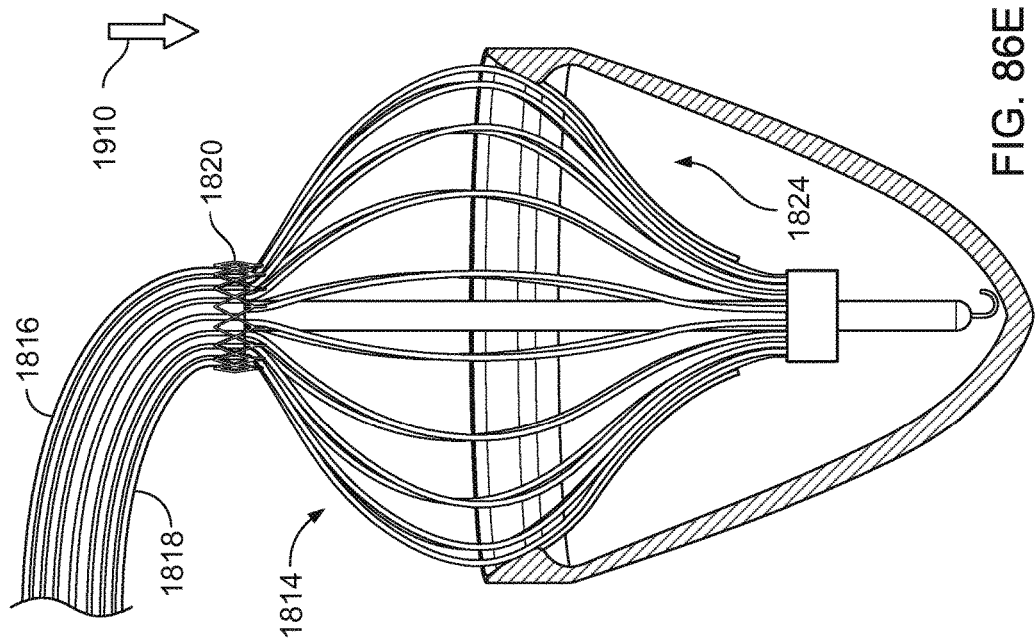
Figure 86D:
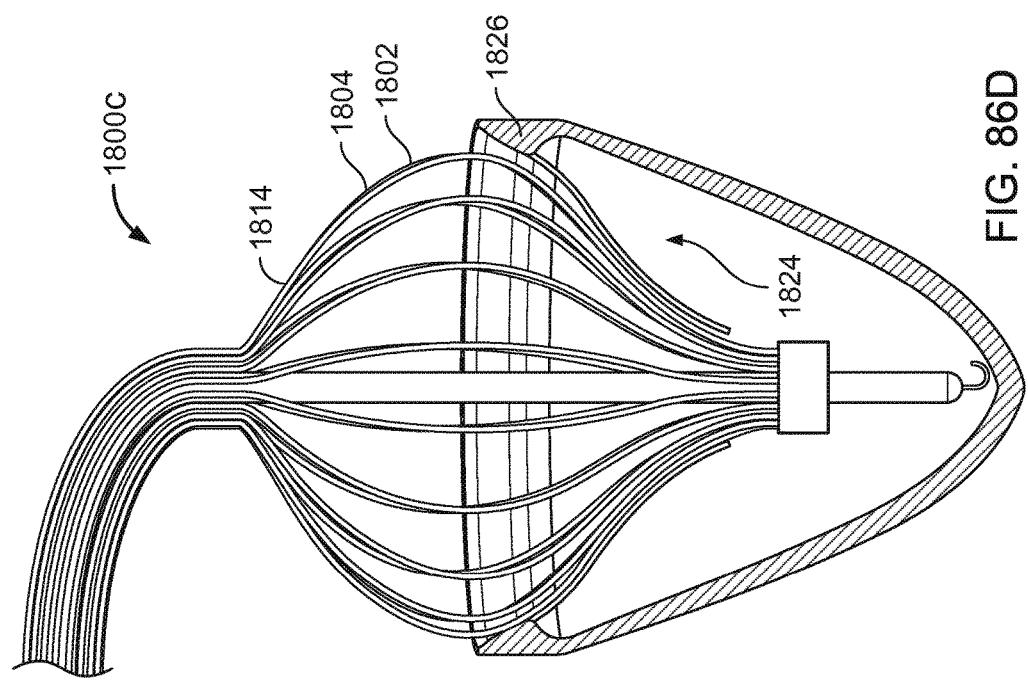

FIG. 86D shows the delivery head 1800c unsheathed and the basket 1814 expanded so that the wires 1802, 1804 contact annular tissue 1826, further securing the delivery head within the annulus 1824 and preparing the basket to guide the delivery of the heart valve support. In some implementations, the basket 1814 automatically springs open when the sheath is removed.

FIG. 86E shows the multiple-lumen tubes 1816, 1818 pulling 1910 the heart valve support 1820 along the wires 1802, 1804 in a direction toward the annulus 1824. The heart valve support 1820 remains contracted as it approaches the basket 1814.

Figure 86G:
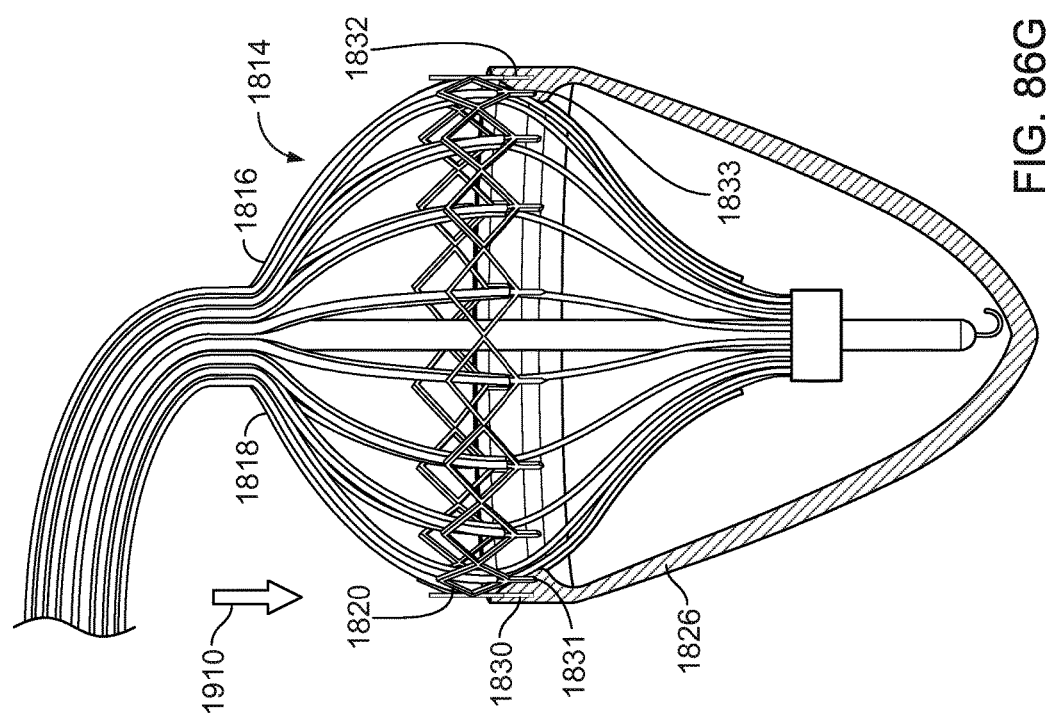
Figure 86F:
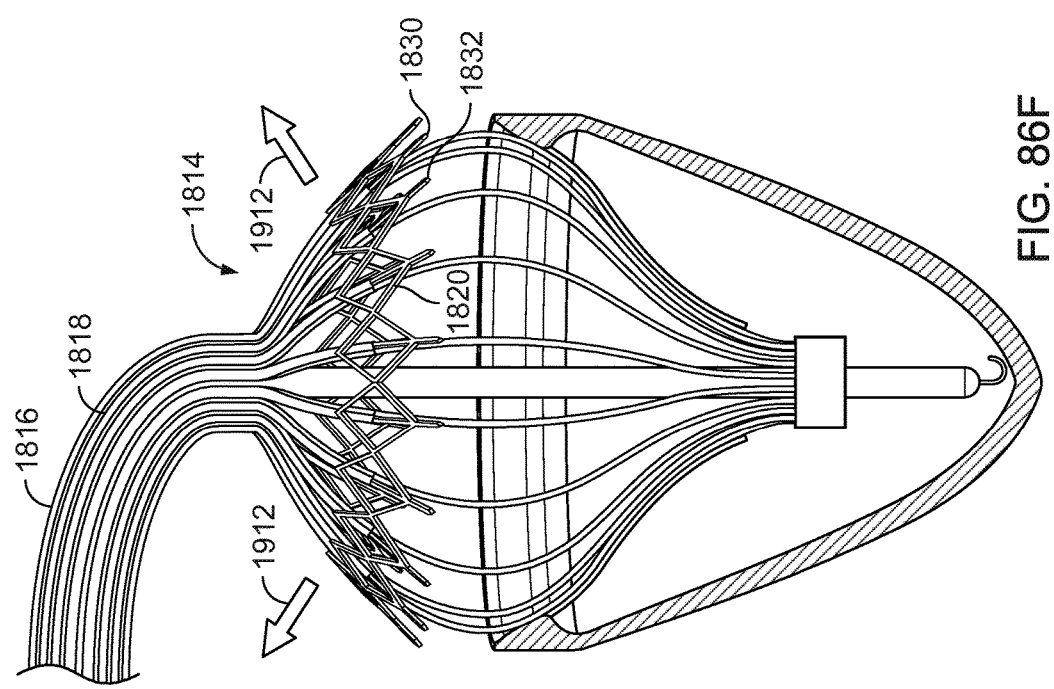

As shown in FIG. 86F, as the multiple-lumen tubes 1816, 1818 pull the heart valve support 1820 along the wires forming the basket 1814, the heart valve support expands 1912 and the anchors 1830, 1832 splay outward.

As shown in FIG. 86G, the multiple-lumen tubes 1816, 1818 continue to pull 1910 the heart valve support 1820 until the anchors 1830, 1832 contact the annular tissue 1826 at locations near the points of contact 1831, 1833 of the basket 1814 and the annular tissue.

As shown in FIG. 86H, a sheath 1874 is advanced 1914 down the delivery head 1800c as the basket 1814 contracts 1916. In some implementations, the sheath 1874 is made of a sufficiently stiff material to cause the basket 1814 to contract 1916 by applying inward pressure to the wires 1802, 1804 as the sheath advances 1914. The contraction of the basket 1814 causes the heart valve support 1820 (still attached to the delivery head) to contract, pulling the annular tissue 1826 inward. (For comparison, the outline of the un-contracted annular tissue 1826a is shown.)

As shown in FIG. 86I the multiple-lumen tubes 1816, 1818 retract 1922 upward away from the basket 1814 to under the sheath 1874. As the multiple-lumen tubes 1816, 1818 retract, they detach from the vertical struts 1838, 1840 of the heart valve support 1820. In some implementations, in response, the vertical struts 1838, 1840 automatically spring into alignment with the diamond sections 1846, 1848 of the heart valve support 1820 in a position that braces the diamond sections and resists horizontal expansion of the diamond sections. At this point, the heart valve support 1820 is in a configuration that it will remain in for the long term to keep the annulus 1824 in a contracted, repaired state.

Figure 86J:
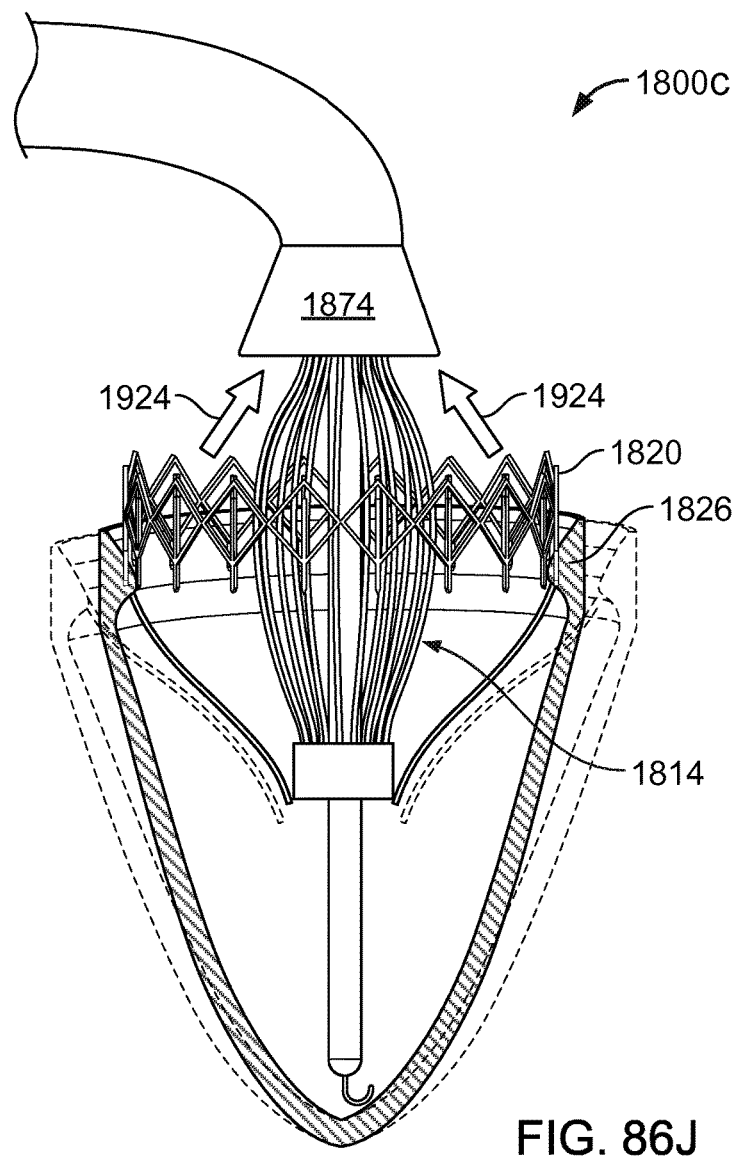

As shown in FIG. 86J, after the multiple-lumen tubes have retracted up along the wires into the sheath 1874, the basket 1814 fully collapses. The entire collapsed basket 1814 can then be pulled 1924 up into the sheath 1874 so that the delivery head 1800c is protected by the sheath as it is removed (for example, removed from a patient). The heart valve support 1820 remains attached to the annular tissue 1826 in a long-term configuration.

Other implementations are within the scope of the following claims.

What is claimed is:

1. An implantable annulus support for modifying a mitral valve annulus from within a left atrium, comprising:
   an expandable tubular body having a proximal end, a distal end, a sidewall therebetween and a longitudinal axis, the sidewall comprising a plurality of struts defining a plurality of distally facing apexes, the plurality of struts including a strut segment inclined radially outward away from the longitudinal axis in a distal direction, the tubular body expandable to a radially enlarged engagement configuration having a first width sufficient to span the mitral valve annulus; and
   a plurality of tissue anchors extending in a distal direction from the distally facing apexes, wherein the plurality of tissue anchors extend in the distal direction at least after deployment from a sheath, wherein axial distal advance of the plurality of tissue anchors causes the plurality of tissue anchors to axially engage tissue;
   wherein the implantable annulus support is contractible using a delivery tool from the radially enlarged engagement configuration for engaging tissue of the mitral valve annulus, to a reduced, deployed configuration for modifying mitral valve annulus geometry, and
   wherein reducing an angle between at least two adjacent struts of the plurality of struts contracts the implantable annulus support and wherein increasing the angle expands the implantable annulus support.

2. An implantable annulus support as in claim 1, wherein the plurality of struts form zig zag shaped sections.

3. An implantable annulus support as in claim 1, wherein the plurality of struts are cut from a tube.

4. An implantable annulus support as in claim 3, wherein the plurality of struts are laser cut from the tube.

5. An implantable annulus support as in claim 1, wherein the sidewall comprises a shape memory material.

6. An implantable annulus support as in claim 1, wherein the sidewall comprises Nitinol.

7. An implantable annulus support as in claim 1, comprising a plurality of barbs on the tissue anchors.

8. An implantable annulus support as in claim 1, wherein the first width is 38 millimeters or more.

9. An implantable annulus support as in claim 1, wherein, in the reduced, deployed configuration, the implantable annulus support contracts to 6.5 millimeters.

10. An implantable annulus support as in claim 1, wherein the implantable annulus support in the reduced, deployed configuration has a second width, wherein the implantable annulus support is configured to be delivered in a delivery configuration, wherein the implantable annulus support in the delivery configuration has a third width, and wherein the first width is greater than the second width and the second width is greater than the third width.

* * * * *